(12) United States Patent
Chen

(10) Patent No.: US 12,156,899 B2
(45) Date of Patent: Dec. 3, 2024

(54) METHODS AND COMPOSITIONS FOR REGENERATING HAIR CELLS AND/OR SUPPORTING CELLS

(71) Applicant: Massachusetts Eye and Ear Infirmary, Boston, MA (US)

(72) Inventor: Zheng-Yi Chen, Somerville, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 25 days.

(21) Appl. No.: 16/842,309

(22) Filed: Apr. 7, 2020

(65) Prior Publication Data
US 2020/0338160 A1  Oct. 29, 2020

Related U.S. Application Data

(63) Continuation of application No. 14/426,520, filed as application No. PCT/US2013/058626 on Sep. 6, 2013, now abandoned.

(60) Provisional application No. 61/698,246, filed on Sep. 7, 2012.

(51) Int. Cl.
| | |
|---|---|
| C12N 5/00 | (2006.01) |
| A61K 31/65 | (2006.01) |
| A61K 38/16 | (2006.01) |
| A61K 38/17 | (2006.01) |
| A61K 48/00 | (2006.01) |
| C12N 5/0793 | (2010.01) |
| A61K 35/30 | (2015.01) |

(52) U.S. Cl.
CPC ............ *A61K 38/177* (2013.01); *A61K 31/65* (2013.01); *A61K 38/16* (2013.01); *A61K 38/1709* (2013.01); *A61K 48/00* (2013.01); *A61K 48/005* (2013.01); *C12N 5/062* (2013.01); *A61K 35/30* (2013.01); *C12N 2501/42* (2013.01); *C12N 2501/606* (2013.01); *C12N 2710/10341* (2013.01)

(58) Field of Classification Search
None
See application file for complete search history.

(56) References Cited

U.S. PATENT DOCUMENTS

| | | |
|---|---|---|
| 3,645,090 A | 2/1972 | Mochizuki et al. |
| 3,940,475 A | 2/1976 | Gross |
| 4,302,204 A | 11/1981 | Wahl et al. |
| 4,358,535 A | 11/1982 | Falkow et al. |
| 5,034,506 A | 7/1991 | Summerton et al. |
| 5,138,045 A | 8/1992 | Cook et al. |
| 5,218,105 A | 6/1993 | Cook et al. |
| 5,258,498 A | 11/1993 | Huston et al. |
| 5,399,363 A | 3/1995 | Liversidge et al. |
| 5,432,272 A | 7/1995 | Benner |
| 5,459,255 A | 10/1995 | Cook et al. |
| 5,543,158 A | 8/1996 | Gref et al. |
| 5,641,515 A | 6/1997 | Ramtoola |
| 6,083,486 A | 7/2000 | Weissleder et al. |
| 6,417,185 B1 | 7/2002 | Goff et al. |
| 6,489,344 B1 | 12/2002 | Nuss et al. |
| 6,541,466 B2 | 4/2003 | Wu et al. |
| 6,608,063 B2 | 8/2003 | Nuss et al. |
| 6,756,511 B2 | 6/2004 | Castro Pineiro et al. |
| 6,890,956 B2 | 5/2005 | Churcher et al. |
| 6,984,626 B2 | 1/2006 | Nadin et al. |
| 7,026,343 B2 | 4/2006 | Prochownik et al. |
| 7,049,296 B2 | 5/2006 | Castro Pineiro et al. |
| 7,101,895 B2 | 9/2006 | Churcher et al. |
| 7,138,400 B2 | 11/2006 | Collins et al. |
| 7,144,910 B2 | 12/2006 | Madin et al. |
| 7,183,303 B2 | 2/2007 | Castro Pineiro et al. |
| 7,206,639 B2 | 4/2007 | Jacobsen et al. |
| 7,300,951 B2 | 11/2007 | Kreft et al. |
| 7,468,365 B2 | 12/2008 | Audia et al. |
| 7,544,511 B2 | 6/2009 | Yang et al. |
| 7,872,027 B2 | 1/2011 | Metallo et al. |
| 8,114,422 B2 | 2/2012 | Fujii et al. |
| 8,188,069 B2 | 5/2012 | Miller et al. |
| 8,188,131 B2 | 5/2012 | Edge et al. |
| 8,226,943 B2 | 7/2012 | Gurney et al. |
| 8,338,482 B2 | 12/2012 | Chen et al. |
| 9,175,265 B2 | 11/2015 | Sieweke |

(Continued)

FOREIGN PATENT DOCUMENTS

| | | |
|---|---|---|
| CN | 101891824 A | 11/2010 |
| EP | 0063879 | 11/1982 |

(Continued)

OTHER PUBLICATIONS

Tsai, Cancer Res., May 2012, vol. 72, No. 10, p. 2622-2633.*
Wikipedia description of Notch pathway, 2017.*
Liao ("The CBF1-independente Notch1 signal pathway activates human cMyc expression partially via transcription factor YY1", Carcinogenesis, 2007, vol. 28, No. 9, p. 1867-1876).*
Palomero (PNAS, Nov. 28, 2006, vol. 103, No. 48, p. 18261-18266).*
Weng (Genes & Develop., 2006, vol. 20, p. 2096-2109).*
Song (J. Immunol., May 1, 2016, vol. 196, Supp. 1).*
AU Office Action in Australian Appln. No. 2013312305, dated Apr. 29, 2021, 3 pages.

(Continued)

*Primary Examiner* — Michael C Wilson
(74) *Attorney, Agent, or Firm* — Fish & Richardson P.C.

(57) ABSTRACT

Provided are methods and compositions for inducing cells of the inner ear (for example, cochlear and utricular hair cells) to reenter to cell cycle and to proliferate. More particularly, the invention relates to the use of agents that increase c-myc activity and/or Notch activity for inducing cell cycle reentry and proliferation of cochlear or utricular hair cells and/or cochlear or utricular supporting cells. The methods and compositions can be used to promote the proliferation of hair cells and/or supporting cells to treat a subject at risk of, or affected with, hearing loss or a subject at risk of, or affected with vestibular dysfunction.

2 Claims, 46 Drawing Sheets

Specification includes a Sequence Listing.

(56) References Cited

U.S. PATENT DOCUMENTS

| | | |
|---|---|---|
| 2004/0029862 A1 | 2/2004 | Belanger et al. |
| 2004/0049038 A1 | 3/2004 | Collins et al. |
| 2004/0186147 A1 | 9/2004 | Hannam et al. |
| 2004/0237127 A1 | 11/2004 | Zoghbi et al. |
| 2005/0119293 A1 | 6/2005 | Collins et al. |
| 2005/0143369 A1 | 6/2005 | Castro Pineiro et al. |
| 2005/0182109 A1 | 8/2005 | Collins et al. |
| 2005/0182111 A1 | 8/2005 | Pineiro et al. |
| 2005/0215602 A1 | 9/2005 | Campbell et al. |
| 2006/0024278 A1 | 2/2006 | Chen |
| 2006/0030837 A1 | 2/2006 | McKenna et al. |
| 2007/0093878 A1 | 4/2007 | Edge et al. |
| 2007/0190046 A1 | 8/2007 | DeMaattos et al. |
| 2008/0008316 A1 | 1/2008 | Pilipchuk |
| 2009/0136466 A1 | 5/2009 | Fritzsch et al. |
| 2009/0181944 A1 | 7/2009 | Boylan et al. |
| 2009/0232780 A1 | 9/2009 | Edge et al. |
| 2009/0258026 A2 | 10/2009 | Siebel et al. |
| 2010/0197660 A1 | 8/2010 | Miller et al. |
| 2011/0020232 A1 | 1/2011 | Eberhart et al. |
| 2011/0251120 A1 | 10/2011 | Wang |
| 2011/0263580 A1 | 10/2011 | Miller |
| 2011/0275719 A1 | 11/2011 | Daniels et al. |
| 2011/0305674 A1 | 12/2011 | Edge et al. |
| 2012/0100569 A1 | 4/2012 | Liu et al. |
| 2012/0107317 A1 | 5/2012 | Lau et al. |
| 2012/0156179 A1 | 6/2012 | Sieweke |
| 2012/0207744 A1 | 8/2012 | Mendlein et al. |
| 2017/0327557 A1 | 11/2017 | Chen |

FOREIGN PATENT DOCUMENTS

| | | |
|---|---|---|
| EP | 1720909 A2 | 11/2006 |
| EP | 2178844 A1 | 4/2010 |
| EP | 2244713 A1 | 11/2010 |
| EP | 1949916 B1 | 8/2011 |
| EP | 2487156 A1 | 8/2012 |
| GB | 2019404 | 10/1979 |
| GB | 2034323 | 6/1980 |
| JP | 2006-117536 A | 5/2006 |
| RU | 38486 | 6/2004 |
| WO | WO-1998/028268 A2 | 7/1998 |
| WO | WO-2001/070677 A1 | 9/2001 |
| WO | WO-2002/047671 A2 | 6/2002 |
| WO | WO-2002/088346 A2 | 11/2002 |
| WO | WO-2003/093251 A1 | 11/2003 |
| WO | WO-2003/093252 A1 | 11/2003 |
| WO | WO-2003/093253 A1 | 11/2003 |
| WO | WO-2003/093264 A1 | 11/2003 |
| WO | WO-2004/039370 A1 | 5/2004 |
| WO | WO-2004/039800 A1 | 5/2004 |
| WO | WO-2004/090110 A2 | 10/2004 |
| WO | WO-2005/014553 A1 | 2/2005 |
| WO | WO 2004/090110 | 4/2005 |
| WO | WO-2005/030731 A1 | 4/2005 |
| WO | WO-2008/076556 A2 | 6/2008 |
| WO | WO-2009/005688 A2 | 1/2009 |
| WO | WO-2009/023453 A1 | 2/2009 |
| WO | WO 2009/005688 | 4/2009 |
| WO | WO 2009/040423 | 4/2009 |
| WO | WO-2009/040423 A1 | 4/2009 |
| WO | WO-2010/060088 A2 | 5/2010 |
| WO | WO-2011/003988 A1 | 1/2011 |
| WO | WO-2011/149762 A2 | 12/2011 |
| WO | WO 2012/080926 | 6/2012 |
| WO | WO-2012/080926 A2 | 6/2012 |
| WO | WO-2013/134022 A1 | 9/2013 |
| WO | WO 2014/039908 | 3/2014 |
| WO | WO 2016/069906 | 5/2016 |

OTHER PUBLICATIONS

AU Office Action in Australian Appln. No. 2013312305, dated Apr. 29, 2019, 3 pages.

AU Office Action in Australian Appln. No. 2013312305, dated Jun. 17, 2017, 2 pages.

CA Office Action in Canadian Appln. No. 2,884,309, dated Jan. 20, 2021, 6 pages.

CN Office Action in Chinese Appln. No. 201380058368.7, dated Jan. 8, 2018, 34 pages (with English translation).

CN Office Action in Chinese Appln. No. 201380058368.7, dated Apr. 13, 2017, 22 pages (with English translation).

CN Office Action in Chinese Appln. No. 201380058368.7, dated May 19, 2016, 6 pages (with English translation).

CN Office Action in Chinese Appln. No. 201380058368.7, dated Sep. 13, 2018, 7 pages (with English translation).

Coclea hair cell, Wikipedia, 2017.

EP Extended European Search Report in European Appln. No. 13834856.0, dated Feb. 17, 2016, 9 pages.

EP Office Action in European Appln. No. 13834856.0, dated Apr. 4, 2018, 7 pages.

EP Office Action in European Appln. No. 13834856.0, dated May 26, 2017, 5 pages.

EP Office Action in European Appln. No. 13834856.0, dated Sep. 10, 2018, 3 pages.

EP Summons to Attend Oral Proceedings in European Appln. No. 13834856.0, dated Feb. 29, 2018, 5 pages.

JP Office Action in Japapnese Appln. No. 2015-531262, dated May 8, 2018, 4 pages (with English translation).

JP Office Action in Japapnese Appln. No. 2015-531262, dated Jun. 6, 2017, 8 pages (with English translation).

Notch patway, Wikipedia, 2017.

Palomero et al., NOTCH1 directly regulates c-MYC and activates a feed-forward-loop transcriptional network promoting leukemic cell growth, PNAS, Nov. 2006, 103(48)18261-18266.

Song et al., "C-Myc regulation by Notch Signaling Modulates T Cell Differentiation," J. Immunol., May, 196(1 Supplement) 121.16.

Tsai et al., "Activation of Ras/PI3K/ERK pathway induces c-Myc stabilization to upregulate argininosuccinate synthetase, leading to arginine deiminase resistance in melanoma cells," Cancer Res., May 2012, 72(10)2622-2633.

Utricular cell, Wikipedia, 2017.

Weng et al., "c-Myc is an important direct target of Notch1 in T-cell acute lymphoblastic leukemia/lymphoma," Genes & Develop., Aug. 2006, 20(15)2096-2109.

Aggarwal BB et al., (2005), 'Curcumin Suppresses the Paclitaxel-induced Nuclear Factor-κβ Pathway in Breast Cancer Cells and Inhibits Lung Metastasis of Human Breast Cancer in Nude Mice,' Clin Cancer Res, 11(20):7490-8.

Ahmed M et al., (2012), 'Eya 1-Six1 Interaction is Sufficient to Induce Hair Cell Fate in the Cochlea by Activating Atoh1 Expression in Cooperation with Sox2,' Dev Cell, 22(2):377-90.

Albright CF et al., (2013), 'Pharmacodynamics of Selective Inhibition of γ-Secretase by Avagacestat®,' J Pharmacol Exp Ther, 344(3):686-95.

Aletsee C et al., (2001), 'The Disintegrin Kistrin Inhibits Neurite Extension from Spiral Ganglion Explants Cultures on Laminin,' Audiol Neurootol, 6(2):57-65.

Alt M and Caselmann WH, (1995), 'Liver-directed Gene Therapy: Molecular Tools and Current Preclinical and Clinical Studies,' J Hepatol, 23(6):746-58.

Andersson ER, and Lendahl U, (2014) "Therapeutic Modulation of Notch Signalling—Are We There Yet?," Nature Reviews: Drug Discovery, 13:357-378.

Ashizawa T et al., (2011), 'Antitumor Activity of a Novel Small Molecule STAT3 Inhibitor Against a Human Lymphoma Cell Line with High STAT3 Activation,' Int J Oncol, 38(5):1245-52.

Best JD et al., (2006), 'In Vivo Characterization of Aβ(40) Changes in Brain and Cerebrospinal Fluid Using the Novel γ-Secretase Inhibitor N-[cis-4-[(4-chlorophenyl)sulfonyl]-4-(2,5-difluorophenyl)cyclohexyl]-1,1,1-trufluoromethanesulfonamide (MRK-560) in the Rat,' J Pharmacol Exp Therapeut, 317(2):786-90.

Brody SL and Crystal RG, (1994), 'Adenovirus-Mediated in vivo Gene Transfer,' Ann NY Acad Sci, 716:90-101.

Brors D et al., (2003), 'EphA4 Provides Repulsive Signals to Developing Cochlear Ganglion Neurites Mediated Through Ephrin-B2 and -B3,' J Comp Neurol, 462(1):90-100.

(56) References Cited

OTHER PUBLICATIONS

Chiarella P et al., (2008), 'Strategies for Effective Naked-DNA Vaccination Against Infectious Diseases,' Recent Pat Antiinfect Drug Discov, 3(2):93-101.
Chung EY et al., (2012), 'CD19 is a Major B Cell Receptor-independent Activator of Myc-Driven B-lymphopagenesis,' J Clin Invest, 122(6):2257-66.
Churcher I et al., (2003), 'Design and Synthesis of Highly Potent Benzodiazepine γ-Secretase Inhibitors: Preparation of (2S,3R)-3-(3,4-difluorphenyl)-2-(4-fluorphenyl)-4-hydroxy-N-((3S)-1-methyl-2-oxo-5-phenyl-2,3-dihydro-1H-benzo[e][1,4]-diazepin-3-yl)buturamide by Use of an Asymmetric Ireland-Claisen Rearrangement,' J Med Chem, 46(12):2275-8.
Clausen DM et al., (2010), 'In Vitro Cytotoxicity and in vivo Efficacy, Pharmacokinetics, and Metabolism of 10074-G5, a Novel Small-molecule Inhibitor of c-Myc/Max Dimerization,' J Pharmacol Exp Ther, 335(3):715-27.
Daudet N et al., (2009), 'Notch Regulation of Progenitor Cell Behavior in Quiescent Regenerating Auditory Epithelium of Mature Birds,' Dev Biol, 326(1):86-100.
Devarajan K et al., (2011), 'A Review of Gene Delivery as Stem Cell Based Therapies for Regenerating Inner Ear Hair Cells,' J Funct Biomater, 2(3):249-70.
Engelhard HH et al., (1998), 'Inhibitory Effects of Phenylbutyrate on the Proliferation, Morphology, Migration and Invasiveness of Malignant Glioma Cells,' J Neurooncol, 37(2):97-108.
Fauq AH et al., (2007), 'A Multigram Chemical Synthesis of the γ-Secretase Inhibitor LY411575 and its Diastereoisomers,' Bioorg Med Chem Lett, 17(22):6392-5 (HHS Public Access version of author manuscript).
Ferry N and Heard JM, (1998), 'Liver-Directed Gene Transfer Vectors,' Hum Gene Ther, 9(14):1975-81.
Fuwa H et al., (2006), 'Synthesis of Biotinylated Photoaffinity Probes Based on Arylsulfonamide γ-Secretase Inhibitors,' Bioorg Med Chem Lett, 16(16):4184-9.
Gillespie LN et al., (2001), 'LIF is More Potent than BDNF in Promoting Neurite Outgrowth of Mammalian Auditory Neurons in vitro,' Neuroreport, 12(2):275-9.
Gray SJ and Samulski RJ, (2008), 'Optimizing Gene Delivery Vectors for the Treatment of Heart Disease,' Expert Opin Biol Ther, 8(7):911-22.
Han Y et al., (2009), 'Effect of c-Myc on the Ultrastructural Structure of Cochlea in Guinea Pigs with Noise Induced Hearing Loss,' Biochem Biophys Res Comm, 390(3):458-62.
Henikoff S and Henikoff JG, (1992), 'Amino Acid Substitution Matrices from Protein Blocks,' Proc Natl Acad Sci, USA, 89(22):10915-9.
Hu ZB et al., (1993), 'Induction of Differentiation of β-cell Leukemia Cell Lines JVM-2 and EHEB by Bryostatin 1,' Leuk Lymphoma, 10(1-2):135-42.
Huang MJ et al., (2006), 'A Small-molecule c-Myc Inhibitor, 10058-F4, Induces Cell-cycle Arrest, Apoptosis, and Myeloid Differentiation of Human Acute Myeloid,' Exp Hematol, 34(11):1480-9.
Hurley NE et al., (2010), 'Modulating the Functional Contributions of c-Myc to the Human Endothelial Cell Cyclic Strain Response,' J Vasc Res, 47(1):80-90.
Imbimbo BP, (2008), 'Therapeutic Potential of γ-Secretase Inhibitors and Modulators,' Curr Top Med Chem, 8(1):54-61.
International Search Report for Application No. PCT/US2013/058626 mailed Jan. 30, 2014 (9 pages).
Ishikawa Y et al., (2013), 'Opposing Functions of Fbxw7 in Keratinocyte Growth, Differentiation and Skin Tumorigenesis Mediated Through Negative Regulation of c-Myc and Notch,' Oncogene, 32(15):1921-32.
Jeon SJ et al., (2011), 'Notch Signaling Alters Sensory or Neuronal Cell Fate Specification of Inner Ear Stem Cells,' J Neurosci, 31(23):8351-8.

Kaltenbach JA et al., (2002), 'Cisplatin-induced Hyperactivity in the Dorsal Cochlear Nucleus and its Relation to Outer Hair Cell Loss: Relevance to Tinnitus,' J Neurophysiol, 88(2):699-714.
Kay MA, (1997), 'Adenoviral Vectors for Hepatic Gene Transfer in Animals,' Chest, 111(Suppl 6):138S-42S.
Kiernan AE et al., (2001), 'The NOTCH Ligand Jagged1 is Required for Inner Ear Sensory Development,' Proc Natl Acad Sci USA, 98(7):3873-8.
Kress, TR et al., (2015) "MYC: Connecting Selective Transcriptional Control to Global RNA Production," Nature Reviews: Cancer 15: 593-607.
Kujawa SG and Liberman MC, (2009), 'Adding Insult to Injury: Cochlear Nerve Degeneration after "Temporary" Noise-Induced Hearing Loss,' J Neurosci, 29(45):14077-85.
Kwan T et al., (2009), 'Development and Regeneration of Inner Ear,' Ann NY Acad Sci, 1170:28-33.
Landy A, (1993), 'Mechanistic and Structural Complexity in the Site-specific Recombination Pathways of Int and FLP,' Curr Opin Genet Dev, 3(5):699-707.
Lanford PJ et al., (1999), 'NOTCH Signaling Pathway Mediates Hair Cell Development in Mammalian Cochlea,' Nat Genet, 21(3):289-92.
Lauber SN et al., (2004), 'The Cooked Food Derived Carcinogen 2-amino-1-methyl-6-phenylimidazo [4,5-b] pyridine is a Potent Oestrogen: A Mechanistic Basis for its Tissue-specific Carcinogenicity,' Carcinogenesis, 25(12):2509-17.
Lee HC et al., (2000), 'Remission in Models of Type 1 Diabetes by Gene Therapy Using a Single-chain Insulin Analogue,' Nature, 408(6811):483-8.
Lee SG et al., (2008), 'Identification of Essential Pathways for Hair Cell Regeneration,' Abstract No. 562, ARO Abstracts, 31st Annual Mid-Winter Research Meeting of the Association for Research in Otolaryngology, Feb. 16-21, 2008, Phoenix, AZ, PA Santi (Ed), Association for Research in Otolaryngology, Mt. Royal, NJ (Pub), 31(2008):191.
Lin CP et al., (2007), 'Small-molecule c-Myc Inhibitor, 10058-F4, Inhibits Proliferation, Downregulates Human Telomerase Reverse Transcriptase and Enhances Chemosensitivity in Human Hepatocellular Carcinoma Cells,' Anticancer Drugs, 18(2):161-70.
Lin V et al., (2011), 'Inhibition of Notch Activity Promotes Nonmitotic Regeneration of Hair Cells in the Adult Mouse Utricles,' J Neurosci, 31(43):15329-39.
Lowy I et al., (1980), 'Isolation of Transforming DNA: Cloning the Hamster APRT Gene,' Cell, 22(3):817-23.
Mangi AA et al., (2003), 'Mesenchymal Stem Cells Modified with Akt Prevent Remodeling and Restore Performance of Infarcted Hearts,' Nat Med, 9(9):1195-201.
McEwan MV et al., (2012), 'Cohesion is Required for Activation of MYC by Esterdiol,' PLoS One, 7(11):e49160.
Melman A et al., (2006), 'hMaxi-K Gene Transfer in Males with Erectile Dysfunction: Results of the First Human Trial,' Hum Gene Ther, 17(12):1165-76.
Mizuma M et al., (2012), 'The γ-Secretase Inhibitor MRK-003 Attenuates Pancreatic Cancer Growth in Preclinical Models,' Mol Cancer Ther, 11(9):1999-2009.
Moon RT et al., (2004), 'WNT and B-catenin Signalling: Diseases and Therapies,' Nat Rev Genet, 5(9):691-701.
Mori H et al., (1997) 'Chemoprevention by Naturally Occurring and Synthetic Agents in Oral, Liver, and Large Bowel Carcinogenesis,' J Cell Biochem Suppl, 27:35-41.
Murtaugh LC et al., (2003), 'Notch Signaling Controls Multiple Steps of Pancreatic Differentiation,' Proc Natl Acad Sci USA, 100(25):14920-5.
Oka K et al., (2000), 'Recent Advances in Liver-Directed Gene Therapy: Implications for the Treatment of Dyslipidemia,' Curr Opin Lipidol, 11(2):179-86.
Oshima K et al., (2010), 'Mechanosensitive Hair Cell-like Cells from Embryonic and Induced Pluripotent Stem Cells,' Cell, 141(4):704-16.
Page BD et al., (2012), 'Small Molecule STAT5-SH2 Domain Inhibitors Exhibit Potent Antileukemia Activity,' J Med Chem, 55(3):1047-55.

(56) References Cited

OTHER PUBLICATIONS

Palomero T et al., (2006), 'Notch1 Directly Regulates c-MYC and Activates a Feed-forward-loop Transcriptional Network Promoting Leukemic Cell Growth,' Proc Natl Acad Sci USA, 103(48):18261-6.
Pan W et al., (2010), 'Notch Signaling is Required for the Generation of Hair Cells and Supporting Cells in the Mammalian Inner Ear,' Proc Natl Acad Sci USA, 107(36):15798-803.
Park S et al., (2004), 'Inhibition of AP-1 Transcription Activator Induces Myc-Dependent Apoptosis in HL60 Cells,' J Cell Biochem, 91(5):973-86.
Petit A et al., (2001), 'New Protease Inhibitors Prevent γ-Secretase-Mediated Production of AB40/42 Without Affecting Notch Cleavage,' Nat Cell Biol, 3(5):507-11.
Purow B, (2012), 'Notch Inhibition as a Promising New Approach to Cancer Therapy,' Adv Exp Med Biol, 727:305-19 (HHS Public Access version of author manuscript).
Sai K et al., (2012), 'Induction of Cell-cycle Arrest and Apoptosis in Glioblastoma Stem-like Cells by WP1193, a Novel Small Molecule Inhibitor of the JAK2/STAT3 Pathway,' J Neurooncol, 107(3):487-501.
Samon JB et al., (2012), 'Preclinical Analysis of the γ-Secretase Inhibitor PF-03084014 in Combination with Glucocorticoids in T-Cell Acute Lymphoblastic Leukemia,' Mol Cancer Ther, 11(7):1565-75.
Shearman MS et al., (2000), 'L-685,458, an Aspartyl Protease Transition State Mimic, is a Potent Inhibitor of Amyloid β-Protein Precursor γ-Secretase Activity,' Biochemistry, 39(30):8698-704.
Shih IM and Wang TL, (2007), 'Notch Signaling, γ-Secretase Inhibitors, and Cancer Therapy,' Cancer Res, 67(5):1879-82.
Shiratori Y et al., (1999), 'Strategy of Liver-directed Gene Therapy: Present Status and Future Prospects,' Liver, 19(4):265-74.
Sirin O and Park F, (2003), 'Regulating Gene Expression Using Self-Inactivating Lentiviral Vectors Containing the Mifepristone-inducible System,' Gene, 323:67-77.
Smetanina Ma et al., (2011), 'Ortho-aminoazotoluene Activates Mouse Constitutive Androstane Receptor (mCAR) and Increases Expression of mCAR Target Genes,' Toxicol Appl Pharmacol, 255(1):76-85 (HHS Public Access version of author manuscript).
Smith-Arica JR and Bartlett JS, (2001), 'Gene Therapy: Recombinant Adeno-Associated Virus Vectors,' Curr Cardiol Rep, 3(1):43-9.
Strayer DS, (1999), 'Viral Gene Delivery,' Expert Opin Investig Drugs, 8(12):2159-72.
Takahashi Y et al., (2003), 'Sulindac Sulfide is a Noncompetitive γ-Secretase Inhibitor that Preferentially Reduces Aγ42 Generation,' J Biol Chem, 278(20):18664-70.
Takebayashi S et al., (2007), 'Multiple Roles of Notch Signaling in Cochlear Development,' Dev Biol, 307(1):165-78.
Thulé PM and Liu JM, (2000), 'Regulated Hepatic Insulin Gene Therapy of STZ-Diabetic Rats,' Gene Ther, 7(20):1744-52.
Tolcher AW et al., (2012), 'Phase I Study of RO4929097, a Gamma Secretase Inhibitor of Notch Signaling, in Patients with Refractory Metastatic of Locally Advanced Solid Tumors,' J Clin Oncol, 30(19):2348-53.
Weihofen A et al., (2002), 'Identification of Signal Peptide Peptidase, a Presenilin-type Aspartic Protease,' Science, 296(5576):2215-8.
Wigler M et al., (1977), 'Transfer of Purified Herpes Virus Thymidine Kinase Gene to Cultured Mouse Cells,' Cell, 11(1):223-32.
Wolfe MS et al., (1998), A Substrate-based Difluoro Ketone Selectively Inhibits Alzheimer's γ-Secretase Activity, J Med Chem, 41(1):6-9.
Written Opinion of the International Searching Authority for Application No. PCT/US2013/058626 mailed Jan. 30, 2014 (12 pages).
Yang NS, (1992), 'Gene Transfer into Mammalian Somatic Cells in vivo,' Crit Rev Biotechnol, 12(4):335-56.
Zhang N et al., (2000), 'A Mutation in the *Lunatic fringe* Gene Suppresses the Effects of Jagged2 Mutation on Inner Hair Cell Development in the Cochlea,' Curr Biol, 10(11): 659-62.

Zhang X et al., (2012), 'Orally Bioavailable Small-molecule Inhibitor of Transcription Factor STAT3 Regresses Human Breast and Lung Cancer Xenografts,' Proc Natl Acad Sci USA, 109(24):9623-8.
Zheng M et al., (2009), 'Studies on the Pharmacokinetics and Metabolism of γ-Secretase Inhibitor BMS-299897, and Exploratory Investigation of CYP Enzyme Induction,' Xenobiotica, 39(7):544-55.
Zine A and de Ribaupierre F, (2002), 'Notch/Notch Ligands and Math1 Expression Patterns in the Organ of Corti of Wild-type and Hes1 and Hes5 Mutant Mice,' Hear Res, 170(1-2):22-31.
Zine A et al., (2000), 'NOTCH Signaling Regulates the Pattern of Auditory Hair Cell Differentiation in Mammals,' Development, 127(15):3373-83.
Ausubel et al., "Preparation of a Specific Retrovirus Producer Cell Line", Current Protocols in Molecular Biology, 2001, 13 pages.
Burns et al., "MYC Gene Delivery to Adult Mouse Utricles Stimulates Proliferation of Postmitotic Supporting Cells In Vitro", PLOS One, Oct. 2012, 7(10):e48704, 15 pages.
Christensen et al., "A Novel Class of Oligonucleotide Analogues Containing 2'-0,3'-C-Linked [3.2.0]Bicycloarabinonucleoside Monomers: Synthesis, Thermal Affinity Studies, and Molecular Modeling", Journal of the American Chemical Society, 1998, 120(22):5458-5463.
CRC's Antisense Research and Applications, 1st ed., Crooke and Lebleu (eds.), 1993, pp. 276-278.
De Mesmaeker et al., "Antisense Oligonucleotides", Accounts of Chemical Research, Sep. 1995, 28(9):366-374.
Fernandez et al., "Membrane Interactions of Antimicrobial Peptides from Australian Frogs," Biochimica et Biophysica Acta (BBA)—Biomembranes, Aug. 2009, 1788(8):1630-1638.
Freier et al., "The Ups and Downs of Nucleic Acid Duplex Stability: Structure-Stability Studies on Chemically-Modified DNA: RNA Duplexes," Nucleic Acids Research, Nov. 1997, 25(22):4429-4443.
Gebeyehu et al., "Novel Biotinylated Nucleotide-Analogs for Labeling and Colorimetric Detection of DNA", Nucleic Acids Research, Jun. 1987, 15(11):4513-4534.
Herdewin, "Heterocyclic Modifications of Oligonucleotides and Antisense Technology", Antisense & Nucleic Acid Drug Development, Aug. 2000, 10(4):297-310.
Kabanov et al., "A New Class of Antivirals: Antisense Oligonucleotides Combined with a Hydrophobic Substituent Effectively Inhibit Influenza Virus Reproduction and Synthesis of Virus-Specific Proteins in MOCK Cells", FEBS Letters, Jan. 1990, 259(2):327-330.
Karagiannis et al., "Rational Design of a Biomimetic Cell Penetrating Peptide Library," ACS Nano, 2013, 7(10):8616-8626, 20 pages.
Kornberg et al., "DNA Replication," The Journal of Biological Chemistry, Jan. 1988, 263(1):1-4.
Kraft et al., "Atoh1 Induces Auditory Hair Cell Recovery in Mice After Ototoxic Injury," The Laryngoscope, Jul. 2011, 123(4):992-999.
Leary et al., "Rapid and Sensitive Colorimetric Method for Visualizing Biotin-Labeled DNA Probes Hybridized to DNA or RNA Immobilized on Nitrocellulose: Bio-Blots", PNAS, Jul. 1983, 80(13):4045-4049.
Letsinger et al., "Cholesteryl-Conjugated Oligonucleotides: Synthesis, Properties, and Activity as Inhibitors of Replication of Human Immunodeficiency Virus in Cell Culture," PNAS, Sep. 1989, 86(17):6553-6556.
Li et al., "Discovery and Characterization of a Peptide that Enhances Endosomal Escape of Delivered Proteins in vitro and in vivo," Journal of the American Chemical Society, Oct. 2015, 137(44):14084-14093.
Manoharan et al., "Chemical Modifications to Improve Uptake and Bioavailability of Antisense Oligonucleotides," Annals of the New York Academy of Sciences, Oct. 1992, 660(1):306-309.
Manoharan et al., "Cholic Acid-Oligonucleotide Conjugates for Antisense Applications," Bioorganic & Medicinal Chemistry Letters, Apr. 1994, 4(8):1053-1060.
Manoharan et al., "Introduction of a Lipophilic Thioether Tether in the Minor Groove of Nucleic Acids for Antisense Applications," Bioorganic & Medicinal Chemistry Letters, Dec. 1993, 3(12):2765-2770.

(56) References Cited

OTHER PUBLICATIONS

Manoharan et al., "Lipidic Nucleic Acids", Tetrahedron Letters, May 1995, 36(21):3651-3654.

Manoharan et al., "Oligonucleotide Conjugates: Alteration of the Pharmacokinetic Properties of Antisense Agents", Nucleosides and Nucleotides, Feb. 2007, 14(3-5):969-973.

Manoharan, "2'-Carbohydrate Modifications in Antisense Oligonucleotide Therapy: Importance of Conformation, Configuration and Conjugation," Biochimica et Biophysica Acta—Gene Structure and Expression, Dec. 1999, 1489(1):117-130.

Meinkoth et al., "Hybridization of Nucleic Acids Immobilized on Solid Supports," Analytical Biochemistry, May 1984, 138(2):267-284.

NeuronBank.org [online], "Coclea hair cell," Sep. 2009, retrieved on Aug. 16, 2017, retrieved from URL<http://www.neuronbank.org/wiki/index.php/Cochlea_hair_cell>, 3 pages.

Nielsen et al., "Sequence-Selective Recognition of DNA by Strand Displacement with a Thymine-Substituted Polyamide," Science, Dec. 1991, 254(5037):1497-1500.

Oberhauser et al., "Effective Incorporation of 2'-O-Methyl-Oligoribonucleotides into Liposomes and Enhanced Cell Association through Modification with Thiocholesterol," Nucleic Acids Research, Feb. 1992, 20(3):533-538.

Office Action in Canadian Appln. No. 2,884,309, dated Feb. 10, 2022, 4 pages.

Oshima et al., "Differential Distribution of Stem Cells in the Auditory and Vestibular Organs of the Inner Ear," Journal of the Association for Research in Otolaryngology, Mar. 2007, 8:18-31.

Rathjen et al., "Properties and Uses of Embryonic Stem Cells: Prospects for Application to Human Biology and Gene Therapy", Reproduction, Fertility and Development, 1998, 10(1):31-47.

Renz et al., "A Colorimetric Method for DNA Hybridization", Nucleic Acids Research, Apr. 1984, 12(8):3435-3444.

Richardson et al., "Biotin and Fluorescent Labeling of RNA Using T4 RNA Ligase," Nucleic Acids Research, Sep. 1983, 11(18):6167-6184.

Rotman, "Measurement of Activity of Single Molecules of Beta-D-Galactosidase", PNAS, Dec. 1961, 47(12):1981-1991.

Saison-Behmoaras et al., "Short Modified Antisense Oligonucleotides Directed Against Ha-ras Point Mutation Induce Selective Cleavage of the mRNA and Inhibit T24 Cells Proliferation", EMBO Journal, May 1991, 10(5):1111-1118.

Scheit, "Nucleotide Analogs—Synthesis and Biological Function", FEBS Letters, Dec. 1980, 122(2):328-329.

Shea et al., "Synthesis, Hybridization Properties and Antiviral Activity of Lipid-Oligodeoxynucleotide Conjugates," Nucleic Acids Research, Jul. 1990, 18(13):3777-3783.

Shu et al., "Renewed proliferation in adult mouse cochlea and regeneration of hair cells," Nature Communications, 2019, 10:5530, 15 pages.

Slowik and Bermingham-McDonogh, "Notch signaling in mammalian hair cell regeneration," Trends in Developmental Biology, 2013, 7:73-89.

Smith et al., "The Synthesis of Oligonucleotides Containing an Aliphatic Amino Group at the 5' Terminus: Synthesis of Fluorescent DNA Primers for Use in DNA Sequence Analysis," Nucleic Acids Research, Apr. 1985, 13(7):2399-2412.

Svinarchuk et al., "Inhibition of HIV Proliferation in MT-4 Cells by Antisense Oligonucleotide Conjugated to Lipophilic Groups," Biochimie, 1993, 75(1-2):49-54.

Thompson et al., "Engineering and Identifying Supercharged Proteins for Macromolecule Delivery into Mammalian Cells," Methods in Enzymology, 2012, 503:293-319.

Toulme, "New Candidates for True Antisense", Nature Biotechnology, 2001, 19:17-18.

Uhlmann, "Recent Advances in Medicinal Chemistry of Antisense Oligonucleotides," Current Opinion in Drug Discovery & Development, Mar. 2000, 3(2):203-213.

Wiles, "Embryonic Stem Cell Differentiation In Vitro," Methods in Enzymology, Jan. 1993, 225:900-918.

Office Action in Australian Appln. No. 2020217408, dated Oct. 10, 2022, 3 pages.

Notice of Acceptance in Australian Appln. No. 2020217408, dated Jul. 21, 2023, 4 pages.

* cited by examiner

FIG. 1A

NP_002458.2 (SEQ ID NO: 1)

```
1   mdffrvvenq qppatmplnv sftnrnydld ydsvqpyfyc deeenfyqqq qqselqppap
61  sediwkkfel lptpplspsr rsglcspsyv avtpfslrgd ndggggsfst adqlemvtel
121 lggdmvnqsf icdpddetfi kniiiqdcmw sgfsaaaklv seklasyqaa rkdsgspnpa
181 rghsvcstss lylqdlsaaa secidpsvvf pyplndsssp kscasqdssa fspssdslls
241 stesspqgsp eplvlheetp pttssdseee qedeeeidvv svekrqapgk rsesgspsag
301 ghskpphspl vlkrchvsth qhnyaappst rkdypaakrv kldsvrvlrq isnnrkctsp
361 rssdteenvk rrthnvlerq rrnelkrsff alrdqipele nnekapkvvi lkkatayils
421 vqaeeqklis eedllrkrre qlkhkleqlr nsca
```

FIG. 1B

C-myc consensus protein sequence (SEQ ID NO: 9)

MPLNVX$_1$FX$_2$NRNYDLDYDSVQPYFX$_3$CDEEENFYX$_4$QQQQSELQPPAPSEDIWKKFELLPTPPLSPS
RRSGLCSPSYVAVX$_5$X$_6$X$_7$FSX$_8$RX$_9$DX$_{10}$DGGGGX$_{11}$FSTADQLEMX$_{12}$TELLGGDMVNQSFICDPDDE
TFIKNIIIQDCMWSGFSAAAKLVSEKLASYQAARKDSX$_{13}$SX$_{14}$X$_{15}$PARGHSVCSTSSLYLQDLX$_{16}$A
AASECIDPSVVFPYPLNDSSSPKSCX$_{17}$SX$_{18}$DSX$_{19}$AFSX$_{20}$SSDSLLSSX$_{21}$ESSPX$_{22}$X$_{23}$X$_{24}$PEPLV
LHEETPPTTSSDSEEEQX$_{25}$DEEEIDVVSVEKRQX$_{26}$PX$_{27}$KRSESGSX$_{28}$X$_{29}$X$_{30}$GGHSKPPHSPLVL
KRCHVSTHQHNYAAPPSTRKDYPAAKRX$_{31}$KLDSX$_{32}$RVLX$_{33}$QISNNRKCX$_{34}$SPRSSDTEENX$_{35}$KRR
THNVLERQRRNELKRSFFALRDQIPELENNEKAPKVVILKKATAYILSX$_{36}$QAX$_{37}$EX$_{38}$KLX$_{39}$SEX$_{40}$
DLLRKRREQLKHKLEQLRNSX$_{41}$A

FIG. 2A

NP_060087.3 (SEQ ID NO: 2)

```
1    mppllapllc lallpalaar gprcsqpget clnggkceaa ngteacvcgg afvgprcqdp
61   npclstpckn agtchvvdrr gvadyacsca lgfsgplclt pldnacltnp crnggtcdll
121  tlteykcrcp pgwsgkscqq adpcasnpca nggqclpfea syichcppsf hgptcrqdvn
181  ecgqkpglcr hggtchnevg syrcvcrath tgpncerpyv pcspspcqng gtcrptgdvt
241  hecaclpgft gqnceenidd cpgnnckngg acvdgvntyn crcppewtgq yctedvdecq
301  lmpnacqngg tchnthggyn cvcvngwtge dcseniddca saacfhgatc hdrvasfyce
361  cphgrtgllc hlndacisnp cnegsncdtn pvngkaictc psgytgpacs qdvdecslga
421  npcehagkci ntlgsfecqc lqgytgprce idvnecvsnp cqndatcldq igefqcicmp
481  gyegvhcevn tdecasspcl hngrcldkin efqcecptgf tghlcqydvd ecastpckng
541  akcldgpnty tcvctegytg thcevdidec dpdpchygsc kdgvatftcl crpgytghhc
601  etninecssq pcrhggtcqd rdnaylcfcl kgttgpncei nlddcasspc dsgtcldkid
661  gyecacepgy tgsmcninid ecagnpchng gtcedgingf tcrcpegyhd ptclsevnec
721  nsnpcvhgac rdslngykcd cdpgwsgtnc dinnnecesn pcvnggtckd mtsgyvctcr
781  egfsgpncqt ninecasnpc lnqgtciddv agykcncllp ytgatcevvl apcapspcrn
841  ggecrqsedy esfscvcptg wqgqtcevdi necvlspcrh gascqnthgg yrchcqagys
901  grncetdidd crpnpchngg sctdgintaf cdclpgfrgt fceedineca sdpcrnganc
961  tdcvdsytct cpagfsgihc enntpdctes scfnggtcvd ginsftclcp pgftgsycqh
1021 dvnecdsqpc lhggtcqdgc gsyrctcpqg ytgpncqnlv hwcdsspckn ggkcwqthtq
1081 yrcecpsgwt glycdvpsvs cevaaqrqgv dvarlcqhgg lcvdagnthh crcqagytgs
1141 ycedlvdecs pspcqngatc tdylggysck cvagyhgvnc seeideclsh pcqnggtcld
1201 lpntykcscp rgtqgvhcei nvddcnppvd pvsrspkcfn ngtcvdqvgg ysctcppgfv
1261 gercegdvne clsnpcdarg tqncvqrvnd fhcecraght grrcesving ckgkpckngg
1321 tcavasntar gfickcpagf egatcendar tcgslrclng gtcisgprsp tclclgpftg
1381 pecqfpassp clggnpcynq gtceptsesp fyrclcpakf ngllchildy sfgggagrdi
1441 ppplieeace lpecqedagn kvcslqcnnh acgwdggdcs lnfndpwknc tqslqcwkyf
1501 sdghcdsqcn sagclfdgfd cqraegqcnp lydqyckdhf sdghcdqgcn saecewdgld
1561 caehvperla agtlvvvvlm ppeqlrnssf hflrelsrvl htnvvfkrda hgqqmifpyy
1621 greeelrkhp ikraaegwaa pdallgqvka sllpggsegg rrrreldpmd vrgsivylei
1681 dnrqcvqass qcfqsatdva aflgalaslg slnipykiea vqsetveppp paqlhfmyva
1741 aaafvllffv gcgvllsrkr rrqhgqlwfp egfkvseask kkrreplged svglkplkna
1801 sdgalmddnq newgdedlet kkfrfeepvv lpdlddqtdh rqwtqqhlda adlrmsamap
1861 tppqgevdad cmdvnvrgpd gftplmiasc sgggletgns eeeedapavi sdfiyqgasl
1921 hnqtdrtget alhlaarysr sdaakrllea sadaniqdnm grtplhaavs adaqgvfqil
1981 irnratdlda rmhdgttpli laarlavegm ledlinshad vnavddlgks alhwaaavnn
2041 vdaavvllkn gankdmqnnr eetplflaar egsyetakvl ldhfanrdit dhmdrlprdi
2101 aqermhhdiv rlldeynlvr spqlhgaplg gtptlspplc spngylgslk pgvqgkkvrk
2161 psskglacgs keakdlkarr kksqdgkgcl ldssgmlspv dslesphgyl sdvassppllp
2221 spfqqspsvp lnhlpgmpdt hlgighlnva akpemaalgg ggrlafetgp prlshlpvas
2281 gtstvlgsss ggalnftvgg stslngqcew lsrlqsgmvp nqynplrgsv apgplstqap
2341 slqhgmvgpl hsslaasals qmmsyqglps trlatqphlv qtqqvqpqnl qmqqqnlqpa
2401 niqqqqslqp pppppqphlg vssaasghlg rsflsgepsq advqplgpss lavhtilpqe
2461 spalptslps slvppvtaaq fltppsqhsy sspvdntpsh qlqvpehpfl tpspespdqw
2521 ssssphsnvs dwsegvsspp tsmqsqiari peafk
```

FIG. 2B

NP_060087.3 residues 1754-2555 (SEQ ID NO: 7)

```
1754                vllsrkr  rrqhgqlwfp  egfkvseask  kkrreplged  svglkplkna
1801  sdgalmddnq  newgdedlet  kkfrfeepvv  lpdlddqtdh  rqwtqqhlda  adlrmsamap
1861  tppqgevdad  cmdvnvrgpd  gftplmiasc  sgggletgns  eeeedapavi  sdfiyqgasl
1921  hnqtdrtget  alhlaarysr  sdaakrllea  sadaniqdnm  grtplhaavs  adaqgvfqil
1981  irnratdlda  rmhdgttpli  laarlavegm  ledlinshad  vnavddlgks  alhwaaavnn
2041  vdaavvllkn  gankdmqnnr  eetplflaar  egsyetakvl  ldhfanrdit  dhmdrlprdi
2101  aqermhhdiv  rlldeynlvr  spqlhgaplg  gtptlspplc  spngylgslk  pgvqgkkvrk
2161  psskglacgs  keakdlkarr  kksqdgkgcl  ldssgmlspv  dslesphgyl  sdvasppllp
2221  spfqqspsvp  lnhlpgmpdt  hlgighlnva  akpemaalgg  ggrlafetgp  prlshlpvas
2281  gtstvlgsss  ggalnftvgg  stslngqcew  lsrlqsgmvp  nqynplrgsv  apgplstqap
2341  slqhgmvgpl  hsslaasals  qmmsyqglps  trlatqphlv  qtqqvqpqnl  qmqqqnlqpa
2401  niqqqqslqp  pppppqphlg  vssaasghlg  rsflsgepsq  advqplgpss  lavhtilpqe
2461  spalptslps  slvppvtaaq  fltppsqhsy  sspvdntpsh  qlqvpehpfl  tpspespdqw
2521  ssssphsnvs  dwsegvsspp  tsmqsqiari  peafk
```

FIG. 2C

Notch Intracellular Domain consensus protein sequence (SEQ ID NO: 10)

VLLSRKRRRQHGQLWFPEGFKVSEASKKKRREPLGEDSVGLKPLKNASDGALMDDNQNEWGDEDLE
TKKFRFEEPVVLPDLX$_1$DQTDHRQWTQQHLDAADLRX$_2$SAMAPTPPQGEVDADCMDVNVRGPDGFTP
LMIASCSGGGLETGNSEEEEDAPAVISDFIYQGASLHNQTDRTGETALHLAARYSRSDAAKRLLEA
SADANIQDNMGRTPLHAAVSADAQGVFQILX$_3$RNRATDLDARMHDGTTPLILAARLAVEGMLEDLIN
SHADVNAVDDLGKSALHWAAAVNNVDAAVVLLKNGANKDMQNNX$_4$EETPLFLAAREGSYETAKVLLD
HFANRDITDHMDRLPRDIAQERMHHDIVRLLDEYNLVRSPQLHGX$_5$X$_6$LGGTPTLSPX$_7$LCSPNGYL
GX$_8$LKX$_9$X$_{10}$X$_{11}$QGKKX$_{12}$RKPSX$_{13}$KGLACX$_{14}$SKEAKDLKARRKKSQDGKGCLLDSSX$_{15}$MLSPVDSL
ESPHGYLSDVASPPLLPSPFQQSPSX$_{16}$PLX$_{17}$HLPGMPDTHLGIX$_{18}$HLNVAAKPEMAALX$_{19}$GGX$_{20}$R
LAFEX$_{21}$X$_{22}$PPRLSHLPVASX$_{23}$X$_{24}$STVLX$_{25}$X$_{26}$X$_{27}$X$_{28}$X$_{29}$GAX$_{30}$NFTVGX$_{31}$X$_{32}$X$_{33}$SLNGQCEWLX
$_{34}$RLQX$_{35}$GMVPX$_{36}$QYNPLRX$_{37}$X$_{38}$VX$_{39}$PGX$_{40}$LSTQAX$_{41}$X$_{42}$LQHX$_{43}$MX$_{44}$GPX$_{45}$HSSLX$_{46}$X$_{47}$X$_{48}$X$_4$
$_9$LSX$_{50}$X$_{51}$X$_{52}$X$_{53}$YQGLPX$_{54}$TRLATQPHLVQTQQVQPQNLQX$_{55}$QX$_{56}$QNLQX$_{57}$X$_{58}$X$_{59}$X$_{60}$X$_{61}$X$_{62}$X$_{63}$
X$_{64}$X$_{65}$X$_{66}$X$_{67}$X$_{68}$X$_{69}$X$_{70}$PPX$_{71}$QPHLX$_{72}$VSSAAX$_{73}$GHLGRSFLSGEPSQADVQPLGPSSLX$_{74}$VHTIL
PQESX$_{75}$ALPTSLPSSX$_{76}$VPPX$_{77}$TX$_{78}$X$_{79}$QFLTPPSQHSYSSX$_{80}$PVDNTPSHQLQVPEHPFLTPSP
ESPDQWSSSSX$_{81}$HSNX$_{82}$SDWSEGX$_{83}$SSPPTX$_{84}$MX$_{85}$SQIX$_{86}$X$_{87}$IPEAFK

FIG. 3A

NP_005163.1 (SEQ ID NO: 3)

```
1    msrllhaeew aevkelgdhh rqpqphhlpq ppppqppat  lqarehpvyp pelslldstd
61   prawlaptlq gictaraaqy llhspelgas eaaaprdevd grgelvrrss ggassskspg
121  pvkvreqlck lkggvvvdel gcsrqrapss kqvngvqkqr rlaanarerr rmhglnhafd
181  qlrnvipsfn ndkklskyet lqmaqiyina lsellqtpsg geqppppas  cksdhhhlrt
241  aasyeggagn ataagaqqas ggsqrptppg scrtrfsapa saggysvqld alhfstfeds
301  altammaqkn lspslpgsil qpvqeenskt sprshrsdge fsphshysds deas
```

FIG. 3B

Atoh1 consensus protein sequence (SEQ ID NO: 11)

MSRLLHAEEWAEVKELGDHHRX$_1$PQPHHX$_2$PX$_3$X$_4$PPX$_5$X$_6$QPPATLQARX$_7$X$_8$PVYPX$_9$ELSLLDSTD
PRAWLX$_{10}$PTLQGX$_{11}$CTARAAQYLLHSPELX$_{12}$ASEAAAPRDEX$_{13}$DX$_{14}$X$_{15}$GELVRRSX$_{16}$X$_{17}$GX$_{18}$X$_{19}$X$_{20}$SKSPGPVKVREQLCKLKGGVVVDELGCSRQRAPSSKQVNGVQKQRRLAANARERRRMHGLNHA
FDQLRNVIPSFNNDKKLSKYETLQMAQIYINALSELLQTPX$_{21}$X$_{22}$GEQPPPPX$_{23}$ASCKX$_{24}$DHHHLR
TAX$_{25}$SYEGGAGX$_{26}$X$_{27}$X$_{28}$X$_{29}$AGAQX$_{30}$AX$_{31}$GGX$_{32}$X$_{33}$RPTPPGX$_{34}$CRTRFSX$_{35}$PASX$_{36}$GGYSVQL
DALHFX$_{37}$X$_{38}$FEDX$_{39}$ALTAMMAQKX$_{40}$LSPSLPGX$_{41}$ILQPVQEX$_{42}$NSKTSPRSHRSDGEFSPHSHY
SDSDEAS

FIG. 4

NM_002467.4 (SEQ ID NO: 4)

```
   1 gaccccgag ctgtgctgct cgcggccgcc accgccgggc cccggccgtc cctggctccc
  61 ctcctgcctc gagaagggca gggcttctca gaggcttggc gggaaaaaga acggagggag
 121 ggatcgcgct gagtataaaa gccggttttc ggggctttat ctaactcgct gtagtaattc
 181 cagcgagagg cagagggagc gagcgggcgg ccggctaggg tggaagagcc gggcgagcag
 241 agctgcgctg cgggcgtcct gggaagggag atccggagcg aatagggggc ttcgcctctg
 301 gcccagccct cccgctgatc ccccagccag cggtccgcaa cccttgccgc atccacgaaa
 361 ctttgcccat agcagcgggc gggcactttg cactggaact acaacaccc gagcaaggac
 421 gcgactctcc cgacgcgggg aggctattct gcccatttgg ggacacttcc ccgccgctgc
 481 caggacccgc ttctctgaaa ggctctcctt gcagctgctt agacgctgga ttttttcgg
 541 gtagtggaaa accagcagcc tcccgcgacg atgcccctca acgttagctt caccaacagg
 601 aactatgacc tcgactacga ctcggtgcag ccgtatttct actgcgacga ggaggagaac
 661 ttctaccagc agcagcagca gagcgagctg cagccccgg cgcccagcga ggatatctgg
 721 aagaaattcg agctgctgcc caccccgccc ctgtcccta gccgccgctc cgggctctgc
 781 tcgccctcct acgttgcggt cacaccctc tccttcggg gagacaacga cggcggtggc
 841 gggagcttct ccacggccga ccagctggag atggtgaccg agctgctggg aggagacatg
 901 gtgaaccaga gtttcatctg cgacccggac gacgagacct tcatcaaaaa catcatcatc
 961 caggactgta tgtggagcgg cttctcggcc gccgccaagc tcgtctcaga gaagctggcc
1021 tcctaccagg ctgcgcgcaa agacagcggc agcccgaacc ccgccgcgg ccacagcgtc
1081 tgctccacct ccagcttgta cctgcaggat ctgagcgccg ccgcctcaga gtgcatcgac
1141 ccctcggtgg tcttcccta ccctctcaac gacagcagct cgcccaagtc ctgcgcctcg
1201 caagactcca gcgccttctc tccgtcctcg gattctctgc tctcctcgac ggagtcctcc
1261 ccgcagggca gccccgagcc cctggtgctc catgaggaga caccgcccac caccagcagc
1321 gactctgagg aggaacaaga agatgaggaa gaaatcgatg ttgtttctgt ggaaaagagg
1381 caggctcctg gcaaaaggtc agagtctgga tcaccttctg ctggaggcca gcaaaacct
1441 cctcacagcc cactggtcct caagaggtgc acgtctcca cacatcagca caactacgca
1501 gcgcctccct ccactcggaa ggactatcct gctgccaaga gggtcaagtt ggacagtgtc
1561 agagtcctga gacagatcag caacaaccga aaatgcacca gcccaggtc ctcggacacc
1621 gaggagaatg tcaagaggcg aacacacaac gtcttggagc gccagaggag aacgagcta
1681 aaacggagct ttttgccct gcgtgaccag atcccggagt tggaaaacaa tgaaaaggcc
1741 cccaaggtag ttatccttaa aaaagccaca gcatacatcc tgtccgtcca agcagaggag
1801 caaaagctca tttctgaaga ggacttgttg cggaaacgac gagaacagtt gaaacacaaa
1861 cttgaacagc tacggaactc ttgtgcgtaa ggaaaagtaa ggaaaacgat tccttctaac
1921 agaaatgtcc tgagcaatca cctatgaact tgtttcaaat gcatgatcaa atgcaacctc
1981 acaaccttgg ctgagtcttg agactgaaag atttagccat aatgtaaact gcctcaaatt
2041 ggactttggg cataaaagaa cttttttatg cttaccatct ttttttttc tttaacagat
2101 ttgtatttaa gaattgtttt taaaaattt taagatttac acaatgtttc tctgtaaata
2161 ttgccattaa atgtaaataa ctttaataaa acgtttatag cagttacaca gaatttcaat
2221 cctagtatat agtacctagt attataggta ctataaaccc taattttttt tatttaagta
2281 cattttgctt tttaaagttg atttttttct attgttttta gaaaaaataa aataactggc
2341 aaatatatca ttgagccaaa tcttaaaaaa aaaaaaaaa
```

FIG. 5A

NM_017617.3 (SEQ ID NO: 5)

```
   1 atgccgccgc tcctggcgcc cctgctctgc ctggcgctgc tgcccgcgct cgccgcacga
  61 ggcccgcgat gctcccagcc cggtgagacc tgcctgaatg gcgggaagtg tgaagcggcc
 121 aatggcacgg aggcctgcgt ctgtggcggg gccttcgtgg gcccgcgatg ccaggacccc
 181 aacccgtgcc tcagcacccc ctgcaagaac gccgggacat gccacgtggt ggaccgcaga
 241 ggcgtggcag actatgcctg cagctgtgcc ctgggcttct ctgggcccct ctgcctgaca
 301 cccctggaca atgcctgcct caccaacccc tgccgcaacg ggggcacctg cgacctgctc
 361 acgctgacgg agtacaagtg ccgctgcccg cccggctggt cagggaaatc gtgccagcag
 421 gctgacccgt gcgcctccaa cccctgcgcc aacggtggcc agtgcctgcc cttcgaggcc
 481 tcctacatct gccactgccc acccagcttc atggcccca cctgccggca ggatgtcaac
 541 gagtgtggcc agaagcccgg gctttgccgc cacggaggca cctgccacaa cgaggtcggc
 601 tcctaccgct gcgtctgccg cgccacccac actgcccca actgcgagcg ccctacgtg
 661 ccctgcagcc cctcgccctg ccagaacggg ggcacctgcc gcccacggg cgacgtcacc
 721 cacgagtgtg cctgcctgcc aggcttcacc ggccagaact gtgaggaaaa tatcgacgat
 781 tgtccaggaa caactgcaa gaacggggt gcctgtgtgg acggcgtgaa cacctacaac
 841 tgccgctgcc cgccagagtg gacaggtcag tactgtaccg aggatgtgga cgagtgccag
 901 ctgatgccaa atgcctgcca gaacggcggg acctgccaca cacccacgg tggctacaac
 961 tgcgtgtgtg tcaacggctg gactggtgag gactgcagcg agaacattga tgactgtgcc
1021 agcgccgcct gcttccacgg cgccacctgc catgaccgtg tggcctcctt ctactgcgag
1081 tgtccccatg gccgcacagg tctgctgtgc cacctcaacg acgcatgcat cagcaacccc
1141 tgtaacgagg ctccaactg cgacaccaac cctgtcaatg gcaaggccat ctgcacctgc
1201 ccctcggggt acacgggccc ggcctgcagc caggacgtgg atgagtgctc gctgggtgcc
1261 aaccctgcg agcatgcggg caagtgcatc aacacgctgg gctccttcga gtgccagtgt
1321 ctgcagggct acacgggccc ccgatgcgag atcgacgtca acgagtgcgt ctcgaacccg
1381 tgccagaacg acgccacctg cctggaccag attggggagt tccagtgcat ctgcatgccc
1441 ggctacgagg tgtgcactg cgaggtcaac acagacgagt gtgccagcag ccctgcctg
1501 cacaatggcc gctgcctgga caagatcaat gagttccagt gcgagtgccc cacgggcttc
1561 actgggcatc tgtgccagta cgatgtggac gagtgtgcca gcacccctg caagaatggt
1621 gccaagtgcc tggacggacc caacacttac acctgtgtgt gcacggaagg gtacacgggg
1681 acgcactgcg aggtggacat cgatgagtgc gaccccgacc cctgccacta cggctcctgc
1741 aaggacggcg tcgccacctt cacctgcctc tgccgcccag gctacacggg ccaccactgc
1801 gagaccaaca tcaacgagtg ctccagccag ccctgccgcc acggggcac ctgccaggac
1861 cgcgacaacg cctacctctg cttctgcctg aaggggacca caggacccaa ctgcgagatc
1921 aacctggatg actgtgccag cagcccctgc gactcgggca cctgtctgga caagatcgat
1981 ggctacgagt gtgcctgtga gccgggctac acagggagca tgtgtaacat caacatcgat
2041 gagtgtgcgg gcaaccctg ccacaacggg ggcacctgcg aggacggcat caatggcttc
2101 acctgccgct gccccgaggg ctaccacgac cccacctgcc tgtctgaggt caatgagtgc
2161 aacagcaacc ctgcgtcca cggggcctgc cgggacagcc tcaacgggta caagtgcgac
2221 tgtgaccctg ggtggagtgg gaccaactgt gacatcaaca caatgagtg tgaatccaac
2281 ccttgtgtca acggcggcac ctgcaaagac atgaccagtg gctacgtgtg cacctgccgg
2341 gagggcttca cggtcccaa ctgccagacc aacatcaacg agtgtgcgtc caacccatgt
2401 ctgaaccagg gcacgtgtat tgacgacgtt gccgggtaca agtgcaactg cctgctgccc
2461 tacacaggtg ccacgtgtga ggtggtgctg gccccgtgtg ccccagccc ctgcagaaac
2521 ggcgggagt gcaggcaatc cgaggactat gagagcttct cctgtgtctg ccccacgggc
2581 tggcaagggc agacctgtga ggtcgacatc aacgagtgcg ttctgagccc gtgccggcac
2641 ggcgcatcct gccagaacac ccacggcggc taccgctgcc actgccaggc cggctacagt
```

FIG. 5A (continued)

NM_017617.3 (SEQ ID NO: 5)

```
2701 gggcgcaact gcgagaccga catcgacgac tgccggccca acccgtgtca caacggggc
2761 tcctgcacag acggcatcaa cacggccttc tgcgactgcc tgcccggctt ccggggcact
2821 ttctgtgagg aggacatcaa cgagtgtgcc agtgacccct gccgcaacgg ggccaactgc
2881 acggactgcg tggacagcta cacgtgcacc tgccccgcag gcttcagcgg gatccactgt
2941 gagaacaaca cgcctgactg cacagagagc tcctgcttca acggtggcac ctgcgtggac
3001 ggcatcaact cgttcacctg cctgtgtcca cccggcttca cgggcagcta ctgccagcac
3061 gatgtcaatg agtgcgactc acagccctgc ctgcatggcg gcacctgtca ggacggctgc
3121 ggctcctaca ggtgcacctg cccccagggc tacactggcc ccaactgcca gaaccttgtg
3181 cactggtgtg actcctcgcc ctgcaagaac ggcggcaaat gctggcagac ccacacccag
3241 taccgctgcg agtgccccag cggctggacc ggcctttact gcgacgtgcc cagcgtgtcc
3301 tgtgaggtgg ctgcgcagcg acaaggtgtt gacgttgccc gcctgtgcca gcatggaggg
3361 ctctgtgtgg acgcgggcaa cacgcaccac tgccgctgcc aggcgggcta cacaggcagc
3421 tactgtgagg acctggtgga cgagtgctca cccagcccct gccagaacgg ggccacctgc
3481 acggactacc tgggcggcta ctcctgcaag tgcgtggccg gctaccacgg ggtgaactgc
3541 tctgaggaga tcgacgagtg cctctcccac ccctgccaga acggggcac ctgcctcgac
3601 ctccccaaca cctacaagtg ctcctgccca cggggcactc agggtgtgca ctgtgagatc
3661 aacgtggacg actgcaatcc ccccgttgac cccgtgtccc ggagccccaa gtgctttaac
3721 aacggcacct gcgtggacca ggtgggcggc tacagctgca cctgcccgcc gggcttcgtg
3781 ggtgagcgct gtgaggggga tgtcaacgag tgcctgtcca atccctgcga cgcccgtggc
3841 acccagaact gcgtgcagcg cgtcaatgac ttccactgcg agtgccgtgc tggtcacacc
3901 gggcgccgct gcgagtccgt catcaatggc tgcaaaggca gccctgcaa gaatggggc
3961 acctgcgccg tggcctccaa caccgcccgc gggttcatct gcaagtgccc tgcgggcttc
4021 gagggcgcca cgtgtgagaa tgacgctcgt acctgcggca gcctgcgctg cctcaacggc
4081 ggcacatgca tctccggccc gcgcagcccc acctgcctgt gcctgggccc cttcacgggc
4141 cccgaatgcc agttcccggc cagcagcccc tgcctgggcg caacccctg ctacaaccag
4201 gggacctgtg agcccacatc cgagagcccc ttctaccgtt gcctgtgccc cgccaaattc
4261 aacgggctct tgtgccacat cctggactac agcttcgggg gtggggccgg gcgcgacatc
4321 cccccgccgc tgatcgagga ggcgtgcgag ctgcccgagt gccaggagga cgcgggcaac
4381 aaggtctgca gcctgcagtg caacaaccac gcgtgcggct gggacggcgg tgactgctcc
4441 ctcaacttca atgacccctg gaagaactgc acgcagtctc tgcagtgctg gaagtacttc
4501 agtgacggcc actgtgacag ccagtgcaac tcagccggct gcctcttcga cggctttgac
4561 tgccagcgtg cggaaggcca gtgcaacccc ctgtacgacc agtactgcaa ggaccacttc
4621 agcgacgggc actgcgacca gggctgcaac agcgcggagt gcgagtggga cgggctggac
4681 tgtgcggagc atgtacccga gaggctggcg gccggcacgc tggtggtggt ggtgctgatg
4741 ccgccggagc agctgcgcaa cagctccttc cacttcctgc gggagctcag ccgcgtgctg
4801 cacaccaacg tggtcttcaa gcgtgacgca cacggccagc agatgatctt ccctactac
4861 ggccgcgagg aggagctgcg caagcacccc atcaagcgtg ccgccgaggg ctgggccgca
4921 cctgacgccc tgctgggcca ggtgaaggcc tcgctgctcc tggtggcag cgagggtggg
4981 cggcggcgga gggagctgga ccccatggac gtccgcggct ccatcgtcta cctggagatt
5041 gacaaccggc agtgtgtgca ggcctcctcg cagtgcttcc agagtgccac cgacgtggcc
5101 gcattcctgg gagcgctcgc ctcgctgggc agcctcaaca tcccctacaa gatcgaggcc
5161 gtgcagagtg agaccgtgga gccgcccccg ccggcgcagc tgcacttcat gtacgtggcg
5221 gcggccgcct ttgtgcttct gttcttcgtg ggctgcgggg tgctgctgtc ccgcaagcgc
5281 cggcggcagc atggccagct ctggttccct gagggcttca aagtgtctga ggccagcaag
```

FIG. 5A (continued)

NM_017617.3 (SEQ ID NO: 5)

```
5341 aagaagcggc gggagcccct cggcgaggac tccgtgggcc tcaagcccct gaagaacgct
5401 tcagacggtg ccctcatgga cgacaaccag aatgagtggg gggacgagga cctggagacc
5461 aagaagttcc ggttcgagga gcccgtggtt ctgcctgacc tggacgacca gacagaccac
5521 cggcagtgga ctcagcagca cctggatgcc gctgacctgc gcatgtctgc catggccccc
5581 acaccgcccc agggtgaggt tgacgccgac tgcatggacg tcaatgtccg cgggcctgat
5641 ggcttcaccc cgctcatgat cgcctcctgc agcgggggcg gcctggagac gggcaacagc
5701 gaggaagagg aggacgcgcc ggccgtcatc tccgacttca tctaccaggg cgccagcctg
5761 cacaaccaga cagaccgcac gggcgagacc gccttgcacc tggccgcccg ctactcacgc
5821 tctgatgccg ccaagcgcct gctggaggcc agcgcagatg ccaacatcca ggacaacatg
5881 ggccgcaccc cgctgcatgc ggctgtgtct gccgacgcac aaggtgtctt ccagatcctg
5941 atccggaacc gagccacaga cctggatgcc cgcatgcatg atggcacgac gccactgatc
6001 ctggctgccc gcctggccgt ggagggcatg ctggaggacc tcatcaactc acacgccgac
6061 gtcaacgccg tagatgacct gggcaagtcc gccctgcact gggccgccgc cgtgaacaat
6121 gtggatgccg cagttgtgct cctgaagaac ggggctaaca agatatgca gaacaacagg
6181 gaggagacac ccctgtttct ggccgcccgg gagggcagct acgagaccgc caaggtgctg
6241 ctggaccact tgccaaccg gacatcacg gatcatatgg accgcctgcc gcgcgacatc
6301 gcacaggagc gcatgcatca cgacatcgtg aggctgctgg acgagtacaa cctggtgcgc
6361 agcccgcagc tgcacggagc cccgctgggg ggcacgccca ccctgtcgcc cccgctctgc
6421 tcgcccaacg gctacctggg cagcctcaag cccggcgtgc agggcaagaa ggtccgcaag
6481 cccagcagca aaggcctggc ctgtggaagc aaggaggcca aggacctcaa ggcacggagg
6541 aagaagtccc aggacggcaa gggctgcctg ctggacagct ccggcatgct ctcgcccgtg
6601 gactccctgg agtcacccca tggctacctg tcagacgtgg cctcgccgcc actgctgccc
6661 tccccgttcc agcagtctcc gtccgtgccc ctcaaccacc tgcctgggat gcccgacacc
6721 cacctgggca tcgggcacct gaacgtggcg gccaagcccg agatggcggc gctgggtggg
6781 ggcggccggc tggcctttga gactggccca cctcgtctct cccacctgcc tgtggcctct
6841 ggcaccagca ccgtcctggg ctccagcagc ggaggggccc tgaatttcac tgtgggcggg
6901 tccaccagtt tgaatggtca atgcgagtgg ctgtcccggc tgcagagcgg catggtgccg
6961 aaccaataca accctctgcg ggggagtgtg gcaccaggcc ccctgagcac acaggccccc
7021 tccctgcagc atggcatggt aggcccgctg cacagtagcc ttgctgccag cgccctgtcc
7081 cagatgatga gctaccaggg cctgcccagc acccggctgg ccacccagcc tcacctggtg
7141 cagacccagc aggtgcagca acaaaactta cagatgcagc agcagaacct gcagccagca
7201 aacatccagc agcagcaaag cctgcagccg ccaccaccac caccacagcc gcaccttggc
7261 gtgagctcag cagccagcgg ccacctgggc cggagcttcc tgagtggaga gccgagccag
7321 gcagacgtgc agccactggg ccccagcagc ctggcggtgc acactattct gccccaggag
7381 agccccgccc tgcccacgtc gctgccatcc tcgctggtcc cacccgtgac cgcagcccag
7441 ttcctgacgc ccccctcgca gcacagctac tcctcgcctg tggacaacac ccccagccac
7501 cagctacagg tgcctgagca ccccttcctc accccgtccc ctgagtcccc tgaccagtgg
7561 tccagctcgt ccccgcattc caacgtctcc gactggtccg agggcgtctc cagccctccc
7621 accagcatgc agtcccagat cgcccgcatt ccggaggcct tcaagtaaac ggcgcgcccc
7681 acgagacccc ggcttccttt cccaagcctt cgggcgtctg tgtgcgctct gtggatgcca
7741 gggccgacca gaggagcctt tttaaaacac atgtttttat acaaataag aacgaggatt
7801 ttaatttttt ttagtattta tttatgtact tttattttac acagaaacac tgccttttta
7861 tttatatgta ctgttttatc tggccccagg tagaaacttt tatctattct gagaaaacaa
7921 gcaagttctg agagccaggg ttttcctacg taggatgaaa agattcttct gtgtttataa
```

FIG. 5A (continued)

NM_017617.3 (SEQ ID NO: 5)

```
7981 aatataaaca aagattcatg atttataaat gccatttatt tattgattcc tttttcaaa
8041 atccaaaaag aaatgatgtt ggagaaggga agttgaacga gcatagtcca aaaagctcct
8101 ggggcgtcca ggccgcgccc ttccccgac gcccacccaa ccccaagcca gcccggccgc
8161 tccaccagca tcacctgcct gttaggagaa gctgcatcca gaggcaaacg gaggcaaagc
8221 tggctcacct tccgcacgcg gattaatttg catctgaaat aggaaacaag tgaaagcata
8281 tgggttagat gttgccatgt gttttagatg gtttcttgca agcatgcttg tgaaaatgtg
8341 ttctcggagt gtgtatgcca agagtgcacc catggtacca atcatgaatc tttgtttcag
8401 gttcagtatt atgtagttgt tcgttggtta tacaagttct tggtccctcc agaaccaccc
8461 cggcccctg cccgttcttg aaatgtaggc atcatgcatg tcaaacatga gatgtgtgga
8521 ctgtggcact tgcctgggtc acacacggag gcatcctacc cttttctggg gaaagacact
8581 gcctgggctg accccggtgg cggcccagc acctcagcct gcacagtgtc cccaggttc
8641 cgaagaagat gctccagcaa cacagcctgg gccccagctc gcgggacccg accccccgtg
8701 ggctcccgtg ttttgtagga gacttgccag agccgggcac attgagctgt gcaacgccgt
8761 gggctgcgtc ctttggtcct gtccccgcag ccctggcagg gggcatgcgg tcgggcaggg
8821 gctggaggga ggcgggggct gcccttgggc caccctcct agtttgggag gagcagattt
8881 ttgcaatacc aagtatagcc tatggcagaa aaatgtctg taaatatgtt tttaaaggtg
8941 gattttgttt aaaaaatctt aatgaatgag tctgttgtgt gtcatgccag tgagggacgt
9001 cagacttggc tcagctcggg gagccttagc cgcccatgca ctggggacgc tccgctgccg
9061 tgccgcctgc actcctcagg gcagcctccc ccggctctac gggggccgcg tggtgccatc
9121 cccagggggc atgaccagat gcgtcccaag atgttgattt ttactgtgtt ttataaaata
9181 gagtgtagtt tacagaaaaa gactttaaaa gtgatctaca tgaggaactg tagatgatgt
9241 atttttttca tcttttttgt taactgattt gcaataaaaa tgatactgat ggtgaaaaaa
9301 aaaaaaaaa
```

FIG. 5B

NM_017617.3 nucleotide positions 5260 to 7665 (SEQ ID NO: 8)

```
5260                                          g tgctgctgtc ccgcaagcgc
5281 cggcggcagc atggccagct ctggttccct gagggcttca aagtgtctga ggccagcaag
5341 aagaagcggc gggagcccct cggcgaggac tccgtgggcc tcaagcccct gaagaacgct
5401 tcagacggtg ccctcatgga cgacaaccag aatgagtggg gggacgagga cctggagacc
5461 aagaagttcc ggttcgagga gccgtggtt ctgcctgacc tggacgacca gacagaccac
5521 cggcagtgga ctcagcagca cctggatgcc gctgacctgc gcatgtctgc catggccccc
5581 acaccgcccc agggtgaggt tgacgccgac tgcatggacg tcaatgtccg cgggcctgat
5641 ggcttcaccc cgctcatgat cgcctcctgc agcggggggcg gcctggagac gggcaacagc
5701 gaggaagagg aggacgcgcc ggccgtcatc tccgacttca tctaccaggg cgccagcctg
5761 cacaaccaga cagaccgcac gggcgagacc gccttgcacc tggccgcccg ctactcacgc
5821 tctgatgccg ccaagcgcct gctggaggcc agcgcagatg ccaacatcca ggacaacatg
5881 ggccgcaccc cgctgcatgc ggctgtgtct gccgacgcac aagtgtctt ccagatcctg
5941 atccggaacc gagccacaga cctggatgcc cgcatgcatg atggcacgac gccactgatc
6001 ctggctgccc gcctggccgt ggagggcatg ctggaggacc tcatcaactc acacgccgac
```

FIG. 5B (continued)

NM_017617.3 nucleotide positions 5260 to 7665 (SEQ ID NO: 8)

```
6061 gtcaacgccg tagatgacct gggcaagtcc gccctgcact gggccgccgc cgtgaacaat
6121 gtggatgccg cagttgtgct cctgaagaac ggggctaaca aagatatgca gaacaacagg
6181 gaggagacac ccctgtttct ggccgcccgg gagggcagct acgagaccgc caaggtgctg
6241 ctggaccact ttgccaaccg ggacatcacg gatcatatgg accgcctgcc gcgcgacatc
6301 gcacaggagc gcatgcatca cgacatcgtg aggctgctgg acgagtacaa cctggtgcgc
6361 agcccgcagc tgcacggagc cccgctgggg ggcacgccca ccctgtcgcc cccgctctgc
6421 tcgcccaacg gctacctggg cagcctcaag cccggcgtgc agggcaagaa ggtccgcaag
6481 cccagcagca aaggcctggc ctgtggaagc aaggaggcca aggacctcaa ggcacggagg
6541 aagaagtccc aggacggcaa gggctgcctg ctggacagct ccggcatgct ctcgcccgtg
6601 gactccctgg agtcacccca tggctacctg tcagacgtgg cctcgccgcc actgctgccc
6661 tccccgttcc agcagtctcc gtccgtgccc ctcaaccacc tgcctgggat gcccgacacc
6721 cacctgggca tcgggcacct gaacgtggcg gccaagcccg agatggcggc gctgggtggg
6781 ggcggccggc tggcctttga gactggccca cctcgtctct cccacctgcc tgtggcctct
6841 ggaccagca ccgtcctggg ctccagcagc ggaggggccc tgaatttcac tgtgggcggg
6901 tccaccagtt tgaatggtca atgcgagtgg ctgtcccggc tgcagagcgg catggtgccg
6961 aaccaataca accctctgcg ggggagtgtg gcaccaggcc ccctgagcac acaggccccc
7021 tccctgcagc atggcatggt aggcccgctg cacagtagcc ttgctgccag cgccctgtcc
7081 cagatgatga gctaccaggg cctgcccagc acccggctgg ccacccagcc tcacctggtg
7141 cagacccagc aggtgcagcc acaaaactta cagatgcagc agcagaacct gcagccagca
7201 aacatccagc agcagcaaag cctgcagccg ccaccaccac caccacagcc gcaccttggc
7261 gtgagctcag cagccagcgg ccacctgggc cggagcttcc tgagtggaga gccgagccag
7321 gcagacgtgc agccactggg ccccagcagc ctggcggtgc acactattct gccccaggag
7381 agccccgccc tgcccacgtc gctgccatcc tcgctggtcc cacccgtgac cgcagcccag
7441 ttcctgacgc cccctcgca gcacagctac tcctcgcctg tggacaacac ccccagccac
7501 cagctacagg tgcctgagca ccccttcctc accccgtccc ctgagtcccc tgaccagtgg
7561 tccagctcgt ccccgcattc caacgtctcc gactggtccg agggcgtctc cagccctccc
7621 accagcatgc agtcccagat cgcccgcatt ccggaggcct tcaag
```

FIG. 6

NM_005172.1 (SEQ ID NO: 6)

```
   1 atgtcccgcc tgctgcatgc agaagagtgg gctgaagtga aggagttggg agaccaccat
  61 cgccagcccc agccgcatca tctcccgcaa ccgccgccgc cgccgcagcc acctgcaact
 121 ttgcaggcga gagagcatcc cgtctacccg cctgagctgt ccctcctgga cagcaccgac
 181 ccacgcgcct ggctggctcc cactttgcag ggcatctgca cggcacgcgc cgcccagtat
 241 ttgctacatt ccccggagct gggtgcctca gaggccgctg cgccccggga cgaggtggac
 301 ggccgggggg agctggtaag gaggagcagc ggcggtgcca gcagcagcaa gagcccgggg
 361 ccggtgaaag tgcgggaaca gctgtgcaag ctgaaaggcg gggtggtggt agacgagctg
 421 ggctgcagcc gccaacgggc cccttccagc aaacaggtga atggggtgca gaagcagaga
 481 cggctagcag ccaacgccag ggagcggcgc aggatgcatg ggctgaacca cgccttcgac
 541 cagctgcgca atgttatccc gtcgttcaac aacgacaaga agctgtccaa atatgagacc
 601 ctgcagatgg cccaaatcta catcaacgcc ttgtccgagc tgctacaaac gcccagcgga
 661 ggggaacagc caccgccgcc tccagcctcc tgcaaaagcg accaccacca ccttcgcacc
 721 gcggcctcct atgaaggggg cgcgggcaac gcgaccgcag ctggggctca gcaggcttcc
 781 ggagggagcc agcggccgac cccgcccggg agttgccgga ctcgcttctc agccccagct
 841 tctgcgggag ggtactcggt gcagctggac gctctgcact tctcgacttt cgaggacagc
 901 gccctgacag cgatgatggc gcaaaagaat ttgtctcctt ctctccccgg gagcatcttg
 961 cagccagtgc aggaggaaaa cagcaaaact tcgcctcggt cccacagaag cgacggggaa
1021 ttttcccccc attcccatta cagtgactcg gatgaggcaa gttag
```

FIG. 19A

NP_005369.2; SEQ ID NO: 12

```
1   mpscststmp gmicknpdle fdslqpcfyp deddfyfggp dstppgediw kkfellptpp
61  lspsrgfaeh sseppswvte mllenelwgs paeedafglg glggltpnpv ilqdcmwsgf
121 sareklerav seklqhgrgp ptagstaqsp gagaaspagr ghggaagagr agaalpaela
181 hpaaecvdpa vvfpfpvnkr epapvpaapa sapaagpava sgagiaapag apgvapprpg
241 grqtsggdhk alstsgedtl sdsddeddee edeeeeidvv tvekrrsssn tkavttftit
301 vrpknaalgp graqsselil krclpihqqh nyaapspyve sedappqkki kseasprplk
361 svippkaksl sprnsdseds errrnhnile rqrrndlrss fltlrdhvpe lvknekaakv
421 lkkateyv hslqaeehql llekeklqar qqqllkkieh artc
```

FIG. 19B

NM_005378.4; SEQ ID NO: 13

```
1    gtcatctgtc tggacgcgct gggtggatgc ggggggctcc tgggaactgt gttggagccg
61   agcaagcgct agccaggcgc aagcgcgcac agactgtagc catccgagga caccccgcc
121  ccccggccc acccggagac acccgcgcag aatcgcctcc ggatccctg cagtcggcgg
181  gagtgttgga ggtcggcgcc ggccccgcc ttccgcgccc ccacgggaa ggaagcaccc
241  ccggtattaa acgaacggg gcggaaagaa gccctcagtc gccggccggg aggcgagccg
301  atgccgagct gctccacgtc caccatgccg ggcatgatct gcaagaaccc agacctcgag
361  tttgactcgc tacagcctg cttctacccg gacgaagatg acttctactt cggcggcccc
421  gactcgaccc ccccggggga ggacatctgg aagaagtttg agctgctgcc cacgccccg
481  ctgtcgccca gccgtggctt cgcggagcac agctccgagc cccgagctg ggtcacggag
541  atgctgcttg agaacgagct gtggggcagc ccggccgagg aggacgcgtt cggcctgggg
601  ggactgggtg gcctcacccc caacccggtc atcctccagg actgcatgtg gagcggcttc
661  tccgcccgcg agaagctgga gcgcgccgtg agcgagaagc tgcagcacgg ccgcgggccg
721  ccaaccgccg gttccaccgc ccagtccccg ggagccggcg ccgccagccc tgcgggtcgc
781  gggcacggcg gggctgcggg agccggccgc gccggggccg ccctgcccgc cgagctcgcc
841  caccccggccg ccgagtgcgt ggatcccgcc gtggtcttcc cctttccgt gaacaagcgc
901  gagccagcgc ccgtgcccgc agccccggcc agtgccccgg cggcgggccc tgcggtcgcc
961  tcggggggcgg gtattgccgc cccagccggg gccccggggg tcgcccctcc gcgcccaggc
1021 ggccgccaga ccagcggcgg cgaccacaag gccctcagta cctccggaga ggacaccctg
1081 agcgattcag atgatgaaga tgatgaagag gaagatgaag aggaagaaat cgacgtggtc
1141 actgtggaga gcggcgttc ctcctccaac accaaggctg tcaccacatt caccatcact
1201 gtgcgtccca gaacgcagc cctgggtccc gggagggctc agtccagcga gctgatcctc
1261 aaacgatgcc ttcccatcca ccagcagcac aactatgccg cccctctcc ctacgtggag
1321 agtgaggatg caccccaca gaagaagata aagagcgagg cgtccccacg tccgctcaag
1381 agtgtcatcc ccccaaaggc taagagcttg agcccccgaa actctgactc ggaggacagt
1441 gagcgtcgca gaaaccacaa catcctggag cgccagcgcc gcaacgacct tcggtccagc
1501 tttctcacgc tcagggacca cgtgccggag ttggtaaaga atgagaaggc cgccaaggtg
1561 gtcattttga aaaaggccac tgagtatgtc cactccctcc aggccgagga gcaccagctt
1621 ttgctggaaa aggaaaaatt gcaggcaaga cagcagcagt tgctaaagaa aattgaacac
1681 gctcggactt gctagacgct tctcaaaact ggacagtcac tgccactttg cacattttga
1741 ttttttttt aaacaaacat tgtgttgaca ttaagaatgt tggtttactt tcaaatcggt
1801 cccctgtcga gttcggctct gggtgggcag taggaccacc agtgtggggt tctgctggga
1861 ccttggagag cctgcatccc aggatgctgg gtggccctgc agcctcctcc acctcacctc
1921 catgacagcg ctaaacgttg gtgacggttg ggagcctctg ggctgttga agtcaccttg
1981 tgtgttccaa gtttccaaac aacagaaagt cattccttct ttttaaaatg gtgcttaagt
2041 tccagcagat gccacataag gggtttgcca tttgataccc ctggggaaca tttctgtaaa
2101 taccattgac acatccgcct tttgtataca tcctgggtaa tgagaggtgg cttttgcggc
```

FIG. 19B (continued)

```
2161 cagtattaga ctggaagttc atacctaagt actgtaataa tacctcaatg tttgaggagc
2221 atgttttgta tacaaatata ttgttaatct ctgttatgta ctgtactaat tcttacactg
2281 cctgtatact ttagtatgac gctgatacat aactaaattt gatacttata ttttcgtatg
2341 aaaatgagtt gtgaaagttt tgagtagata ttactttatc acttttgaa ctaagaaact
2401 tttgtaaaga aatttactat atatatatgc cttttccta gcctgtttct tcctgttaat
2461 gtatttgttc atgtttggtg catagaactg ggtaaatgca aagttctgtg tttaatttct
2521 tcaaaatgta tatatttagt gctgcatctt atagcacttt gaaatacctc atgtttatga
2581 aaataaatag cttaaaatta aatgaaaaaa aaa
```

FIG. 20A

NP_077719.2; SEQ ID NO: 14

```
   1  mpalrpallw allalwlcca apahalqcrd gyepcvnegm cvtyhngtgy ckcpegflge
  61  ycqhrdpcek nrcqnggtcv aqamlgkatc rcasgftged cqystshpcf vsrpclnggt
 121  chmlsrdtye ctcqvgftgk ecqwtdacls hpcangstct tvanqfsckc ltgftgqkce
 181  tdvnecdipg hcqhggtcln lpgsyqcqcp qgftgqycds lyvpcapspc vnggtcrqtg
 241  dftfecnclp gfegstcern iddcpnhrcq nggvcvdgvn tyncrcppqw tgqfctedvd
 301  ecllqpnacq nggtcanrng gygcvcvngw sgddcsenid dcafasctpg stcidrvasf
 361  scmcpegkag llchlddaci snpchkgalc dtnplngqyi ctcpqgykga dctedvdeca
 421  mansnpceha gkcvntdgaf hceclkgyag prcemdinec hsdpcqndat cldkiggftc
 481  lcmpgfkgvh celeinecqs npcvnngqcv dkvnrfqclc ppgftgpvcq ididdcsstp
 541  clngakcidh pngyecqcat gftgvlceen idncdpdpch hgqcqdgids ytcicnpgym
 601  gaicsdqide cysspclndg rcidlvngyq cncqpgtsgv nceinfddca snpcihgicm
 661  dginryscvc spgftgqrcn ididecasnp crkgatcing vngfrcicpe gphhpscysq
 721  vneclsnpci hgnctgglsg ykclcdagwv gincevdkne clsnpcqngg tcdnlvngyr
 781  ctckkgfkgy ncqvnideca snpclnqgtc fddisgytch cvlpytgknc qtvlapcspn
 841  pcenaavcke spnfesytcl capgwqgqrc tididecisk pcmnhglchn tqgsymcecp
 901  pgfsgmdcee diddclanpc qnggscmdgv ntfsclclpg ftgdkcqtdm neclsepckn
 961  ggtcsdyvns ytckcqagfd gvhcennine ctesscfngg tcvdginsfs clcpvgftgs
1021  fclheinecs shpclnegtc vdglgtyrcs cplgytgknc qtlvnlcsrs pcknkgtcvq
1081  kkaesqclcp sgwagaycdv pnvscdiaas rrgvlvehlc qhsgvcinag nthycqcplg
1141  ytgsyceeql decasnpcqh gatcsdfigg yrcecvpgyq gvnceyevde cqnqpcqngg
1201  tcidlvnhfk cscppgtrgl lceeniddca rgphclnggq cmdriggysc rclpgfager
1261  cegdinecls npcssegsld ciqltndylc vcrsaftgrh cetfvdvcpq mpclnggtca
1321  vasnmpdgfi crcppgfsga rcqsscgqvk crkgeqcvht asgprcfcps prdcesgcas
1381  spcqhggsch pqrqppyysc qcappfsgsr celytappst ppatclsqyc adkardgvcd
1441  eacnshacqw dggdcsltme npwancsspl pcwdyinnqc delcntvecl fdnfecqgns
1501  ktckydkyca dhfkdnhcdq gcnseecgwd gldcaadqpe nlaegtlviv vlmppeqllq
1561  darsflralg tllhtnlrik rdsqgelmvy pyygeksaam kkqrmtrrsl pgeqeqevag
1621  skvfleidnr qcvqdsdhcf kntdaaaall ashaiqgtls yplvsvvses ltpertqlly
1681  llavavviil fiillgvima krkrkhgslw lpegftlrrd asnhkrrepv gqdavglknl
1741  svqvseanli gtgtsehwvd degpqpkkvk aedeallsee ddpidrrpwt qqhleaadir
1801  rtpslaltpp qaeqevdvld vnvrgpdgct plmlaslrgg ssdlsdeded aedssaniit
1861  dlvyqgaslq aqtdrtgema lhlaarysra daakrlldag adanaqdnmg rcplhaavaa
1921  daqgvfqili rnrvtdldar mndgttplil aarlavegmv aelincqadv navddhgksa
1981  lhwaaavnnv eatllllkng anrdmqdnke etplflaare gsyeaakill dhfanrditd
2041  hmdrlprdva rdrmhhdivr lldeynvtps ppgtvltsal spvicgpnrs flslkhtpmg
2101  kksrrpsaks tmptslpnla keakdakgsr rkkslsekvq lsessvtlsp vdslesphty
2161  vsdttsspmi tspgilqasp npmlataapp apvhaqhals fsnlhemqpl ahgastvlps
2221  vsqllshhhi vspgsgsags lsrlhpvpvp adwmnrmevn etqynemfgm vlapaegthp
2281  giapqsrppe gkhittprep lppivtfqli pkgsiaqpag apqpqstcpp avagplptmy
2341  qipemarlps vafptammpq qdgqvaqtil payhpfpasv gkyptppsqh syassnaaer
2401  tpshsghlqg ehpyltpspe spdqwssssp hsasdwsdvt tsptpggagg gqrgpgthms
2461  epphnnmqvy a
```

FIG. 20B

NM_024408.3; SEQ ID NO: 15

```
   1 gcttgcggtg ggaggaggcg gctgaggcgg aaggacacac gaggctgctt cgttgcacac
  61 ccgagaaagt ttcagccaaa cttcgggcgg cggctgaggc ggcggccgag gagcggcgga
 121 ctcggggcgc ggggagtcga ggcatttgcg cctgggcttc ggagcgtagc gccagggcct
 181 gagcctttga agcaggagga ggggaggaga gagtggggct cctctatcgg gaccccctcc
 241 ccatgtggat ctgcccaggc ggcggcggcg gcggcggagg aggaggcgac cgagaagatg
 301 cccgccctgc gccccgctct gctgtgggcg ctgctggcgc tctggctgtg ctgcgcggcc
 361 cccgcgcatg cattgcagtg tcgagatggc tatgaaccct gtgtaaatga aggaatgtgt
 421 gttacctacc acaatggcac aggatactgc aaatgtccag aaggcttctt gggggaatat
 481 tgtcaacatc gagacccctg tgagaagaac cgctgccaga atggtgggac ttgtgtggcc
 541 caggccatgc tggggaaagc cacgtgccga tgtgcctcag gtttacagg agaggactgc
 601 cagtactcaa catctcatcc atgctttgtg tctcgaccct gcctgaatgg cggcacatgc
 661 catatgctca gccgggatac ctatgagtgc acctgtcaag tcgggtttac aggtaaggag
 721 tgccaatgga cggatgcctg cctgtctcat ccctgtgcaa atggaagtac ctgtaccact
 781 gtggccaacc agttctcctg caaatgcctc acaggcttca gggcagaa atgtgagact
 841 gatgtcaatg agtgtgacat tccaggacac tgccagcatg gtggcacctg cctcaacctg
 901 cctggttcct accagtgcca gtgccctcag gcttcacag gccagtactg tgacagcctg
 961 tatgtgccct gtgcaccctc accttgtgtc aatggaggca cctgtcggca gactggtgac
1021 ttcacttttg agtgcaactg ccttccaggt tttgaaggga gcacctgtga ggaatatatt
1081 gatgactgcc ctaaccacag gtgtcagaat ggaggggttt gtgtggatgg ggtcaacact
1141 tacaactgcc gctgtccccc acaatggaca ggacagttct gcacagagga tgtggatgaa
1201 tgcctgctgc agcccaatgc ctgtcaaaat gggggcacct gtgccaaccg caatggaggc
1261 tatggctgtg tatgtgtcaa cggctggagt ggagatgact gcagtgagaa cattgatgat
1321 tgtgccttcg cctcctgtac tccaggctcc acctgcatcg accgtgtggc ctccttctct
1381 tgcatgtgcc cagaggggaa ggcaggtctc ctgtgtcatc tggatgatgc atgcatcagc
1441 aatccttgcc acaagggggc actgtgtgac accaaccccc taaatgggca atatatttgc
1501 acctgcccac aaggctacaa aggggctgac tgcacagaag atgtggatga atgtgccatg
1561 gccaatagca atccttgtga gcatgcagga aaatgtgtga cacggatgg cgccttccac
1621 tgtgagtgtc tgaagggtta tgcaggacct cgttgtgaga tggacatcaa tgagtgccat
1681 tcagacccct gccagaatga tgctacctgt ctggataaga ttggaggctt cacatgtctg
1741 tgcatgccag gtttcaaagg tgtgcattgt gaattagaaa taaatgaatg tcagagcaac
1801 ccttgtgtga caatgggca gtgtgtggat aaagtcaatc gtttccagtg cctgtgtcct
1861 cctggtttca ctgggccagt ttgccagatt gatattgatg actgttccag tactccgtgt
1921 ctgaatgggg caaagtgtat cgatcacccg aatggctatg aatgccagtg tgccacaggt
1981 ttcactggtg tgttgtgtga ggagaacatt gacaactgtg accccgatcc ttgccaccat
2041 ggtcagtgtc aggatggtat tgattcctac acctgcatct gcaatcccgg gtacatgggc
2101 gccatctgca gtgaccagat tgatgaatgt tacagcagcc cttgcctgaa cgatggtcgc
2161 tgcattgacc tggtcaatgg ctaccagtgc aactgccagc caggcacgtc aggggttaat
2221 tgtgaaatta attttgatga ctgtgcaagt aaccttgta tccatggaat ctgtatggat
2281 ggcattaatc gctacagttg tgtctgctca ccaggattca gggcagag atgtaacatt
2341 gacattgatg agtgtgcctc caatcctgt cgcaagggtg aacatgtat aacggtgtg
2401 aatggtttcc gctgtatatg ccccgaggga ccccatcacc cagctgcta ctcacaggtg
2461 aacgaatgcc tgagcaatcc ctgcatccat ggaaactgta ctggaggtct cagtggatat
2521 aagtgtctct gtgatgcagg ctgggttggc atcaactgtg aagtggacaa aaatgaatgc
2581 ctttcgaatc catgccagaa tggaggaact tgtgacaatc tggtgaatgg atacaggtgt
2641 acttgcaaga agggcttaa aggctataac tgccaggtga atattgatga atgtgcctca
2701 aatccatgcc tgaaccaagg aacctgcttt gatgacataa gtggctacac ttgccactgt
2761 gtgctgccat acacaggcaa gaattgtcag acagtattgg ctccctgttc cccaaaccct
2821 tgtgagaatg ctgctgtttt caaagagtca ccaaattttg agagttatac ttgcttgtgt
2881 gctcctggct ggcaaggtca gcggtgtacc attgacattg acgagtgtat ctccaagccc
2941 tgcatgaacc atggtctctg ccataacacc cagggcagct acatgtgtga atgtccacca
3001 ggcttcagtg gtatggactg tgaggaggac attgatgact gccttgccaa tccttgccag
```

FIG. 20B (continued)

```
3061 aatggaggtt cctgtatgga tggagtgaat actttctcct gcctctgcct tccgggtttc
3121 actggggata agtgccagac agacatgaat gagtgtctga gtgaaccctg taagaatgga
3181 gggacctgct ctgactacgt caacagttac acttgcaagt gccaggcagg atttgatgga
3241 gtccattgtg agaacaacat caatgagtgc actgagagct cctgtttcaa tggtggcaca
3301 tgtgttgatg ggattaactc cttctcttgc ttgtgccctg tgggtttcac tggatccttc
3361 tgcctccatg agatcaatga atgcagctct catccatgcc tgaatgaggg aacgtgtgtt
3421 gatggcctgg gtacctaccg ctgcagctgc ccctgggct acactgggaa aaactgtcag
3481 accctggtga atctctgcag tcggtctcca tgtaaaaaca aggtacttg cgttcagaaa
3541 aaagcagagt cccagtgcct atgtccatct ggatgggctg gtgcctattg tgacgtgccc
3601 aatgtctctt gtgacatagc agcctccagg agaggtgtgc ttgttgaaca cttgtgccag
3661 cactcaggtg tctgcatcaa tgctggcaac acgcattact gtcagtgccc cctgggctat
3721 actgggagct actgtgagga gcaactcgat gagtgtgcgt ccaaccctg ccagcacggg
3781 gcaacatgca gtgacttcat tggtggatac agatgcgagt gtgtcccagg ctatcaggt
3841 gtcaactgtg agtatgaagt ggatgagtgc cagaatcagc cctgccagaa tggaggcacc
3901 tgtattgacc ttgtgaacca tttcaagtgc tcttgcccac caggcactcg ggcctactc
3961 tgtgaagaga cattgatga ctgtgcccgg gtccccatt gccttaatgg tggtcagtgc
4021 atggatagga ttggaggcta cagttgtcgc tgcttgcctg gctttgctgg ggagcgttgt
4081 gaggagaca tcaacgagtg cctctccaac ccctgcagct ctgagggcag cctggactgt
4141 atacagctca ccaatgacta cctgtgtgtt tgccgtagtg cctttactgg ccggcactgt
4201 gaaaccttcg tcgatgtgtg tccccagatg ccctgcctga atggagggac ttgtgctgtg
4261 gccagtaaca tgcctgatgg tttcatttgc cgttgtcccc cgggattttc cggggcaagg
4321 tgccagagca gctgtggaca agtgaaatgt aggaagggg agcagtgtgt gcacaccgcc
4381 tctggacccc gctgcttctg ccccagtccc cgggactgcg agtcaggctg tgccagtagc
4441 ccctgccagc acggggcag ctgccaccct cagcgccagc ctccttatta ctcctgccag
4501 tgtgccccac cattctcggg tagccgctgt gaactctaca cggcacccc cagcacccct
4561 cctgccacct gtctgagcca gtattgtgcc gacaaagctc gggatggcgt ctgtgatgag
4621 gcctgcaaca gccatgcctg ccagtgggat gggggtgact gttctctcac catggagaac
4681 ccctgggcca actgctcctc cccacttccc tgctggatt atatcaacaa ccagtgtgat
4741 gagctgtgca acacggtcga gtgcctgttt gacaactttg aatgccaggg aacagcaag
4801 acatgcaagt atgacaaata ctgtgcagac cacttcaaag acaaccactg tgaccagggg
4861 tgcaacagtg aggagtgtgg ttgggatggg ctggactgtg ctgctgacca acctgagaac
4921 ctggcagaag gtaccctggt tattgtggta ttgatgccac ctgaacaact gctccaggat
4981 gctcgcagct tcttgcgggc actgggtacc ctgctccaca ccaacctgcg cattaagcgg
5041 gactcccagg gggaactcat ggtgtacccc tattatggtg agaagtcagc tgctatgaag
5101 aaacagagga tgacacgcag atcccttcct ggtgaacaag aacaggaggt ggctggctct
5161 aaagtctttc tggaaattga caaccgccag tgtgttcaag actcagacca ctgcttcaag
5221 aacacggatg cagcagcagc tctcctggcc tctcacgcca tacagggac cctgtcatac
5281 cctcttgtgt ctgtcgtcag tgaatccctg actccagaac gcactcagct cctctatctc
5341 cttgctgttg ctgttgtcat cattctgttt attattctgc tggggtaat catggcaaaa
5401 cgaaagcgta agcatggctc tctctggctg cctgaaggtt tcactcttcg ccgagatgca
5461 agcaatcaca agcgtcgtga gccagtggga caggatgctg tgggctgaa aaatctctca
5521 gtgcaagtct cagaagctaa cctaattggt actggaacaa gtgaacactg ggtcgatgat
5581 gaagggcccc agccaaagaa agtaaaggct gaagatgagg ccttactctc agaagaagat
5641 gaccccattg atcgacggcc atggacacag cagcaccttg aagctgcaga catccgtagg
5701 acaccatcgc tggctctcac ccctcctcag gcagagcagg aggtggatgt gttagatgtg
5761 aatgtccgtg gcccagatgg ctgcacccca ttgatgttgg cttctctccg aggaggcagc
5821 tcagatttga gtgatgaaga tgaagatgca gaggactctt ctgctaacat catcacagac
5881 ttggtctacc agggtgccag cctccaggcc cagacagacc ggactggtga gatggccctg
5941 caccttgcag cccgctactc acgggctgat gctgccaagc gtctcctgga tgcaggtgca
6001 gatgccaatg cccaggacaa catgggccgc tgtccactcc atgctgcagt ggcagctgat
6061 gcccaaggtg tcttccagat tctgattcgc aaccgagtaa ctgatctaga tgccaggatg
6121 aatgatggta ctacaccct gatcctggct gcccgcctgg ctgtgaggg aatggtggca
6181 gaactgatca actgccaagc ggatgtgaat gcagtggatg accatggaaa atctgctctt
6241 cactgggcag ctgctgtcaa taatgtggag gcaactcttt tgttgttgaa aaatggggcc
6301 aaccgagaca tgcaggacaa caaggaagag acacctctgt ttcttgctgc ccgggagggg
```

FIG. 20B (continued)

```
6361 agctatgaag cagccaagat cctgttagac cattttgcca atcgagacat cacagaccat
6421 atggatcgtc ttccccggga tgtggctcgg gatcgcatgc accatgacat tgtgcgcctt
6481 ctggatgaat acaatgtgac cccaagccct ccaggcaccg tgttgacttc tgctctctca
6541 cctgtcatct gtgggcccaa cagatctttc ctcagcctga agcacacccc aatgggcaag
6601 aagtctagac ggcccagtgc caagagtacc atgcctacta gcctccctaa ccttgccaag
6661 gaggcaaagg atgccaaggg tagtaggagg aagaagtctc tgagtgagaa ggtccaactg
6721 tctgagagtt cagtaacttt atccctgtt gattccctag aatctcctca cacgtatgtt
6781 tccgacacca catcctctcc aatgattaca tccctggga tcttacaggc ctcacccaac
6841 cctatgttgg ccactgccgc ccctcctgcc ccagtccatg cccagcatgc actatctttt
6901 tctaaccttc atgaaatgca gcctttggca catggggcca gcactgtgct tccctcagtg
6961 agccagttgc tatcccacca ccacattgtg tctccaggca gtggcagtgc tggaagcttg
7021 agtaggctcc atccagtccc agtcccagca gattggatga accgcatgga ggtgaatgag
7081 acccagtaca atgagatgtt tggtatggtc ctggctccag ctgagggcac ccatcctggc
7141 atagctcccc agagcaggcc acctgaaggg aagcacataa ccaccctcg ggagcccttg
7201 ccccccattg tgactttcca gctcatccct aaaggcagta ttgcccaacc agcggggct
7261 ccccagcctc agtccacctg ccctccagct gttgcgggcc cctgccac catgtaccag
7321 attccagaaa tggcccgttt gccagtgtg gcttcccca ctgccatgat gcccagcag
7381 gacgggcagg tagctcagac cattctccca gcctatcatc ctttccagc tctgtgggc
7441 aagtacccca cacccccttc acagcacagt tatgcttcct caaatgctgc tgagcgaaca
7501 cccagtcaca gtggtcacct ccagggtgag catccctacc tgacaccatc cccagagtct
7561 cctgaccagt ggtcaagttc atcaccccac tctgcttctg actggtcaga tgtgaccacc
7621 agccctaccc ctggggggtgc tggaggaggt cagcggggac ctgggacaca catgtctgag
7681 ccaccacaca acaacatgca ggtttatgcg tgagagagtc cacctccagt gtagagacat
7741 aactgacttt tgtaaatgct gctgaggaac aaatgaaggt catccgggag agaaatgaag
7801 aaatctctgg agccagcttc tagaggtagg aaagagaaga tgttcttatt cagataatgc
7861 aagagaagca attcgtcagt ttcactgggt atctgcaagg cttattgatt attctaatct
7921 aataagacaa gtttgtggaa atgcaagatg aatacaagcc ttgggtccat gtttactctc
7981 ttctatttgg agaataagat ggatgcttat tgaagcccag acattcttgc agcttggact
8041 gcatttaag ccctgcaggc ttctgccata tccatgagaa gattctacac tagcgtcctg
8101 tgggaatta tgccctggaa ttctgcctga attgacctac gcatctcctc ctccttggac
8161 attcttttgt cttcatttgg tgcttttggt tttgcacctc tccgtgattg tagccctacc
8221 agcatgttat agggcaagac ctttgtgctt ttgatcattc tggcccatga aagcaacttt
8281 ggtctccttt cccctcctgt cttcccggta tcccttggag tctcacaagg tttactttgg
8341 tatggttctc agcacaaacc tttcaagtat gttgtttctt tggaaaatgg acatactgta
8401 ttgtgttctc ctgcatatat cattcctgga gagagaaggg gagaagaata cttttcttca
8461 acaaattttg ggggcaggag atcccttcaa gaggctgcac cttaattttt cttgtctgtg
8521 tgcaggtctt catataaact ttaccaggaa gaagggtgtg agtttgttgt ttttctgtgt
8581 atgggcctgg tcagtgtaaa gttttatcct tgatagtcta gttactatga ccctccccac
8641 ttttttaaaa ccagaaaaag gtttggaatg ttggaatgac caagagacaa gttaactcgt
8701 gcaagagcca gttacccacc cacaggtccc cctacttcct gccaagcatt ccattgactg
8761 cctgtatgga acacatttgt cccagatctg agcattctag gcctgtttca ctcactcacc
8821 cagcatatga aactagtctt aactgttgag ccttttcctt catatccaca gaagacactg
8881 tctcaaatgt tgtacccttg ccatttagga ctgaactttc cttagcccaa gggacccagt
8941 gacagttgtc ttccgtttgt cagatgatca gtctctactg attatcttgc tgcttaaagg
9001 cctgctcacc aatctttctt tcacaccgtg tggtccgtgt tactggtata cccagtatgt
9061 tctcactgaa gacatggact ttatatgttc aagtgcagga attggaaagt tggacttgtt
9121 ttctatgatc caaaacagcc ctataagaag gttggaaaag gaggaactat atagcagcct
9181 ttgctatttt ctgctaccat ttctttttcct ctgaagcggc catgacattc cctttggcaa
9241 ctaacgtaga aactcaacag aacattttcc tttcctagag tcaccttta gatgataatg
9301 gacaactata gacttgctca ttgttcagac tgattgcccc tcacctgaat ccactctctg
9361 tattcatgct cttggcaatt tctttgactt tcttttaagg gcagaagcat tttagttaat
9421 tgtagataaa gaatagtttt cttcctcttc tccttgggcc agttaataat tggtccatgg
9481 ctacactgca acttccgtcc agtgctgtga tgcccatgac acctgcaaaa taagttctgc
9541 ctgggcattt tgtagatatt aacaggtgaa ttcccgactc ttttggtttg aatgacagtt
9601 ctcattcctt ctatggctgc aagtatgcat cagtgcttcc cacttacctg atttgtctgt
```

FIG. 20B (continued)

```
 9661 cggtggcccc atatggaaac cctgcgtgtc tgttggcata atagtttaca aatggttttt
 9721 tcagtcctat ccaaatttat tgaaccaaca aaaataatta cttctgccct gagataagca
 9781 gattaagttt gttcattctc tgctttattc tctccatgtg gcaacattct gtcagcctct
 9841 ttcatagtgt gcaaacattt tatcattcta aatggtgact ctctgccctt ggacccattt
 9901 attattcaca gatggggaga acctatctgc atggacctct gtggaccaca gcgtacctgc
 9961 ccctttctgc cctcctgctc cagccccact tctgaaagta tcagctactg atccagccac
10021 tggatatttt atatcctccc ttttccttaa gcacaatgtc agaccaaatt gcttgtttct
10081 ttttcttgga ctactttaat ttggatcctt tgggtttgga gaaagggaat gtgaaagctg
10141 tcattacaga caacaggttt cagtgatgag gaggacaaca ctgcctttca aacttttttac
10201 tgatctctta gattttaaga actcttgaat tgtgtggtat ctaataaaag ggaaggtaag
10261 atggataatc actttctcat ttgggttctg aattggagac tcagttttta tgagacacat
10321 cttttatgcc atgtatagat cctcccctgc tattttttggt ttatttttat tgttataaat
10381 gctttctttc tttgactcct cttctgcctg cctttgggga taggtttttt tgtttgttta
10441 tttgcttcct ctgttttgtt ttaagcatca ttttcttatg tgaggtgggg aagggaaagg
10501 tatgagggaa agagagtctg agaattaaaa tattttagta taagcaattg gctgtgatgc
10561 tcaaatccat tgcatcctct tattgaattt gccaatttgt aattttgca taataaagaa
10621 ccaaaggtgt aatgttttgt tgagaggtgg tttagggatt ttggccctaa ccaatacatt
10681 gaatgtatga tgactatttg ggaggacaca tttatgtacc cagaggcccc cactaataag
10741 tggtactatg gttacttcct tgtgtacatt tctcttaaaa gtgatattat atctgtttgt
10801 atgagaaacc cagtaaccaa taaaatgacc gcatattcct gactaaacgt agtaaggaaa
10861 atgcacactt tgtttttact tttccgtttc attctaaagg tagttaagat gaaatttata
10921 tgaaagcatt tttatcacaa aataaaaaag gtttgccaag ctcagtggtg ttgtatttt
10981 tattttccaa tactgcatcc atggcctggc agtgttacct catgatgtca taatttgctg
11041 agagagcaaa ttttcttttc tttctgaatc ccacaaagcc tagcaccaaa cttctttttt
11101 tcttccttta attagatcat aaataaatga tcctggggaa aaagcatctg tcaaatagga
11161 aacatcacaa aactgagcac tcttctgtgc actagccata gctggtgaca aacagatggt
11221 tgctcaggga caaggtgcct tccaatggaa atgcgaagta gttgctatag caagaattgg
11281 gaactgggat ataagtcata atattaatta tgctgttatg taaatgattg gtttgtaaca
11341 ttccttaagt gaaatttgtg tagaacttaa tatacaggat tataaaataa tattttgtgt
11401 ataaatttgt tataagttca cattcataca tttatttata aagtcagtga gatatttgaa
11461 catgaaaaaa aaaa
```

FIG. 21A

NP_000426.2; SEQ ID NO: 16

```
   1 mgpgargrrr rrrpmspppp pppvralpll lllagpgaaa ppcldgspca nggrctqlps
  61 reaaclcppg wvgercqled pchsgpcagr gvcqssvvag tarfscrcpr gfrgpdcslp
 121 dpclsspcah garcsvgpdg rflcscppgy qgrscrsdvd ecrvgepcrh ggtclntpgs
 181 frcqcpagyt gplcenpavp capspcrngg tcrqsgdlty dcaclpgfeg qncevnvddc
 241 pghrclnggt cvdgvntync qcppewtgqf ctedvdecql qpnachnggt cfntlgghsc
 301 vcvngwtges csqniddcat avcfhgatch drvasfycac pmgktgllch lddacvsnpc
 361 hedaicdtnp vngraictcp pgftggacdq dvdecsigan pcehlgrcvn tqgsflcqcg
 421 rgytgprcet dvneclsgpc rnqatcldri gqftcicmag ftgtycevdi decqsspcvn
 481 ggvckdrvng fsctcpsgfs gstcqldvde castpcrnga kcvdqpdgye crcaegfegt
 541 lcdrnvddcs pdpchhgrcv dgiasfscac apgytgtrce sqvdecrsqp crhggkcldl
 601 vdkylcrcps gttgvncevn iddcasnpct fgvcrdginr ydcvcqpgft gplcnveine
 661 casspcgegg scvdgengfr clcppgslpp lclppshpca hepcshgicy dapggfrcvc
 721 epgwsgprcs qslardaces qpcraggtcs sdgmgfhctc ppgvqgrqce llspctpnpc
 781 ehggrcesap gqlpvcscpq gwqgprcqqd vdecagpapc gphgictnla gsfsctchgg
 841 ytgpscdqdi ndcdpnpcln ggscqdgvgs fscsclpgfa gprcardvde clsnpcgpgt
 901 ctdhvasftc tcppgyggfh ceqdlpdcsp sscfnggtcv dgvnsfsclc rpgytgahcq
 961 headpclsrp clhggvcsaa hpgfrctcle sftgpqcqtl vdwcsrqpcq nggrcvqtga
1021 yclcppgwsg rlcdirslpc reaaaqigvr leqlcqaggq cvdedsshyc vcpegrtgsh
1081 ceqevdpcla qpcqhggtcr gymggymcec lpgyngdnce ddvdecasqp cqhggscidl
1141 varylcscpp gtlgvlcein eddcgpgppl dsgprclhng tcvdlvggfr ctcppgytgl
1201 rceadinecr sgachaahtr dclqdpgggf rclchagfsg prcqtvlspc esqpcqhggq
1261 crpspgpggg ltftchcaqp fwgprcerva rscrelqcpv gvpcqqtprg prcacppgls
1321 gpscrsfpgs ppgasnasca aapclhggsc rpaplapffr cacaqgwtgp rceapaaape
1381 vseeprcpra acqakrgdqr cdrecnspgc gwdggdcsls vgdpwrqcea lqcwrlfnns
1441 rcdpacsspa clydnfdcha ggrertcnpv yekycadhfa dgrcdqgcnt eecgwdgldc
1501 asevpallar gvlvltvllp peellrssad flqrlsailr tslrfrldah gqamvfpyhr
1561 pspgseprar relapevigs vvmleidnrl clqspendhc fpdaqsaady lgalsaverl
1621 dfpyplrdvr geplepppeps vpllpllvag avlllvilvl gvmvarrkre hstlwfpegf
1681 slhkdvasgh kgrrepvgqd algmknmakg eslmgevatd wmdtecpeak rlkveepgmg
1741 aeeavdcrqw tqhhlvaadi rvapamaltp pqgdadadgm dvnvrgpdgf tplmlasfcg
1801 galepmptee deaddtsasi isdlicqgaq lgartdrtge talhlaarya radaakrlld
1861 agadtnaqdh sgrtplhtav tadaqgvfqi lirnrstdld armadgstal ilaarlaveg
1921 mveeliasha dvnavdelgk salhwaaavn nveatlallk ngankdmqds keetplflaa
1981 regsyeaakl lldhfanrei tdhldrlprd vaqerlhqdi vrlldqpsgp rsppgphglg
2041 pllcppgafl pglkaaqsgs kksrrppgka glgpqgprgr gkkltlacpg pladssvtls
2101 pvdsldsprp fggppaspgg fplegpyaaa tatavslaql ggpgraglgr qppggcvlsl
2161 gllnpvavpl dwarlpppap pgpsfllpla pgpqllnpgt pvspqerppp ylavpghgee
2221 ypaagahssp pkarflrvps ehpyltpspe spehwaspsp pslsdwsest pspatatgam
    2281tgalpaq plplsvpssl aqaqtqlgpq pevtpkrqvl a
```

FIG. 21B

NM_000435.2; SEQ ID NO: 17

```
  1 gcggcgcgga ggctggcccg ggacgcgccc ggagcccagg gaaggaggga ggagggagg
 61 gtcgcggccg gccgccatgg ggccggggc cgtggccgc cgccgccgcc gtcgcccgat
121 gtcgccgcca ccgccaccgc cacccgtgcg ggcgctgccc ctgctgctgc tgctagcggg
181 gccgggggct gcagcccccc cttgcctgga cggaagcccg tgtgcaaatg gaggtcgttg
241 cacccagctg ccctcccggg aggctgcctg cctgtgcccg cctggctggg tgggtgagcg
```

FIG. 21B (continued)

```
 301 gtgtcagctg gaggacccct gtcactcagg ccctgtgct ggccgtggtg tctgccagag
 361 ttcagtggtg gctggcaccg cccgattctc atgccggtgc cccgtggct tccgaggccc
 421 tgactgctcc ctgccagatc cctgcctcag cagcccttgt gcccacggtg cccgctgctc
 481 agtggggccc gatggacgct tcctctgctc ctgcccacct ggctaccagg gccgcagctg
 541 ccgaagcgac gtggatgagt gccgggtggg tgagccctgc cgccatggtg gcacctgcct
 601 caacacacct ggctccttcc gctgccagtg tccagctggc tacacagggc cactatgtga
 661 gaaccccgcg gtgccctgtg caccctcacc atgccgtaac gggggcacct gcaggcagag
 721 tggcgacctc acttacgact gtgcctgtct tcctgggttt gagggtcaga attgtgaagt
 781 gaacgtggac gactgtccag acaccgatg tctcaatggg gggacatgcg tggatggcgt
 841 caacacctat aactgccagt gcctcctga gtggacaggc cagttctgca cggaggacgt
 901 ggatgagtgt cagctgcagc ccaacgcctg ccacaatggg ggtacctgct caacacgct
 961 gggtggccac agctgcgtgt gtgtcaatgg ctggacaggc gagagctgca gtcagaatat
1021 cgatgactgt gccacagccg tgtgcttcca tggggccacc tgccatgacc gcgtggcttc
1081 tttctactgt gcctgcccca tgggcaagac tggcctcctg tgtcacctgg atgacgcctg
1141 tgtcagcaac ccctgccacg aggatgctat ctgtgacaca atccggtga acggccgggc
1201 catttgcacc tgtcctcccg gcttcacggg tggggcatgt gaccaggatg tggacgagtg
1261 ctctatcggc gccaaccct gcgagcactt gggcaggtgc gtgaacacgc agggctcctt
1321 cctgtgccag tgcggtcgtg gctacactgg acctcgctgt gagaccgatg tcaacgagtg
1381 tctgtcgggg ccctgccgaa accaggccac gtgcctcgac cgcataggcc agttcacctg
1441 tatctgtatg gcaggcttca caggaaccta ttgcgaggtg acattgacg agtgtcagag
1501 tagccctgt gtcaacggtg ggtctgcaa ggaccgagtc aatggcttca gctgcacctg
1561 cccctcgggc ttcagcggct ccacgtgtca gctggacgtg gacgaatgcg ccagcacgcc
1621 ctgcaggaat ggcgccaaat gcgtggacca gcccgatggc tacgagtgcc gctgtgccga
1681 gggctttgag ggcacgctgt gtgatcgcaa cgtggacgac tgctccctg acccatgcca
1741 ccatggtcgc tgcgtggatg gcatcgccag cttctcatgt gcctgtgctc ctggctacac
1801 gggcacacgc tgcgagagcc aggtggacga atgccgcagc cagccctgcc gccatggcgg
1861 caaatgccta gacctggtgg acaagtacct ctgccgctgc ccttctggga ccacaggtgt
1921 gaactgcgaa gtgaacattg acgactgtgc cagcaacccc tgcaccttg gagtctgccg
1981 tgatggcatc aaccgctacg actgtgtctg ccaacctggc ttcacagggc ccctttgtaa
2041 cgtggagatc aatgagtgtg cttccagccc atgcggcgag ggaggttcct gtgtggatgg
2101 ggaaaatggc ttccgctgcc tctgcccgcc tggctccttg ccccactct gcctcccccc
2161 gagccatccc tgtgcccatg agccctgcag tcacggcatc tgctatgatg cacctggcgg
2221 gttccgctgt gtgtgtgagc ctggctggag tggccccgc tgcagccaga gcctggcccg
2281 agacgcctgt gagtcccagc cgtgcagggc cggtgggaca tgcagcagcg atggaatggg
2341 tttccactgc acctgcccgc ctggtgtcca gggacgtcag tgtgaactcc tctcccctg
2401 caccccgaac ccctgtgagc atggggccg ctgcgagtct gccctggcc agctgcctgt
2461 ctgctcctgc ccagggct ggcaaggccc acgatgccag caggatgtgg acgagtgtgc
2521 tggccccgca ccctgtggcc ctcatggtat ctgcaccaac ctggcaggga gtttcagctg
2581 cacctgccat ggagggtaca ctggcccttc ctgcgatcag acatcaatg actgtgaccc
2641 caacccatgc ctgaacggtg gctcgtgcca agacggcgtg ggctcctttt cctgctcctg
2701 cctccctggt ttcgccggcc cacgatgcgc ccgcgatgtg atgagtgcc tgagcaaccc
2761 ctgcggcccg ggcacctgta ccgaccacgt ggcctccttc acctgcacct gcccgccagg
2821 ctacggaggc ttccactgcg aacaggacct gcccgactgc agccccagct cctgcttcaa
2881 tggcgggacc tgtgtggacg gcgtgaactc gttcagctgc ctgtgccgtc cggctacac
2941 aggagcccac tgccaacatg aggcagaccc ctgcctctcg cggccctgcc tacacggggg
3001 cgtctgcagc gccgccacc ctggcttccg ctgcacctgc ctcgagagct tcacgggccc
3061 gcagtgccag acgctggtgg attggtgcag ccgccagcct tgtcaaaacg gggtcgctg
3121 cgtccagact ggggccatt gcctttgtcc ccctggatgg agcggacgcc tctgtgacat
3181 ccgaagcttg ccctgcaggg aggccgcagc ccagatcggg gtgcggctgg agcagctgtg
3241 tcaggcgggt gggcagtgtg tggatgaaga cagctcccac tactgcgtgt gcccagaggg
3301 ccgtactggt agccactgtg agcaggaggt ggacccctgc ttgcccagc cctgccagca
3361 tgggggggacc tgccgtggct atatggggggg ctacatgtgt gagtgtcttc ctggctacaa
3421 tggtgataac tgtgaggacg acgtggacga gtgtgcctcc cagcccctgcc agcacggggg
3481 ttcatgcatt gacctcgtgg cccgctatct ctgctcctgt cccccaggaa cgctggggt
3541 gctctgcgag attaatgagg atgactgcgg cccaggccca ccgctggact cagggccccg
```

FIG. 21B (continued)

```
3601 gtgcctacac aatggcacct gcgtggacct ggtgggtggt ttccgctgca cctgtccccc
3661 aggatacact ggtttgcgct gcgaggcaga catcaatgag tgtcgctcag gtgcctgcca
3721 cgcggcacac acccgggact gcctgcagga cccaggcgga ggtttccgtt gcctttgtca
3781 tgctggcttc tcaggtcctc gctgtcagac tgtcctgtct ccctgcgagt cccagccatg
3841 ccagcatgga ggccagtgcc gtcctagccc gggtcctggg ggtgggctga ccttcacctg
3901 tcactgtgcc cagccgttct ggggtccgcg ttgcgagcgg gtggcgcgct cctgccggga
3961 gctgcagtgc ccggtgggcg tcccatgcca gcagacgccc cgcgggccgc gctgcgcctg
4021 cccccaggg ttgtcgggac cctcctgccg cagcttcccg gggtcgccgc cggggccag
4081 caacgccagc tgcgcggccg cccctgtct ccacggggc tcctgccgcc ccgcgccgct
4141 cgcgcccttc ttccgctgcg cttgcgcgca gggctggacc gggccgcgct gcgaggcgcc
4201 cgccgcggca cccgaggtct cggaggagcc gcggtgcccg cgccgcct gccaggccaa
4261 gcgcggggac cagcgctgcg accgcgagtg caacagccca ggctgcggct gggacggcgg
4321 cgactgctcg ctgagcgtgg gcgacccctg gcggcaatgc gaggcgctgc agtgctggcg
4381 cctcttcaac aacagccgct gcgaccccgc ctgcagctcg cccgcctgcc tctacgacaa
4441 cttcgactgc cacgccggtg gccgcgagcg cacttgcaac ccggtgtacg agaagtactg
4501 cgccgaccac tttgccgacg gccgctgcga ccagggctgc aacacggagg agtgcggctg
4561 ggatgggctg gattgtgcca gcgaggtgcc ggccctgctg gcccgcggcg tgctggtgct
4621 cacagtgctg ctgccgccag aggagctact gcgttccagc gccgactttc tgcagcggct
4681 cagcgccatc ctgcgcacct cgctgcgctt ccgcctggac gcgcacggcc aggccatggt
4741 cttcccttac caccggccta gtcctggctc cgaaccccgg gcccgtcggg agctggcccc
4801 cgaggtgatc ggctcggtag taatgctgga gattgacaac cggctctgcc tgcagtcgcc
4861 tgagaatgat cactgcttcc ccgatgccca gagcgccgct gactacctgg gagcgttgtc
4921 agcggtggag cgcctggact tcccgtaccc actgcgggac gtgcgggggg agccgctgga
4981 gcctccagaa cccagcgtcc cgctgctgcc actgctagtg gcgggcgctg tcttgctgct
5041 ggtcattctc gtcctgggtg tcatggtggc ccggcgcaag cgcgagcaca gcaccctctg
5101 gttccctgag ggcttctcac tgcacaagga cgtggcctct ggtcacaagg gccggcggga
5161 acccgtgggc caggacgcgc tgggcatgaa gaacatggcc aagggtgaga gcctgatggg
5221 ggaggtggcc acagactgga tggacacaga gtgcccagag gccaagcggc taaaggtaga
5281 ggagccaggc atgggggctg aggaggctgt ggattgccgt cagtggactc aacaccatct
5341 ggttgctgct gacatccgcg tggcaccagc catggcactg acaccaccac agggcgacgc
5401 agatgctgat ggcatggatg tcaatgtgcg tgcccagat ggcttcaccc cgctaatgct
5461 ggcttccttc tgtgggggg ctctggagcc aatgccaact gaagaggatg aggcagatga
5521 cacatcagct agcatcatct ccgacctgat ctgccagggg gctcagcttg ggcacggac
5581 tgaccgtact ggcgagactg ctttgcacct ggctgcccgt tatgcccgtg ctgatgcagc
5641 caagcggctg ctggatgctg gggcagacac caatgcccag gaccactcag gccgcactcc
5701 cctgcacaca gctgtcacag ccgatgccca gggtgtcttc cagattctca tccgaaaccg
5761 ctctacagac ttggatgccc gcatggcaga tggctcaacg gcactgatcc tggcggcccg
5821 cctggcagta gagggcatgg tggaagagct catcgccagc catgctgatg tcaatgctgt
5881 ggatgagctt gggaaatcag ccttacactg gctgcggct gtgaacaacg tggaagccac
5941 tttggccctg ctcaaaaatg gagccaataa ggacatgcag gatagcaagg aggagacccc
6001 cctattcctg gccgcccgcg agggcagcta tgaggctgcc aagctgctgt tggaccactt
6061 tgccaaccgt gagatcaccg accacctgga caggctgccg cgggacgtag cccaggagag
6121 actgcaccag gacatcgtgc gcttgctgga tcaacccagt gggccccgca gcccccccgg
6181 tccccacggc ctggggcctc tgctctgtcc tccaggggcc ttcctccctg gcctcaaagc
6241 ggcacagtcg gggtccaaga agagcaggag gcccccggg aaggcggggc tggggccgca
6301 gggcccccgg gggcggggca agaagctgac gctggcctgc ccgggccccc tggctgacag
6361 ctcggtcacg ctgtcgcccg tggactcgct ggactccccg cggcctttcg gtgggccccc
6421 tgcttcccct ggtggcttcc ccttgaggg gccctatgca gctgccactg ccactgcagt
6481 gtctctggca cagcttggtg gccaggccg gcgggtcta ggcgccagc ccctggagg
6541 atgtgtactc agcctgggcc tgctgaaccc tgtggctgtg cccctcgatt gggcccggct
6601 gcccccacct gccctccag gccctcgtt cctgctgcca ctggcgccgg accccagct
6661 gctcaaccca gggacccccg tctccccgca ggagcggccc ccgccttacc tggcagtccc
6721 aggacatggc gaggagtacc cggcggctgg ggcacacagc agcccccaa aggcccgctt
6781 cctgcgggtt cccagtgagc acccttacct gaccccatcc cccgaatccc ctgagcactg
6841 ggccagcccc tcacctccct ccctctcaga ctggtccgaa tccacgccta gcccagccac
```

FIG. 21B (continued)

```
6901 tgccactggg gccatggcca ccaccactgg ggcactgcct gcccagccac ttcccttgtc
6961 tgttcccagc tcccttgctc aggcccagac ccagctgggg ccccagccgg aagttacccc
7021 caagaggcaa gtgttggcct gagacgctcg tcagttctta gatcttgggg gcctaaagag
7081 accccgtcc tgcctccttt ctttctctgt ctcttccttc cttttagtct ttttcatcct
7141 cttctctttc caccaaccct cctgcatcct tgccttgcag cgtgaccgag ataggtcatc
7201 agcccagggc ttcagtcttc ctttatttat aatgggtggg ggctaccacc caccctctca
7261 gtcttgtgaa gagtctggga cctccttctt ccccacttct ctcttccctc attcctttct
7321 ctctccttct ggcctctcat ttccttacac tctgacatga atgaattatt attatttta
7381 ttttttcttt ttttttaca ttttgtatag aaacaaattc atttaaacaa acttattatt
7441 attattttt acaaaatata tatatggaga tgctccctcc ccctgtgaac cccccagtgc
7501 ccccgtgggg ctgagtctgt gggcccattc ggccaagctg gattctgtgt acctagtaca
7561 caggcatgac tgggatcccg tgtaccgagt acacgaccca ggtatgtacc aagtaggcac
7621 ccttgggcgc acccactggg gccaggggtc ggggagtgt tgggagcctc ctccccaccc
7681 cacctccctc acttcactgc attccagatg ggacatgttc catagccttg ctggggaagg
7741 gcccactgcc aactccctct gccccagccc cacccttggc catctccctt tgggaactag
7801 ggggctgctg gtgggaaatg ggagccaggg cagatgtatg cattcctttg tgtccctgta
7861 aatgtgggac tacaagaaga ggagctgcct gagtggtact ttctcttcct ggtaatcctc
7921 tggcccagcc tcatggcaga atagaggtat ttttaggcta tttttgtaat atggcttctg
7981 gtcaaaatcc ctgtgtagct gaattcccaa gccctgcatt gtacagcccc ccactcccct
8041 caccacctaa taaggaata gttaacactc aaaaaaaaaa aaaaaaaa
```

FIG. 22A

NP_004548.3; SEQ ID NO: 18

```
1     mqppslllll lllllllcvsv vrprgllcgs fpepcanggt clslslgqgt cqcapgflge
61    tcqfpdpcqn aqlcqnggsc qallpaplgl psspspltps flctclpgft gercqakled
121   pcppsfcskr grchiqasgr pqcscmpgwt geqcqlrdfc sanpcvnggv clatypqiqc
181   hcppgfegha cerdvnecfq dpgpcpkgts chntlgsfqc lcpvgqegpr celragpcpp
241   rgcsnggtcq lmpekdstfh lclcppgfig pdcevnpdnc vshqcqnggt cqdgldtytc
301   lcpetwtgwd csedvdecet qgpphcrngg tcqnsagsfh cvcvsgwggt sceenlddci
361   aatcapgstc idrvgsfscl cppgrtgllc hledmclsqp chgdaqcstn pltgstlclc
421   qpgysgptch qdldeclmaq qgpspcehgg sclntpgsfn clcppgytgs rceadhnecl
481   sqpchpgstc ldllatfhcl cppglegqlc evetnecasa pclnhadchd llngfqcicl
541   pgfsgtrcee didecrsspc anggqcqdqp gafhckclpg fegprcqtev declsdpcpv
601   gascldlpga ffclcpsgft gqlcevplca pnlcqpkqic kdqkdkancl cpdgspgcap
661   pednctchhg hcqrsscvcd vgwtgpecea elggcisapc ahggtcypqp sgynctcptg
721   ytgptcseem tachsgpcln ggscnspgg yyctcppsht gpqcqtstdy cvsapcfngg
781   tcvnrpgtfs clcamgfqgp rcegklrpsc adspcrnrat cqdspqggprc lcptgytggs
841   cqtlmdlcaq kpcprnshcl qtgpsfhclc lqgwtgplcn lplsscqkaa lsqgidvssl
901   chngglcvds gpsyfchcpp gfqgslcqdh vnpcesrpcq ngatcmaqps gylcqcapgy
961   dgqncskeld acqsqpchnh gtctpkpggf hcacppgfvg lrcegdvdec ldqpchptgt
1021  aachslanaf ycqclpghtg qwceveidpc hsqpcfhggt ceatagsplg fichcpkgfe
1081  gptcshraps cgfhhchhgg lclpspkpgf pprcaclsgy ggpdcltppa pkgcgppspc
1141  lyngscsett glggpgfrcs cphsspgprc qkpgakgceg rsgdgacdag csgpggnwdg
1201  gdcslgvpdp wkgcpshsrc wllfrdgqch pqcdseeclf dgydcetppa ctpaydqych
1261  dhfhnghcek gcntaecgwd ggdcrpedgd pewgpslall vvlsppaldq qlfalarvls
1321  ltlrvglwvr kdrdgrdmvy pypgaraeek lggtrdptyq eraapqtqpl gketdslsag
1381  fvvvmgvdls rcgpdhpasr cpwdpglllr flaamaavga lepllpgpll avhphagtap
1441  panqlpwpvl cspvagvill algallvlql irrrrehga lwlppgftrr prtqsaphrr
1501  rpplgedsig lkalkpkaev dedgvvmcsg peegeevgqa eetgppstcq lwslsggcga
1561  lpqaamltpp qesemeapdl dtrgpdgvtp lmsavccgev qsgtfqgawl gcpepwepll
1621  dggacpqaht vgtgetplhl aarfsrptaa rrlleaganp nqpdragrtp lhaavaadar
1681  evcqlllrsr qtavdarted gttplmlaar lavedlveel iaaqadvgar dkwgktalhw
1741  aaavnnaraa rsllqagadk daqdnreqtp lflaaregav evaqlllglg aarelrdqag
1801  lapadvahqr nhwdlltlle gagppearhk atpgreagpf prartvsvsv pphgggalpr
1861  crtlsagagp rgggaclqar twsvdlaarg ggayshcrsl sgvgagggpt prgrrfsagm
1921  rgprpnpaim rgrygvaagr ggrvstddwp cdwvalgacg sasnipippp cltpspergs
1981  pqldcgppal qempinqgge gkk
```

FIG. 22B

NM_004557.3; SEQ ID NO: 19

```
1     agacgtgagg cttgcagcag gccgaggagg aagaagaggg gcagtgggag cagaggaggt
61    ggctcctgcc ccagtgagag ctctgagggt ccctgcctga agagggacag ggaccggggc
121   ttggagaagg ggctgtggaa tgcagccccc ttcactgctg ctgctgctgc tgctgctgct
181   gctgctatgt gtctcagtgg tcagacccag agggctgctg tgtgggagtt cccagaacc
241   ctgtgccaat ggaggcacct gcctgagcct gtctctggga caagggacct gccagtgtgc
301   ccctggcttc ctgggtgaga cgtgccagtt cctgaccccc tgccagaacg cccagctctg
361   ccaaaatgga ggcagctgcc aagccctgct cccgctccc ctaggctcc cagctctcc
421   ctctccattg acacccagct tcttgtgcac ttgcctccct ggcttcactg gtgagagatg
481   ccaggccaag cttgaagacc cttgtcctcc ctccttctgt tccaaaaggg gccgctgcca
541   catccaggcc tcgggccgcc cacagtgctc ctgcatgcct ggatggacag gtgagcagtg
```

FIG. 22B (continued)

```
 601 ccagcttcgg gacttctgtt cagccaaccc atgtgttaat ggaggggtgt gtctggccac
 661 ataccccag atccagtgcc actgcccacc gggcttcgag ggccatgcct gtgaacgtga
 721 tgtcaacgag tgcttccagg acccaggacc ctgccccaaa ggcacctcct gccataacac
 781 cctgggctcc ttccagtgcc tctgccctgt ggggcaggag ggtccacgtt gtgagctgcg
 841 ggcaggaccc tgccctccta ggggctgttc aatggggggc acctgccagc tgatgccaga
 901 gaaagactcc acctttcacc tctgcctctg tcccccaggt ttcataggcc cagactgtga
 961 ggtgaatcca gacaactgtg tcagccacca gtgtcagaat gggggcactt gccaggatgg
1021 gctggacacc tacacctgcc tctgcccaga aacctggaca ggctgggact gctccgaaga
1081 tgtggatgag tgtgagaccc agggtccccc tcactgcaga acggggca cctgccagaa
1141 ctctgctggt agctttcact gcgtgtgtgt gagtggctgg ggcggcacaa gctgtgagga
1201 gaacctggat gactgtattg ctgccacctg tgccccggga tccacctgca ttgaccgggt
1261 gggctctttc tcctgcctct gcccacctgg acgcacagga ctcctgtgcc acttggaaga
1321 catgtgtctg agccagccgt gccatgggga tgcccaatgc agcaccaacc ccctcacagg
1381 ctccacactc tgcctgtgtc agcctggcta ttcggggccc acctgccacc aggacctgga
1441 cgagtgtctg atggcccagc aaggcccaag tccctgtgaa catggcggtt cctgcctcaa
1501 cactcctggc tccttcaact gcctctgtcc acctggctac acaggctccc gttgtgaggc
1561 tgatcacaat gagtgcctct cccagccctg ccacccagga agcacctgtc tggacctact
1621 tgccaccttc cactgcctct gcccgccagg cttagaaggg cagctctgtg aggtggagac
1681 caacgagtgt gcctcagctc cctgcctgaa ccacgcggat tgccatgacc tgctcaacgg
1741 cttccagtgc atctgcctgc ctggattctc cggcacccga tgtgaggagg atatcgatga
1801 gtgcagaagc tctccctgtg ccaatggtgg gcagtgccag gaccagcctg gagccttcca
1861 ctgcaagtgt ctcccaggct ttgaagggcc acgctgtcaa acagaggtgg atgagtgcct
1921 gagtgaccca tgtcccgttg gagccagctg ccttgatctt ccaggagcct tcttttgcct
1981 ctgcccctct ggtttcacag gccagctctg tgaggttccc ctgtgtgctc caacctgtg
2041 ccagcccaag cagatatgta aggaccagaa agacaaggcc aactgcctct gtcctgatgg
2101 aagccctggc tgtgccccac ctgaggacaa ctgcacctgc caccacgggc actgccagag
2161 atcctcatgt gtgtgtgacg tgggttggac ggggccagag tgtgaggcag agctagggg
2221 ctgcatctct gcaccctgtg cccatgggggg gacctgctac ccccagccct ctggctacaa
2281 ctgcacctgc cctacaggct acacaggacc cacctgtagt gaggagatga cagcttgtca
2341 ctcagggcca tgtctcaatg gcggctcctg caaccctagc cctggaggct actactgcac
2401 ctgcctcca agccacacag ggccccagtg ccaaaccagc actgactact gtgtgtctgc
2461 cccgtgcttc aatgggggta cctgtgtgaa caggcctggc accttctcct gcctctgtgc
2521 catgggcttc cagggcccgc gctgtgaggg aaagctccgc cccagctgtg cagacagccc
2581 ctgtaggaat agggcaacct gccaggacag ccctcagggt ccccgctgcc tctgccccac
2641 tggctacacc ggaggcagct gccagactct gatggactta tgtgcccaga agccctgccc
2701 acgcaattcc cactgcctcc agactgggcc ctccttccac tgcttgtgcc tccagggatg
2761 gaccgggcct ctctgcaacc ttccactgtc ctcctgccag aaggctgcac tgagccaagg
2821 catagacgtc tcttccccttt gccacaatgg aggcctctgt gtcgacagcg gcccctccta
2881 tttctgccac tgcccccctg gattccaagg cagcctgtgc caggatcacg tgaacccatg
2941 tgagtccagg ccttgccaga acggggccac ctgcatggcc cagcccagtg ggtatctctg
3001 ccagtgtgcc ccaggctacg atggacagaa ctgctcaaag gaactcgatg cttgtcagtc
3061 ccaaccctgt cacaaccatg gaacctgtac tcccaaacct ggaggattcc actgtgcctg
3121 ccctccaggc tttgtggggc tacgctgtga gggagacgtg gacgagtgtc tggaccagcc
3181 ctgccacccc acaggcactg cagcctgcca ctctctggcc aatgccttct actgccagtg
3241 tctgcctgga cacacaggcc agtggtgtga ggtggagata gacccctgcc acagccaacc
3301 ctgctttcat ggagggacct gtgaggccac agcaggatca cccctgggtt tcatctgcca
3361 ctgccccaag ggttttgaag gccccacctg cagccacagg gcccttcct gcggcttcca
3421 tcactgccac cacggaggcc tgtgtctgcc ctcccctaag ccaggcttcc caccacgctg
3481 tgcctgcctc agtggctatg ggggtcctga ctgcctgacc ccaccagctc ctaaaggctg
3541 tggccctccc tccccatgcc tatacaatgg cagctgctca gagaccacgg gcttgggggg
3601 cccaggcttt cgatgctcct gccctcacag ctctccaggg ccccggtgtc agaaacccgg
3661 agccaagggg tgtgagggca aagtggaga tggggcctgc gatgctggct gcagtggccc
3721 gggaggaaac tgggatggag gggactgctc tctgggagtc ccagacccct ggaagggctg
3781 cccctcccac tctcggtgct ggcttctctt ccgggacggg cagtgccacc cacagtgtga
3841 ctctgaagag tgtctgtttg atggctacga ctgtgagacc cctccagcct gcactccagc
```

FIG. 22B (continued)

```
3901 ctatgaccag tactgccatg atcacttcca caacgggcac tgtgagaaag gctgcaacac
3961 tgcagagtgt ggctgggatg gaggtgactg caggcctgaa gatggggacc cagagtgggg
4021 gccctccctg gccctgctgg tggtactgag ccccccagcc ctagaccagc agctgtttgc
4081 cctggcccgg gtgctgtccc tgactctgag ggtaggactc tgggtaagga aggatcgtga
4141 tggcagggac atggtgtacc cctatcctgg ggcccgggct gaagaaaagc taggaggaac
4201 tcgggacccc acctatcagg agagagcagc ccctcaaacg cagcccctgg gcaaggagac
4261 cgactccctc agtgctgggt tgtggtggt catggtgtg gatttgtccc gctgtggccc
4321 tgaccacccg gcatcccgct gtccctggga ccctgggctt ctactccgct tccttgctgc
4381 gatggctgca gtgggagccc tggagcccct gctgcctgga ccactgctgg ctgtccaccc
4441 tcatgcaggg accgcacccc ctgccaacca gcttccctgg cctgtgctgt gctcccagt
4501 ggccggggtg attctcctgg ccctaggggc tcttctcgtc ctccagctca tccggcgtcg
4561 acgccgagag catggagctc tctggctgcc cctggtttc actcgacggc ctcggactca
4621 gtcagctccc caccgacgcc ggcccccact aggcgaggac agcattggtc tcaaggcact
4681 gaagccaaag gcagaagttg atgaggatgg agttgtgatg tgctcaggcc ctgaggaggg
4741 agaggaggtg ggccaggctg aagaaacagg cccaccctcc acgtgccagc tctggtctct
4801 gagtggtggc tgtggggcgc tccctcaggc agccatgcta actcctcccc aggaatctga
4861 gatggaagcc cctgacctgg acaccgtgg acctgatggg gtgacacccc tgatgtcagc
4921 agtttgctgt ggggaagtac agtccgggac cttccaaggg gcatggttgg gatgtcctga
4981 gccctgggaa cctctgctgg atggaggggc ctgtccccag gctcacaccg tgggcactgg
5041 ggagaccccc ctgcacctgg ctgccgatt ctcccggcca accgctgccc gccgcctcct
5101 tgaggctgga gccaacccca accagccaga ccgggcaggg cgcacacccc ttcatgctgc
5161 tgtggctgct gatgctcggg aggtctgcca gcttctgctc cgtagcagac aaactgcagt
5221 ggacgctcgc acagaggacg ggaccacacc cttgatgctg gctgccaggc tggcggtgga
5281 agacctggtt gaagaactga ttgcagccca agcagacgtg ggggccagag ataaatgggg
5341 gaaaactgcg ctgcactggg ctgctgccgt gaacaacgcc cgagccgccc gctcgcttct
5401 ccaggccgga gccgataaag atgcccagga caacagggag cagacgccgc tattcctggc
5461 ggcgcgggaa ggagcggtgg aagtagccca gctactgctg gggctggggg cagcccgaga
5521 gctgcgggac caggctgggc tagcgccggc ggacgtcgct caccaacgta accactggga
5581 tctgctgacg ctgctggaag gggctggcc accagaggcc cgtcacaaag ccacgccggg
5641 ccgcgaggct gggcccttcc cgcgcgcacg gacggtgtca gtaagcgtgc ccccgcatgg
5701 gggcggggct ctgccgcgct gccggacgct gtcagccgga gcaggccctc gtggggcgg
5761 agcttgtctg caggctcgga cttggtccgt agacttggct gcgcgggggg cggggccta
5821 ttctcattgc cggagcctct cgggagtagg agcaggagga ggcccgaccc ctcgcggccg
5881 taggttttct gcaggcatgc gcgggcctcg gccaaccct gcgataatgc gaggaagata
5941 cggagtggct gccgggcgcg gaggcagggt ctcaacggat gactggccct gtgattgggt
6001 ggccctggga gcttgcggtt ctgcctccaa cattccgatc ccgcctcctt gccttactcc
6061 gtccccggag cgggatcac ctcaacttga ctgtggtccc ccagccctcc aagaaatgcc
6121 cataaaccaa ggaggagagg gtaaaaaata gaagaataca tggtagggag gaattccaaa
6181 aatgattacc cattaaaagg caggctggaa ggccttcctg gttttaagat ggatccccca
6241 aaatgaaggg ttgtgagttt agtttctctc ctaaaatgaa tgtatgccca ccagagcaga
6301 catcttccac gtggagaagc tgcagctctg gaaagagggt ttaagatgct aggatgaggc
6361 aggcccagtc ctcctccaga aaataagaca ggccacagga gggcagagtg gagtggaaat
6421 acccctaagt tggaaccaag aattgcaggc atatgggatg taagatgttc tttcctatat
6481 atggtttcca aagggtgccc ctatgatcca ttgtccccac tgcccacaaa tggctgacaa
6541 atatttattg ggcacctact atgtgccagg cactgtgtag gtgctgaaaa gtggccaagg
6601 gccaccccg ctgatgactc cttgcattcc ctcccctcac aacaaagaac tccactgtgg
6661 ggatgaagcg cttcttctag ccactgctat cgctatttaa gaaccctaaa tctgtcaccc
6721 ataataaagc tgatttgaag tgttaaaaaa aaaaaaaaaa aa
```

FIG. 23A

NP_660161.1; SEQ ID NO: 20

```
1    mksckpsgpp agarvappca ggtecagtca gagrlesaar rrlaanarer rrmqglntaf
61   drlrrvvpqw gqdkklskye tlqmalsyim altrilaeae rfgserdwvg lhcehfgrdh
121  ylpfpgaklp geselysqrl fgfqpepfqm at
```

FIG. 23B

NM_145178.3; SEQ ID NO: 21

```
1     ctgcactctc cgacagctac tgcgctaaaa gcgctccttc cctgagcttc gggaaagagt
61    tcatcttcct gcaaaggagt ctcaggcttt cccagaggac ttgaaaggcc ttcctcgaac
121   cagccacacc aaactctgct gcagaaggtt tccttctctt tttcaacttc atgttgagaa
181   aatgactttc tcttgagcat ctcattttcc cctaaatttg ggcaagtgaa gagatatcag
241   cctggtcatc cagtagaaca gaaggccgag tcccgcactc ccccactgta aactatttga
301   ttgcacgtga gttgctttgt ttatgactta tttgctcaga agaggcacgt tgggaagcgg
361   ctcgagagac cagcccacgc gcaggtcctg agcgggcggg cgtgcgaggt cggcgcctcg
421   ctgcttgggg ccggggatga agtcctgcaa gcccagcggc ccgccggcgg gagcgcgcgt
481   tgcacccccg tgcgcgggcg gcaccgagtg cgcgggcacg tgcgccgggg ccgggcggct
541   ggagagcgcg gcgcgcaggc gcctggcggc caacgcgcgc gagcgccgcc gcatgcaggg
601   gctcaacact gccttcgacc gcttacgcag ggtggttccc cagtggggcc aggataaaaa
661   gctgtccaag tacgagaccc tgcagatggc cctgagctac atcatggctc tgacccggat
721   cctggccgag gccgagcgat cggctcgga gcgggactgg gtgggtctcc actgtgagca
781   cttcggccgc gaccactacc tcccgttccc gggcgcgaag ctgccgggcg agagcgagct
841   gtacagccag agactcttcg gcttccagcc cgagcccttc cagatggcca cctagggcgc
901   gcgcctccgc gggggtgggt gtccggcagc cgctccgagc ctcggccctg ccccaagtag
961   cccagaagcc tccggcggcc caggattcta aggatgcaat cctcgaggaa aattagtcga
1021  ttctcagatt accttttattc gcatcatcag acctatggac gcaatcattt aattgccttt
1081  cttttcccct cctcctttgt attttgtaga tttcattaat ggatcttgtg aatgggttga
1141  ttgctgtgaa aataatgccc ccttttccct tttctgggct actttgaggg aaaacaatct
1201  taagaaaaat aggattaagc tattctgttc cagtcctcag agaaataatc actttcttaa
1261  actttgtgag tttgtcctgt tcgggtgaag ttacagtatc cattacttgt gtttgctcac
1321  aacagagcta ccttcctgtt gtgtaaatgc gttttgctt tagtgcattg tgtgtgcaag
1381  catgaagtag aaacactttt ttttctgggt acagtacat gggtatcggt gctctgtatt
1441  tttttaaact gtgtacacat tattaaaata tacattttat aaaatataaa taaaacgtg
1501  gatttgtttt tcatgccaaa aaaaaaaaaa aaaa
```

FIG. 24

Atoh1 enhancer (SEQ ID NO: 22)

```
   1  TCCAAGGTCC GGCAATGAAG TTTGCATAAC AAACGTTTGG CAGCTCCCTC TCTCACACCC
  61  CATTAACAAG CTGTAACATA TAGCTGCAGG TTGCTATAAT CTCATTAATA TTTTGGAAAC
 121  TTGAATATTG AGTATTTCTG AGCGCTCATT CCCCATATGC CAGACCACTC CTGCCATGCT
 181  GACTGGTTCC TTTCTCTCCA TTATTAGCAA TTAGCTTCTA CCTTCCAAAG TCAGATCCAA
 241  GTATCTAAGA TACTACCAAA GGCATCAACT ATGTATGCAA GTTAGGCATG CTTAATATCA
 301  CCCAAACAAA CAAAGAGTCA GCACTTCTTA AAGTAATGAA GATAGATAAA TCGGGTTAGT
 361  TCTTTGGGAC ACCGCTGTTG TTTTCCAGAG TTTTTCTATA CTTTAAGCAG CTTGTTTTAT
 421  ATTCTGTCTT TGCCCTCAGC CAGCTAACAT TTTATTTGTT GAGGGTTTTG GCTCACCACA
 481  CTTTTGGAAA CTTATTTGAT TTCACGGGGA GCTGAAGGAA GATTGTTTTT GGCAACAGGC
 541  AAGTTTAACA CGTTCTTCAT GGGGCATTGC GAATGGCACA TCTACCAGAA AGGGAGGGGG
 601  AGTAACTTCC TCGTGCTGAA CCAGCAGGAG ACCAGAGCTT TCCTGAGGTC TTCCTATTGA
 661  TTTTAAAGAT TTAAAACTGA GCCCCAAAGT TGTAATGTTA TTGAAGTTTG TCTTGGAATA
 721  TACATCTCCT CTGCTAACTT AAAAGTTCAA GAAAGGAAAG GAAAGAAATA GAACCCCTTG
 781  CTAACTACAA CCTAGACTGA GAGGTGAAGA TCGCGGGCAA AGACAGGTGG TCACTGAAAC
 841  GTTTGCAGTT CTTTTCTTCC GAAGGCTTAG GACACAGGGT AAGGAGGAGC TAAAATAAAG
 901  CCGAGTGTAC GTTTAGTCTT CTCTGCACCC CAGGCCTAGT GTCTCCCAG GCAAGGAGTC
 961  ACCCCCTTTG CTTCTGGCTC CTAACTGAAA AAGGCAAAAG GGAGTGGAGA ATGGGTTAAA
1021  TCCCAGGACA CAGGGGAGAG GCAGGGAGG AGAGAAGTCG GAGGAAGATA AAGGAAAGGA
1081  CAGGAACCAA GAAGCGTGGG GGTAGTTTGC CGTAATGTGA GTGTTTCTTA ATTAGAGAGC
1141  GGCTGACAAT AGAGGGGCTG GCAGAGGCTC CTGGCCCCGG TGCGGAGCGT CTGGAGCGGA
1201  GCACGCGCTG TCAGCTGGTG AGCGCACTCG CTTTCAGGCC GCTCCCCGGG GAGCTGAGCG
1261  GCCACATTTA ACACCGTCGT CACCCTCCCC GGCCTCCTCA ACATCGGCCT CCTCCTCGTA
1321  GACAGCCTTG CTCGGCCCCC CACCGGCAGA GTTTACAGAA GCCAGAGCCT CTCGCCGTTC
1381  CCCCG
```

FIG. 25

Pou4f3 promoter (SEQ ID NO: 23)

```
   1   AGGGGGTGGC ACGGCGCGGC GCGGCGCGGC GCGGCGCGGC GCGGCGGGTG TCTCACAGTT
  61   GGCCTCTGGC TCCCTGGTCC CTCTGGGCAT CTCGGATCCT CCCTGGGCTG GGCAGACAAT
 121   GAGAGGCAGC GGCCGACAGG CGAGTCCAGT AGCAGCTGTG CAGGCGGAGG TTACATGTGA
 181   GAAGTTTGTG AAAGAAACTG AGAGAAAGAG AGAGGAAGGC AAGGCAGGCT GCAGACACCT
 241   GGCCCCGGTG CCTCACCAGC TGCCCTCCTG CGATGGCATC TTGAGTTCGG GCAGCTCCTA
 301   TCGAAGCCAT CTTGCCTGGC ATCCTCCCCG CCCCCTCTCC AGCATGCCTA GGTGAGGCTG
 361   AGCTGATGGA GGCTTAGCTG TGGTTCCAAC TAACTGCCCT GTACCAGCAG AGGAAGCTAG
 421   CTTAGTTCAA AACCTAGTAA AGCAAACACT CTGTCAGGGG AACTTGCCTT CCCCTTCACA
 481   TTGAGCATTC CTCTGGCAGG AGTCCTGAAG AAGATTTATT AATATGTCCA TTCTAAAATG
 541   ACATAGACTT CTTAAGGACT GTTTGGACA CATAAGAACT GATAAGACTC ACCCTCTAAA
 601   AGTCTCCAGA GTCTTTGAAG GAACAGACAT TCATCGTCAC ATGCTTTGA AGAGATAACA
 661   GAGCAGGGCT GGAGAAATGG CTCAGCAGTT AAGAAGACTT CCAGAGGACC TGGTGAGATT
 721   CCCAGTCCCC TGTAATTCCA GTTCAGTGA ATCTGATGCC TTCTTCTGGC AGCAGCACT
 781   CACGCTAGAC ACAAATGTGG TATACAAACA TACATGCAAG CAAAACAAAA GTGTGTGTTA
 841   AGTGTTTGTG CATCATGTGC ATACTACGTG CCTGGTAAGG CCAGAAGAAG ATGTTGGATC
 901   CCCTGGAACT CTTAGAGATG GTTGTGAGCT GCCATGTAGG TGCTGGAAAT TGTATCAGGG
 961   CCCTCTGGAG AGGTCAATAA ATGCTCTTAA GTGTTGAGCC ATCTCTCCAC TCCTCATATA
1021   CATTAAAGGA ATAATTTTTT TGTACAGGCT ACAGGGGAGG TTGAGGCAGG AAGGTCTCAA
1081   GGCCAAGGCC AGGCTTAGTT ACATAGAGGG AACTGTCTCA AAATAAGAGT GGAGGATCTG
1141   GAGAAATGGA AAGAGCACTG TTGTTCTTAC AGGGGACCAA TTCCTAGCAT CCACATGGAG
1201   GTCCAAGATC CTTTTCTGAC TCTGAAGGTA TCAGACACTC ATATGGTAGA CATACATACA
1261   TGCAGGCAAA ACACTTATAC ACATAAGATA ATCTGAAAAA AATTAATAAA GGGGGGAATC
1321   TAACTCATTG GCAGACCACT CGCCTTGAAT GCACGAGGCC CTAGGTTCAG TTTATCATAT
1381   GCAGAGAGTA GAGTTAGTCA CATTGGGATA GACAATAAGC AGAGAGAAGC GGGATGCTAG
1441   CTGTCTCCTT TCTTCCATTG TGTGTGTGTA TATATATATA TGTATACATA TATATACACA
1501   CACACATATA CATACACACA CACACACACA CACACACACA CACACTGTAT ATACTGTAGT
1561   TGTCTTCAGC CATACCAGAA GAGGGCATCA GATCCTATTA CAGCTGATTT TGAGCCACCT
1621   TGTGGTTGCT GGGAGTTGAA CTTAAGACCT TGGCAAGAGC AGCCAATGCT CTTAACCACT
1681   GGGCCGTCTC TCCAATCCCC TCCCTTTCTC CATTTTGTTC CTTTGTGTAT ACCCGCCCTT
1741   GGGATGATGA CACTTGGATC CAAGGTGGAT CTTCTCTCCT CGATCAATCC TTCAAGAAAC
1801   ACCTCACACG TGTCCTTCTT AAGTTTTCTC TTTTTTCCAA GACAGGATTT CTCTGTGTAG
1861   CCATGGCTGG CCTGTAACCA TCTTTATAGA CCAGGCTGGC CTCGAACTCA CAGAGATCCA
1921   CCTGCTAATG AAAGAACTCA GTGGGGAAAC CCCCACTCAG CTCCCGATTC GGCGTGCACC
1981   CAAGAATCGC GAATAGAACA CAACACCTTG ATGTAACAAC AAGAGGTTTT TTAATGGCGG
2041   AGCTCCGGGT CGAAACGTAT CTCACACAAC AGGAGACAGT GGATTCGACC ACGAGGCTTA
2101   GAAGCTAGGG GTTTTTATAG AAAAGGAGTG GGGCTGGGGA AGGAATTGAC GCGGTTTCAC
2161   ATGATTGGTC CATTTAAACA TCAGCAGCCT GTAACATTTA ACTTAGGTCA GAGGGGTGGG
2221   AGCTAGGGAG GCGAAGGGCT TGCCCGGGCA TGTCCTGGTC TGTTCTGCTG TGTTCTCAGC
2281   CCCAGGTTTC AAAGCGCACA AACAACTCTT TGGGCTATTT AACATACATT ACATGAATTA
2341   CAGTTTTATT TCCTTTCACT TCTACTGTCT GAGTGCTTGG CCTAAAGGCG TGCTCCACCA
2401   CCTGGATCCT TAGGCTTGCC AACCACATCT ACTCCTTGTT ACTTAACACT GAAATACACC
2461   ACTTTAGCCA CAACATTCCA TCCTGTCCCC CAAGTGTTCC GATATATCGT ATCTCATAAC
2521   GCAAAACATT CTATCCAATT TCAAGAATTC CCATAGTTAT AAAAGTCCCA ACATGATTGA
2581   AAAGTCCAAG TTCAATAAAA TCTCTGGGTC TCCAAGAAAA TCCTTAAATG TGAGTTCTGG
2641   TAACAATCCA GAAATATTCT ACATCCAATA TACAATGGTA CCAGGTGAAC ATCACATTCC
2701   AAAAGACGGG AAGGAGAGCA TAGAACAAAT GGATGGGACC AAGTCAAGAC TAAAACCCAG
2761   GAGAGGAAAT ACGAAACTCT GCAGCTCCAT TTGTAGCACC GAGGGCACGT CATATAATGA
2821   CGTGCGGTTG AAGATGGTTG TTAGCTGCTG TGTGGGTCCT GGGTTCTCTG GATGAACATT
2881   GACTAGTAAA AAAATTTTTT TGAATGAATT AATTTACTTA TCTTCTGGGT GAGGCAGGAT
2941   CTGAATGTGG AGGCCAGAGG GCAACTGTGG GAGTCACTTG TCTCCTATGT GTTAGATCTG
3001   GGGAGACAAC TGAGGAATCC AGGTCCCCAA GCTTCATGCC AGGCACCTTT ACTAGCGGAG
3061   TCATCTCACT GACCTTGGCA CTCATCACTT AATAACAGT TACCTTTTAA TTCATTCATT
3121   TAATTTAATT AATGATAATT CCACAGCATT CAACTCAATC CTTTTTCTGG CCATATGGTT
3181   TTCAAAATCT TTTGCTGTCT TGAGTCTCAT TATAAACCCA ACTAAACACA ATGACCACAA
3241   CACCTAACTA AATGCTATGC TGTCTTGAAA TGTCCTCCAC CAAATGTGTC TGTCACCCAT
3301   GTTTCCCTAC ACACACAAAG TTTATGGACA CAGACAAAAT ACTTTGCCAG AATAGAATTC
```

FIG. 25 (continued)

```
3361  AAATGATCTT TAGTCAAGCT CCCAATAGAG ACCTCATTTG CATCGAAAAC CTCAGGGGGC
3421  CAAGCTTTCA TCCTTTGAGT CTAGTCCACT GAACTCTTGT GCATCTAGAC CACTGAACTC
3481  CAGACAGAAT TCCCCACCAA GCTCTGCTCA CCACACTCTC AGCACCTCTA GTCTACCTTC
3541  CCCTACCAAC CCCCTTCAAG CAAACAAGTT CCAAAGGCGT GAGAACTAGC TGGTTAGCAA
3601  GAATGTAACT TCTGGGTGCC AACTTTCTGT ATTAGATAGT TTTTTCCTCA CTAATCAGAT
3661  ACTTGATAGA AACAACTTAA GAGAGAGAAG ATATATTTTG TATCCAGTGT CAGAGTTTTC
3721  AGTGTGAGAG AGCTAGAGCA CAGAATTCTG TGCTGGGTCC CGAGGTAGAG AAAGGAGAAT
3781  GCTAGCTCCT GTCAACTTTC CCTCTTTAAC CCATTTATTC CAGCAAAGTC CAAAGCCATG
3841  AGGATGGCAC CACTCACATT CAAGATGAGT CTTTTTTTTT TTTTTGCCC CTTACTTAAT
3901  CCTCACACTC ACAGGTAGAT CTCACCAGTC TTTCAGGTAA TTCTAAATAT AGTCTAGTTG
3961  ACAAGGAGGA TTAAACCACC ACAGCCCTTG TCAAACCTC TGAGTCCGAG TTTTCGTGCT
4021  CTGTTTTATG AAACTGGAGT TGCTTCTTTC TTATTCATTC TAATGTTGAA AGCCACTAGC
4081  CCACAGAAAA ATGTCCTTGT CCCTGATTTG AATCTCTCTG GAGAACACAG TGCTCTGAGT
4141  CCTGATTTAT GTGGCAATCT CATGTCCTGG CCAAGATCTT GGTTTTTGT TTTTTGTTTT
4201  GTTTTGTTTT TTTTGTTTTT TTTTTTTTTT TTTTTTTTTT TGAGATAGGG TCTCACTTAT
4261  GTAGCCCTGG CTGTCCTGAA ACTCCCTATG TAGACCAGGC TGGCCTTGAA CTCACAGAGA
4321  TCCACCTGCC TCTGCCTCCT CAAGTGCCAC TACACTGCCT TAAACCCTAA GATCTTGAAA
4381  CAGTGCTCTC TGTATCTGCA GAACCTGCCA TGAAATCCAG CTAGCAGTGG GTATTTCAAA
4441  GACCTTATAG AATGAAAAAA ATGTGACTCC TTTGGTGCCC TTGACTGAAC CCTGAGATTA
4501  TTTTTGGACT CAATGGGTGT AGGGTATTTC CTTATTTGTT TGTGCTCTAG GTGGGGTCCC
4561  CATTATGTAG CTTAGCTGAC CTTGAACTCT TGATGTAGAA CAGACTGCCC CCCCCACCTG
4621  TCTCTCTATG TGTGTTTTAA TTACAATAAA ATGCCACGGT ATAAGCGTAA GTTTACCTCA
4681  GGCCAACCTC TCTTGCATGA CCAACTACAA ATAGTAGTTG ACTGGTTTTT ATTAGATTTT
4741  CATCTAATTG AATTTAAGTT TGTAAGTTCT GAAAAAAATG TGTCCTAAGG CTTATCTTGT
4801  ACTTTCATCC CCCCCCCGC CCACCAATCT ATTATTTTAT GTGTATGGAG GTTTTGTATG
4861  TATATATGTT TGTGTACCTC CTATGTGAAG TACCCCTGGA GGTCCGAAAA GGGCATCAGA
4921  TTCATTGGAA TTAACAAATA GTTCTGAGCT ACCATGTGTG TGCTGGGAAC TGAACTTGGG
4981  TCTTCTGAAA GACCCAGCCA ATGCTCTTAA TCTCAGGGTC ACTTCTACAG ACCCTGCCGT
5041  TGCAATTTTT AAAAATTATT TGTTGTTCCC TTGTCATCAT GTGTGTGTCT CCCTGCCCTT
5101  GTTCCACCCC CATTCCCCAC CGATTTCCCC AGCATTATCT AAAGACCTTG ATAAGGCCTG
5161  TGGTGTGACA GAAAACAGTT GATAAAGGAG ATCAGCATTA CCTTTTTACA GGTCCTTTAA
5221  AAAGCCAAGT AAGTACATGT ATGACTACAC TTAATTGATT TTTAAATTT CAGCCCCTTT
5281  CTGTAGCTGG GTGTCTTTGC ATGTAGTTTC ACTCTGTCTC CATCAATAGG TTTATGTTCA
5341  GGCAAAGCCA TAATCAGATT TTCTAAGAGT CATCTCCAGT GACAATTATT CAGGTCTTAT
5401  TACTATTAAT TATTATTTAA TATTTAATTA ATTGATTAAC AATCATTATT AATCATTAGT
5461  TTTTCATGTT ATTATTCGTT TCGTTTGTT TAAGATCTCG CACAGCCCAA GCTGGCCTTG
5521  AACTCAGTCT GTCATCCATG TGAGTACAGA ACTCCAGTT TCCTTCACCC ACATCCCAAG
5581  TGCTGAGGTT ACAGGTGTGA ACAGCCACAT CTATCTTACA GATTTACAAT GGTTTCATGC
5641  CCTTTTCTGA TGCTATAGAA TAAAGAAAAT GTATTTTGC CAGCTAAAGA AGAAAAAAT
5701  GATTCCCTTA CAATTTGTAT TTCTTATCTT TCAGGCTAAT TGATGATTGA GTTCCAACCA
5761  GGTTGACTAT AGCAATGTAT AAAAGATTAA TTTTAAAGTG TGACACAAAA ATAAATATTC
5821  AAAATGGTGG ACACACACAC ACACACACAC ACAGAGGCTA GTTTTACTGA TAGGTGTCAG
5881  CTTACTACTG ACCATTGCTA GTGGACCTTA TGGGAAGAAA AGACAGAAAG GTGTTTTCTA
5941  GGGGCCTGAG GGAAGTAGTG GTATTGTCCT GGTCAGCATT TTTTGATGAC TTATTTTATT
6001  TTATGTGCAT TGATGTTTTG CCTACATATA TGTCTGTTGA ACCGCATTGG ATCCCCTGAA
6061  ACTGCAGTTA CAGGCTACCA TGTGGGTGTT GGGAATTGAG CCCAGGTCCT CTGGAAGATC
6121  AGTCAGTGTT GTTAACCACT GAGCCATCTC TCCAGTCCCA CCTAGTCAGT ATTTTCCAAG
6181  TCCATGAGTG ACAGAGCAGT GAAGGGGATG GGTATGAATG CGTCTTTCCC AAGTATTCCT
6241  CTTCACAGAC AACGAGGATA TTATGGCATG AAAAGAGACC CTTAAGAGGC TCCATGGGGT
6301  CAGGCAAAAT GTAGGTCCAC TACCTCCATG TTTATTCCCG CTTCCCTTTT GGACTCCACA
6361  CTGGTCAGGA AACAATACTG AGGAGTCTTA AAAGCTAGTG GGAGATAAAA ATCACCCATG
6421  TTTGACTTCT GGGGACTTGA GGGGCTTGTG TTGTGGCACA AAGCCAGTAA TAAGGAGAGG
6481  AACAGTTCAC ATCTGCAGAG AGACCACATC CCTGGAGAGA CTGCAGGCTG TTCTTTAGGT
6541  TAAAAGGAG GTGCTAACAT TTGTTCCATC CTTTCAACAT GTTGGATGCC GTTTCAAGTG
6601  CTTACCACCA AGTAACCCTC ACTACAGTAG GGGAAACTAC TGTATGCATC TGTATACAGA
6661  TGGGCACTGC AGTATAGAGG CCTCAAGATG ACTGTCTCCT GGCCTCTCAG CCAGTAGAAG
6721  TAGAAGCAGC AGTGTGCTCT GAGTCTGATG GCAGCATGCA CTGGGTTGTG AAGAAGTGTC
6781  CTGAGTGCAC AGTGAGGTCA TCATCATCAT CCTTCTCCTC CAGCAAGACC CAAGAAAGCT
```

FIG. 25 (continued)

```
6841  ACCTGAGTAC CATTTCAGTT GGCCTCCCTC ACAGATTGAT GATTGATTGA TTGATTGATT
6901  GTTGTTGTTG TTTTGCCACA GCAAGGAAGG ACCTAGAATG TGTTTTGGGA TGAGTTGAGA
6961  AAGGACTGGC TGGCAGTCCT GAGGAAAGAG GGGGAGCCAG GTCAGTGTAG GGTGTCATCT
7021  TAGACTAAAT TCATCCCTGG GTCCTAGACT TTCCACACTC TGCCCCCTCA GTGTTAAGAT
7081  TCTGGGAAAC CCAGCACTCT TGAGCACAGA GACAGTGCTG CAGGACACAG CTGGGCAGGA
7141  AGAATTTCTC TTCCAACCCG AAGGCAGCTC CCAGCCGGC CACAGTCCCA GGATTCCCCA
7201  TCCATTATTC ATGGTGTTTA TTAGCTCCCA GGAAGGGAGA GGAAAGAAGG AGAGGAGGCG
7261  CTAGGGAAAT AGGGGACACA GAGGATGGGG CAGAGACAAA CTTAGGACCC TTAAGTTGGG
7321  GGAACTTCTA AAGGAAGAAG AGGAGGCTAA GAGGTGAAGA GCCCAAAGTC AGACATGGTG
7381  TTGGCTCCAA ACCAGTGAGT GAATGACACT GCTCACAGGT AGGAGATCTT GGGCTAACTT
7441  ATTTGGCTCT TGTTTCCTTT GGCTGTCTAA TGGGATAGCA GTAGCTACTC TGTAGTGTCC
7501  TGTAGGAACG TTGGTCCTAT ACACTAACAA TACTTTTTAA ATATTGAGTG CTCAATACTT
7561  TTCTCATTAT GTTATTATTA TTATTATTAT TATTATTATT ATTATTATTA TTATCATTGC
7621  CTCGCACAAA TCAGTAGCTC AAAAATGATA GCTGTTGTTA CAGGTATTGG GGCTGCTAAG
7681  CTCTACAGAA GTATGCAGAA GAATTGCTCC AGCTAGGCCA GCTGTCCTCT ACTGTTCCTT
7741  AGCAAGCTTT CTGGGGGGTG GGGGGGAAAG GGAGAACTTG GCCCACAAGT TCTGTTTCTC
7801  AGATGAAAGC TGAAACAGCC AGGGTTAGGA AGAAGCCACA GGCTTGTGGA TCAGGAAGCC
7861  TTTCTTCCAC CCAAGCTCAC AGAGGGAGT ATCACCCGAT AAGCATTCTG GTAACCTCTG
7921  GTCCTTGCCC AGGCTGGTTT CTGAGTTTGG AGGCACCTTT TCGCTATGCA CTGGGATGCA
7981  GGCTTTGAGC TTCAGACTCA GAGCACCTTG AAAATAGCCA GTTTGGGGTG TGTGTGTGTG
8041  TGTGTGTGTG TGTGTGTGTG TGTGTGTGTG TCTCAGGAGC TTAAGTCTGC CCTTTCATCC
8101  AGGCAGCTCG AGCTGGACA GGACAGAGGT TTAGGACTTT ATGCAAAGAA GTCCAGGAGG
8161  AAGAAGAAAG AATCTGTAAA GTCTGGCAAG CTGGAGCCAG GTGGGCGGG GCGGACAGGA
8221  AGAGGCCCTG CCAGGCCGGG GTATAAATGC TGTGGAGGGG GGCGGCCGCA TCAGGCTCAG
8281  AGTGGCGCGC CGAGACCTGC GGTCCCGCCT TGCCTCCCGG GCCGCCCCTG CGAGTCCCGG
8341  GCGCGTGTGC ACGTCTGCGC GTGCCCGGGC CCTTCCTGGC AGACTGCTTG TAAGATGAGT
8401  GAAGAAGCAG GTGGGGGAGA GGGGAGGCAG CAAGCGAGAG GGCGAGGGGA GCGCTGGCGC
8461  TGAGCGGCGC TCACTTGGAG CGCGGAGAGC TAGCAAGACG A
```

FIG. 26

Myo7a promoter (SEQ ID NO: 24)

```
   1    CTAGAGGGAT CTGTCTGTTT CATTTTTCCC GTACCCCGCA CCCCCCCACA CACAAGGGTA
  61    AAGACAGAGG GCACAATGGG TAGCTGACCT CTGGTCAGAA GGATGAGCAA GGAAGGCCTT
 121    GGGAATCACA GATAAAAGCT GGCCTTGCTG GTTACCTAGT GAGTCAGAGC CCAGCTCTGT
 181    GGAATCCTTC AGGTTCCCTG CTTCCAGTCA GTGTGGGGCT GGCTTTGCTG AGCTCTGCCC
 241    ATCTCAGGCC CTGGGGACAT GGGGGCACAC AGTTCCTGCT CTGCAGCAGC CTTCCAGCAA
 301    CTGGGGAAAA TGTACAAATC ATGTCTGATC GAAGTACTGT AGTGTCCTTG ATAAGCAGTG
 361    TCCCTAGGAG CTGACTCTTA GTCTCTGAGT TCAAGATCTG TGCCCTGTTC TAGTGGAGAG
 421    GAGAGACTTA CATGCAGGCC ACAGACGGAG GTGGCAGAGC AGAGATCCTG GGAAGGTGCG
 481    GTAGCTAGAG CTAGGAATTT ATGGGCAGGG CCACGGGTAG AAGCTGGGTC GGGTTGTGGA
 541    AAACGAAATG ATGGAATACG ACGATAGATT GGATTTGAAG GGGCGAGGGT TGTATGAACT
 601    AAGACCAGTT CTGCAGTGGT TCAGATGTGG TGCCCTTAAG AGGCTCAGGT GCCAGAAACC
 661    AGTGCCCCTT CTGGATAGGG CAGAAAACAG GCAGAACCTG GAGAGGTACG GTGGAGCATG
 721    AGGTGGTAAG GACACACACC ATCTCAGGTG GTTTGTTTTG GGGAAAACAA GCATGGATTT
 781    CTAGGTTTCT CCGATCGGGT GACCTGCTTA GCCGAGTTTG GGTGCTGAGG AAATGTCTCC
 841    GTTATGGTTC TGAGACCACT TTCTCACCCA CCCACTGCCT TCCCAGCATG CACCTCAGCC
 901    TCAACGAAGC ACACCTGCCC CAGTTGCCGC CTTGTCGATT GGGCTCTGGA TGCTCCAACC
 961    TGTGTCTCTC CCACTCTGTG TAGGCTCATG CTACTCACCT GACTCATAAG TATCAGTTTC
1021    GTAGGTGAAG GCTGCGTTGG GTGCAAGTCA ACCTTGGACC CTGGTCTCAC TGTGGCACCC
1081    TGGTATGAGG AAGTTGACCG GCTTTTCCTT AGTCTTGTAG CAGTTGGCTG TGCCCAGCAG
1141    GTGGCACCAT TGCACCATTG ATTCTCCCCA CTCCATACCA CTATAGATTC CACCCCACCC
1201    TATTCCCCTC CCCACCTTAA CCCACCCACC CCCACCGAAA AGCAGCTTTC CTGAGTAGAT
1261    GTCCCAGCTG GCAAGTGTGG GCAGAAGAAG GGGCCAGGTC TCAGGAGGAG GAGGAGGAGG
1321    AGGAGGAGGA GGAAGAGGAA GAGGAGTCCT TCAGCCTCCT TCCTCATCTA CCATGATGAG
1381    TATTTGTGTC CTGTTCATTC CCACCCACTC CCTTTTTTAA ATCACACATT TAAATCACAC
1441    ACACACACAC ACACACACAC ACACACACAC ACACACACAC ACACCGGGTA AGTCTGTCCT
1501    GCGTGAGGTG GCTCCTACTC AGGTGGCTTT GCAAACTGTC TGGATAACAG CACACTCAAG
1561    ACTCCTAGGA CAGGCTGTGG GGGCCAGTTG TAGAGCCTGG GGGTGGGGTG CATCTTGGGG
1621    AGTCCTGGTT TGGATGTTGT GTCCAGCCAA GGCTCCAGGT ATTGCCAAGC CTGCTCATTT
1681    ATATGGTCTC TAGTAGTGCC CTGACGAGGG AAGCTGGGTG AGCAGGGGAG GCTACTGGGA
1741    ACTGAGACCC AGCAAAATCA TGAGGAAGAT GGGACGTGAT CAGGTGTCCT AACCATGCAG
1801    AGATGGCAGG TAGTAACACA TGTGACAAGA GACCCTGAGG TCCTGATGGT TGGCCCCAGG
1861    CCCGAGGTTC CCACTGGCCA GCAGTGCCCC CTGGAGCTTC TATGCCTTGC ATCCCTGCTG
1921    GTTAGCTTTA CACAGCACCT TGGGCAACCT CTAGACGTTA GTCAGCAGCC CCAGCACAGC
1981    CCGCCCCTCA TGCTGATGTC ACCACATCCA GACCTTCGAG GCCCCAGGGG CTCCGCCTCC
2041    TGGGAGAAGG CTTTGGAGGG AGAGGGCGGG TGGCAGTGCA GGCTGGACAG CTGCCCTGAA
2101    CAGAAAGAAA GAGTGACCCA GGGAGACAAG AAACAGAGTA GCCCAAGGGA AGCCCACAGC
2161    AGCAGCAGAT CAAGGCTCAA GCTGGAGCTG AAAATTTGCA GGCTCCAGCC TCAGCTTCCA
2221    GAGTCCTCCT GACCTGTGAC CCCTGGCTCC TGGCTGGGAG GTGGTGACTC GGAGGGTGTG
2281    GATAAAACCC AGGTAAGGAT GGGCTGCCCT GGCTGGAACT TTTGGACTGG GGAGGAGTTA
2341    CAGGCTGGGG CCTCCTCTGG AGCCTCTGCC CTTAGGTTCC TGGGACTGGA CTCCCCTGAA
2401    CCTACAGGGG CCTTGCCACC ATAGGCATGG AAAGAAAATG CCCCGAGCCG TGCACATGGA
2461    GGCTTATGCC CTAGATGAGG GAATAGCTGA AGAGCACAGG GCCTGTGGAG TTGTTTCCGG
2521    GTTGGAGCTG GGTCAGGGGT ATCCAGAGGC AGGGGTGAAA GATGGGAGTG GAGGCTGGGG
2581    GGGCAAGTGT GGATGCCTCT CTCTGCTTGG TCTTTTGGTC ATCTCCCTGA TAATCTATCT
2641    CTCCTTGCAC ACGTTGTTTC TTCTTTGTGT GCCTTACATT CTCTATCCGT GACCCAAGAA
2701    CATGAAGGTT ACCATCTGGG GTTGCCCAGG GGTCAAGGTA AAATCAGTTG TGGGTCTAGG
2761    GAAAAAAACA AAACAAAACA AAAACTATG GTTCTTTGTT CTCAATTTGA AAAGCAACAG
2821    TCTTACACAC TAGTCTAGTC TGGGATGGAG AGGTAGAGCC TCATGCATGG GGTAGAAGAG
2881    ACCTGAGCTT TTCCATGGGT CTTCAGCTCT ACCCTCCAAG TCTACAGTCC CAGTCTGTCC
2941    TGCAGCCTTG TACCAGCATG AGTGAGGCAG GGGCCAGGCA GCCTCTTCAG ACGCCAGCTC
3001    TCATAACTAC TGCTGCTGCC TTTGGGATTA TCCCCCTGCC AGGACCCCAG CGTGGTGTAG
3061    GTCTCCCGAA GGACCATATG CCCATAGAGA CCCAGGGCGT GGGGTCAGGG CTCAGGTGTC
3121    AGGCAGTGTC GTGGGCAGAG GATCAGATGT CCCAGTGCCT CTGAATGGAC CCTTGTGAAA
3181    ACTTAATGCT CACTCGAGGG GCAGGCAGG CAGGGATGGA GGGGCCTCAC ACCAAGACCT
3241    ATGGGCTGGG GCTGCTTCTG GTGACCACAC TCGAGGCAGC AAATCCATCT CGAGCCTATT
3301    CCTGGGTCCA GCTCTGTGCT GGATGAGGTA AGAGATGAGG GCCACGAACA GGTGTTAGAT
```

FIG. 26 (continued)

```
3361  CATTCTGCCA TGTGTCCTAA AACTCCTAAA GCAGTCCTGA ACCAGGAGCA GAGTCCAAAT
3421  CTTACTTAGT GCCAAGTCTT CCCTGCCCTG CTGTGTGACC TTGGGTAAGA GATAGTCCTT
3481  CTCTGAACTT TGGGCAGCCT CAGGACATTA GTCCCTGTCC CAGCACAGCC CACCCCTCAC
3541  GCTGATGTCT GGTACAGGGC TGACTACACT CCTTTCAAAG CCCTTTGGGA TGACGAGGGC
3601  AGCTTTGGGC AGTGGAGGTG GTGACGGTAA CTGAGGCTCT GGTCACATAG ACTGAGCTTT
3661  AATCAGAAGG ATGGAAACCA AGAAAGATTT CCGTGAGGGA GGAGGGGTAG GGGTGGGGTT
3721  GGGGAGGAGT CTAGGTGGCC CTGCAGATCC AAGCTGCCTG GGCTCAGGGC GTGCCATGGT
3781  CTCTTCCCAC AGAGCTGTGT CTGGTCACTC CGGCAGGTGT GCTGACGTAG AAG
```

FIG. 27

Hes5 promoter (SEQ ID NO: 25)

```
   1  ACCTCTGTCA GAGCTCGGGT GAGGGTTGTG GCAGGGACTA AGGGAGGTGA ATTCTGCACT
  61  TATATCTTGC ACTGGACAGA CCATCCTGTG CTGCCTCAAA GCCAAGCCTT CCCCTCTGTC
 121  CCAGATGCTT CCATCCATGG TAACCCAACA ACCCCTTGTG CTAAGAGCTT CTGGAGCAAG
 181  ACCTTCGGAA TAGATCATTT ACAGCAGTGG GTCACTACCA TAGCAGGAGG GCGTTTCCCT
 241  AGTGGGCACT GTGAAGGCCC TTCAGTTCCT GAGCTCAGAC ATGGCTGACA TCCATCCAGA
 301  GAACCTGGTT TCATTCCACA CTGGCTATTG TGCTCTGATG CCAGCCTCCT GGTTTGGGCC
 361  TGGCTAGGTC TTAGGTTGAC CCTAGGAGGA AGCACGGGGC CTTATCTCCT CCCTCAGCCC
 421  CTGCAGAGTA TTGGGGAAAT AGTACAGGTT CCAGATGGAG GGACGCTCCT ACATGGCCAT
 481  CCCCTAGGTG TCTAGGGTGT GACTAGTAAG GTCACCTGGT TAGGAACCAC GGTTATCAGT
 541  TCTTACAAAG AGGCCCATCC ACACTGGCAC AGCATTCATA TGGGGGCTTA TTTTTAGGTC
 601  TCCCACCTTC TACCTGCCAA CACAAAATGC TGAATGAAAC TGGAACACAC ACACAGAGGC
 661  ATGCACGCGC GCGCCCGCAC GAGCTGAGGG GGATGTCATG AGAGGAGTTA AGGGCAGCCA
 721  TGGTTTCCTA AAAGCCACGC GGGAGTAGTG ATCACGGACA GCATGAAGGA GGCACGGTCC
 781  TCCTGTTTCA GAGATGCATG TGGCACCTGG TGACACAAGA GCAGTCCAGA TACCCTGTGG
 841  GTTCAGGGGT TCCTGAGGGC TTCCTAGGTA TGGGGCTTTG TGCTAGGCAT TATCCAAAGC
 901  AAATTCAGCT AGCCTAGAAG TACGCTTGGC AGGCTCCGCG CGTGGCCATT TCTAGCTGCG
 961  GAGAAGTCAC TCCTCTCAAC TGACAGAACT GGCAATAAAG CGCCTAAATT CTAAATACAT
1021  GAGTCCCTCT CTCATCCTGT ACCTGCGAAT GGCATGGCGG CAGCATCTGT TTGAGAGAAT
1081  GTGGCCCACT TTAACCCACT GTGCCTGTGG GCAACAGGTC CCAGCTGGGG AGGGTGCCCA
1141  CTCCTCTGGA AGTCGCTGTC TGTTCATTGT AAAACTCTCA TTTCTCTGCG CCTGTGGCCT
1201  CTGCCAGCCA GCGGTGGGGA GCCTCTGGGG AGTGGGAGGG AAGAAGGGAG AGAAGGGGGG
1261  GGGAGAGCAC TCCTTCCTGC CCTCCCCACC TCCCCGCGGC CTGGGAAAAG GCAGCATATT
1321  GAGGCGCGGG GCTCTCAGCA TCAGGCCCCG GGATGCTAAT GAGGGCGAGC GCGTTCCCAC
1381  AGCCCGGACA TTGTGCCGCG CGGCCCACCT GCTCCTCGGG GAGCGACCAT TGTGCCCGCG
1441  CCAATTCACA GGCAATTTAG CGTGCGCTAA TGGGCCGGCG CCTTTGTGCG GCCGGCGCCG
1501  CCATTGGCCG CCGAGTGTGG GAACGGCCGC GGCGCCCGGA CCCCAGGCGC CGGGCCGCTG
1561  CCCGCGCCTA TATAGGGCTG GCGTGCTGGG GTCCAGGTCG
```

FIG. 28

GFAP promoter (SEQ ID NO: 26)

```
   1 AGGAGCTCCC ACCTCCCTCT CTGTGCTGGG ACTCACAGAG GGAGACCTCA GGAGGCAGTC
  61 TGTCCATCAC ATGTCCAAAT GCAGAGCATA CCCTGGGCTG GGCGCAGTGG CGCACAACTG
 121 TAATTCCAGC ACTTTGGGAG GCTGATGTGG AAGGATCACT TGAGCCCAGA AGTTCTAGAC
 181 CAGCCTGGGC AACATGGCAA GACCCTATCT CTACAAAAAA AGTTAAAAAA TCAGCCACGT
 241 GTGGTGACAC ACACCTGTAG TCCCAGCTAT TCAGGAGGCT GAGGTGAGGG GATCACTTAA
 301 GGCTGGGAGG TTGAGGCTGC AGTGAGTCGT GGTTGCGCCA CTGCACTCCA GCCTGGGCAA
 361 CAGTGAGACC CTGTCTCAAA AGACAAAAAA AAAAAAAAAA AAAAAAGAA CATATCCTGG
 421 TGTGGAGTAG GGGACGCTGC TCTGACAGAG GCTCGGGGGC CTGAGCTGGC TCTGTGAGCT
 481 GGGGAGGAGG CAGACAGCCA GGCCTTGTCT GCAAGCAGAC CTGGCAGCAT GGGCTGGCC
 541 GCCCCCCAGG GCCTCCTCTT CATGCCCAGT GAATGACTCA CCTTGGCACA GACACAATGT
 601 TCGGGGTGGG CACAGTGCCT GCTTCCCGCC GCACCCCAGC CCCCCTCAAA TGCCTTCCGA
 661 GAAGCCCATT GAGCAGGGGG CTTGCATTGC ACCCCAGCCT GACAGCCTGG CATCTTGGGA
 721 TAAAAGCAGC ACAGCCCCCT AGGGGCTGCC CTTGCTGTGT GGCGCCACCG GCGGTGGAGA
 781 ACAAGGCTCT ATTCAGCCTG TGCCCAGGAA AGGGGATCAG GGGATGCCCA GGCATGGACA
 841 GTGGGTGGCA GGGGGGGAGA GGAGGGCTGT CTGCTTCCCA GAAGTCCAAG GACACAAATG
 901 GGTGAGGGGA CTGGGCAGGG TTCTGACCCT GTGGGACCAG AGTGGAGGGC GTAGATGGAC
 961 CTGAAGTCTC CAGGGACAAC AGGGCCCAGG TCTCAGGCTC CTAGTTGGGC CCAGTGGCTC
1021 CAGCGTTTCC AAACCCATCC ATCCCCAGAG GTTCTTCCCA TCTCTCCAGG CTGATGTGTG
1081 GGAACTCGAG GAAATAAATC TCCAGTGGGA GACGGAGGGG TGGCCAGGGA AACGGGGCGC
1141 TGCAGGAATA AAGACGAGCC AGCACAGCCA GCTCATGTGT AACGGCTTTG TGGAGCTGTC
1201 AAGGCCTGGT CTCTGGGAGA GAGGCACAGG GAGGCCAGAC AAGGAAGGGG TGACCTGGAG
1261 GGACAGATCC AGGGGCTAAA GTCCTGATAA GGCAAGAGAG TGCCGGCCCC CTCTTGCCCT
1321 ATCAGGACCT CCACTGCCAC ATAGAGGCCA TGATTGACCC TTAGACAAAG GGCTGGTGTC
1381 CAATCCCAGC CCCCAGCCCC AGAACTCCAG GGAATGAATG GGCAGAGAGC AGGAATGTGG
1441 GACATCTGTG TTCAAGGGAA GGACTCCAGG AGTCTGCTGG GAATGAGGCC TAGTAGGAAA
1501 TGAGGTGGCC CTTGAGGGTA CAGAACAGGT TCATTCTTCG CCAAATTCCC AGCACCTTGC
1561 AGGCACTTAC AGCTGAGTGA GATAATGCCT GGGTTATGAA ATCAAAAAGT TGGAAAGCAG
1621 GTCAGAGGTC ATCTGGTACA GCCCTTCCTT CCCTTTTTTT TTTTTTTTTT TGTGAGACAA
1681 GGTCTCTCTC TGTTGCCCAG GCTGGAGTGG CGCAAACACA GCTCACTGCA GCCTCAACCT
1741 ACTGGGCTCA AGCAATCCTC CAGCCTCAGC CTCCCAAAGT GCTGGGATTA CAAGCATGAG
1801 CCACCCCACT CAGCCCTTTC CTTCCTTTTT AATTGATGCA TAATAATTGT AAGTATTCAT
1861 CATGGTCCAA CCAACCCTTT CTTGACCCAC CTTCCTAGAG AGAGGGTCCT CTTGCTTCAG
1921 CGGTCAGGGC CCCAGACCCA TGGTCTGGCT CCAGGTACCA CCTGCCTCAT GCAGGAGTTG
1981 GCGTGCCCAG GAAGCTCTGC CTCTGGGCAC AGTGACCTCA GTGGGGTGAG GGGAGCTCTC
2041 CCCATAGCTG GGCTGCGGCC CAACCCCACC CCCTCAGGCT ATGCCAGGGG GTGTTGCCAG
2101 GGGCACCCGG GCATCGCCAG TCTAGCCCAC TCCTTCATAA AGCCCTCGCA TCCCAGGAGC
2161 GAGCAGAGCC AGAGCAGGAT GGAGAGGAGA CGCATCACCT CCGCTGCTCG C
```

METHODS AND COMPOSITIONS FOR REGENERATING HAIR CELLS AND/OR SUPPORTING CELLS

CROSS REFERENCE TO RELATED APPLICATION

This application is a continuation of U.S. patent application Ser. No. 14/426,520, filed Mar. 6, 2015, which is the U.S. national stage of International Application Number PCT/US2013/058626, filed Sep. 6, 2013, which claims priority to and the benefit of U.S. Provisional Patent Application No. 61/698,246, which was filed on Sep. 7, 2012, the entire contents of which are incorporated by reference herein.

GOVERNMENT FUNDING

This invention was made with government support under Grant Number DC006908 awarded by the National Institute of Health. The Government has certain rights in the invention.

FIELD OF THE INVENTION

The field of the invention relates generally to methods and compositions for inducing inner ear cells to reenter the cell cycle and to proliferate. More particularly, the invention relates to increasing c-myc and/or Notch activity within cells to induce cell cycle reentry and proliferation of hair cells and/or supporting cells of the inner ear.

BACKGROUND OF THE INVENTION

One of the most common types of hearing loss is sensorineural deafness that is caused by the loss of hair cells or hair cell function. Hair cells are sensory cells in the cochlea responsible for transduction of sound into an electrical signal. The human inner ear contains only about 15,000 hair cells per cochlea at birth, and, although these cells can be lost as a result of various genetic or environmental factors (e.g., noise exposure, ototoxic drug toxicity, viral infection, aging, and genetic defects), the lost or damaged cells cannot be replaced. Hair cells also are found in the utricle of the vestibule, an organ which regulates balance. Therefore, hair cell regeneration is an important approach to restoring hearing and vestibular function.

Studies of regeneration of hair cells in mature mammalian inner ear to date have focused on transdifferentiation of existing supporting cells. Supporting cells underlie, at least partially surround, and physically support sensory hair cells within the inner ear. Examples of supporting cells include inner rod (pillar cells), outer rod (pillar cells), inner phalangeal cells, outer phalangeal cells (of Deiters), cells of Held, cells of Hensen, cells of Claudius, cells of Boettcher, interdental cells and auditory teeth (of Huschke). Transdifferentiation of supporting cells to hair cells by overexpression or activation of Protein Atonal Homolog 1 (Atoh1) in supporting cells or by exposure of supporting cells to Atoh1 agonists is one such approach to generating new hair cells. One limitation to this approach, however, is that transdifferentiation of supporting cells to hair cells diminishes the existing population of supporting cells, which can impair inner ear function. In addition, overexpression of Atoh1 in aged inner ear or flat epithelium, which lacks supporting cells, is not sufficient to induce hair cells. Furthermore, it is not clear if all types of supporting cells can be transdifferentiated into hair cells upon Atoh1 overexpression.

Other studies of hair cell regeneration have examined cell cycle reentry for hair cells in embryonic or neonatal mice by, for example, blocking Rb1 and p27kip1. However similar manipulations in the adult inner ear have not induced cell cycle reentry. In addition, the hair cells in embryonic and neonatal mice that reenter the cell cycle in general subsequently die.

Over 150 types of genetic deafness are due to mutations in genes that affect both hair cells and supporting cells. For example, mutations in Myosin VIIa (Myo7a) cause hair cell stereocilia abnormalities that lead to permanent deafness. Mutations in GJB2 (connexin 26) cause damage to supporting cells that lead to the most common form of genetic deafness. Approaches (e.g., gene therapy and anti-sense oligonucleotide therapy) have been developed as potential treatments for hereditary deafness. However most of these defects occur during embryonic development. By birth, affected hair cells and supporting cells already have died or are severely degenerated, making intervention difficult. Therefore, to treat genetic deafness, there is an ongoing need to regenerate hair cells and/or supporting cells in utero and after birth, which can be combined with other approaches to correct the genetic defects underlying the disease.

In addition, inner ear non-sensory cells (e.g., fibrocytes in the ligament) play essential roles in hearing. Inner ear non-sensory cells can be damaged by factors such as noise and aging, which contribute to hearing loss. These cell types, like many of those in the inner ear, lack the capacity to regenerate spontaneously after damage.

Because spontaneous regeneration does not occur in the mammalian inner ear, recovery from hearing loss requires intervention to replace any inner ear cell types that are lost or degenerated. Therefore, there is an ongoing need to regenerate hair and/or supporting cells within the mammalian ear, in particular in the inner ear, to replace those lost, for example, by genetic or environmental factors. The regenerated hair and supporting cells may be used to slow the loss of hearing and/or vestibular function and/or partially or fully to restore loss of hearing and/or vestibular function.

SUMMARY OF THE INVENTION

The invention is based, in part, upon the discovery that increasing c-myc activity, Notch activity, or both c-myc and Notch activity in an ear cell, for example, a cell of an inner ear, promotes cell cycle reentry and proliferation of the cell. When the cell is, for example, a hair cell or a supporting cell, it is contemplated that proliferation and subsequent differentiation of the cell into hair and/or supporting cells can restore or improve hearing and/or vestibular function.

In one aspect, the invention relates to a method of inducing proliferation or cell cycle reentry of a differentiated cochlear cell or a utricular cell. The method comprises increasing both c-myc activity and Notch activity within the cell sufficient to induce proliferation or cell cycle reentry of the cochlear cell or utricular cell. Upon entry into the cell cycle, the cell may dedifferentiate but retain aspects of its differentiated state. In certain embodiments, the cochlear or utricular cell can be, for example, a hair cell or a supporting cell. The method may also include the step of inhibiting c-myc and/or Notch activity after proliferation of the cochlear or the utricular hair or supporting cell to induce differentiation or transdifferentiation of the cell and/or at least one of its daughter cells into a hair cell. Inhibition of c-myc and/or Notch activity after proliferation can be important in promoting cell survival.

In another aspect, the invention relates to a method for regenerating a cochlear or utricular hair cell. The method includes increasing both c-myc activity and Notch activity within the hair cell thereby to induce cell proliferation to produce one, two or more daughter hair cells, and, after cell proliferation, decreasing c-myc and/or Notch activity to induce and/or maintain differentiation of the daughter hair cells. In certain embodiments, the cochlear or utricular cell can be, for example, a hair cell or a supporting cell. These steps can be performed in vivo (for example, in the inner ear of a mammal, in particular the cochlea or utricle), or ex vivo, wherein the resulting cells are cultured and/or introduced into the inner ear of a recipient.

In another aspect, the invention relates to a method for reducing the loss of, maintaining, or promoting hearing in a subject. The method comprises increasing both c-myc activity and Notch activity within a hair cell and/or a supporting cell of the inner ear thereby to induce cell proliferation to produce daughter cells, and, after cell proliferation, decreasing c-myc and/or Notch activity, and permitting daughter cells of hair cell origin to differentiate into hair cells or permitting daughter cells of supporting cell origin to transdifferentiate into hair cells thereby to reduce the loss of, maintain or promote hearing in the subject. The daughter cells of supporting cell origin can be induced to transdifferentiate into hair cells by activating Atoh1 activity, for example, by gene expression, by administration of an effective amount of Atoh1 or an Atoh1 agonist. The steps can be performed in vivo (for example, in the inner ear of a mammal, in particular in the cochlea), or ex vivo, wherein the resulting cells are cultured and/or introduced into the inner ear of the subject.

In another aspect, the invention relates to a method for reducing the loss of, maintaining, or promoting vestibular function in a subject. The method comprises increasing both c-myc activity and Notch activity within a hair cell and/or a supporting cell of the inner ear thereby to induce cell proliferation to produce daughter cells, and, after cell proliferation, decreasing c-myc and/or Notch activity, and permitting daughter cells of hair cell origin to differentiate into hair cells or permitting daughter cells of supporting cell origin to transdifferentiate into hair cells thereby to reduce the loss of, maintain or promote vestibular function in the subject. The daughter cells of supporting cell origin can be induced to transdifferentiate into hair cells by activating Atoh1 activity, for example, by gene expression, by administration of an effective amount of Atoh1 or an Atoh1 agonist. The steps can be performed in vivo (for example, in the inner ear of a mammal, in particular in the utricle), or ex vivo, wherein the resulting cells are cultured and/or introduced into the inner ear of the subject.

In each of the foregoing aspects of the invention, c-myc activity may be increased by contacting the cell with an effective amount of a c-myc protein or a c-myc activator. After c-myc activity is increased, c-myc activity can be inhibited to limit proliferation of the cochlear cell or utricular cell and/or to promote survival of the cochlear cell or utricular cell. Similarly, in each of the foregoing aspects of the invention, Notch activity may be increased by contacting the cell with an effective amount of a Notch protein, a Notch Intracellular Domain (NICD) protein or a Notch activator. Notch activity can be inhibited by contacting the cell with an effective amount of a Notch inhibitor.

In certain embodiments, the c-myc protein or c-myc activator may be administered to the inner ear of a subject.

In certain embodiments, the Notch protein, NICD protein, Notch activator, and/or Notch inhibitor may be administered to the inner ear of a subject. In other embodiments, the c-myc protein or c-myc activator may be co-administered together with the Notch protein, the NICD protein, the Notch activator, and/or the Notch inhibitor to the inner ear of the subject.

The foregoing aspects and embodiments of the invention may be more fully understood by reference to the following figures, detailed description and claims.

BRIEF DESCRIPTION OF THE DRAWINGS

The objects and features of the invention may be more fully understood by reference to the drawings described herein.

FIG. 1A shows the full-length protein sequence of human c-myc (NP_002458.2; SEQ ID NO: 1), and FIG. 1B shows the c-myc protein consensus protein sequence (SEQ ID NO: 9).

FIG. 2A shows the full-length protein sequence of human Notch (NP_060087.3; SEQ ID NO: 2), FIG. 2B shows the protein sequence of human Notch intracellular domain (NP_060087.3 residues 1754-2555; SEQ ID NO: 7), and FIG. 2C shows a consensus protein sequence of the Notch Intracellular domain (SEQ ID NO: 10).

FIG. 3A shows the full-length protein sequence of human Atoh1 (NP_005163.1; SEQ ID NO: 3) and FIG. 3B shows an Atoh1 consensus protein sequence (SEQ ID NO: 11).

FIG. 4 shows the nucleic acid sequence of human c-myc mRNA (NM_002467.4; SEQ ID NO: 4).

FIG. 5A shows the nucleic acid sequence of human Notch mRNA (NM_017617.3; SEQ ID NO: 5) and FIG. 5B shows the nucleotide sequence of human Notch intracellular domain (NM_017617.3 nucleotide positions 5260 to 7665; SEQ ID NO: 8).

FIG. 6 shows the nucleic acid sequence of human Atoh1 mRNA (NM_005172.1; SEQ ID NO: 6).

(open arrows, panels K, M, and O), demonstrating that proliferating supporting cells survive 35 days post-injection. Closed arrows in panels K, L, M, and O show Myo7a+/BrdU+ hair cells. Arrowhead in panels K,L,M, and O show Myo7a+/Sox2+/BrdU+ hair cell.

Figure 9:
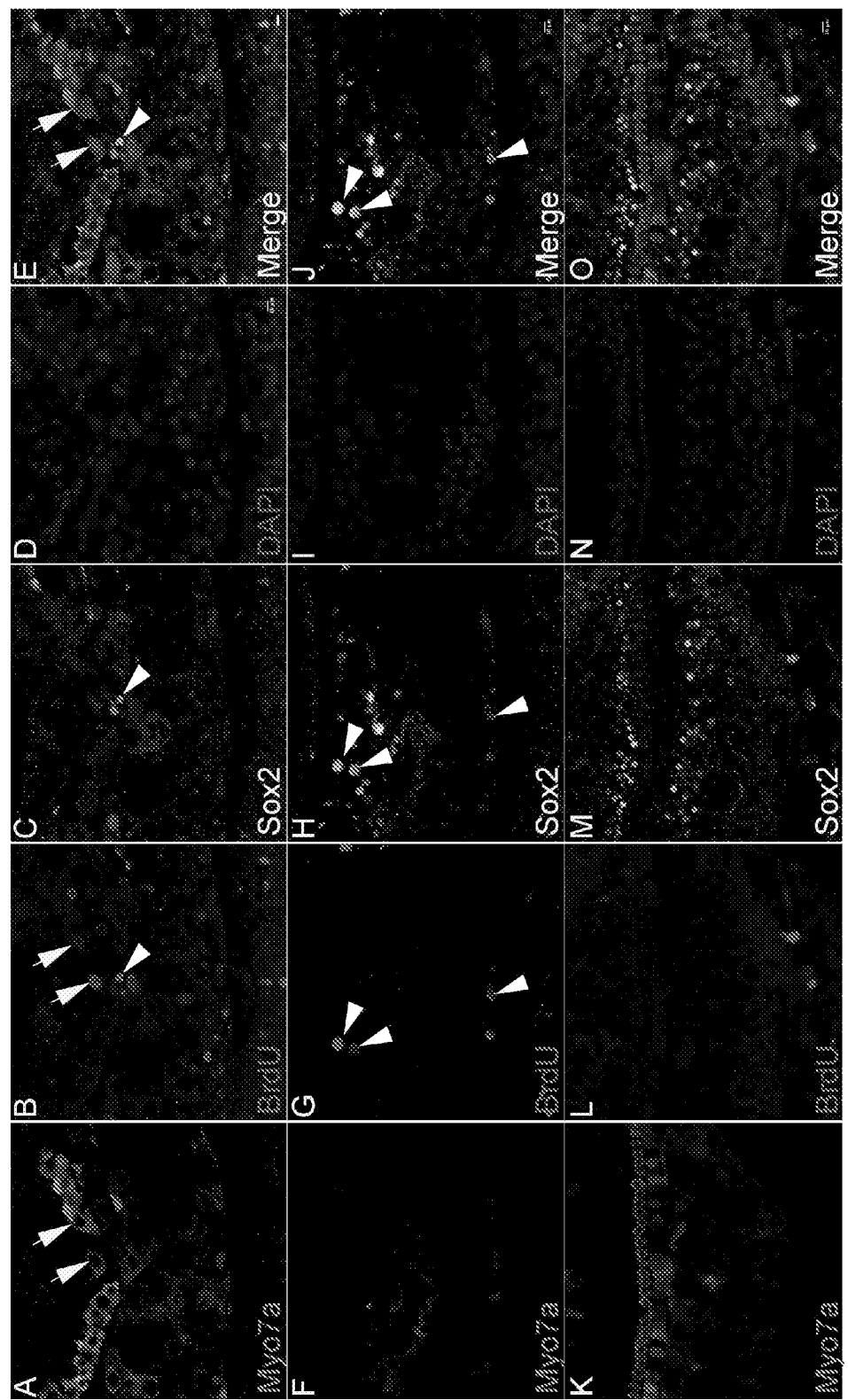

FIG. 9 shows cochlear hair and supporting cells double-labeled with cell-type specific markers and BrdU in the cochlear epithelium of aged NICD$^{flox/flox}$ mice injected with an Ad-Cre-GFP/Ad-Myc mixture over the course of 15 days. Panels A, F, and K show Myo7a labeling of hair cells. Panels B, G, and L show BrdU labeling of dividing cells. Panels C, H, and M show Sox2 labeling of supporting cells. Panels D, I, and N show DAPI labeling of cell nuclei. Panels E, J, and O show merged images. Panels A-J show Myo7a+/BrdU+ hair cells (panels A, B, and E; arrows) and Sox2+/BrdU+ supporting cells (panels B, C, E, G, H, and J; arrowheads) following injection with Ad-Myc and Ad-Cre-GFP adenovirus. Panels K-O show the same staining in 17-month old NICD$^{flox/flox}$ mice injected with Ad-Cre-GFP virus alone. No BrdU labeled hair cells or supporting cells were found in the latter group. Scale bars: 10 µM.

Figure 10:
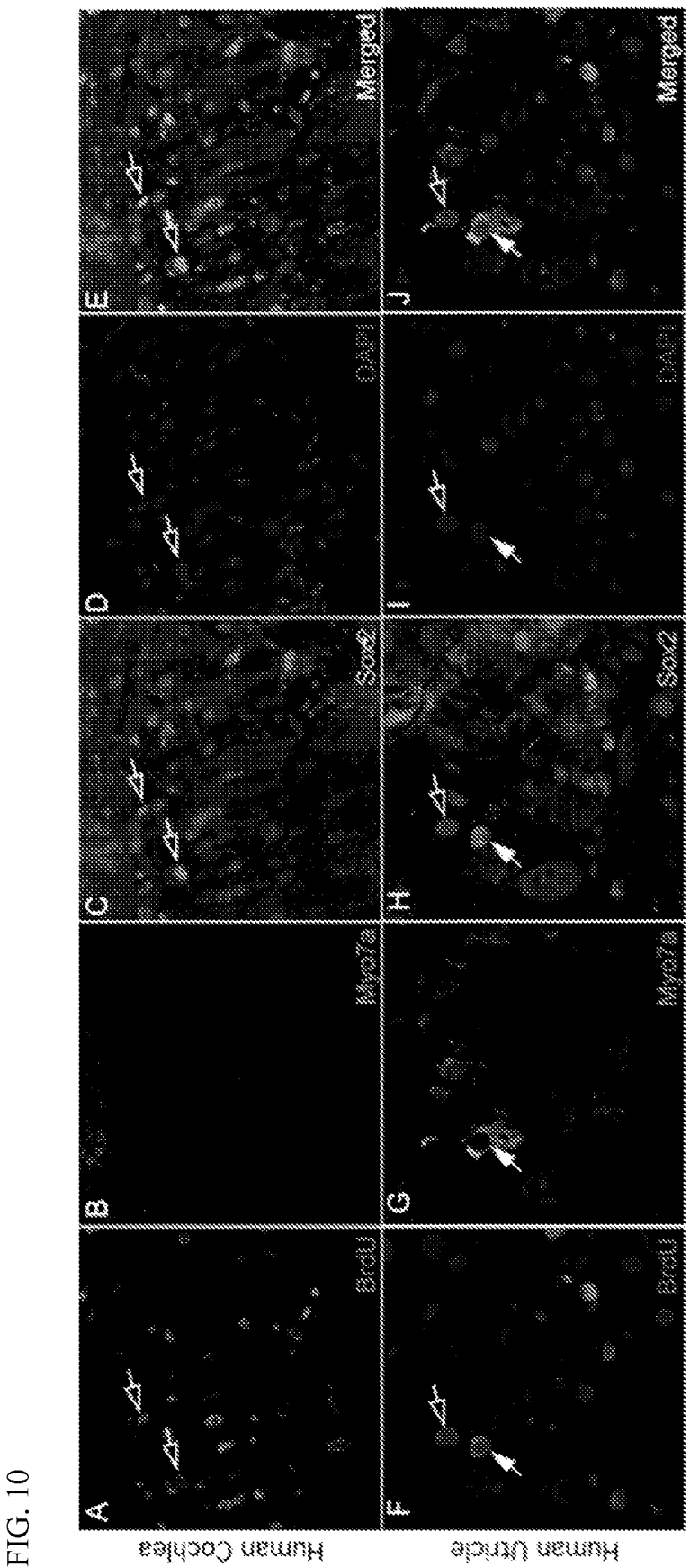

FIG. 10 shows BrdU (panels A and F), Myo7a (panels B and G) and Sox2 (panels C and H) labeled hair and supporting cells in cultured adult human cochlear (panels A-E) and utricular (panels F-J) tissue transduced with Ad-Myc/Ad-NICD for 10 days. Open arrows (panels A, C, D, E, F, H, I, and J) indicate proliferating supporting cells (Sox2+/BrdU+) and solid arrow (panels F-J) indicates a proliferating hair cell (Myo7a+/BrdU+). Nuclear staining is shown by DAPI (D and I).

Figure 11:
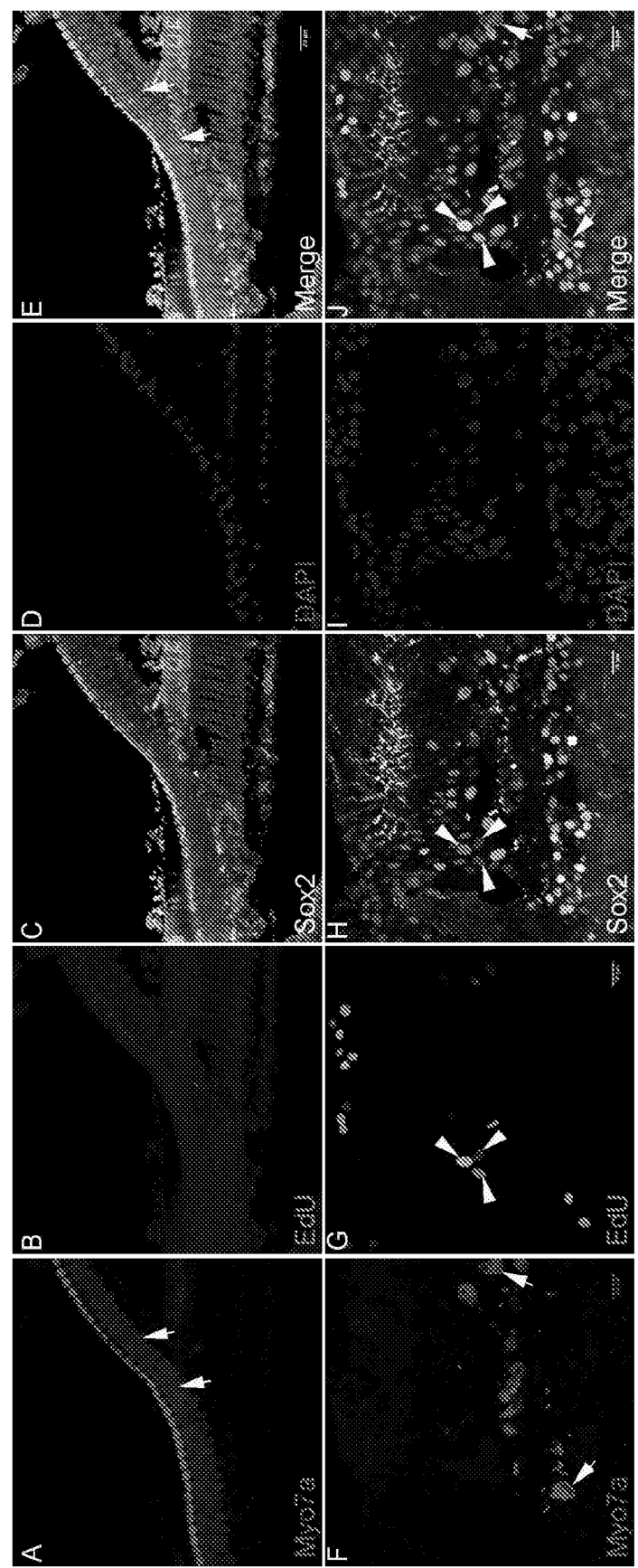

FIG. 11 shows Myo7+ hair (panels A and F) and Sox2+ supporting (panels C and H) cells in adult monkey cochlear cultures. Dividing cells were labeled with EdU (panels B and G). Panels A-E show Ad-GFP infected control monkey cochlea, in which no EdU+ cells were identified. Panels G, H, and J show EdU+/Sox2+ supporting cells (arrowheads) in monkey cochlea cultures exposed to Ad-Myc/Ad-NICD virus. In both control and Ad-Myc/Ad-NICD virus infected cultures, no hair cells were observed to re-enter the cell cycle (panels A, E, F, and J; arrows). Scale bars: 20 µM.

Figure 12:
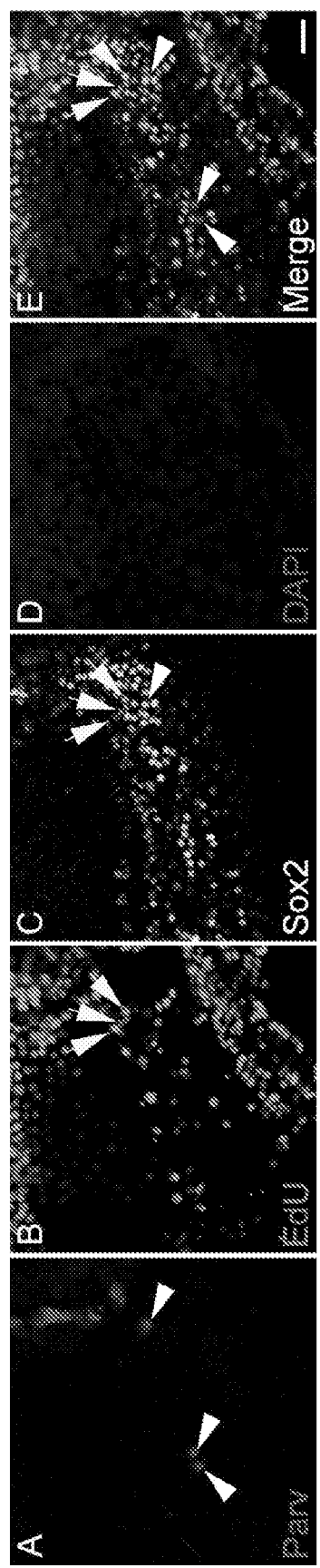

FIG. 12 shows selective induction of proliferation in supporting cells (arrows; panels B, C, and E), but not inner hair cells (arrowheads; panels A, C, and E), of rtTa/tet-on-Myc/tet-on-NICD mice exposed to doxycycline administered by an implanted osmotic pump for 9 days to induce expression of NICD and Myc. Cells that reentered the cell cycle were labeled via daily EdU (panel B) administration during the same period. Cell nuclei were stained for DAPI (panel D). Inner hair cells were stained for Parvalbumin (Parv; panel A). Supporting cells were stained for Sox2 (panel C). A single Parv+ hair cell is shown that also expressed Sox2 due to Notch activation (rightmost arrowhead in panels A, C, and E). Outer hair cells are not shown as they were lost during surgical implantation of the osmotic pump. Scale bar: 20 µM.

Figure 13:
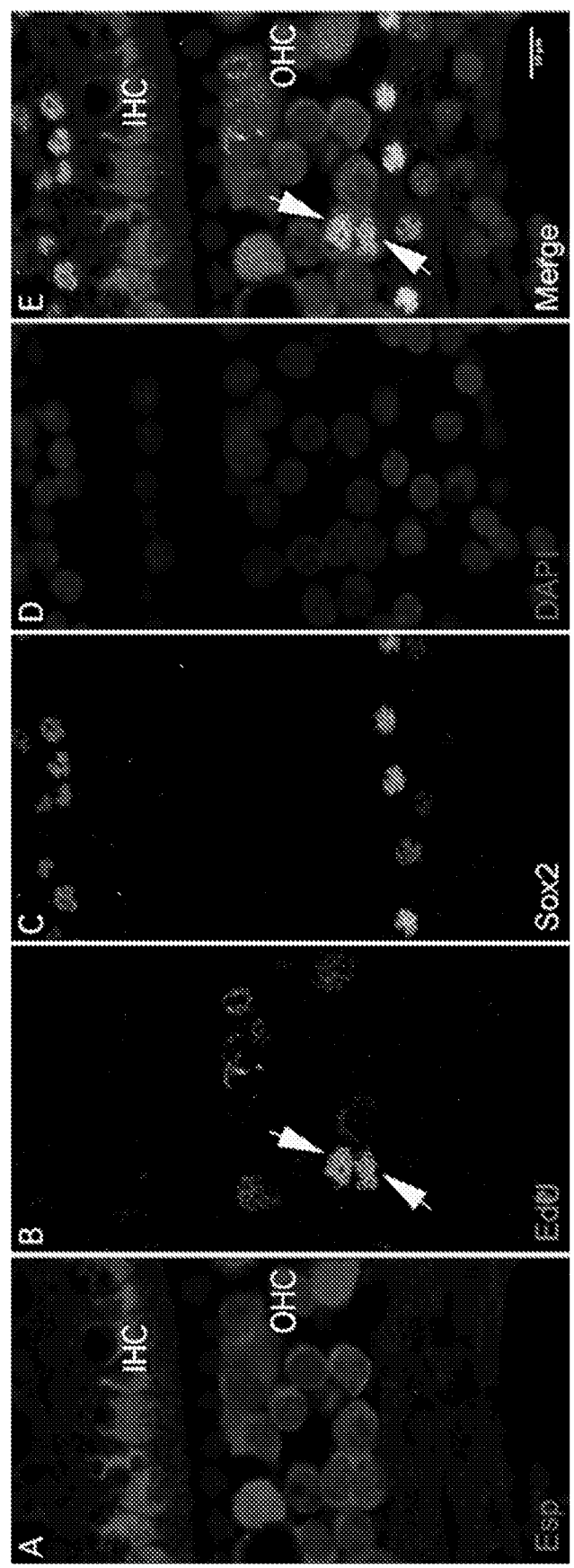

FIG. 13 shows outer hair cells are selectively induced to undergo cell cycle reentry following exposure to elevated c-Myc and Notch activity in vivo. rtTa/tet-on-Myc/tet-on-NICD mice were exposed to doxycycline administered by an implanted osmotic pump for 12 days to induce expression of NICD and Myc, after which tissue was harvested for staining. Cells that reentered the cell cycle were labeled via daily EdU (panel B) administration during the period of doxycycline exposure. Cell nuclei were stained for DAPI (panel D). Inner and outer hair cells were stained for Espin (Esp; panel A). Supporting cells were stained for Sox2 (panel C). Note that outer hair cells were spared during implantation of the osmotic pump in this experiment, as opposed to the experiment shown in FIG. 12. A dividing Esp+/EdU+ outer hair cell is shown in FIG. 13 (panels B and E; arrows), demonstrating selective induction of outer hair cell proliferation at this level of exposure to elevated c-Myc and Notch activity.

Figure 14:
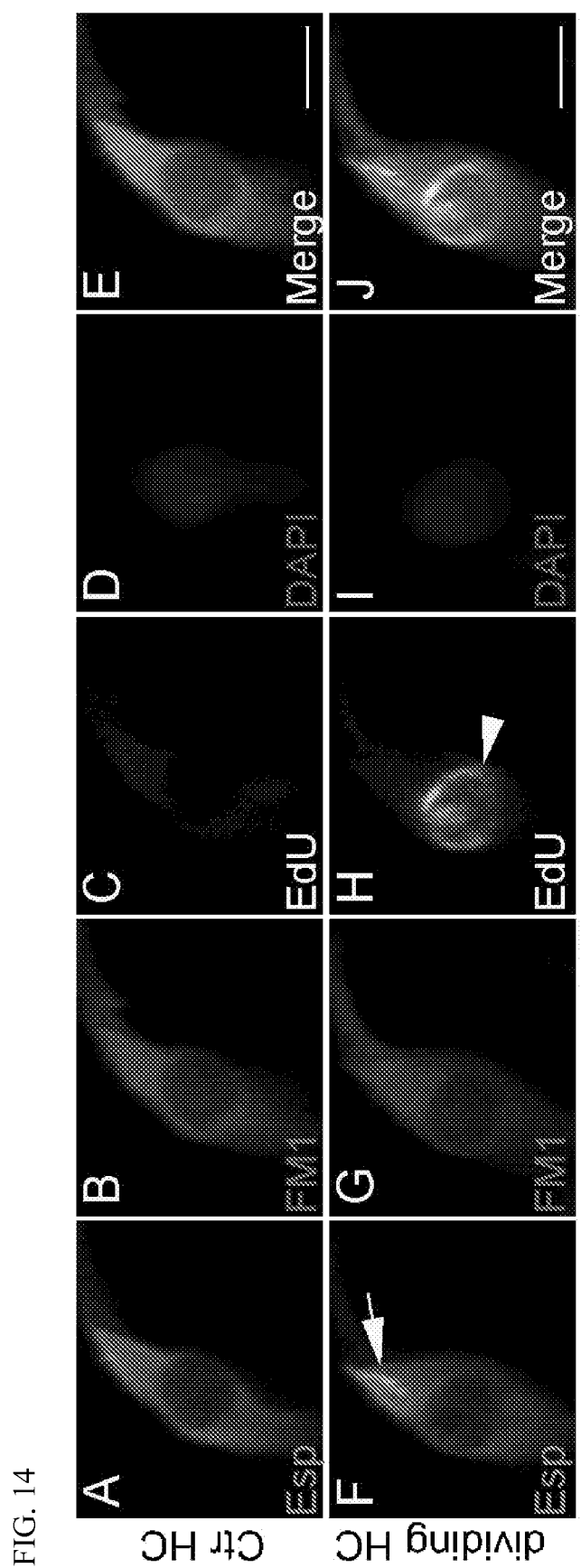

FIG. 14 shows Espin-positive (Esp+) hair cells labeled with FM-143FX (FM1) to reveal cells with functional membrane channels. Cochlea of 45-day-old NICD$^{flox/flox}$ mice were exposed to Ad-Myc/Ad-Cre-GFP virus and EdU was injected once daily for 5 days following virus injection to label dividing cells. 35 days post-virus injection, cochlea were harvested, briefly exposed to FM1, fixed, and stained. Panels A-E show an Esp+/FM1+/EdU– control hair cell that has not undergone cell cycle reentry, but which expresses Esp and takes up FM1. Panels F-J show an Esp+/FM1+/EdU+ hair cell in a cochlea exposed to Ad-Myc/Ad-NICD virus, indicating the presence of functional membrane channels in a cell that has undergone cell cycle reentry. Arrowhead (panel H) indicates EdU labeling; arrow (panel F) indicates the presence of Esp+ hair bundles. Scale bars: 10 µM.

Figure 15:
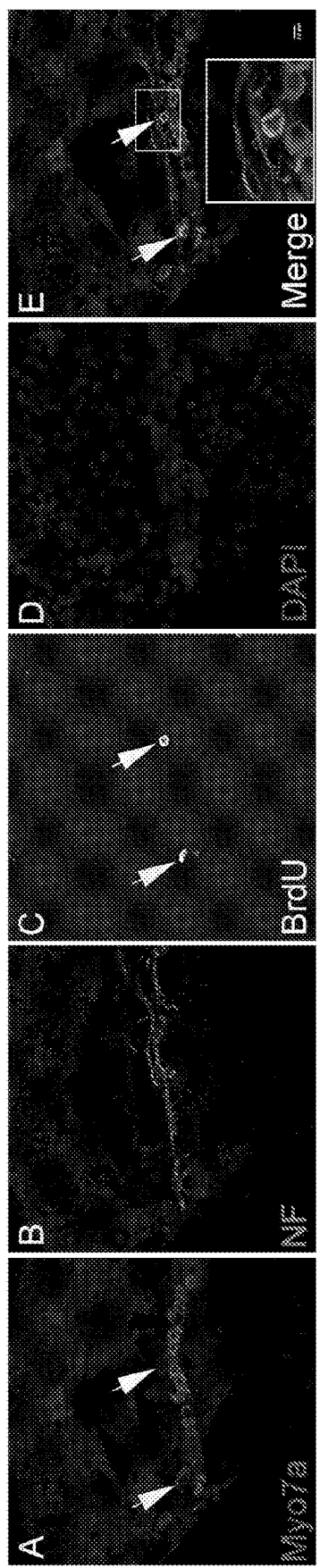

FIG. 15 shows that production of Myo7a+ hair cells induced to undergo cell proliferation following exposure to elevated levels of c-Myc and Notch activity is accompanied by production of neurofilament-positive (NF+; panel B) neurofibers. Cochlea of 45-day-old NICD$^{flox/flox}$ mice were exposed to Ad-Myc/Ad-Cre-GFP virus and BrdU was injected once daily for 15 days following virus injection to label dividing cells (panel C). Tissue was harvested and stained 20 days post-virus injection. Panel A shows Myo7+ hair cells. Cell nuclei were stained using DAPI (panel D). Panel E shows a merge of all stains and an enlarged view of the boxed area indicated by the rightmost arrow in the panel. Arrows (panels A, C, and E) indicate Myo7a+/BrdU+ hair cells in contact with NF+ ganglion neuron neurofibers. Scale bar: 10 µM.

Figure 16:
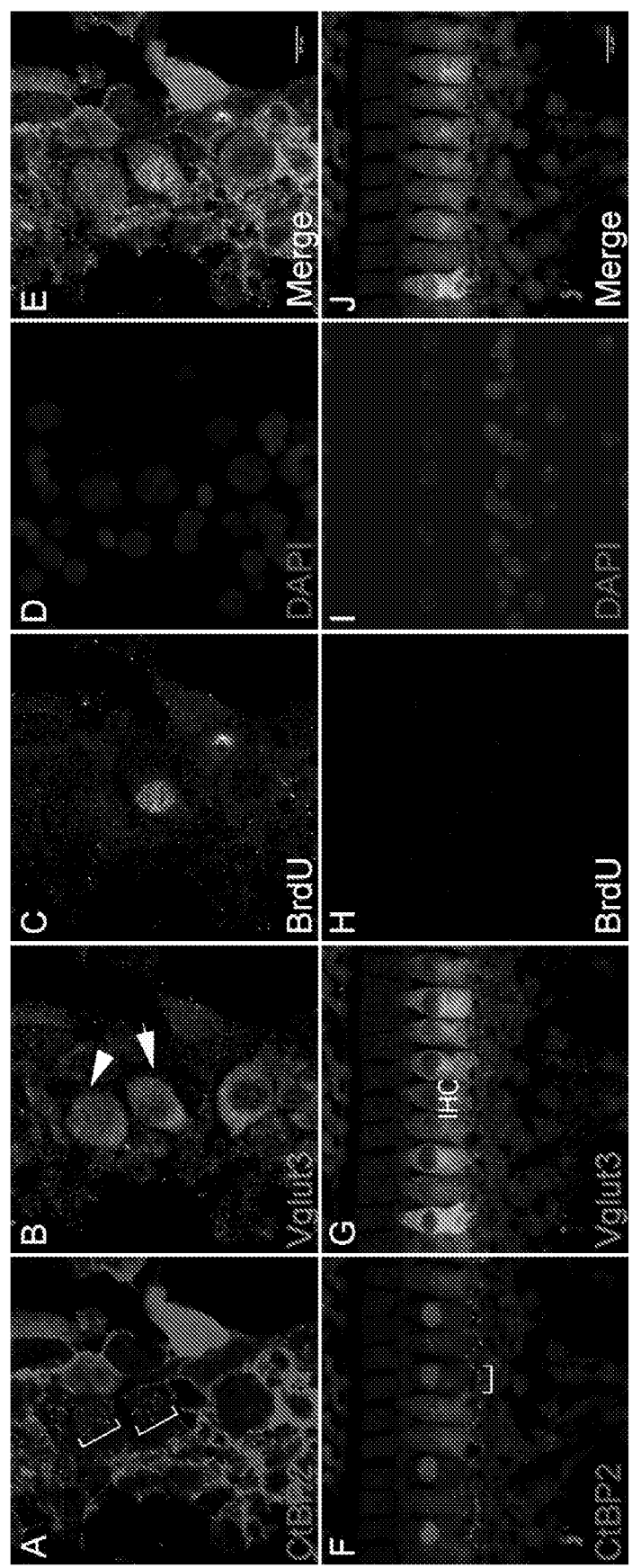

FIG. 16 shows an example of an inner hair cell induced to proliferate via exposure to elevated levels of c-Myc and Notch activity and expressing an inner hair cell-specific marker (Vglut3; panels B and G) and a marker of functional synapses (CtBP2; panels A and F; brackets). Cochlea of 45-day-old NICD$^{flox/flox}$ mice were exposed to Ad-Myc/Ad-Cre-GFP (panels A-E) or Ad-GFP (panels F-J) virus via a single injection of virus, and BrdU was injected once daily for 15 days following virus injection to label dividing cells (panels C and H). Tissue was then harvested and stained. Cell nuclei were stained with DAPI (panels D and I). Panels A-E show a CtBP2+/VGlut3+/BrdU+ inner hair cell (panel B; arrow) induced to proliferate following exposure to elevated c-Myc and Notch activity, and a CtBP2+/Vglut3+/BrdU– inner hair cell (panel B; arrowhead) that did not undergo cell cycle reentry. Panels F-J show inner hair cells exposed to Ad-GFP that did not stain positive for BrdU but expressed the inner hair cell-specific marker Vglut3 and the presynaptic marker CtBP2. IHC=inner hair cell layer.

Figure 17:
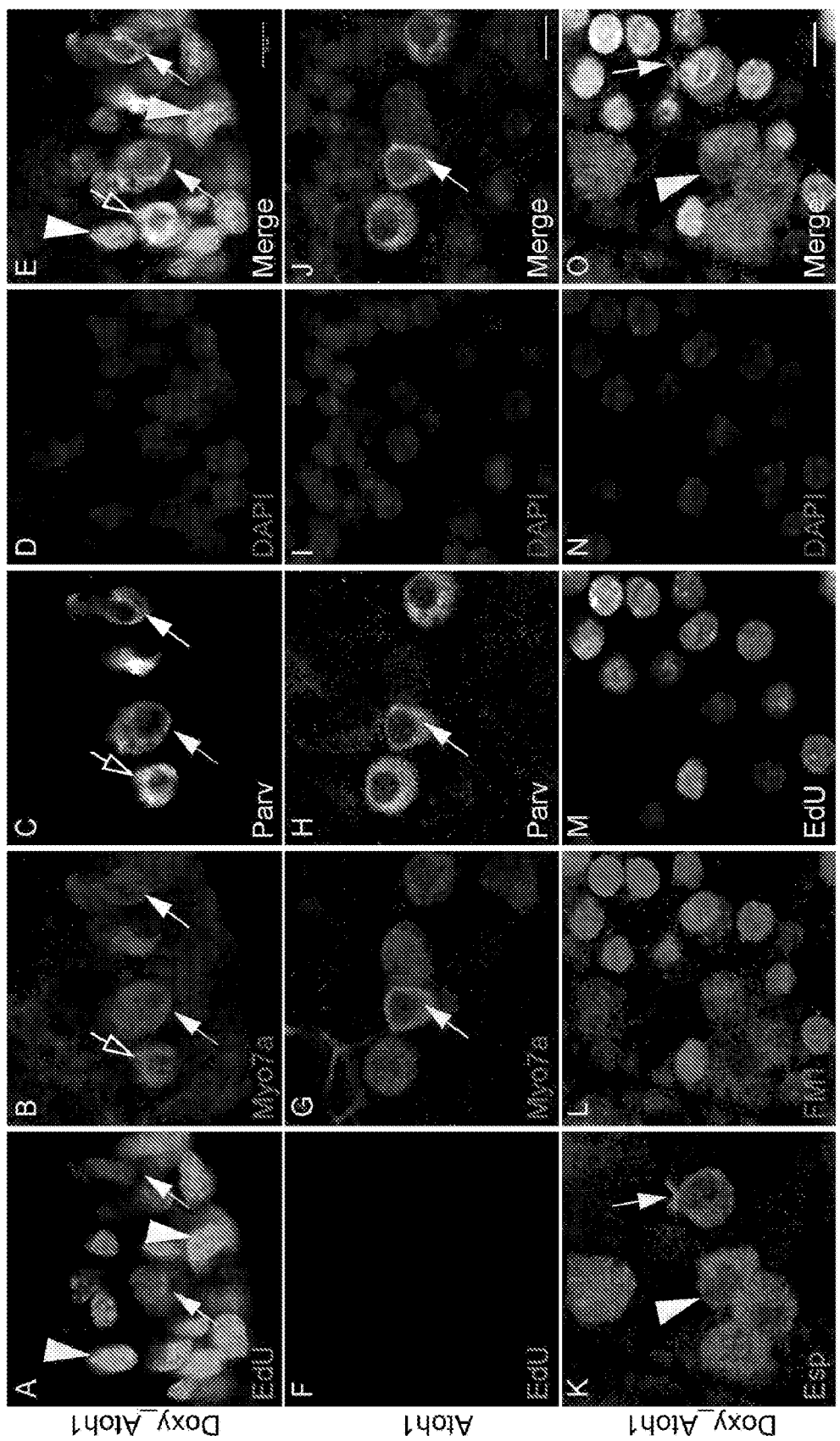

FIG. 17 shows cultured cochlear support cells from doxycycline-inducible rtTa/tet-on-Myc/tet-on-Notch mice induced to transdifferentiate or proliferate and transdifferentiate to functional hair cells following exposure to either Atoh1-expressing adenovirus alone (panels F-J) or doxycycline and Atoh1-expressing adenovirus (Ad-Atoh1; panels A-E and K-O). Cochlea from adult rtTa/tet-on-Myc/tet-on-Notch mice were dissected and cultured for 5 days in the presence (panels A-E and K-O) or absence (panels F-J) of doxycycline, followed by Ad-Atoh1 infection and an additional 14 days of culture. EdU was added daily to label dividing cells (panels A, F, and M). Cell nuclei were stained with DAPI (panels D, I, and N). Panels A-E show supporting cells exposed to doxycycline followed by Ad-Atoh1, and labeled with EdU, reenter the cell cycle and/or transdifferentiate into Myo7a+/Parv+ hair cells (closed arrows in panels A, B, C, and E). Open arrow in panels B, C, and E indicates the presence of a Myo7a+/Parv+ supporting cell that has transdifferentiated into a hair cell, but has not undergone cell cycle reentry. Arrowhead in panels A and E indicates an EdU+ supporting cell. Panels F-J shows supporting cells exposed to Ad-Atoh1, but not doxycycline, transdifferentiate to Myo7a+/Parv+ hair cells. Arrow in panels G, H, and J indicates a supporting cell that has transdifferentiated into a Myo7a+/Parv+ hair cell, but which has not undergone cell cycle reentry. Panels K-O show supporting cells exposed to doxycycline followed by Ad-Atoh1 and labeled with FM1 (panel L) and Edu (panel M) have Esp+ hair bundles (panel K) and take up FM1 dye. Arrow in panels K and O indicates an Esp+/FM1+/EdU+ hair cell displaying stereocilia derived from a transdifferentiated supporting cell that has undergone cell cycle reentry. Arrowhead in panels K and O indicates an Esp+/FM1+/EdU− hair cell derived from a transdifferentiated supporting cell that has not undergone cell cycle reentry. Scale bar: 10 μM.

Figure 18:
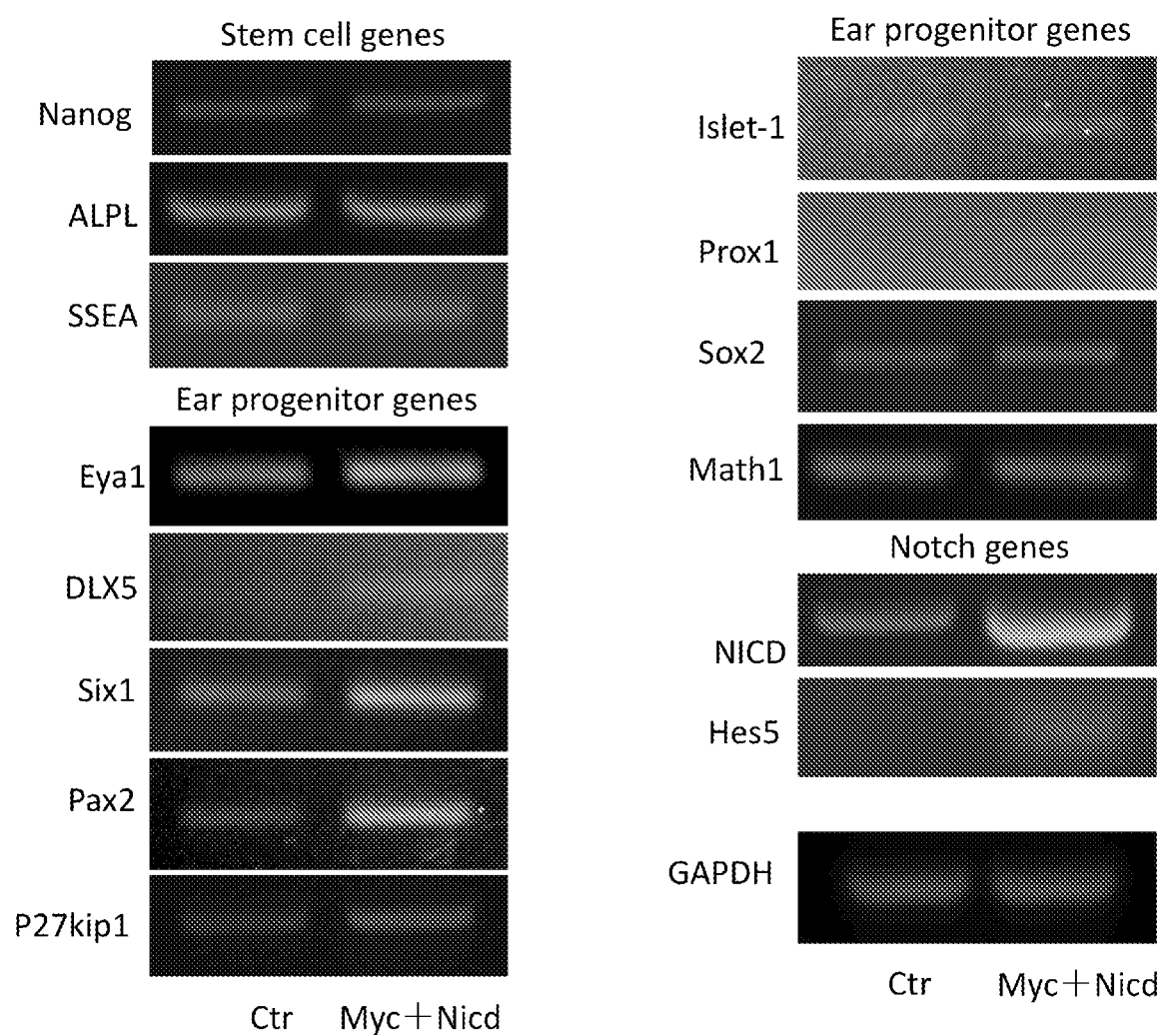

FIG. 18 shows the results of semi-quantitative RT-PCR analysis of sets of mRNA transcripts produced in control cochlear cells and in cochlear cells following exposure to elevated c-Myc and NICD levels. Adult NICD$^{flox/flox}$ mouse cochleas were exposed to Ad-Myc/Ad-Cre-GFP (Myc+ Nicd) or Ad-GFP (Ctr) and cultured for 4 days, mRNA was extracted, and semi-quantitative RT-PCT was performed. Changes in expression of stem cell genes (Nanog, ALPL, and SSEA) and ear progenitor cell genes/Notch genes (Eya1, DLX5, Six1, Pax2, p27kip1, Islet-1, Sox2, Math1, NICD, Prox1, and Hes5) was examined. GAPDH expression was used as an internal control.

FIG. 19A shows the full-length protein sequence of human N-myc (NP_005369.2; SEQ ID NO: 12) and FIG. 19B shows the nucleic acid sequence of human N-myc (NM_005378.4; SEQ ID NO: 13).

FIG. 20A shows the full-length protein sequence of human Notch2 (NP_077719.2; SEQ ID NO: 14) and FIG. 20B shows the nucleic acid sequence of human Notch2 (NM_024408.3; SEQ ID NO: 15).

FIG. 21A shows the full-length protein sequence of human Notch3 (NP_000426.2; SEQ ID NO: 16) and FIG. 21B shows the nucleic acid sequence of human Notch3 (NM_000435.2; SEQ ID NO: 17).

FIG. 22A shows the full-length protein sequence of human Notch4 (NP_004548.3; SEQ ID NO: 18) and FIG. 22B shows the nucleic acid sequence of human Notch4 (NM_004557.3; SEQ ID NO: 19).

FIG. 23A shows the full-length protein sequence of human Atoh7 (NP_660161.1; SEQ ID NO: 20) and FIG. 23B shows the nucleic acid sequence of human Atoh7 (NM_145178.3; SEQ ID NO: 21).

FIG. 24 shows the nucleic acid sequence for an Atoh1 enhancer (SEQ ID NO: 22), which controls expression in hair cells.

FIG. 25 shows the nucleic acid sequence for a Pou4f3 promoter (SEQ ID NO: 23), which controls expression in hair cells.

FIG. 26 shows the nucleic acid sequence for a Myo7a promoter (SEQ ID NO: 24), which controls expression in hair cells.

FIG. 27 shows the nucleic acid sequence for a Hes5 promoter (SEQ ID NO: 25), which controls expression in vestibular supporting cells and cochlear inner phalangeal cells, Deiters cells and Pillar cells.

FIG. 28 shows the nucleic acid sequence for a GFAP promoter (SEQ ID NO: 26), which controls expression in vestibular supporting cells and cochlear inner phalangeal cells, Deiters cells and Pillar cells.

DETAILED DESCRIPTION

The invention relates to methods and compositions for inducing cell cycle reentry and proliferation of hair and/or supporting cells in the ear, in particular, the inner ear. The methods and compositions can be used to increase a population of hair cells and/or supporting cells diminished by environmental or genetic factors. Using the methods and compositions described herein, it may be possible to preserve or improve hearing and/or vestibular function in the inner ear.

As demonstrated herein, simultaneously increasing c-myc and Notch activity appears to be an important step in inducing cell cycle reentry and proliferation in cells of the inner ear. As shown in the Examples below, overexpression of c-myc and Notch in the inner ear of a mammal results in the reentry of hair and supporting cells into the cell cycle and the proliferation of those cells. The proliferation of hair cells (or the proliferation of supporting cells followed by transdifferentiation of those cells into hair cells) may lead to improved hearing and/or vestibular function in a subject.

Definitions

For convenience, certain terms in the specification, examples, and appended claims are collected in this section.

As used herein, the term "effective amount" is understood to mean the amount of an active agent, for example, a c-myc or Notch activator, that is sufficient to induce cell cycle reentry and/or proliferation of the cells of the inner ear (e.g., a hair cell or a supporting cell). The cells are contacted with amounts of the active agent effective to induce cell cycle reentry and/or proliferation.

As used herein, "pharmaceutically acceptable" or "pharmacologically acceptable" mean molecular entities and compositions that do not produce an adverse, allergic or other untoward reaction when administered to an animal, or to a human, as appropriate. The term, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The term "subject" is used throughout the specification to describe an animal, human or non-human, to whom treatment according to the methods of the present invention is provided. Veterinary and non-veterinary applications are contemplated. The term includes, but is not limited to, birds and mammals, e.g., humans, other primates, pigs, rodents such as mice and rats, rabbits, guinea pigs, hamsters, cows, horses, cats, dogs, sheep and goats. Typical subjects include humans, farm animals, and domestic pets such as cats and dogs.

As used herein "target cell" and "target cells" refers to a cell or cells that are capable of reentering the cell cycle and/or proliferating and/or transdifferentiating to or towards a cell or cells that have or result in having characteristics of auditory or vestibular hair cells. Target cells include, but are not limited to, e.g., hair cells, e.g., inner ear hair cells, which includes auditory hair cells (inner and outer hair cells) and vestibular hair cells (located in the utricle, saccule and three semi-circular canals, for example), progenitor cells (e.g., inner ear progenitor cells), supporting cells (e.g., Deiters' cells, pillar cells, inner phalangeal cells, tectal cells and Hensen's cells), supporting cells expressing one or more of $p27_{kip}$, p75, S100A, Jagged-1, Prox1, and/or germ cells. "Inner hair cell" refers to a sensory cell of the inner ear that is anatomically situated in the organ of Corti above the basilar membrane. "Outer hair cell" refers to a sensory cell of the inner ear that is anatomically situated in the organ of Corti below the tectorial membrane near the center of the basilar membrane. Examples of target cells also include fibrocytes, marginal cells or interdental cells expressing one or more of Gjb2, Slc26a4 and Gjb6. As described herein, prior to treatment with the methods, compounds, and compositions described herein, each of these target cells can be identified using a defined set of one or more markers (e.g., cell surface markers) that is unique to the target cell. A different set of one or more markers (e.g., cell surface markers) can also be used to identify target cells have characteristics of an auditory hair cell or supporting cell.

As used herein, the term "host cell" refers to cells transfected, infected, or transduced in vivo, ex vivo, or in vitro with a recombinant vector or a polynucleotide. Host cells may include packaging cells, producer cells, and cells infected with viral vectors. In particular embodiments, host cells infected with viral vector of the invention are administered to a subject in need of therapy. In certain embodiments, the term "target cell" is used interchangeably with host cell and refers to transfected, infected, or transduced cells of a desired cell type.

The term "vector" is used herein to refer to a nucleic acid molecule capable transferring or transporting another nucleic acid molecule. The transferred nucleic acid is generally linked to, for example, inserted into, the vector nucleic acid molecule. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial or yeast artificial chromosomes, and viral vectors. Useful viral vectors include, for example, adenoviruses, replication defective retroviruses, and lentiviruses.

As used herein, the term "viral vector" refers either to a nucleic acid molecule that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s). The term "viral vector" may also refer either to a virus or viral particle capable of transferring a nucleic acid into a cell or to the transferred nucleic acid itself. Viral vectors and transfer plasmids contain structural and/or functional genetic elements that are primarily derived from a virus.

The term "retroviral vector" refers to a viral vector or plasmid containing structural and functional genetic elements, or portions thereof, that are primarily derived from a retrovirus.

The term "lentiviral vector" refers to a viral vector or plasmid containing structural and functional genetic elements, or portions thereof, that are primarily derived from a lentivirus.

The terms "lentiviral vector" or "lentiviral expression vector" may be used to refer to lentiviral transfer plasmids and/or infectious lentiviral particles. It is understood that nucleic acid sequence elements such as cloning sites, promoters, regulatory elements, heterologous nucleic acids, etc., are present in RNA form in the lentiviral particles of the invention and are present in DNA form in the DNA plasmids of the invention.

The term "hybrid" refers to a vector, LTR or other nucleic acid containing both retroviral (e.g., lentiviral) sequences and non-lentiviral viral sequences. A hybrid vector may refer to a vector or transfer plasmid comprising retroviral (e.g., lentiviral) sequences for reverse transcription, replication, integration and/or packaging. In some embodiments of the invention, a hybrid vector may be used to practice the invention described herein.

The term "transduction" refers to the delivery of a gene(s) or other polynucleotide sequence using a retroviral or lentiviral vector by means of viral infection rather than by transfection. In certain embodiments, a cell (e.g., a target cell) is "transduced" if it comprises a gene or other polynucleotide sequence delivered to the cell by infection using a viral (e.g., adenoviral) or retroviral vector. In particular embodiments, a transduced cell comprises one or more genes or other polynucleotide sequences delivered by a retroviral or lentiviral vector in its cellular genome.

As used herein, the term "c-myc" refers to a multifunctional, nuclear phosphoprotein that plays a role in cell cycle progression, apoptosis and cellular transformation and/or has an amino sequence or consensus amino acid sequence set forth in Section 1(i) below. The full length sequence of human c-myc appears, for example, in the NCBI protein database under accession no. NP_002458.2 (see ncbi.nlm.nih.gov and SEQ ID NO: 1). A consensus sequence for c-myc built from an alignment of human, rat, mouse and chimpanzee using ClustalW is set forth in SEQ ID NO: 9. C-myc functions as a transcription factor that regulates transcription of specific target genes. Mutations, overexpression, rearrangement and translocation of this gene have been associated with a variety of hematopoietic tumors, leukemias and lymphomas, including Burkitt lymphoma. C-myc is also known in the art as MYC, v-myc myelocytomatosis viral oncogene homolog (avian), transcription factor p64, bHLHe39, MRTL, avian myelocytomatosis viral oncogene homolog, v-myc avian myelocytomatosis viral oncogene homolog, myc proto-oncogene protein, class E basic helix-loop-helix protein 39, myc-related translation/localization regulatory factor, and proto-oncogene c-Myc, and BHLHE39.

As used herein, the term, "Notch" refers to the Notch family of signaling proteins, which includes Notch1, Notch2, Notch3 and Notch4, a NICD, and/or a protein having an amino acid sequence or consensus amino acid sequence set forth in Section (1)(i) below. The full length sequence of human Notch1 appears, for example, in the NCBI protein database under accession no. NP_060087.3 (see ncbi.nlm.nih.gov and SEQ ID NO: 2). Members of this Type 1 transmembrane protein family share structural characteristics including an extracellular domain consisting of multiple epidermal growth factor-like (EGF) repeats, and an intracellular domain consisting of multiple, different domain types. Notch family members play a role in a variety of developmental processes by controlling cell fate decisions.

Notch1 is cleaved in the trans-Golgi network, and presented on the cell surface as a heterodimer. Notch1 functions as a receptor for membrane bound ligands Jagged1, Jagged2 and Delta1 to regulate cell-fate determination. Upon ligand activation through the released notch intracellular domain (NICD) it forms a transcriptional activator complex with RBPJ/RBPSUH and activates genes of the enhancer of split locus. Notch 1 affects the implementation of differentiation, proliferation and apoptotic programs.

Disclosed herein is a method of inducing proliferation or cell cycle reentry of a differentiated cochlear cell or a utricular cell. The method comprises increasing c-myc, Notch or both c-myc activity and Notch activity within the cell sufficient to induce proliferation or cell cycle reentry of the cochlear cell or utricular cell.

In certain embodiments, the method includes increasing c-myc activity within a cell when Notch activity is already increased, for example, when Notch1 has been upregulated in response to damage to the inner ear. In certain embodiments, the invention relates to a method of inducing proliferation or cell cycle reentry of a differentiated cochlear cell or a utricular cell in which Notch activity is increased in response to damage to the cochlear cell or utricular cell, as compared to the level of Notch activity in undamaged cochlear cells or utricular cells, respectively. The method comprises increasing c-myc activity within the cochlear cell or utricular cell sufficient to induce proliferation or cell cycle reentry of the cochlear cell or utricular cell.

In other embodiments, the method includes increasing Notch activity within a cell, when c-myc activity is already increased. (See, for example, Lee et al. (2008) ASSOC. RES. OTOLARYNGOL. ABS.: 762.) In particular, the invention relates to a method of inducing proliferation or cell cycle reentry of a differentiated cochlear cell or a utricular cell in which c-myc activity is increased in response to damage to the cochlear cell or utricular cell, as compared to the level of c-myc activity in undamaged cochlear cells or utricular cells, respectively. The method comprises increasing Notch activity within the cochlear cell or utricular cell sufficient to induce proliferation or cell cycle reentry of the cochlear cell or utricular cell.

After c-myc activity, Notch activity, or both c-myc and Notch activities, as appropriate, is or are increased, Notch may be inhibited according to methods known in the art and/or described herein to cause proliferating supporting cells to transdifferentiate into hair cells. Alternatively, or in addition, after c-myc activity, Notch activity, or both c-myc and Notch activity is or are increased, as appropriate, Atoh1 activity can be increased to cause proliferating supporting cells to transdifferentiate into hair cells. Methods of increasing Atoh1 activity (including use of Atoh1 agonists) are known in the art (see, for example, U.S. Pat. No. 8,188,131; U.S. Patent Publication No. 20110305674; U.S. Patent Publication No. 20090232780; Kwan et al. (2009) INT'L SYMPOSIUM ON OLFACTION AND TASTE: ANN. N.Y. ACAD. SCI. 1170:28-33; Daudet et al. (2009) DEV. BIO. 326:86-100; Takebayashi et al. (2007) DEV. BIO. 307:165-178; and Ahmed et al. (2012) DEV. CELL 22(2):377-390.)

Also disclosed is a method of regenerating a cochlear or utricular hair cell. The method includes (a) increasing c-myc, Notch, or both c-myc activity and Notch activity, as appropriate, \within the hair cell thereby to induce cell proliferation to produce one, two or more daughter cells, and (b) after cell proliferation, decreasing Notch activity to induce differentiation of at least one of the cell and the daughter cells to produce a differentiated cochlear or utricular hair cell. The process can occur in vivo or ex vivo. In one embodiment, Notch activity is decreased in a cell that originated from a supporting cell to cause the supporting cell to transdifferentiate into a hair cell. In another embodiment, Atoh1 activity is increased in a cell that originated from a supporting cell to cause the supporting cell to transdifferentiate into a hair cell.

In certain embodiments, after c-myc and Notch induce proliferation within a hair cell or supporting cell, c-myc activity is decreased to induce differentiation of at least one of the cell and the daughter cell to produce a differentiated cochlear or utricular hair cell. Decreasing c-myc activity after proliferation can promote survival of the proliferating cell.

Also disclosed is a method for reducing the loss of, maintaining, or promoting hearing in a subject. The method comprises increasing c-myc activity, Notch activity, or both c-myc activity and Notch activity, as appropriate, within a hair cell and/or a supporting cell of the inner ear thereby to induce cell proliferation to produce daughter cells, and, after cell proliferation, decreasing c-myc and/or Notch activity, and permitting daughter cells of hair cell origin to differentiate into hair cells or permitting daughter cells of supporting cell origin to transdifferentiate into hair cells thereby to reduce the loss of, maintain or promote hearing in the subject. The daughter cells of supporting cell origin can be induced to transdifferentiate into hair cells by activating Atoh1 activity, for example, by gene expression, by administration of an effective amount of Atoh1 or an Atoh1 agonist. The steps can be performed in vivo (for example, in the inner ear of a mammal, in particular in the cochlea), or ex vivo, wherein the resulting cells are cultured and/or introduced into the inner ear of the subject.

Also disclosed is a method for reducing the loss of, maintaining, or promoting vestibular function in a subject. The method comprises increasing c-myc activity, Notch activity, or both c-myc activity and Notch activity, as appropriate, within a hair cell and/or a supporting cell of the inner ear thereby to induce cell proliferation to produce daughter cells, and, after cell proliferation, decreasing c-myc and/or Notch activity, and permitting daughter cells of hair cell origin to differentiate into hair cells or permitting daughter cells of supporting cell origin to transdifferentiate into hair cells thereby to reduce the loss of, maintain or promote vestibular function in the subject. The daughter cells of supporting cell origin can be induced to transdifferentiate into hair cells by activating Atoh1 activity, for example, by gene expression, by administration of an effective amount of Atoh1 or an Atoh1 agonist. The steps can be performed in vivo (for example, in the inner ear of a mammal, in particular in the utricle), or ex vivo, wherein the resulting cells are cultured and/or introduced into the inner ear of the subject.

The methods and compositions described herein can be used for treating subjects who have, or who are at risk for developing, an auditory disorder resulting from a loss of auditory hair cells, e.g., sensorineural hair cell loss. Patients having an auditory disorder can be identified using standard hearing tests known in the art. The method can comprise (a) increasing c-myc activity, Notch activity, or both c-myc activity and Notch activity, as appropriate, within the hair cell of the subject thereby to induce cell proliferation to produce a daughter cell, and (b) after cell proliferation, decreasing Notch activity to induce differentiation of at least one of the cell and the daughter cell to produce a differentiated cochlear or utricular hair cell. This can be accomplished by administering an agent or agents to the subject to modulate c-myc and Notch activity. Alternatively, the process can occur in cells (e.g., cochlear and/or utricular cells) ex vivo, after which the resulting cells are transplanted into the inner ear of the subject. In certain embodiments, the methods and compositions described herein can be used to promote growth of neurites from the ganglion neurons of the inner ear. For example, the regeneration of hair cells may promote the growth of new neurites from ganglion neurons and formation of new synapses with the regenerated hair cells to transmit sound and balance signals from the hair cells to the brain.

In certain embodiments, the methods and compositions described herein can be used to promote growth of neurites from the ganglion neurons of the inner ear. For example, the regeneration of hair cells may promote the growth of new neurites from ganglion neurons and formation of new synapses with the regenerated hair cells to transmit sound and balance signals from the hair cells to the brain. In some embodiments, the methods and compositions described herein can be used to reestablish proper synaptic connections between hair cells and auditory neurons to treat, for example, auditory neuropathy.

Subjects with sensorineural hair cell loss experience the degeneration of cochlea hair cells, which frequently results in the loss of spiral ganglion neurons in regions of hair cell loss. Such subjects may also experience loss of supporting cells in the organ of Corti, and degeneration of the limbus, spiral ligament, and stria vascularis in the temporal bone material.

In certain embodiments, the present invention can be used to treat hair cell loss and any disorder that arises as a consequence of cell loss in the ear, such as hearing impairments, deafness, vestibular disorders, tinnitus (see, Kaltenbach et al. (2002) J Neurophysiol, 88(2). 699-714s), and hyperacusis (Kujawa et al. (2009) J. Neurosci. 29(45): 14077-14085), for example, by promoting differentiation (e.g., complete or partial differentiation) of one or more cells into one or more cells capable of functioning as sensory cells of the ear, e.g., hair cells.

In certain embodiments, the subject can have sensorineural hearing loss, which results from damage or malfunction of the sensory part (the cochlea) or non-sensory part (the limbus, spiral ligament and stria vascularis) or the neural part (the auditory nerve) of the ear, or conductive hearing loss, which is caused by blockage or damage in the outer and/or middle ear. Alternatively or in addition, the subject can have mixed hearing loss caused by a problem in both the conductive pathway (in the outer or middle ear) and in the nerve pathway (the inner ear). An example of a mixed hearing loss is a conductive loss due to a middle-ear infection combined with a sensorineural loss due to damage associated with aging.

In certain embodiments, the subject may be deaf or have a hearing loss for any reason, or as a result of any type of event. For example, a subject may be deaf because of a genetic or congenital defect; for example, a human subject can have been deaf since birth, or can be deaf or hard-of-hearing as a result of a gradual loss of hearing due to a genetic or congenital defect. In another example, a human subject can be deaf or hard-of-hearing as a result of a traumatic event, such as a physical trauma to a structure of the ear, or a sudden loud noise, or a prolonged exposure to loud noises. For example, prolonged exposures to concerts, airport runways, and construction areas can cause inner ear damage and subsequent hearing loss.

In certain embodiments, a subject can experience chemical-induced ototoxicity, wherein ototoxins include therapeutic drugs including antineoplastic agents, salicylates, quinines, and aminoglycoside antibiotics, contaminants in foods or medicinals, and environmental or industrial pollutants.

In certain embodiments, a subject can have a hearing disorder that results from aging. Alternatively or in addition, the subject can have tinnitus (characterized by ringing in the ears) or hyperacusis (heightened sensitivity to sound).

In addition, the methods and compositions described herein can be used to treat a subject having a vestibular dysfunction, including bilateral and unilateral vestibular dysfunction. Vestibular dysfunction is an inner ear dysfunction characterized by symptoms that include dizziness, imbalance, vertigo, nausea, and fuzzy vision and may be accompanied by hearing problems, fatigue and changes in cognitive functioning. Vestibular dysfunction can be the result of a genetic or congenital defect; an infection, such as a viral or bacterial infection; or an injury, such as a traumatic or nontraumatic injury. Vestibular dysfunction is most commonly tested by measuring individual symptoms of the disorder (e.g., vertigo, nausea, and fuzzy vision).

Alternatively or in addition, the methods and compositions described herein can be used prophylactically, such as to prevent, reduce or delay progression of hearing loss, deafness, or other auditory disorders associated with loss of inner ear function. For example, a composition containing one or more of the agents can be administered with (e.g., before, after or concurrently with) a second composition, such as an active agent that may affect hearing loss. Such ototoxic drugs include the antibiotics neomycin, kanamycin, amikacin, viomycin, gentamycin, tobramycin, erythromycin, vancomycin, and streptomycin; chemotherapeutics such as cisplatin; nonsteroidal anti-inflammatory drugs (NSAIDs) such as choline magnesium trisalicylate, diclofenac, diflunisal, fenoprofen, flurbiprofen, ibuprofen, indomethacin, ketoprofen, meclofenamate, nabumetone, naproxen, oxaprozin, phenylbutazone, piroxicam, salsalate, sulindac, and tolmetin; diuretics; salicylates such as aspirin; and certain malaria treatments such as quinine and chloroquine. For example, a human undergoing chemotherapy can be treated using the compounds and methods described herein. The chemotherapeutic agent cisplatin, for example, is known to cause hearing loss. Therefore, a composition containing one or more agents that increase the activity of c-myc and Notch can be administered with cisplatin therapy (e.g., before, after or concurrently with) to prevent or lessen the severity of the cisplatin side effect. Such a composition can be administered before, after and/or simultaneously with the second therapeutic agent. The two agents may be administered by different routes of administration.

In certain embodiments, the methods and compositions described herein can be used to increase the levels (e.g., protein levels) and/or activity (e.g., biological activity) of c-myc and Notch in cells (e.g., inner ear cells). Exemplary methods and compositions include, but are not limited to methods and compositions for increasing c-myc or Notch expression (e.g., transcription and/or translation) or levels (e.g., concentration) in cells. It is contemplated that such modulation can be achieved in hair cells and/or supporting cells in vivo and ex vivo.

1. Methods and Compositions for Increasing C-myc and Notch and Atoh1 Activity (i) C-myc, Notch, or Atoh1 Polypeptides It is contemplated that c-myc, Notch, and Atoh1 proteins, including full length proteins, biologically active fragments, and homologs of c-myc and Notch can be introduced into target cells using techniques known in the art.

Exemplary c-myc polypeptides include, for example, NP_002458.2 (SEQ ID NO: 1), as referenced in the NCBI protein database. Exemplary Notch polypeptides include, for example, NP_060087.3 (SEQ ID NO: 2), as referenced in the NCBI protein database. Exemplary Atoh1 polypeptides include, for example, NP_005163.1 (SEQ ID NO: 3), as referenced in the NCBI protein database.

In certain embodiments, nucleic acid sequences encoding c-myc, Notch, and Atoh1 family members may be used in accordance with the methods described herein. Exemplary c-myc family members include N-myc, referenced in the NCBI protein database as NP_005369.2 (SEQ ID NO: 12). Exemplary Notch family members include Notch2, referenced in the NCBI protein database as NP_077719.2 (SEQ ID NO: 14); Notch3, referenced in the NCBI protein database as NP_000426.2 (SEQ ID NO: 16); and Notch4, referenced in the NCBI protein database as NP_004548.3 (SEQ ID NO: 18). Exemplary Atoh1 family members include Atoh7, referenced in the NCBI protein database as NP_660161.1 (SEQ ID NO: 20).

In certain embodiments, a protein sequence of the invention may comprise a consensus protein sequence or a nucleotide sequence encoding a consensus protein sequence. Consensus protein sequences of c-myc, Notch intracellular domain, and Atoh1 of the invention are set forth below.

A consensus protein sequence of c-myc built from human, mouse, rat and chimpanzee sequences using ClustalW is as follows:

MPLNVX$_1$FX$_2$NRNYDLDYDSVQPYFX$_3$
CDEEENFYX$_4$QQQQSELQPPAPSEDIW
KKFELLPTPPLSPSRRSGLCSPSYVAVX$_5$X$_6$
X$_7$F$_8$XRX$_9$DX$_{10}$DGGGGX$_{11}$FSTADQLEMX$_{12}$TE
LLGGDMVNQSFICDPDDETFIKNIIQDCM
WSGFSAAAKLVSEKLASYQAARKDSX$_{13}$SX$_{14}$X$_{15}$
PARGHSVCSTSSLYLQDLX$_{16}$AAASECIDPSVVF
PYPLNDSSSPKSCX$_{17}$SX$_{18}$DSX$_{19}$AFSX$_{20}$
SSDSLLSSX$_{21}$ESSPX$_{22}$X$_{23}$X$_{24}$PEPLVLHEETP
PTTSSDSEEEQX$_{25}$DEEEIDVVSVEKRQX$_{26}$PX$_{27}$
KRSESGSX28X$_{29}$X$_{30}$GGHSKPPHSPLVLKR
CHVSTHQHNYAAPPSTRKDYPAAKRX$_{31}$KLD
SX$_{32}$RVLX$_{33}$QISNNRKCX$_{34}$SPRSSDTEENX$_{35}$
KRRTHNVLERQRRNELKRSFFALRDQIPELE
NNEKAPKVVILKKATAYILSX$_{36}$QAX$_{37}$EX$_{38}$
KLX$_{39}$SEX$_{40}$DLLRKRREQLKHKLEQLRNSX$_{41}$A (SEQ ID NO: 9), wherein X$_1$ is S or N; X$_2$ is T or A; X$_3$ is Y or I; X$_4$ is Q or H; X$_5$ is T or A; X$_6$ is P or T; X$_7$ is S or a bond; X$_8$ is L or P; X$_9$ is G or E; X$_{10}$ is N or D; X$_{11}$ is S or N; X$_{12}$ is V or M; X$_{13}$ is G or T; X$_{14}$ is P or L; X$_{15}$ is N or S; X$_{16}$ is S or T; X$_{17}$ is P or A or T; X$_{18}$ is Q or S; X$_{19}$ is S or T; X$_{20}$ is P or S; X$_{21}$ is T or a bond; X$_{22}$ is Q or R; X$_{23}$ is A or G; X$_{24}$ is S or T; X$_{25}$ is E or D; X$_{26}$ is A or T or P; X$_{27}$ is G or A; X$_{28}$ is P or S; X$_{29}$ is P or S; X$_{30}$ is A or S; X$_{31}$ is V or A; X$_{32}$V or G; X$_{33}$ is K or R; X$_{34}$ is T or S; X$_{35}$ is D or V; X$_{36}$ is V or I; X$_{37}$ is E or D; X$_{38}$ is Q or H; X$_{39}$ is T or I; X$_{40}$ is E or K; and X$_{41}$ is C or G.

A consensus protein sequence of the Notch intracellular domain build from human, rat and mouse sequences using ClustalW is as follows:

VLLSRKRRRQHGQLWFPEGFKVSEASKKKRRE-
PLGEDSVGLKPLKNASDGAL MDDNQNEWGDED-
LETKKFRFEEPVVLPDLX$_1$
DQTDHRQWTQQHLDAADLRX$_2$SAMAPTP PQGEV-
DADCMDVNVRGPDGFTPLMIASCSGGGLETGN-
SEEEEDAPAVISDFIYQGASLHN QTDRTGETALH-
LAARYSRSDAA
KRLLEASADANIQDNMGRTPLHAAVSADAQGV
FQILX$_3$RNRATDLDARMIIDGTTPLILAARLA
VEGMLEDLINSHADVNAVDDLGKSALHWAAAVN
NVDAAVVLLKNGANKDMQNNX$_4$EETPLFLAA
REGSYETAKVLLDHFANRDITDHMDRLP RDIAQER-
MHHDIVRLLDEYNLVRSPQLHGX$_5$
X$_6$LGGTPTLSPX$_7$LCSPNGYLGX$_8$LKX$_9$X$_{10}$X$_{11}$
QGKKX$_{12}$RKPSX$_{13}$KGLACX$_{14}$SKEAKDLKARR
KKSQDGKGCLLDSSX$_{15}$MLSPVDSLESPH
GYLSDVASPPLLPSPFQQSPSX$_{16}$PLX$_{17}$HLPGM
PDTHLGIX$_{18}$HLNVAAKPEMAALX$_{19}$GGX$_{20}$
RLAFEX$_{21}$X$_{22}$PPRLSHLPVASX$_{23}$X$_{24}$STVLX$_{25}$X$_{26}$
X$_{27}$X$_{28}$X$_{29}$GAX$_{30}$NFTVGX$_{31}$X$_{32}$X$_{33}$SLNGQC
EWLX$_{34}$RLQX$_{35}$GMVPX$_{36}$QYNPLRX$_{37}$X$_{38}$VX$_{39}$
PGX$_{40}$LSTQAX$_{41}$X$_{42}$LQHX$_{43}$MX$_{44}$GPX$_{45}$HSSL
X$_{46}$X$_{47}$X$_{48}$X$_{49}$L SX$_{50}$X$_{51}$X$_{52}$X$_{53}$YQGLPX$_{54}$
TRLATQPHLVQTQQVQPQNLQX$_{55}$QX$_{56}$
QNLQX$_{57}$X$_{58}$X$_{59}$X$_{60}$X$_{61}$X$_{62}$X$_{63}$X$_{64}$X$_{65}$X$_{66}$X$_{67}$X$_{68}$
X$_{69}$X$_{70}$PPX$_{71}$QPHLX$_{72}$VSSAAX$_{73}$GHLGRSFL
SGEPSQADV QPLGPSSLX$_{74}$VHTILPQESX$_{75}$
ALPTSLPSSX$_{76}$VPPX$_{77}$TX$_{78}$X$_{79}$QFLTPPSQHS
YSSX$_{80}$PVDNTP SHQLQVPEHPFLT
PSPESPDQWSSSSXiHSNX$_2$SDWSEGX$_3$
SSPPTX$_4$MX$_5$SQIX$_6$X$_7$IPEA FK (SEQ ID NO: 10), wherein X$_1$ is D or S; X$_2$ is M or V; X$_3$ is L or I; X$_4$ is K or R; X$_5$ is T or A; X$_6$ is A or P; X$_7$ is T or P; X$_8$ is S or N; X$_9$ is S or P; X$_{10}$ is A or G; X$_{11}$ is T or V; X$_{12}$ is A or V; X$_{13}$ is T or S; X$_{14}$ is G or S; X$_{15}$ is G or S; X$_{16}$ is M or V; X$_{17}$ is S or N; X$_{18}$ is S or G; X$_{19}$ is A or G; X$_{20}$ is S or G; X$_{21}$ is P or T; X$_{22}$ is P or G; X$_{23}$ is S or G; X$_{24}$ is A or T; X$_{25}$ is S or G; X$_{26}$ is T or S; X$_{27}$ is N or S; X$_{28}$ is G or S; X$_{29}$ is T or G; X$_{30}$ is M or L; X$_{31}$ is A or G; X$_{32}$ is P or S; X$_{33}$ is A or T; X$_{34}$ is P or S; X$_{35}$ is N or S; X$_{36}$ is S or N; X$_{37}$ is P or G; X$_{38}$ is G or S; X$_{39}$ is T or A; X$_{40}$ is T or P; X$_{41}$ is A or P; X$_{42}$ is G or S; X$_{43}$ is G or S; X$_{44}$ is M or V; X$_{45}$ is L or I; X$_{46}$ is S or A; X$_{47}$ is T or A; X$_{48}$ is N or S; X$_{49}$ is T or A; X$_{50}$ is P or Q; X$_{51}$ is M or I; X$_{52}$ is M or I; X$_{53}$ is S or a bond; X$_{54}$ is S or N; X$_{55}$ is L or I or M; X$_{56}$ is Q or P; X$_{57}$ is a bond or P; X$_{58}$ is a bond or A; X$_{59}$ is a bond or N; X$_{60}$ is a bond or I; X$_{61}$ is a bond or Q; X$_{62}$ is a bond or Q; X$_{63}$ is a bond or Q; X$_{64}$ is a bond or Q; X$_{65}$ is a bond or S; X$_{66}$ is a bond or L; X$_{67}$ is a bond or Q; X$_{68}$ is a bond or P; X$_{69}$ is a bond or P; X$_{70}$ is a bond or P; X$_{71}$ is P or S; X$_{72}$ is S or G; X$_{73}$ is N or S; X$_{74}$ is P or A; X$_{75}$ is Q or P; X$_{76}$ is M or L; X$_{77}$ is M or V; X$_{78}$ is T or A; X$_{79}$ is T or A; X$_{80}$ is S or a bond; X$_{81}$ is P or R; X$_{82}$ is I or V; X$_{83}$ is I or V; X$_{84}$ is T or S; X$_{85}$ is P or Q; X$_{86}$ is T or A; X$_{87}$ is H or R.

A consensus protein sequence of Atoh1 built from human, mouse and chimpanzee sequences using ClustalW is as follows:

MSRLLHAEEWAEVKELGDHHRX$^1$PQPHHX$_2$
PX$_3$X$_4$PPX$_5$X$_6$QPPATLQARX$_7$X$_8$PV
YPX$_9$ELSLLDSTDPRAWLX$_{10}$PTLQGX$_{11}$
CTARAAQYLLHSPELX$_{12}$ASEAAAPRDEX$_{13}$
DX$_{14}$X$_{15}$GELVRRSX$_{16}$X$_{17}$GX$_{18}$X$_{19}$X$_{20}$SKSPG
PVKVREQLCKLKGGVVVDELGCSRQRAPSSKQVNG
VQKQRRLAANARERRRMHGLNHAFDQLRN-
VIPSFNNDKKLSKYETLQMAQIYINALSEL
LQTPX$_{21}$X$_{22}$GEQPPPPX$_{23}$ASCKX$_{24}$DHII
HLRTAX$_{25}$SYEGGAGX$_{26}$X$_{27}$X$_{28}$X$_{29}$AGAQX$_{30}$AX$_{31}$G
GX$_{32}$X$_{33}$RPTPPGX$_{34}$CRTRFSX$_{35}$PASX$_{36}$GGYSVQL
DALHFX$_{37}$X$_8$sFEDX$_{39}$ALTAMMAQKX$_{40}$L
SPSLPGX$_{41}$ILQPVQEX$_{42}$NSKTSPRSHRSD
GEFSPHSHYSDSDEAS (SEQ ID NO: 11), wherein X$_1$ is Q or H; X$_2$ is L or V; X$_3$ is Q or a bond; X$_4$ is P or a bond; X$_5$ is P or a bond; X$_6$ is P or a bond; X$_7$ is E or D; X$_8$ is H or L; X$_9$ is P or A; X$_{10}$ is A or T; X$_{11}$ is I or L; X$_{12}$ is S or G;

$X_{13}$ is V or A; $X_{14}$ is G or S; $X_{15}$ is R or Q; $X_{16}$ is S or G; $X_{17}$ is G or C; $X_{18}$ is A or G; $X_{19}$ is S or a bond; $X_{20}$ is S or L; $X_{21}$ is S or N; $X_{22}$ is G or V; $X_{23}$ is P or T; $X_{24}$ is S or N; $X_{25}$ is A or S; $X_{26}$ is A or N; $X_{27}$ is A or S; $X_{28}$ is T or A; $X_{29}$ is A or V; $X_{30}$ is Q or P; $X_{31}$ is S or P; $X_{32}$ is S or G; $X_{33}$ is Q or P; $X_{34}$ is S or P; $X_{35}$ is A or G; $X_{36}$ is A or S; $X_{37}$ is S or P; $X_{38}$ is T or A; $X_{39}$ is S or R; $X_{40}$ is N or D; $X_{41}$ is S or G; and $X_{42}$ is E or D.

As used herein, the term "Atoh1" refers to a protein belonging to the basic helix-loop-helix (BHLH) family of transcription factors that is involved in the formation of hair cells in an inner ear of a mammal, and/or is a protein having an amino sequence or consensus sequence as set forth herein.

The c-myc, Notch, or Atoh1 polypeptides can be used in combination with compositions to enhance uptake of the polypeptides into biological cells. In certain embodiments, the Atoh1, c-myc, or Notch polypeptides can be mutated to include amino acid sequences that enhance uptake of the polypeptides into a biological cell. In certain embodiments, Atoh1, c-myc, or Notch polypeptides can be altered or mutated to increase the stability and/or activity of the polypeptide (e.g., c-myc, Notch or Atoh-1 point mutants). In certain embodiments, c-myc, Notch or Atoh1 polypeptides can be altered to increase nuclear translocation of the polypeptide. In certain embodiments, altered c-myc, Notch or Atoh1 polypeptides or biologically active fragments of c-myc, Notch, or Atoh1 retain at least 50%, 60%, 70%, 80%, 90%, or 95% of the biological activity of full length, wild type respective c-myc, Notch or Atoh1 protein in the species that is the same species as the subject that is or will be treated with the methods and compositions described herein.

In certain embodiments, c-myc polypeptides sequences can be 50%, 60%, 70%, 80%, 85%, 90%, 95%, 98%, 99%, or 100% identical to NP_002458.2 (SEQ ID NO.: 1). In certain embodiments, Notch polypeptides sequences are 50%, 60%, 70%, 80%, 85%, 90%, 95%, 98%, 99%, or 100% identical to NP_060087.3 (SEQ ID NO.: 2). In certain embodiments, Atoh1 polypeptides sequences can be 50%, 60%, 70%, 80%, 85%, 90%, 95%, 98%, 99%, or 100% identical to NP_005163.1 (SEQ ID NO.: 3). In certain embodiments, agents encoded by modified Atoh1, c-myc, or Notch nucleic acid sequences and Atoh1, c-myc, or Notch polypeptide sequences possess at least a portion of the activity (e.g., biological activity) of the molecules encoded by the corresponding, e.g., unmodified, full-length Atoh1, c-myc, or Notch nucleic acid sequences and Atoh1, c-myc, or Notch polypeptide sequences. For example, molecules encoded by modified Atoh1, c-myc, or Notch nucleic acid sequences and modified Atoh1, c-myc, or Notch polypeptides retain 50%, 60%, 70%, 80%, 85%, 90%, 95%, 98%, 99%, or 100% of the activity (e.g., biological activity) of the molecules encoded by the corresponding, e.g., unmodified, respective Atoh1, c-myc, or Notch nucleic acid sequences and/or full length Atoh1, c-myc, or Notch polypeptide sequences.

In certain embodiments, the c-myc protein of the invention comprises functional domains at least 50%, 60%, 70%, 80%, 85%, 90%, 95%, 98%, 99%, or 100% identical to a Myc-N domain comprising amino acid residues 16-360 of SEQ ID NO: 1, a helix-loop-helix domain comprising amino acid residues 370-426 of SEQ ID NO: 1, a Myc leucine zipper domain comprising amino acid residues 423-454 of SEQ ID NO: 1, and/or surrounding and/or intervening sequences of SEQ ID NO: 1. In certain embodiments, the Notch protein of the invention comprises functional domains at least 50%, 60%, 70%, 80%, 85%, 90%, 95%, 98%, 99%, or 100% identical to a Notch intracellular domain comprising amino acid residues 1754-2555 of SEQ ID NO: 2. In certain embodiments, the Atoh1 protein of the invention comprises functional domains at least 50%, 60%, 70%, 80%, 85%, 90%, 95%, 98%, 99%, or 100% identical to a basic helix-loop-helix domain comprising amino acids 158-214 of SEQ ID NO: 3, a helix-loop-helix domain comprising amino acids 172-216 of SEQ ID NO: 3, and/or surrounding and/or intervening sequences of SEQ ID NO: 3.

In certain embodiments, the c-myc and Notch proteins of the invention can be administered to cells as a single protein containing both c-myc and Notch (or active domains thereof), preferably separated by a cleavable linker. Examples of cleavable linkers are known in the art (see, e.g., U.S. Pat. Nos. 5,258,498 and 6,083,486.)

C-myc, Notch or Atoh1 levels (e.g., protein levels) and/or activity (e.g., biological activity) in target cells and/or in the nucleus of target cells can be assessed using standard methods such as Western Blotting, in situ hybridization, reverse transcriptase polymerase chain reaction, immunocytochemistry, viral titer detection, and genetic reporter assays. Increases in c-myc, Notch or Atoh1 levels (e.g., protein levels) and/or activity (e.g., biological activity) in target cells and/or in the nucleus of target cells can be assessed by comparing c-myc, Notch or Atoh1 levels and/or activity in a first cell sample or a standard with c-myc, Notch or Atoh1 levels and/or activity in a second cell sample, e.g., contacting the cell sample with an agent contemplated to increase c-myc, Notch or Atoh1 levels and/or activity.

Sequence identity may be determined in various ways that are within the skill in the art, e.g., using publicly available computer software such as BLAST, BLAST-2, ALIGN or Megalign (DNASTAR) software, which are used to perform sequence alignments and then calculate sequence identity. Exemplary software programs available from the National Center for Biotechnology Information (NCBI) on the website ncbi.nlm.nih.gov include blastp, blastn, blastx, tblastn and tblastx. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are used at the default settings. The default scoring matrix used by blastp, blastx, tblastn, and tblastx is the BLOSUM62 matrix (Henikoff et al., (1992) PROC. NATL. ACAD. SCI. USA 89:10915-10919). In one approach, the percent identity can be determined using the default parameters of blastp, version 2.2.26 available from the NCBI.

(ii) DNA Encoding Atoh1, C-myc, or Notch

Atoh1, c-myc, or Notch can be expressed in target cells using one or more expression constructs known in the art. Such expression constructs include, but are not limited to, naked DNA, viral, and non-viral expression vectors. Exemplary c-myc nucleic acid sequences that may be expressed in target cells include, for example, NM_002467.4 (SEQ ID NO: 4), as referenced in the NCBI gene database. Exemplary Notch nucleic acid sequences that may be expressed include, for example, NM_017617.3 (SEQ ID NO: 5), as referenced in the NCBI gene database. Exemplary Atoh1 nucleic acid sequences that may be expressed in target cells include, for example, NM_005172.1 (SEQ ID NO: 6), as referenced in the NCBI gene database.

In certain embodiments, c-myc, Notch, and Atoh1 family members may be used. Exemplary c-myc family members include N-myc, referenced in the NCBI gene database as NM_005378.4 (SEQ ID NO: 13). Exemplary Notch family members include Notch2, referenced in the NCBI gene database as NM_024408.3 (SEQ ID NO: 15); Notch3, referenced in the NCBI gene database as NM_000435.2 (SEQ ID NO: 17); and Notch4, referenced in the NCBI gene database as NM_004557.3 (SEQ ID NO: 19). Exemplary Atoh1 family members include Atoh7, referenced in the NCBI gene database as NM_145178.3 (SEQ ID NO: 21).

In certain embodiments, DNA encoding c-myc, Notch or Atoh1 can be an unmodified wild type sequence. Alternatively, DNA encoding c-myc, Notch or Atoh1 can be modified using standard techniques. For example, DNA encoding c-myc, Notch or Atoh1 can be modified or mutated, e.g., to increase the stability of the DNA or resulting polypeptide. Polypeptides resulting from such altered DNAs should retain the biological activity of wild type c-myc, Notch or Atoh1. In certain embodiments, DNA encoding Atoh1, c-myc, or Notch can be altered to increase nuclear translocation of the resulting polypeptide. In certain embodiments, DNA encoding c-myc, Notch or Atoh1 can be modified using standard molecular biological techniques to include an additional DNA sequence that can encode one or more of, e.g., detectable polypeptides, signal peptides, and protease cleavage sites.

In certain embodiments, c-myc nucleic acid sequences can be 50%, 60%, 70%, 80%, 85%, 90%, 95%, 98%, 99%, or 100% identical to NM_002467.4 (SEQ ID NO: 4). In certain embodiments, Notch nucleic acid sequences are 50%, 60%, 70%, 80%, 85%, 90%, 95%, 98%, 99%, or 100% identical to NM_017617.3 (SEQ ID NO: 5). In certain embodiments, Atoh1 nucleic acid sequences are 50%, 60%, 70%, 80%, 85%, 90%, 95%, 98%, 99%, or 100% identical to NM_005172.1 (SEQ ID NO: 6).

In certain embodiments, the c-myc nucleic acid sequence of the invention comprises functional domains at least 50%, 60%, 70%, 80%, 85%, 90%, 95%, 98%, 99%, or 100% identical to DNA encoding a Myc-N domain comprising amino acid residues 16-360 of SEQ ID NO: 1, a helix-loop-helix domain comprising amino acid residues 370-426 of SEQ ID NO: 1, DNA encoding a Myc leucine zipper domain comprising amino acid residues 423-454 of SEQ ID NO: 1, and/or DNA encoding the surrounding and/or intervening sequences of SEQ ID NO: 1. In certain embodiments, the Notch nucleic acid sequence of the invention comprises functional domains at least 50%, 60%, 70%, 80%, 85%, 90%, 95%, 98%, 99%, or 100% identical to DNA encoding a Notch intracellular domain comprising amino acid residues 1754-2555 of SEQ ID NO: 2. In certain embodiments, the Atoh1 nucleic acid sequence of the invention comprises functional domains at least 50%, 60%, 70%, 80%, 85%, 90%, 95%, 98%, 99%, or 100% identical to DNA encoding a basic helix-loop-helix domain comprising amino acids 158-214 of SEQ ID NO: 3, DNA encoding a helix-loop-helix domain comprising amino acids 172-216 of SEQ ID NO: 3, and/or DNA encoding surrounding and/or intervening sequences of SEQ ID NO: 3.

(iii) C-myc, Notch or Atoh1 Pathway Modulators

In certain embodiments, c-myc or Notch levels (e.g., protein levels) and/or activity (e.g., biological activity) can be increased or decreased using compounds or compositions that target c-myc or Notch, or one or more components of the c-myc or Notch pathway. Similarly, Atoh1 levels (e.g., protein levels) and/or activity (e.g., biological activity) can be increased using compounds that target Atoh1 or one or more components of the Atoh1 pathway.

Exemplary c-myc activators include microRNAs that target FBXW-7 (Ishikawa Y et al., Oncogene 2012 Jun. 4; doi:10.1038/onc.2012.213) and activators that increase c-myc expression levels or activity such as nordihydroguaiaretic acid (NDGA) (Park S et al. (2004) J. CELL BIOCHEM. 91(5):973-86), CD19 (Chung et a.l, (2012) J. CLIN. INVEST. 122(6):2257-2266, cohesin (McEwan et al, (2012) PLoS ONE 7(11): e49160), bryostatin 1 (Hu et al. (1993) LEUK. LYMPHOMA 10(1-2):135-42), 2'-3-dimethyl-4-aminoazobenzene (ortho-aminoazotoluene, OAT) (Smetanina et al. (2011) TOXICOL. APPL. PHARMACOL. 255(1):76-85), 2-amino-1-methyl-6-phenylimidazo[4,5-b]pyridine (PhIP) (Lauber et a. (2004) CARCINOGENESIS 25(12):2509-17), β-estradiol (U.S. Pat. No. 7,544,511 B2), RU38486 (U.S. Pat. No. 7,544,511 B2), dexamethasone (U.S. Pat. No. 7,544,511 B2), thyroid hormones (U.S. Pat. No. 7,544,511 B2), retinoids (U.S. Pat. No. 7,544,511 B2), and ecdysone (U.S. Pat. No. 7,544,511 B2).

Exemplary c-myc inhibitors include 7-nitro-N-(2-phenylphenyl)-2,1,3-benzoxadiazol-4-amine (10074-G5) (Clausen D M et al., (2010) J. PHARMACOL. EXP. THER. 335(3):715-27), thioxothiazolidinone [Z-E]-5-[4-ethylbenzylidene]-2-thioxo-1,3-thiazolidin-4-one (10058-F4) (Clausen et al. (2010) J. PHARMACOL. EXP. THER. 335(3):715-27; Lin C P et al. (2007) ANTICANCER DRUGS. 18(2):161-70; Huang et al. (2006) EXP. HEMATOL. 34(11):1480-9), 4-phenylbutyrate (phenylbutyrate) (Engelhard et al. (1998) J. NEUROONCOL. 37(2):97-108), Compound 0012 (Hurley et al. (2010) J. VASC. RES. 47(1): 80-90), curcumin (Aggarwal et al. (2005) CLIN. CANCER RES. 11(20):7490-8), magnesium hydroxide (Mori et al. (1997) J. CELL BIOCHEM. SUPPL. 27:35-41), BP-1-102 (Zhang et al. (2012) PROC. NATL. ACAD. SCI. U.S.A. 109(24):9623-8), WP1193 (Sai et al. (2012) J. NEUROONCOL. 107(3):487-501), BP-1-107 (Page et al. (2012) J. MED. CHEM. 55(3):1047-55), BP-1-108 (Page et al. (2012) J. MED. CHEM. 55(3):1047-55), SF-1-087 (Page et al. (2012) J. MED. CHEM. 55(3):1047-55), SF-1-088 (Page et al. (2012) J. MED. CHEM. 55(3):1047-55), STX-0119 (Ashizawa et al. (2011) INT. J. ONCOL. 38(5):1245-52), substituted thiazol-4-one compounds (U.S. Pat. No. 7,872,027), (Z,E)-5-(4-ethylbenzylidene)-2-thioxothiazolidin-4-one (10058-F4) (U.S. Pat. No. 7,026,343), S2T1-60TD (U.S. Publication No. 20120107317A1), Quarfloxin (CX-3543) (U.S. Publication No. 20120107317A1), benzoylanthranilic acid (U.S. Publication No. 20120107317A1), cationic porphyrin TMPyP4 (U.S. Publication No. 20120107317A1), tyrphostin and tryphostin-like compounds (European Patent No. EP2487156A1), AG490 (European Patent No. EP2487156A1), FBXW-7 expression vectors (Ishikawa Y et al., supra), and siRNAs targeting c-Myc transcript (Id.).

Exemplary Notch activators include microRNAs that target FBXW-7 (Ishikawa Y et al. supra), AG-370, 5 (U.S. Pat. No. 8,114,422), AG-1296 (6,7-dimethoxy-3-phenylquinoxaline) (Id.), nigericin·Na (Id.), cytochalasin D (Id.), FCCP (carbonylcyanide-4-(trifluoromethoxy)-phenylhydrazone) (Id.), SP60012 (Id.), and vectors that produce protein of or isolated protein of Jagged-1, Jagged-2, Jagged-3, Serrate, any member of the Jagged/Serrate protein family, Delta, Delta-like-1, Delta-like-3, Delta-like-4, Delta-like homolog-1 (DLK1), any member of the Delta protein family, and any portion of any of these proteins (PCT Publication WO2004090110A3). Exemplary Notch activators may also include chemical activators such as valproic acid (VPA, see, U.S. Pat. No. 8,338,482), resveratrol and phenethyl isothiocyanate.

Exemplary Notch inhibitors include gamma-secretase inhibitors such as an arylsulfonamide, a benzodiazepine, L-685,458 (U.S. Patent Publication No. 2001/0305674), MK-0752 (Purow B. (2012) ADV. EXP. MED. BIOL. 727:305-

19; Imbimbo BP (2008) CURR. TOP. MED. CHEM. 8(1):54-61), DAPT ([N-(3,5-Difluorophenacetyl)-L-alanyl]-S-phenylglycine t-butyl ester) (Id.; Ishikawa Y et al. supra; PCT Publication WO2011149762A3), LY-374973 (N—[N-(3,5-Difluorophenacetyl)-L-alanyl]-S-phenylglycine t-butyl ester) (PCT Publication WO2011149762A3), N-[(3,5-Difluorophenyl)acetyl]-L-alanyl-2-phenyl]glycine-1,1-dimethylethyl ester (Id.); Lilly GSI L685,458 (Purow B, supra), compound E ((2S)-2-{[(3,5-Difluorophenyl)acetyl]amino}-N-[(3S)-1-methyl-2-oxo-5-phenyl-2,3-dihydro-1H-1,4-benzodiazepin-3-yl]propanamide) (Purow B, supra), DBZ (dibenzazepine) (Purow B, supra), isocoumarin (Purow B, supra), JLK6 (7-amino-4-chloro-3-methoxyisocoumarin) (Purow B (2012) ADV. EXP. MED. BIOL. 727:305-19), Compound 18 ([11-endo]-N-(5,6,7,8,9,10-hexahydro-6,9-methano benzo[9][8]annulen-11-yl)-thiophene-2-sulfonamide) (Purow B, supra), E2012 (Imbimbo BP, supra; PCT Publication WO2009005688A3), MRK560 (Imbimbo BP, supra), LY-411575 (Imbimbo BP, supra), LY-450139 (Imbimbo BP, supra; PCT Publication WO2009005688A3), γ-secretase inhibitor XII (PCT Publication WO2011149762A3; PCT Publication WO2009005688A3), 2, 2-dimethyl-N—((S)-6-oxo-6, 7-dihydro-5H-dibenzo(b,d)azepin-7-yl)-N'-(2, 2,3,3,3-pentafluoro-propyl)-malonamide (U.S. Patent Publication No. 20090181944A1), GSI-IX (EP1949916B1), GSI-X (EP1949916B1), tocopherol derivatives (PCT Publication WO2009040423A1), [(2S)-2-{[(3,5-Difluorophenyl)acetyl]amino}-N-[(3S)1-methyl-2-oxo-5-phenyl-2,3-dihydro-1H-1,4-benzodiazepin-3-yl] propanamide] (PCT Publication WO2009005688A3), N—[N-(3,5-difluorophenacetyl)-L-alanyl]-Sphenylglycine-t-butylester (Id.), [1,1'-Biphenyl]-4-acetic acid (Id.), 2-fluoro-alpha-methyl (Id.), NGX-555 (Id.), LY-411575 (Id.), Cellzome (Id.), 2-Thiophenesulfonamide (Id.), 5-chloro-N-[(1S)-3,3,3-trifluoro-1-(hydroxymethyl)-2-(trifluoromethyl) propyl] (Id.), NIC5-15 (Id.), BMS (Id.), CHF-5074 (Id.), BMS-299897 (Imbimbo BP, supra), RO4929097; L-685458 ((5S)-(t-Butoxycarbonylamino)-6-phenyl-(4R)hydroxy-(2R)benzylhexanoyl)-L-leu-L-phe-amide); BMS-708163 (Avagacestat); BMS-299897 (2-[(1R)-1-[[(4-Chlorophenyl) sulfonyl](2,5-difluorophenyl)amino]ethyl-5-fluorobenzenebutanoic acid); MK-0752; YO-01027; MDL28170 (Sigma); LY411575 (N-2((2S)-2-(3,5-difluorophenyl)-2-hydroxyethanoyl)-N1-((7S)-5-methyl-6-oxo-6,7-dihydro-5H-dibenzo[b,d]azepin-7-yl)-1-alaninamide, see U.S. Pat. No. 6,541,466); ELN-46719 (2-hydroxy-valeric acid amide analog of LY411575 (where LY411575 is the 3,5-difluoromandelic acid amide) (U.S. Pat. No. 6,541,466)); PF-03084014 ((S)-2-((S)-5,7-difluoro-1,2,3,4-tetrahydronaphthalen-3-ylamino)-N-(1-(2-methyl-1-(neopentylamino)propan-2-yl)-1H-imidazol-4-yl)pentanamide, Samon et al., MOL CANCER THER 2012; 11:1565-1575); and Compound E ((2S)-2-{[(3,5-Diflurophenyl)acetyl]amino}-N-[(3S)-1-methyl-2-oxo-5-phenyl-2,3-dihydro-1H-1,4-benzodiazepin-3-yl]propanamide; see WO 98/28268 and Samon et al., MOL CANCER THER 2012; 11:1565-1575; available from Alexis Biochemicals)), or pharmaceutically acceptable salts thereof. In some embodiments, suitable gamma secretase inhibitors include: semagacestat (also known as LY450139, (2S)-2-hydroxy-3-methyl-N-[(1S)-1-methyl-2-oxo-2-[[(1S)-2,3,4,5-tetrahydro-3-methyl-2-oxo-1H-3-benzazepin-1-yl]amino]ethyl]butanamide, available from Eli Lilly; WO 02/47671 and U.S. Pat. No. 7,468,365); LY411575 (N-2((2S)-2-(3,5-difluorophenyl)-2-hydroxyethanoyl)-N1-((7S)-5-methyl-6-oxo-6,7-dihydro-5H-dibenzo[b,d]azepin-7-yl)-L-alaninamide, available from Eli Lilly, Fauq et al., (2007) BIOORG MED CHEM LETT 17: 6392-5); begacestat (also known as GSI-953, U.S. Pat. No. 7,300,951); arylsulfonamides (AS, Fuwa et al., (2006) BIOORG MED CHEM LETT. 16(16):4184-4189); N—[N-(3,5-difluorophenacetyl)-L-alanyl]-(S)-phenylglycine t-butyl ester (DAPT, Shih et al., (2007) CANCER RES. 67: 1879-1882); N—[N-3, 5-Difluorophenacetyl]-L-alanyl-S-phenylglycine Methyl Ester (also known as DAPM, gamma-Secretase Inhibitor XVI, available from EMD Millipore); Compound W (3,5-bis(4-Nitrophenoxy)benzoic acid, available from Tocris Bioscience); L-685,458 ((5S)-(tert-Butoxycarbonylamino)-6-phenyl-(4R)-hydroxy-(2R)-benzylhexanoyl)-L-leucy-L-phenylalaninamide, available from Sigma-Aldrich, Shearmen et al., (2000) BIOCHEMISTRY 39, 8698-8704); BMS-289948 (4-chloro-N-(2,5-difluorophenyl)-N-((1R)-{4-fluoro-2-[3-(1H-imidazol-1-yl)propyl]phenyl}ethyl) benzenesulfonamide hydrochloride, available from Bristol Myers Squibb); BMS-299897 (4-[2-((1R)-1-{[(4-chlorophenyl)sulfonyl]-2,5-difluoroanilino}ethyl)-5-fluorophenyl]butanoic acid, available from Bristol Myers Squibb, see Zheng et al., (2009) XENOBIOTICA 39(7):544-55); avagacestat (also known as BMS-708163, (R)-2-(4-chloro-N-(2-fluoro-4-(1,2,4-oxadiazol-3-yl)benzyl)phenylsulfonamido)-5,5,5-trifluoropentanamide, available from Bristol Myers Squibb, Albright et al., (2013) J PHARMACOL. EXP. THER. 344(3):686-695); MK-0752 (3-(4-((4-chlorophenyl)sulfonyl)-4-(2,5-difluorophenyl)cyclohexyl)propanoic acid, available from Merck); MRK-003 ((3'R,6R,9R)-5'-(2,2,2-trifluoroethyl)-2-((E)-3-(4-(trifluoromethyl)piperidin-1-yl)prop-1-en-1-yl)-5,6,7,8,9,10-hexahydrospiro[6,9-methanobenzo[8]annulene-11,3'-[1,2,5]thiadiazolidine] 1',1'-dioxide, available from Merck, Mizuma et al., (2012) MOL CANCER THER. 11(9):1999-2009); MRK-560 (N-[cis-4-[(4-Chlorophenyl)sulfonyl]-4-(2,5-difluorophenyl)cyclohexyl]-1,1,1-trifluoro-methanesulfonamide, Best et. al., (2006) J PHARMACOL EXP THER. 317(2):786-90); RO-4929097 (also known as R4733, (S)-2, 2-dimethyl-N1-(6-oxo-6,7-dihydro-5H-dibenzo[b,d]azepin-7-yl)-N3-(2,2,3,3,3-pentafluoropropyl)malonamide, available from Hoffman-La Roche Inc., Tolcher et al., (2012) J CLIN. ONCOL. 30(19):2348-2353); JLK6 (also known as 7-Amino-4-chloro-3-methoxyisocoumarin, available from Santa Cruz Biotechnology, Inc., Petit et al., (2001) NAT. CELL. BIOL. 3: 507-511); Tarenflurbil (also known as (R)-Flurbiprofen, (2R)-2-(3-fluoro-4-phenylphenyl)propanoic acid); ALX-260-127 (also known as Compound 11, described by Wolfe et al., (1998) J. MED. CHEM. 41: 6); Sulindac sulfide (SSide, et al., (2003) J BIOL CHEM. 278(20): 18664-70); 1,1,1-trifluoro-N-(4-[5-fluoro-2-(trifluoromethyl)phenyl]-4-{[4 (trifluoromethyl)phenyl] sulfonyl}cyclohexyl)methanesulfonamide (U.S. Patent Publication No. 20110275719); N-[trans-3-[(4-chlorophenyl) sulfonyl]-3-(2,5-difluorophenyl)cyclobutyl]-1,1,1-trifluoromethanesulfonamide (U.S. Patent Publication No. 20110263580); N-[cis-3-[(4-chlorophenyl)sulfonyl]-3-(2,5-difluorophenyl)cyclobutyl]-1,1,1-trifluoromethanesulfonamide (U.S. Patent Publication No. 20110263580); N-[cis-3-[(4-chlorophenyl)sulfonyl]-3-(2-cyano-5-fluorophenyl) cyclobutyl]-1,1,1-trifluoromethanesulfonamide (U.S. Patent Publication No. 20110263580); N-[cis-3-[(4-chlorophenyl) sulfonyl]-3-(2,5-dichlorophenyl)cyclobutyl]-1,1,1-trifluoromethanesulfonamide (U.S. Patent Publication No. 20110263580); N-(cis-3-(2,5-difluorophenyl)-3-{[4-(trifluoromethyl)phenyl]sulfonyl}cyclobutyl)-1,1,1-trifluoromethanesulfonamide (U.S. Patent Publication No. 20110263580); N-{cis-3-(5-chloro-2-fluorophenyl)-3-[(4-chlorophenyl)sulfonyl]cyclobutyl}-1,1,1-trifluoromethanesulfonamide (U.S. Patent Publication No. 20110263580); N-{cis-3-(2,5-difluorophenyl)-3-[(4-fluorophenyl)sulfonyl]

cyclobutyl}-1,1,1-trifluoromethanesulfonamide (U.S. Patent Publication No. 20110263580); N-{cis-3-(2,5-difluorophenyl)-3-[(3,4-difluorophenyl)sulfonyl]cyclobutyl}-1,1,1-trifluoromethanesulfonamide (U.S. Patent Publication No. 20110263580); N-[cis-3-[(4-cyanophenyl)sulfonyl]-3-(2,5-difluorophenyl)cyclobutyl]-1,1,1-trifluoromethanesulfonamide (U.S. Patent Publication No. 20110263580); 4-{[cis-3-[(4-chlorophenyl)sulfonyl]-3-(2,5-difluorophenyl)cyclobutyl][trifluoromethyl) sulfonyl]amino}butanoic acid (U.S. Patent Publication No. 20110263580); N-[cis-3-[(4-chlorophenyl)sulfonyl]-3-(2,5-difluorophenyl)cyclobutyl]-1,1,1-trifluoro-N-[2-(tetrahydro-2-pyran-2-yloxy)ethyl]methanesulfonamide (U.S. Patent Publication No. 20110263580); Methyl{[cis-3-[(4-chlorophenyl)sulfonyl]-3-(2,5-difluorophenyl)cyclobutyl][(trifluoromethyl)sulfonyl]amino}acetate (U.S. Patent Publication No. 20110263580); N-[3-[(4-chlorophenyl)sulfonyl]-3-(2,5-difluorophenyl)cyclobutyl]-1,1,1-trifluoro-N-methylmethanesulfonamide (U.S. Patent Publication No. 20110263580); N-[3-[(4-chlorophenyl)sulfonyl]-3-(2,5-difluorophenyl)cyclobutyl]-1,1,1-trifluoro-N-methylmethanesulfonamide (U.S. Patent Publication No. 20110263580); Methyl 4-{[cis-3-[(4-chlorophenyl)sulfonyl]-3-(2,5-difluorophenyl)cyclobutyl] [(trifluoro-methyl)sulfonyl]amino}butanoate (U.S. Patent Publication No. 20110263580); N-[cis-3-[(4-chlorophenyl)sulfonyl]-3-(2,5-difluorophenyl)cyclobutyl]-N-[(trifluoromethyl)sulfonyl]glycine (U.S. Patent Publication No. 20110263580); N-[cis-3-[(4-chlorophenyl)sulfonyl]-3-(2,5-difluorophenyl)-1-methylcyclobutyl]-1,1,1-trifluoromethanesulfonamide (U.S. Patent Publication No. 20110263580); N-(cis-3-(2,5-difluorophenyl)-1-methyl-3-{[4-(trifluoromethyl)phenyl]sulfonyl}cyclobutyl)-1,1,1-trifluoromethanesulfonamide (U.S. Patent Publication No. 20110263580); N-[cis-3-[(4-chlorophenyl)sulfonyl]-3-(2,5-difluorophenyl)cyclobutyl]-1,1,1-trifluoro-N-[(trifluoromethyl)sulfonyl]methanesulfonamide (U.S. Patent Publication No. 20110263580); Sodium[cis-3-[(4-chlorophenyl)sulfonyl]-3-(2,5-difluorophenyl)cyclobutyl][(trifluoromethyl)sulfonyl]azanide (U.S. Patent Publication No. 20110263580); Potassium[cis-3-[(4-chlorophenyl)sulfonyl]-3-(2,5-difluorophenyl)cyclo butyl][(trifluoromethyl)sulfonyl]azanide (U.S. Patent Publication No. 20110263580); N-[cis-3-[(4-trifluoromethoxyphenyl)sulfonyl]-3-(2,5-difluorophenyl)cyclobutyl]-1,1,1-trifluoromethanesulfonamide (U.S. Patent Publication No. 20110263580); 1,1,1-trifluoro-N-(4-[5-fluoro-2-(trifluoromethyl)phenyl]-4-{[4-(trifluoromethyl)phenyl]sulfonyl}cyclohexyl)methanesulfonamide (U.S. Patent Publication No. 20110263580); gamma-Secretase Inhibitor I (also known as Z-Leu-Leu-Nle-CHO, benzyloxycarbonyl-leucyl-leucyl-norleucinal, available from Calbiochem); gamma-secretase inhibitor

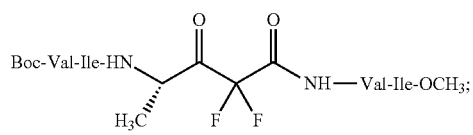

(MOL)(CDX) (available from Calbiochem); gamma secretase inhibitor III, (N-Benzyloxycarbonyl-Leu-leucinal, available from Calbiochem); gamma secretase inhibitor IV, (N-(2-Naphthoyl)-Val-phenylalaninal, available from Calbiochem); gamma-secretase inhibitor V (also known as Z-LF-CHO, N-Benzyloxycarbonyl-Leu-phenylalaninal, available from EMD Millipore); gamma-secretase inhibitor VI (1-(S)-endo-N-(1,3,3)-Trimethylbicyclo[2.2.1]hept-2-yl)-4-fluorophenyl Sulfonamide, available from EMD Millipore); gamma secretase inhibitor VII, (also known as Compound A, MOC-LL-CHO, Menthyloxycarbonyl-LL-CHO, available from Calbiochem); gamma secretase inhibitor X, ({1S-Benzyl-4R-[1-(1S-carbamoyl-2-phenethylcarbamoyl)-1S-3-methylbutylcarbamoyl]-2R-hydroxy-5-phenylpentyl}carbamic acid tert-butyl ester, available from Calbiochem); gamma secretase inhibitor XI, (7-Amino-4-chloro-3-methoxyisocoumarin, available from Calbiochem); gamma secretase inhibitor XII, (also known as Z-Ile-Leu-CHO, Shih and Wang, (2007) CANCER RES. 67: 1879-1882); gamma secretase inhibitor XIII, (Z-Tyr-Ile-Leu-CHO, available from Calbiochem); gamma secretase inhibitor XIV, (Z-Cys(t-Bu)-Ile-Leu-CHO, available from Calbiochem); gamma secretase inhibitor XVII, (also known as WPE-III-31C)

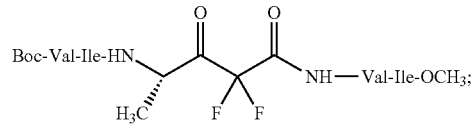

(MOL)(CDX) (available from Calbiochem); gamma secretase inhibitor XIX, (also known as benzodiazepine, (2S,3R)-3-(3,4-Difluorophenyl)-2-(4-fluorophenyl)-4-hydroxy-N-((3S)-2-oxo-5-phenyl-2,3-dihydro-1H-benzo[e][1,4]diazepin-3-yl)-butyramide, Churcher et al., (2003) J MED CHEM. 46(12):2275-8); gamma secretase inhibitor XX, (also known as dibenzazepine, (S,S)-2-[2-(3,5-Difluorophenyl)acetylamino]-N-(5-methyl-6-oxo-6,7-dihydro-5H-dibenzo[b,d]azepin-7-yl)propionamide,

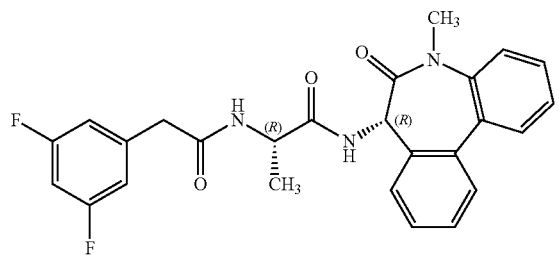

(MOL)(CDX) (Weihofen et al., Science 296: 2215-2218, 2002, available from Calbiochem); gamma secretase inhibitor XXI, ((S,S)-2-[2-(3,5-Difluorophenyl)-acetylamino]-N-(1-methyl-2-oxo-5-phenyl-2,3-dihydro-1H-benzo[e][1,4]diazepin-3-yl)-propionamide, available from Calbiochem); 5-methyl-2-propan-2-ylcyclohexyl)N-[4-methyl-1-[(4-methyl-1-oxopentan-2-yl)amino]-1-oxopentan-2-yl]carbamate (available from HDH Pharma Inc.); N-trans-3,5-Dimethoxycinnamoyl-Ile-leucinal (available from Calbiochem); N-tert-Butyloxycarbonyl-Gly-Val-Valinal; isovaleryl-V V-Sta-A-Sta-OCH3 (available from Calbiochem); diethyl-(5-phenyl-3H-azepin-2-yl)-amine (U.S. Pat. No. 8,188,069); diethyl-(5-isopropyl-3H-azepin-2-yl)-amine (U.S. Pat. No. 8,188,069); diethyl-(4-phenyl-3H-azepin-2-yl)-amine (U.S. Pat. No. 8,188,069); diethyl-(6-phenyl-3H-azepin-2-yl)-amine (U.S. Pat. No. 8,188,069); 5-phenyl-1,3-dihydro-azepin-2-one (U.S. Pat. No. 8,188,069); 5-Isopropyl-1,3-dihydro-azepin-2-one (U.S. Pat. No. 8,188,069); 4-phenyl-1,3-dihydro-azepin-2-one (U.S. Pat.

No. 8,188,069); 6-phenyl-1,3-dihydro-azepin-2-one (U.S. Pat. No. 8,188,069); 2-butoxy-5-phenyl-3H-azepine (U.S. Pat. No. 8,188,069); 1-methyl-5-phenyl-1,3-dihydro-azepin-2-one (U.S. Pat. No. 8,188,069); 5-isopropyl-1-methyl-1,3-dihydro-azepin-2-one (U.S. Pat. No. 8,188,069); 1-methyl-4-phenyl-1,3-dihydro-azepin-2-one (U.S. Pat. No. 8,188,069); 1-methyl-6-phenyl-1,3-dihydro-azepin-2-one (U.S. Pat. No. 8,188,069); 1-methyl-5-phenyl-1H-azepine-2,3-dione-3-oxime (U.S. Pat. No. 8,188,069); 5-isopropyl-1-methyl-1H-azepine-2,3-dione-3-oxime (U.S. Pat. No. 8,188,069); 1-methyl-6-phenyl-1H-azepine-2,3-dione-3-oxime (U.S. Pat. No. 8,188,069); 1-methyl-4-phenyl-1H-azepine-2,3-dione-3-oxime (U.S. Pat. No. 8,188,069); 3-amino-1-methyl-5-phenyl-1,3-dihydro-azepin-2-one (U.S. Pat. No. 8,188,069); 3-amino-5-isopropyl-1-methyl-1,3-dihydro-azepin-2-one (U.S. Pat. No. 8,188,069); 3-amino-1-methyl-4-phenyl-1,3-dihydro-azepin-2-one (U.S. Pat. No. 8,188,069); 3-amino-1-methyl-6-phenyl-1,3-dihydro-azepin-2-one (U.S. Pat. No. 8,188,069); (S)-[1-(1-methyl-2-oxo-5-phenyl-2,3-dihydro-1H-azepin-3-ylcarbamoyl)-ethyl]-carbamic acid tertbutyl ester (U.S. Pat. No. 8,188,069); [(S)-1-(5-isopropyl-1-methyl-2-oxo-2,3-dihydro-1H-azepin-3-ylcarbamoyl)-ethyl]carbamic acid tert-butyl ester (U.S. Pat. No. 8,188,069); [(S)-1-(1-methyl-2-oxo-4-phenyl-2,3-dihydro-1H-azepin-3-ylcarbamoyl)-ethyl]carbamic acid tert-butyl ester (U.S. Pat. No. 8,188,069); [(S)-1-(1-methyl-2-oxo-6-phenyl-2,3-dihydro-1H-azepin-3-ylcarbamoyl)-ethyl]-carbamic acid tert-butyl ester (U.S. Pat. No. 8,188,069); (S)-2-amino-N-(1-methyl-2-oxo-5-phenyl-2,3-dihydro-1H-azepin-3-yl)-propionamide (U.S. Pat. No. 8,188,069); (S)-2-amino-N-(5-isopropyl-1-methyl-2-oxo-2,3-dihydro-1H-azepin-3-yl)propionarnide (U.S. Pat. No. 8,188,069); (S)-2-Amino-N-(I-methyl-2-oxo-6-phenyl-2,3-dihydro-1H-azepin-3-yl)propionamide hydrochloride (U.S. Pat. No. 8,188,069); (S)-2-Amino-N-(I-methyl-2-oxo-4-phenyl-2,3-dihydro-1H-azepin-3-yl)propionamide hydrochloride (U.S. Pat. No. 8,188,069); (S)-2-fluoro-3-methyl-butyric acid (U.S. Pat. No. 8,188,069); (S)-2-hydroxy-3-methyl-N—[(S)-1-((S)-1-methyl-2-oxo-5-phenyl-2,3-dihydro-1H-azepin-3-ylcarbamoyl)-ethyl]-butyramide (U.S. Pat. No. 8,188,069); (S)-2-fluoro-3-methyl-N—[(S)-1-(1-methyl-2-oxo-5-phenyl-2,3-dihydro-1H-azepin-3-ylcarbamoyl)-ethyl]-butyramide (U.S. Pat. No. 8,188,069); (S)-2-hydroxy-N—[(S)-1-(5-isopropyl-1-methyl-2-oxo-2,3-dihydro-1H-azepin-3-ylcarbamoyl)ethyl]-3-methyl-butyramide (U.S. Pat. No. 8,188,069); (S)-2-hydroxy-3-methyl-N—[(S)-1-(1-methyl-2-oxo-4-phenyl-2,3-dihydro-1H-azepin-3-ylcarbamoyl)-ethyl]-butyramide (U.S. Pat. No. 8,188,069); (S)-2-hydroxy-3-methyl-N—[(S)-1-(1-methyl-2-oxo-6-phenyl-2,3-dihydro-1H-azepin-3-ylcarbamoyl)-ethyl]-butyramide (U.S. Pat. No. 8,188,069); and(S)-2-fluoro-3-methyl-N—[(S)-1-(1-methyl-2-oxo-6-phenyl-2,3-dihydro-1H-azepin-3-ylcarbamoyl)-ethyl]-butyramide (U.S. Pat. No. 8,188,069), and pharmaceutically acceptable salts thereof.

Additional examples of gamma-secretase inhibitors are disclosed in U.S. Patent Application Publication Nos. 2004/0029862, 2004/0049038, 2004/0186147, 2005/0215602, 2005/0182111, 2005/0182109, 2005/0143369, 2005/0119293, 2007/0190046, 2008/008316, 2010/0197660 and 2011/0020232; U.S. Pat. Nos. 6,756,511; 6,890,956; 6,984,626; 7,049,296; 7,101,895; 7,138,400; 7,144,910; 7,183,303; 8,188,069; and International Publication Nos. WO 1998/28268; WO 2001/70677, WO 2002/049038, WO 2004/186147, WO 2003/093253, WO 2003/093251, WO 2003/093252, WO 2003/093264, WO 2005/030731, WO 2005/014553, WO 2004/039800, WO 2004/039370, WO 2009/023453, EP 1720909, EP 2178844, EP 2244713.

Additional exemplary Notch inhibitors include nonsteroidal anti-inflammatory drugs (NSAIDs) such as flurbiprofen (Purow B, supra), MPC-7869 (Imbimbo BP, supra), ibuprofen (Id.), sulindac sulphide, indomethacin, alpha-secretase inhibitors (ASIs) (Purow B, supra), the Na+/H+ antiporter Monensin (Id.); small molecules that block Notch binding to interacting proteins such as Jagged, Numb, Numb-like, CBF1 transcription factor, and mastermind-like (MAML) (Id.; Ishikawa Y et al, supra.); antibodies that bind Notch proteins or Notch ligands such as Delta-Like-4 (Purow B, supra); stapled peptides that bind Notch such as SAHM1 (Id.); dominant-negative forms of genes such as MAML (Id; Ishikawa Y et al., supra), Numb/Numb-Like (Purow B, supra), and FBXW-7 (Id.); expression vectors that increase levels of Notch regulators such as FBXW-7 (Id.; Ishikawa Y et al., supra); siRNAs that target Notch transcripts (Purow B, supra); microRNAs such as miR-326, miR-34a, microRNA-206, and miR-124 (Id.); and Notch antibodies (U.S. Pat. No. 8,226,943, U.S. Publication No. 20090258026A2, PCT Publication WO2012080926A2).

Exemplary Atoh1 activators include, for example, β-Catenin or β-catenin pathway agonists, e.g., Wnt ligands, DSH/DVL1, 2, 3, LRP6δN, WNT3A, WNT5A, and WNT3A, 5A. Additional Wnt/β-catenin pathway activators and inhibitors are reviewed in the art (Moon et al., Nature Reviews Genetics, 5:689-699, 2004). In some embodiments, suitable Wnt/β-catenin pathway agonists can include antibodies and antigen binding fragments thereof, and peptides that bind specifically to frizzled (Fzd) family of receptors.

Kinase inhibitors, e.g., casein kinase 1 (CK1) and glycogen synthase kinase 3 β (GSK3β) inhibitors can also act as β-Catenin or β-catenin pathway agonists to activate Atoh1. GSK3β inhibitors include, but are not limited to, lithium chloride (LiCl), Purvalanol A, olomoucine, alsterpaullone, kenpaullone, benzyl-2-methyl-1,2,4-thiadiazolidine-3,5-dione (TDZD-8), 2-thio(3-iodobenzyl)-5-(1-pyridyl)-[1,3,4]-oxadiazole (GSK3 inhibitor II), 2,4-dibenzyl-5-oxothiadiazolidine-3-thione (OTDZT), (2′Z,3′E)-6-Bromoindirubin-3′-oxime (BIO), α-4-Dibromoacetophenone (i.e., Tau Protein Kinase I (TPK I) Inhibitor), 2-Chloro-1-(4,5-dibromo-thiophen-2-yl)-ethanone, N-(4-Methoxybenzyl)-N′-(5-nitro-1,3-thiazol-2-yl)urea (AR-A014418), and indirubins (e.g., indirubin-5-sulfonamide; indirubin-5-sulfonic acid (2-hydroxyethyl)-amide indirubin-3′-monoxime; 5-iodo-indirubin-3′-monoxime; 5-fluoroindirubin; 5,5′-dibromoindirubin; 5-nitroindirubin; 5-chloroindirubin; 5-methylindirubin, 5-bromoindirubin), 4-Benzyl-2-methyl-1,2,4-thiadiazolidine-3,5-dione (TDZD-8), 2-thio(3-iodobenzyl)-5-(1-pyridyl)-[1,3,4]-oxadiazole (GSK3 inhibitor II), 2,4-Dibenzyl-5-oxothiadiazolidine-3-thione (OTDZT), (2′Z,3′E)-6-Bromoindirubin-3′-oxime (BIO), α-4-Dibromoacetophenone (i.e., Tau Protein Kinase I (TPK I) Inhibitor), 2-Chloro-1-(4,5-dibromo-thiophen-2-yl)-ethanone, (vi)N-(4-Methoxybenzyl)-N′-(5-nitro-1,3-thiazol-2-yl)urea (AR-A014418), and H-KEAPPAPPQSpP-NH2 (L803) or its cell-permeable derivative Myr-N-GKEAPPAPPQSpP-NH2 (L803-mts). Other GSK3β inhibitors are disclosed in U.S. Pat. Nos. 6,417,185; 6,489,344; and 6,608,063. In some embodiments, suitable kinase inhibitors can include RNAi and siRNA designed to decrease GSK3β and/or CK1 protein levels. In some embodiments, useful kinase inhibitors include FGF pathway inhibitors. In some embodiments, FGF pathway inhibitors include, for example, SU5402.

Additional Atoh1 activators include gamma secretase inhibitors (e.g., arylsulfonamides, dibenzazepines, benzodiazepines, N—[N-(3,5-difluorophenacetyl)-L-alanyl]-(S)-phenylglycine t-butyl ester (DAPT; EMD Biosciences, San Diego, CA, USA), L-685,458, or MK0752ho, in addition to those listed above under Notch inhibitors), gentamycin, and the combination of transcription factors Eya1 and Six1 (and optionally Sox2), as described in Ahmed et al. (2012) DEV. CELL 22(2):377-390.

Additional Atoh1 activators are described in U.S. Pat. No. 8,188,131, including a compound represented by Formula I:

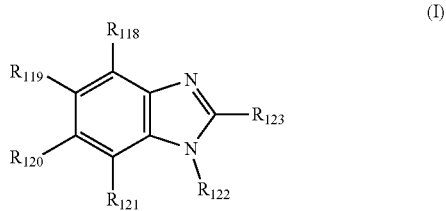

(I)

wherein:
each of $R_{118}$, $R_{119}$, $R_{120}$, and $R_{121}$ is, independently selected from H, halo, OH, CN, $NO_2$, $C_1$-$C_3$ alkyl, $C_1$-$C_3$ haloalkyl, $C_1$-$C_3$ alkoxy, and $C_1$-$C_3$ haloalkoxy;
$R_{122}$ is hydrogen or —Z—$R^a$; wherein:
Z is O or a bond; and
$R^a$ is:
  (i) $C_1$-$C_6$ alkyl or $C_1$-$C_6$ haloalkyl, each of which is optionally substituted with from 1-3 $R^b$; or
  (ii) $C_3$-$C_{10}$ cycloalkyl, $C_3$-$C_{10}$ cycloalkenyl, each of which is optionally substituted with from 1-5 $R^c$; or
  (iii) $C_7$-$C_{11}$ aralkyl, or heteroaralkyl including 6-11 atoms, each of which is optionally substituted with from 1-5 $R^c$;
  (iv) $C_6$-$C_{10}$ aryl or heteroaryl including 5-10 atoms, each of which is optionally substituted with from 1-5 $R^d$;
$R_{123}$ is:
  (i) hydrogen; or
  (ii) $C_1$-$C_6$ alkyl or $C_1$-$C_6$ haloalkyl, each of which is optionally substituted with from 1-3 $R^b$; or
  (iii) $C_6$-$C_{10}$ aryl or heteroaryl including 5-10 atoms, each of which is optionally substituted with from 1-5 $R^d$; or
  (iv) $C_7$-$C_{11}$ aralkyl, or heteroaralkyl including 6-11 atoms, each of which is optionally substituted with from 1-5 $R^c$; or
  (v) ($C_1$-$C_6$ alkyl)-$Z^1$—($C_6$-$C_{10}$ aryl), wherein Z is O, S, NH, or N($CH_3$); the alkyl portion is optionally substituted with from 1-3 $R^b$; and the aryl portion is optionally substituted with from 1-5 $R^d$; or
  (vi) ($C_1$-$C_6$ alkyl)-$Z^2$-(heteroaryl including 5-10 atoms), wherein $Z^2$ is O, S, NH, or N($CH_3$); the alkyl portion is optionally substituted with from 1-3 $R^b$; and the heteroaryl portion is optionally substituted with from 1-5 $R^d$; or
  (vii) ($C_1$-$C_6$ alkyl)-$Z^3$ ($C_3$-$C_{10}$ cycloalkyl), wherein $Z^3$ is O, S, NH, or N($CH_3$); the alkyl portion is optionally substituted with from 1-3 R; and the cycloalkyl portion is optionally substituted with from 1-5 $R^c$;
$R^b$ at each occurrence is, independently:
  (i) NH; NH($C_1$-$C_3$ alkyl); N($C_1$-$C_3$ alkyl)$_2$; hydroxy; $C_1$-$C_6$ alkoxy or $C_1$-$C_6$ haloalkoxy; or
  (ii) $C_3$-$C_7$ cycloalkyl optionally substituted with from 1-3 substituents independently selected from $C_1$-$C_6$ alkyl, NH; NH($C_1$-$C_3$ alkyl); N($C_1$-$C_3$ alkyl)$_2$; hydroxy; $C_1$-$C_6$ alkoxy or $C_1$-$C_6$ haloalkoxy;
$R^c$ at each occurrence is, independently:
  (i) halo; $NH_2$; NH($C_1$-$C_3$ alkyl); N($C_1$-$C_3$ alkyl)$_2$; hydroxy; $C_1$-$C_6$ alkoxy; $C_1$-$C_6$ haloalkoxy; or oxo; or
  (ii) $C_1$-$C_6$ alkyl or $C_1$-$C_6$ haloalkyl; and
$R^d$ at each occurrence is, independently:
  (i) halo; $NH_2$; NH($C_1$-$C_3$ alkyl); N($C_1$-$C_3$ alkyl)$_2$; hydroxy; $C_1$-$C_6$ alkoxy or $C_1$-$C_6$ haloalkoxy; nitro; NHC(O)($C_1$-$C_3$ alkyl); or cyano; or
  (ii) $C_1$-$C_6$ alkyl or $C_1$-$C_6$ haloalkyl; or a pharmaceutically acceptable salt thereof.

Other exemplary Atoh1 activators described in U.S. Pat. No. 8,188,131 include 4-(4-chlorophenyl)-1-(5H-pyrimido[5,4-b]indol-4-yl)-1H-pyrazol-3-amine; 6-chloro-1-(2-chlorobenzyloxy)-2-phenyl-1H-benzo[d]imidazole; 6-chloro-1-(2-chlorobenzyloxy)-2-(4-methoxyphenyl)-1H-benzo[d]imidazole; 6-chloro-2-(4-methoxyphenyl)-1-(4-methylbenzyloxy)-1H-benzo[d]imidazole; 6-chloro-1-(3,5-dimethylbenzyloxy)-2-(4-methoxyphenyl)-1H-benzo[d]imidazole; 6-chloro-1-(4-methoxybenzyloxy)-2-(4-methoxyphenyl)-1H-benzo[d]imidazole; 1-(4-methylbenzyloxy)-6-nitro-2-phenyl-1H-benzo[d]imidazole; 4-(1H-benzo[d] imidazol-2-yl)phenol; 2,5-dichloro-N-((1-methyl-H-benzo[d]imidazol-2-yl)methyl)aniline; 4-(2-(1-methyl-1H-benzo[d]imidazol-2-yl)ethyl)aniline; 2-((2-methoxyphenoxy)methyl)-1H-benzo[d]imidazole; 2-((4-fluorophenoxy)methyl)-1-methyl-1H-benzo[d]imidazole; 2-(phenylthiomethyl)-1H-benzo[d]imidazole; 3-(6-methyl-1H-benzo[d]imidazole-2-yl)-2H-chromen-2-imine; N-(2-(1H-benzo[d]imidazole-2-yl)phenyl)isobutyramide; 2-(o-tolyloxymethyl)-1H-benzo[d]imidazole; 2-(4-methoxyphenyl)-1-phenethyl-1H-benzo[d]imidazole; N-(6-bromobenzo[d]thiazole-2-yl)thiophene-2-carboxamide; N-(benzo[d]thiazole-2-yl)-1-methyl-1H-pyrazole-5-carboxamide; 2-(4-fluorobenzylthio)benzo[d]thiazole; 5-chloro-N-methylbenzo[d]thiazole-2-amine; N-(6-acetamidobenzo[d]thiazol-2-yl)furan-2-carboxamide; N-(6-fluorobenzo[d]thiazole-2-yl)-3-methoxybenzamide; 2-(benzo[d]oxazol-2-ylthio)-N-(2-chlorophenyl)acetamide; 5-chloro-2-phenylbenzo[d]oxazole; 5-methyl-2-m-tolylbenzo[d]oxazole; 2-(4-isobutoxyphenyl)-3-(naphthalen-2-yl)-2,3-dihydroquinazolin-4(1H)-one; N-(2-(2-(4-fluorophenyl)-2-oxoethylthio)-4-oxoquinazolin-3(4H)-yl)benzamide; 2-(4-chlorophenyl)-4-(4-methoxyphenyl)-1,4-dihydrobenzo[4,5]imidazo [1,2-a]pyrimidine; 2-(3-pyridyl)-4-(4-bromophenyl)-1,4-dihydrobenzo[4,5]imidazo [1,2-a]pyrimidine; N-sec-butyl-1,7,7-trimethyl-9-oxo-8,9-dihydro-7H-furo[3,2-f]chromene-2-carboxamide; N-(3-carbamoyl-5,6-dihydro-4H-cyclopenta[b]thiophen-2-yl)benzofuran-2-carboxamide; 3-chloro-N-(5-chloropyridin-2-yl)benzo[b]thiophene-2-carboxamide; 3-chloro-N-((tetrahydrofuran-2-yl)methyl)benzo[b]thiophene-2-carboxamide; N-(3-(5-chloro-3-methylbenzo[b]thiopen-2-yl)-1H-pyrazol-5-yl) acetamide; 2-(naphthalen-2-yl)-1H-indole; 2-(pyridin-2-yl)-1H-indole; N-(2-chlorophenyl)-2-(1H-indole-3-yl)-2-oxoacetamide; 2-m-tolylquinoline; 2-(4-(2-methoxyphenyl)piperazin-1-yl)quinolone; 2-(1H-benzo[d][1,2,3]triazol-1-yl)-N-(2,3-dihydro-1H-inden-2-yl)acetamide; 1-phenethyl-1H-benzo[d][1,2,3]triazole; 7-(4-fluorobenzyloxy)-2H-chromen-2-one; N-(2,4-dichlorophenyl)-8-methoxy-2H-chromene-3-carboxamide; N-(3-chlorophenyl)-8-methyl-3,4-dihydroquinoline-1(2H)-carbothioamide; 7-methoxy-5-methyl-2-phenyl-4H-chromen-4-one; 2-(3,4-dimethylphenyl)quinoxaline; 4-bromo-N-(5-chloropyridin-2-yl)benzamide; 3-amino-6,7,8,9-tetrahydro-5H-cyclohepta[e]thieno[2,3-b]pyridine-2-carboxamide; (Z)-3-methyl-N'-

(nicotinoyloxy)benzimidamide; N,N-diethyl-6-methoxythieno[2,3-b]quinoline-2-carboxamide; 6-(4-methoxyphenyl)-1,2,3,4-tetrahydro-1,5-naphthyridine; 5-bromo-N-(2-(phenylthio)ethyl) nicotinamide; N-(6-methylpyridin-2-yl)-2,3-dihydrobenzo[b][1,4]dioxine-6-carboxamide; 2-(4-methylbenzylthio)oxazolo [4,5-b]pyridine; N-(2-methoxyethyl)-5-p-tolylpyrimidin-2-amine; 4-(5-(benzo[b]thiophen-2-yl)pyrimidin-2-yl)morpholino; 4-(5-(4-fluorophenyl)pyrimidin-2-yl)morpholino; N-(4-bromo-3-methylphenyl)quinazoline-4-amine; N-(4-methoxyphenyl)quinazolin-4-amine; N-(3-methoxyphenyl)-9H-purin-6-amine; N,N-diethyl-1-m-tolyl-1H-pyrazolo[3,4-d]pyrimidin-4-amine; (5-(4-bromophenyl)furan-2-yl)(morpholino)methanone; (Z)-4-bromo-N'-(furan-2-carbonyloxy)benzimidamide; N-(4-iodophenyl)furan-2-carboxamide; 5-(5-(2,4-difluorophenyl)furan-2-yl)-1-(methylsulfonyl)-1H-pyrazole; 1-(3-amino-5-(4-tert-butylphenyl)thiophen-2-yl)ethanone; N-(3-cayano-4,5,6,7-tetrahydrobenzo[b]thiophen-2-yl)-2-fluorobenzamide; N-(5-chloropyridin-2-yl)thiophene-2-carboxamide; N-(2-(4-fluorophenoxy)ethyl)thiophene-2-carboxamide; 2,5-dimethyl-N-phenyl-1-(thiophen-2-ylmethyl)-1H-pyrrole-3-carboxamide; N-(3-cyanothiophen-2-yl)-4-isopropoxybenzamide; 2-(4-methoxyphenoxy)-N-(thiazol-2-yl)acetamide; 4-(4-methoxyphenyl)-N-(3-methylpyridin-2-yl)thiazol-2-amine; 4-(biphenyl-4-yl)thiazol-2-amine; 4-(4-(4-methoxyphenyl)thiazol-2-yl)-3-methylisoxazol-5-amine; N-(2-methoxyphenyl)-4-phenylthiazol-2-amine; 1-(4-amino-2-(m-tolylamino)thiazol-5-yl)-2-methylpropan-1-one; 4-(4-chlorophenyl)-1-(5H-pyrimido[5,4-b]indol-4-yl)-1H-pyrazol-3-amine; 2-(4-chlorophenyl)-6-ethyl-5-methylpyrazolo[1,5-a]pyrimidin-7(4H)-one; 5-methoxy-2-(5-phenyl-1H-pyrazol-3-yl)phenol; (3-(4-bromophenyl)-1-phenyl-1H-pyrazol-4-yl)methanol; N-(2,5-dichlorophenyl)-1-ethyl-1H-pyrazole-3-carboxamide; 4-chloro-1-methyl-N-(2-oxo-2-phenylethyl)-1H-pyrazole-3-carboxamide; N-(3-(5-tert-butyl-2-methylfuran-3-yl)-1H-pyrazole-5-yl)benzamide; N-(5-methylisoxazol-3-yl)benzo[d][1,3]dioxole-5-carboxamide; (5-(4-bromophenyl)isoxazole-3-yl)(morpholino)methanone; N-(4-bromophenyl)-5-isopropylisoxazole-3-carboxamide; 5-((4-chloro-2-methylphenoxy)methyl)-3-(pyridin-4-yl)-1,2,4-oxadiazole; 5-(2-methoxyphenyl)-3-p-tolyl-1,2,4-oxadiazole; 5-(phenoxymethyl)-3-(pyridin-3-yl)-1,2,4-oxadiazole; 5-(2-chloro-4-methylphenyl)-3-(pyridin-3-yl)-1,2,4-oxadiazole; 3-(2-chlorophenyl)-5-p-tolyl-1,2,4-oxadiazole; 5-(piperidin-1-ylmethyl)-3-p-toyl-1,2,4-oxadiazole; 5-(4-bromophenyl)-3-(pyridin-3-yl)-1,2,4-oxadiazole; 5-(2-bromophenyl)-3-(4-bromophenyl)-1,2,4-oxadiazole; 5-(2-bromo-5-methoxyphenyl)-3-(thiophenyl-2-yl)-1,2,4-oxadiazole; 3-(2-fluorophenyl)-N-(3-(piperidin-1-yl)propyl)-1,2,4-oxadiazol-5-amine; 2-(2-chlorobenzoyl)-N-(4-fluorophenyl)hydrazinecarbothioamide; 2-(methylamino)-N-phenethylbenzamide; 4-tert-butyl-N-((tetrahydrofuran-2-yl)methyl)benzamide; 2-phenyl-5-o-tolyl-1,3,4-oxadiazole; 4-(3-(4-chlorophenyl)-4,5-dihydro-1H-1,2,4-triazole-5-yl)-N,N-dimethylaniline; 7-methoxy-2-(4-methoxyphenyl)-1,10b-dihydrospiro[benzo[e]pyrazolo[1,5-c][1,3]oxazine-5,1'-cyclohexane]; 6-oxo-2-(4-(3-(trifluoromethyl)phenoxy)phenyl)-1,4,5,6-tetrahydropyridine-3-carbonitrile; 6-(4-methoxyphenyl)imidazo[2,1-b]thiazole; 2-(2-bromophenoxy)-N-(4H-1,2,4-triazol-3-yl)acetamide; 1-(indolin-1-yl)-2-phenoxyethanone; 2-(4-chlorophenyl)-6,7,8,9-tetrahydrobenzo[e]imidazo [1,2-b][1,2,4]triazine; and pharmaceutically acceptable salts thereof.

2. Delivery of Agents for Modulating c-myc, Notch and Atoh1

Delivery of Proteins, Activators and Inhibitors

The method of delivery of modulators of c-myc, Notch or Atoh1 activity will depend, in part, upon whether the hair cells or supporting cells are being contacted with the agents of interest in vivo or ex vivo. In the in vivo approach, the agents are delivered into the inner ear of a mammal. In the ex vivo approach, cells are contacted with the agents ex vivo. The resulting hair cells can then be transplanted into the inner ear of a recipient using techniques known and used in the art.

In certain embodiments, c-myc activity is increased by administering c-myc protein or a c-myc activator in the inner ear of a recipient to give, for example, a final concentration of greater than about 30 µM, for example, in the range of about 30 µM to about 1000 µM. In certain embodiments, the c-myc protein or c-myc activator can be administered in an amount sufficient to give a final concentration of greater than about 30 µM. For example, the c-myc protein or c-myc activator may be administered in an amount sufficient to give a final concentration in the range from about 30 µM to about 1000 µM, 50 µM to about 1000 µM, 80 µM to about 1000 µM, about 100 µM to about 1000 µM, about 150 µM to about 1000 µM, from about 200 µM to about 800 µM, or from about 200 µM to about 600 µM.

In other embodiments, c-myc protein or a c-myc activator is administered at a dose from about 0.025 mg to about 4 mg, from about 0.035 mg to about 2 mg, from about 0.05 mg to about 2 mg, from about 0.1 mg to about 2 mg, from about 0.2 mg to about 1 mg, or from about 0.2 mg to about 0.8 mg of the c-myc protein or c-myc activator can be administered locally to the inner ear of a mammal. In one embodiment, 0.5 mg of c-myc protein or c-myc activator is administered locally to the inner ear. In certain other embodiments, from about 0.05 mg to about 2 mg, from about 0.2 mg to about 2 mg, from about 0.05 mg to about 1.5 mg, from about 0.15 mg to about 1.5 mg, from about 0.4 mg to about 1 mg, or from about 0.5 mg to about 0.8 mg of c-myc protein or c-myc activator can be administered locally to the inner ear of a mammal.

In certain embodiments, Notch activity is increased by administering a Notch protein, a NICD protein or a Notch activator to an inner ear of a recipient to give a final concentration of greater than about 30 µM, for example, in the range of about 30 µM to about 1000 µM. In certain embodiments, a Notch protein, NICD protein or Notch activator can be administered in an amount sufficient to give a final concentration of greater than about 30 µM. For example, the Notch protein, NICD protein or Notch activator may be administered in an amount sufficient to give a final concentration in the range from about 30 µM to about 1000 µM, 50 µM to about 1000 µM, 80 µM to about 1000 µM, about 100 µM to about 1000 µM, about 150 µM to about 1000 µM, from about 200 µM to about 800 µM, or from about 200 µM to about 600 µM.

In other embodiments, Notch protein, NICD protein or Notch activator is administered at a dose from about 0.025 mg to about 4 mg, from about 0.035 mg to about 2 mg, from about 0.05 mg to about 2 mg, from about 0.1 mg to about 2 mg, from about 0.2 mg to about 1 mg, or from about 0.2 mg to about 0.8 mg of the Notch protein, NICD protein or Notch activator can be administered locally to the inner ear of a mammal. In one embodiment, 0.5 mg of Notch protein, NICD protein or Notch activator is administered locally to the inner ear of a mammal. In certain other embodiments, from about 0.05 mg to about 2 mg, from about 0.2 mg to about 2 mg, from about 0.05 mg to about 1.5 mg, from about 0.15 mg to about 1.5 mg, from about 0.4 mg to about 1 mg, or from about 0.5 mg to about 0.8 mg of Notch protein, NICD protein or Notch activator can be administered locally to the inner ear of a mammal.

In certain embodiments, after cell proliferation has occurred, Notch activity is inhibited by administering a Notch inhibitor. A Notch inhibitor can be administered to give a final concentration of greater than about 30 µM, for example, in the range of about 30 µM to about 1000 µM. In certain embodiments, a Notch inhibitor can be administered in an amount sufficient to give a final concentration of greater than about 30 µM. For example, the Notch inhibitor may be administered in an amount sufficient to give a final concentration in the range from about 30 µM to about 1000 µM, 50 µM to about 1000 µM, 80 µM to about 1000 µM, about 100 µM to about 1000 µM, about 150 µM to about 1000 µM, from about 200 µM to about 800 µM, or from about 200 µM to about 600 µM. In certain embodiments, the Notch inhibitor is administered in an amount sufficient to give a final concentration of about 400 µM.

In other embodiments, a Notch inhibitor is administered at a dose from about 0.025 mg to about 4 mg, from about 0.035 mg to about 2 mg, from about 0.05 mg to about 2 mg, from about 0.1 mg to about 2 mg, from about 0.2 mg to about 1 mg, or from about 0.2 mg to about 0.8 mg of the Notch inhibitor can be administered locally to the inner ear of a mammal. In one embodiment, 0.5 mg of Notch inhibitor is administered locally to the inner ear of a mammal. In certain other embodiments, from about 0.05 mg to about 2 mg, from about 0.2 mg to about 2 mg, from about 0.05 mg to about 1.5 mg, from about 0.15 mg to about 1.5 mg, from about 0.4 mg to about 1 mg, or from about 0.5 mg to about 0.8 mg of Notch inhibitor can be administered locally to the inner ear of a mammal. In certain embodiments, about 0.7 mg Notch inhibitor is administered locally to the inner ear of a mammal.

In certain embodiments, Atoh1 activity is increased by administering Atoh1 protein or an Atoh1 activator in the inner ear of a recipient to give, for example, a final concentration of greater than about 30 µM, for example, in the range of about 30 µM to about 1000 µM. In certain embodiments, the Atoh1protein or Atoh1 activator can be administered in an amount sufficient to give a final concentration of greater than about 30 µM. For example, the Atoh1protein or Atoh1 activator may be administered in an amount sufficient to give a final concentration in the range from about 30 µM to about 1000 µM, 50 µM to about 1000 µM, 80 µM to about 1000 µM, about 100 µM to about 1000 µM, about 150 µM to about 1000 µM, from about 200 µM to about 800 µM, or from about 200 µM to about 600 µM.

In other embodiments, Atoh1 protein or a Atoh1 activator is administered at a dose from about 0.025 mg to about 4 mg, from about 0.035 mg to about 2 mg, from about 0.05 mg to about 2 mg, from about 0.1 mg to about 2 mg, from about 0.2 mg to about 1 mg, or from about 0.2 mg to about 0.8 mg of the Atoh1 protein or Atoh1 activator can be administered locally to the inner ear of a mammal. In one embodiment, 0.5 mg of Atoh1 protein or Atoh1 activator is administered locally to the inner ear. In certain other embodiments, from about 0.05 mg to about 2 mg, from about 0.2 mg to about 2 mg, from about 0.05 mg to about 1.5 mg, from about 0.15 mg to about 1.5 mg, from about 0.4 mg to about 1 mg, or from about 0.5 mg to about 0.8 mg of Atoh1 protein or Atoh1 activator can be administered locally to the inner ear of a mammal.

Delivery of DNA

In some aspects, the activity of c-myc, Notch or Atoh1 can be increased in a target cell using expression constructs known in the art, e.g., naked DNA constructs, DNA vector based constructs, and/or viral vector and/or viral based constructs to express nucleic acids encoding a desired c-myc, Notch or Atoh1 protein. In certain embodiments, a single DNA construct expressing c-myc and Notch or NICD as two separate genes can be delivered into the inner ear of a subject. In certain embodiments, a single DNA construct expressing c-myc and Notch or NICD and Atoh1 as three separate genes can be delivered into the inner ear of a subject.

Exemplary expression constructs can be formulated as a pharmaceutical composition, e.g., for administration to a subject.

DNA constructs and the therapeutic use of such constructs are well known to those of skill in the art (see, e.g., Chiarella et al. (2008) RECENT PATENTS ANTI-INFECT. DRUG DISC. 3:93-101; Gray et al. (2008) EXPERT OPIN. BIOL. THER. 8:911-922; Melman et al. (2008) HUM. GENE THER. 17:1165-1176). Naked DNA constructs typically include one or more therapeutic nucleic acids (e.g., DNA encoding c-myc and/or Notch) and a promoter sequence. A naked DNA construct can be a DNA vector, commonly referred to as pDNA. Naked DNA typically do not integrate into chromosomal DNA. Generally, naked DNA constructs do not require, or are not used in conjunction with, the presence of lipids, polymers, or viral proteins. Such constructs may also include one or more of the non-therapeutic components described herein.

DNA vectors are known in the art and typically are circular double stranded DNA molecules. DNA vectors usually range in size from three to five kilo-base pairs (e.g., including inserted therapeutic nucleic acids). Like naked DNA, DNA vectors can be used to deliver and express one or more therapeutic proteins in target cells. DNA vectors do not integrate into chromosomal DNA.

Generally, DNA vectors include at least one promoter sequence that allows for replication in a target cell. Uptake of a DNA vector may be facilitated by combining the DNA vector with, for example, a cationic lipid, and forming a DNA complex. Typically, viral vectors are double stranded circular DNA molecules that are derived from a virus. Viral vectors typically are larger in size than naked DNA and DNA vector constructs and have a greater capacity for the introduction of foreign (i.e., not virally encoded) genes. Like naked DNA and DNA vectors, viral vectors can be used to deliver and express one or more therapeutic nucleic acids in target cells. Unlike naked DNA and DNA vectors, certain viral vectors stably incorporate themselves into chromosomal DNA. Typically, viral vectors include at least one promoter sequence that allows for replication of one or more vector encoded nucleic acids, e.g., a therapeutic nucleic acid, in a host cell. Viral vectors may optionally include one or more non-therapeutic components described herein. Advantageously, uptake of a viral vector into a target cell does not require additional components, e.g., cationic lipids. Rather, viral vectors transfect or infect cells directly upon contact with a target cell.

The approaches described herein include the use of retroviral vectors, adenovirus-derived vectors, and/or adeno-associated viral vectors as recombinant gene delivery systems for the transfer of exogenous genes in vivo, particularly into humans. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14, and other standard laboratory manuals.

Viruses that are used as transduction agents of DNA vectors and viral vectors such as adenoviruses, retroviruses, and lentiviruses may be used in practicing the present invention. Illustrative retroviruses include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus. As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV).

In certain embodiments, an adenovirus can be used in accordance with the methods described herein. The genome of an adenovirus can be manipulated such that it encodes and expresses a gene product of interest but is inactivated in terms of its ability to replicate in a normal lytic viral life cycle. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors.

Adeno-associated virus is a naturally occurring defective virus that requires another virus, such as an adenovirus or a herpes virus, as a helper virus for efficient replication and a productive life cycle. It is also one of the few viruses that may integrate its DNA into non-dividing cells, and exhibits a high frequency of stable integration.

In various embodiments, one or more viral vectors that expresses a therapeutic transgene or transgenes encoding a polypeptide or polypeptides of the invention (e.g., Atoh1, Notch, c-myc) is administered by direct injection to a cell, tissue, or organ of a subject, in vivo.

In various other embodiments, cells are transduced in vitro or ex vivo with such a vector encapsulated in a virus, and optionally expanded ex vivo. The transduced cells are then administered to the inner ear of a subject. Cells suitable for transduction include, but are not limited to stem cells, progenitor cells, and differentiated cells. In certain embodiments, the transduced cells are embryonic stem cells, bone marrow stem cells, umbilical cord stem cells, placental stem cells, mesenchymal stem cells, neural stem cells, liver stem cells, pancreatic stem cells, cardiac stem cells, kidney stem cells, hematopoietic stem cells, inner ear hair cells, iPS cells, inner ear supporting cells, cochlear cells, or utricular cells.

In particular embodiments, host cells transduced with viral vector of the invention that expresses one or more polypeptides, are administered to a subject to treat and/or prevent an auditory disease, disorder, or condition. Other methods relating to the use of viral vectors, which may be utilized according to certain embodiments of the present invention, can be found in, e.g., Kay (1997) CHEST 111(6 Supp.):138S-142S; Ferry et al. (1998) HUM. GENE THER. 9:1975-81; Shiratory et al. (1999) LIVER 19:265-74; Oka et al. (2000) CURR. OPIN. LIPIDOL. 11:179-86; Thule et al. (2000) Gene Ther. 7: 1744-52; Yang (1992) CRIT. REV. BIOTECHNOL. 12:335-56; Alt (1995) J. HEPATOL. 23:746-58; Brody et al. (1994) ANN. N. Y. ACAD. SCI. 716:90-101; Strayer. (1999) EXPERT OPIN. INVESTIG. DRUGS 8:2159-2172; Smith-Arica et al. (2001) CURR. CARDIOL. REP. 3:43-49; and Lee et al. (2000) NATURE 408:483-8.

In some embodiments of the invention, it may be desirable to use a cell, cell type, cell lineage or tissue specific expression control sequence to achieve cell type specific, lineage specific, or tissue specific expression of a desired polynucleotide sequence, for example, to express a particular nucleic acid encoding a polypeptide in only a subset of cell types, cell lineages, or tissues, or during specific stages of development. Illustrative examples of cell, cell type, cell lineage or tissue specific expression control sequences include, but are not limited to: an Atoh1 enhancer for all hair cells (see, e.g., FIG. 24); a Pou4f3 promoter for all hair cells (see, e.g., FIG. 25); a Myo7a promoter for all hair cells (see, e.g., FIG. 26); a Hes5 promoter for vestibular supporting cells and cochlear inner phalangeal cells, Deiters cells and Pillar cells (see, e.g., FIG. 27); and GFAP promoter for vestibular supporting cells and cochlear inner phalangeal cells, Deiters cells and Pillar cells (see, e.g., FIG. 28).

Certain embodiments of the invention provide conditional expression of a polynucleotide of interest. For example, expression is controlled by subjecting a cell, tissue, organism, etc., to a treatment or condition that causes the polynucleotide to be expressed or that causes an increase or decrease in expression of the polynucleotide encoded by the polynucleotide of interest. Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, GENE, 323: 67), the cumate inducible gene switch (WO 2002/088346), tetracycline-dependent regulatory systems, etc.

Conditional expression can also be achieved by using a site specific DNA recombinase. According to certain embodiments of the invention the vector comprises at least one (typically two) site(s) for recombination mediated by a site specific recombinase. As used herein, the terms "recombinase" or "site specific recombinase" include excisive or integrative proteins, enzymes, co-factors or associated proteins that are involved in recombination reactions involving one or more recombination sites (e.g., two, three, four, five, seven, ten, twelve, fifteen, twenty, thirty, fifty, etc.), which may be wild-type proteins (see Landy (1993) CURRENT OPINION IN BIOTECHNOLOGY 3:699-707), or mutants, derivatives (e.g., fusion proteins containing the recombination protein sequences or fragments thereof), fragments, and variants thereof. Illustrative examples of recombinases suitable for use in particular embodiments of the present invention include, but are not limited to: Cre, Int, IF, Xis, Flp, Fis, Hin, Gin, OC31, Cin, Tn3 resolvase, TndX, XerC, XerD, TnpX, Hjc, Gin, SpCCE1. and ParA.

The vectors may comprise one or more recombination sites for any of a wide variety of site specific recombinases. It is to be understood that the target site for a site specific recombinase is in addition to any site(s) required for integration of a vector (e.g., a retroviral vector or lentiviral vector).

In certain embodiments, vectors comprise a selection gene, also termed a selectable marker. Typical selection genes encode proteins that (a) confer resistance to antibiotics or other toxins, e.g., ampicillin, neomycin, hygromycin, methotrexate, Zeocin, Blastocidin, or tetracycline, (b) complement auxotrophic deficiencies, or (c) supply critical nutrients not available from complex media, e.g., the gene encoding D-alanine racemase for Bacilli. Any number of selection systems may be used to recover transformed cell lines. These include, but are not limited to, the herpes simplex virus thymidine kinase (Wigler et al., (1977) CELL 11:223-232) and adenine phosphoribosyltransferase (Lowy et al., (1990) CELL 22:817-823) genes which can be employed in tk– or aprt– cells, respectively.

All the molecular biological techniques required to generate an expression construct described herein are standard techniques that will be appreciated by one of skill in the art.

In certain embodiments, DNA delivery may occur auricularly, parenterally, intravenously, intramuscularly, or even intraperitoneally as described, for example, in U.S. Pat. Nos. 5,543,158; 5,641,515; and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

In certain embodiments, DNA delivery may occur by use of liposomes, nanocapsules, microparticles, microspheres, lipid particles, vesicles, optionally mixing with cell penetrating polypeptides, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

Exemplary formulations for ex vivo DNA delivery may also include the use of various transfection agents known in the art, such as calcium phosphate, electroporation, heat shock and various liposome formulations (i.e., lipid-mediated transfection). Particular embodiments of the invention may comprise other formulations, such as those that are well known in the pharmaceutical art, and are described, for example, in Remington: The Science and Practice of Pharmacy, 20th Edition. Baltimore, MD: Lippincott Williams & Wilkins, 2000.

Duration of Delivery

The duration of c-myc, Notch and Atoh1 activation can be varied to achieve a desired result. For example, it may be beneficial to expose a target cell to a c-myc protein or c-myc activator and a Notch protein, NICD protein, or a Notch activator for one to six days, one week, two weeks, three weeks, one month, three months, six months, nine months, one year, two years or more. Alternatively, when c-myc is increased by constitutive activation (e.g., using an adenovirus to overexpress c-myc), the duration of increased c-myc activity can be controlled by administering a c-myc inhibitor following administration of a myc protein or a myc activator. Inhibiting c-myc activity after a period of increased c-myc activity can be used to control proliferation, promote cell survival, and avoid tumorigenesis.

Similarly, the duration of increased Notch activity can be controlled by administering a Notch inhibitor, as discussed above, following administration of a Notch protein, NICD protein, or a Notch activator.

Route of Administration and Formulation

The route of administration will vary depending on the disease being treated. Hair cell loss, sensorineural hearing loss, and vestibular disorders can be treated using direct therapy using systemic administration and/or local administration. In certain embodiments, the route of administration can be determined by a subject's health care provider or clinician, for example following an evaluation of the subject.

The invention provides (i) a composition for use in proliferating or regenerating a cochlear or a utricular hair cell, (ii) a composition for use in proliferating or regenerating a cochlear or a utricular supporting cell, (iii) a composition for use in reducing the loss of, maintaining, or promoting hearing in a subject, and (iv) a composition for use in reducing the loss of, maintaining, or promoting vestibular function in a subject. Accordingly, the invention provides a first composition comprising an agent, for example, each of the agents discussed hereinabove, for example, an agent that increases c-myc activity and/or an agent that increases Notch activity within a hair or supporting cell, either alone or in combination with a pharmaceutically acceptable carrier for use in each of the foregoing approaches. In addition, the invention provides a second composition comprising an agent, for each of the agents discussed hereinabove, for example, an agent that reduces or inhibits c-myc activity and/or an agent that reduces or inhibits Notch activity within a hair or supporting cell, either alone or in combination with in a pharmaceutically acceptable carrier for use in each of the foregoing approaches. When supporting cells are regenerated, the invention provides a third composition comprising an agent, for example, an agent for increasing Atoh1 activity, to induce transdifferentiation of a proliferated supporting cell into a hair cell.

In certain embodiments, a c-myc protein or c-myc activator and a Notch protein, NICD protein or Notch activator can be formulated as a pharmaceutical composition containing the appropriate carriers and/or excipients.

The c-myc protein or activator and/or the Notch protein, NICD protein, or Notch activator, and/or the Atoh1 protein or activator can be solubilized in a carrier, for example, a viscoelastic carrier, that is introduced locally into the inner ear. In other embodiments, the c-myc protein or activator and/or the Notch protein, NICD protein, or Notch activator, and/or Atoh1 protein or activator can be solubilized in a liposome or microsphere. Methods for delivery of a drug or combination of drugs in liposomes and/or microspheres are well-known in the art.

In addition, it is contemplated that the c-myc protein or activator and/or the Notch protein, NICD protein, or Notch activator, and/or Atoh1 protein or activator can be formulated so as to permit release of one or more proteins and/or activators over a prolonged period of time. A release system can include a matrix of a biodegradable material or a material, which releases the incorporated active agents. The active agents can be homogeneously or heterogeneously distributed within a release system. A variety of release systems may be useful in the practice of the invention, however, the choice of the appropriate system will depend upon the rate of release required by a particular drug regime. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic.

In certain embodiments, the agents can be administered to a subject, e.g., a subject identified as being in need of treatment for hair cell loss, using a systemic route of administration. Systemic routes of administration can include, but are not limited to, parenteral routes of administration, e.g., intravenous injection, intramuscular injection, and intraperitoneal injection; enteral routes of administration, e.g., administration by the oral route, lozenges, compressed tablets, pills, tablets, capsules, drops (e.g., ear drops), syrups, suspensions and emulsions; rectal administration, e.g., a rectal suppository or enema; a vaginal suppository; a urethral suppository; transdermal routes of administration; and inhalation (e.g., nasal sprays).

Alternatively or in addition, the agents can be administered to a subject, e.g., a subject identified as being in need of treatment for hair cell loss, using a local route of administration. Such local routes of administration include administering one or more compounds into the ear of a subject and/or the inner ear of a subject, for example, by injection and/or using a pump.

In certain embodiments, the agents may be injected into the ear (e.g., auricular administration), such as into the luminae of the cochlea (e.g., the Scala media, Sc vestibulae, and Sc tympani). For example, the agents can be administered by intratympanic injection (e.g., into the middle ear), and/or injections into the outer, middle, and/or inner ear. Such methods are routinely used in the art, for example, for the administration of steroids and antibiotics into human ears. Injection can be, for example, through the round window of the ear or through the cochlea capsule.

In other embodiments, the agents can be delivered via nanoparticles, for example, protein-coated nanoparticles. Nanoparticles can be targeted to cells of interest based on cell-type specific receptor affinity for ligands coating the nanoparticles. The dosage of the agent can be modulated by regulating the number of nanoparticles administered per dose.

Alternatively, the agent may be administered to the inner ear using a catheter or pump. A catheter or pump can, for example, direct the agent into the cochlea luminae or the round window of the ear. Exemplary drug delivery systems suitable for administering one or more compounds into an ear, e.g., a human ear, are described in U.S. Patent Publication No. 2006/0030837 and U.S. Pat. No. 7,206,639. In certain embodiments, a catheter or pump can be positioned, e.g., in the ear (e.g., the outer, middle, and/or inner ear) of a subject during a surgical procedure.

Alternatively or in addition, the agents can be delivered in combination with a mechanical device such as a cochlea implant or a hearing aid, which is worn in the outer ear. An exemplary cochlea implant that is suitable for use with the present invention is described in U.S. Patent Publication No. 2007/0093878.

In certain embodiments, the modes of administration described above may be combined in any order and can be simultaneous or interspersed. For example, the agents may be administered to a subject simultaneously or sequentially. It will be appreciated that when administered simultaneously, the agents may be in the same pharmaceutically acceptable carrier (e.g., solubilized in the same viscoelastic carrier that is introduced into the inner ear) or the two agents may be dissolved or dispersed in separate pharmaceutical carriers, which are administered at the same time. Alternatively, the agents may be provided in separate dosage forms and administered sequentially.

Alternatively or in addition, the agents may be administered according to any of the Food and Drug Administration approved methods, for example, as described in CDER Data Standards Manual, version number 004 (which is available at fda.give/cder/dsm/DRG/drg00301.htm).

3. Delivery of Agents to Hair Cells and Supporting Cells Ex Vivo

It is understood that the concepts for delivering agents of interest to hair cells and supporting cells in vivo can also apply to the delivery of the agents of interest to hair cells and supporting cells ex vivo. The hair cells and supporting cells can be harvested and cultured using techniques known and used in the art. The agents (protein expression vectors, activators and inhibitors (for example, as discussed above)) can then be contacted with the cultured hair cells or supporting cells to induce the cells to reenter the cell cycle, and proliferate. Thereafter, once the cells have proliferated, the c-myc and Notch activities can be inhibited using appropriate inhibitors, for example, those discussed above. The resulting hair cells can then be maintained in culture for any number of uses, including, for example, to study the biological, biophysical, physiological and pharmacological characteristics of hair cells and/or supporting cells. Alternatively, the resulting hair cells can then be implanted in to the inner ear of a recipient using standard surgical procedures.

In certain embodiments, suitable cells can be derived from a mammal, such as a human, mouse, rat, pig, sheep, goat, or non-human primate. In certain embodiments, the cells can be harvested from the inner ear of a subject, and cells can be obtained from the cochlea organ of Corti, the modiolus (center) of the cochlea, the spiral ganglion of the cochlea, the vestibular sensory epithelia of the saccular macula, the utricular macula, or the cristae of the semicircular canals. Alternatively or in addition, methods include obtaining tissue from the inner ear of the animal, where the tissue includes at least a portion of the utricular maculae.

Tissue isolated from a subject can be suspended in a neutral buffer, such as phosphate buffered saline (PBS), and subsequently exposed to a tissue-digesting enzyme (e.g., trypsin, leupeptin, chymotrypsin, and the like) or a combination of enzymes, or a mechanical (e.g., physical) force, such as trituration, to break the tissue into smaller pieces. Alternatively, or in addition, both mechanisms of tissue disruption can be used. For example, the tissue can be incubated in about 0.05% enzyme (e.g., about 0.001%, 0.01%, 0.03%, 0.07%, or 1.0% of enzyme) for about 5, 10, 15, 20, or 30 minutes, and following incubation, the cells can be mechanically disrupted. The disrupted tissue can be passed through a device, such as a filter or bore pipette, that separates a stem cell or progenitor cell from a differentiated cell or cellular debris. The separation of the cells can include the passage of cells through a series of filters having progressively smaller pore size. For example, the filter pore size can range from about 80 µm or less, about 70 µm or less, about 60 µm or less, about 50 µm or less, about 40 µm or less, about 30 µm or less, about 35 µm or less, or about 20 µm or less.

Partially and/or fully differentiated cells, e.g., generated by the methods described above, can be maintained in culture for a variety of uses, including, for example, to study the biological, biophysical, physiological and pharmacological characteristics of hair cells and/or supporting cells. Cell cultures can be established using inner ear cells from subjects with hearing loss and/or loss in vestibular function to develop potential treatments (e.g., to screen for drugs effective in treating the hearing loss and/or loss in vestibular function). Further, the methods of the present invention can be used in combination with induced pluripotent stem (iPS) cell technology to establish cell lines (e.g., hair cell lines and/or supporting cell lines). For example, fibroblasts from a subject with hearing loss can be induced to form iPS cells using known techniques (see, for example, Oshima et al. (2010) CELL 141(4):704-716). However, because the numbers of cells generated using iPS cell technology is limited, the methods provided herein can be used in combination with iPS cell technology to produce sufficient numbers of cells to establish cell lines (e.g., hair cell lines and/or supporting cell lines).

Partially and/or fully differentiated cells, e.g., generated by the methods described above, can be transplanted or implanted, such as in the form of a cell suspension, into the ear by injection, such as into the luminae of the cochlea. Injection can be, for example, through the round window of the ear or through the bony capsule surrounding the cochlea. The cells can be injected through the round window into the auditory nerve trunk in the internal auditory meatus or into the scala tympani. In certain embodiments, the cells described herein can be used in a cochlea implant, for example, as described in U.S. Patent Publication No. 2007/0093878.

To improve the ability of transplanted or implanted cells to engraft, cells can be modified prior to differentiation. For example, the cells can be engineered to overexpress one or more anti-apoptotic genes. The Fak tyrosine kinase or Akt genes are candidate anti-apoptotic genes that can be used for this purpose; overexpression of FAK or Akt can prevent cell death in spiral ganglion cells and encourage engraftment when transplanted into another tissue, such as an explanted organ of Corti (see, for example, Mangi et al., (2003) NAT. MED. 9:1195-201). Neural progenitor cells overexpressing $\alpha_v\beta_3$ integrin may have an enhanced ability to extend neurites into a tissue explant, as the integrin has been shown to mediate neurite extension from spiral ganglion neurons on laminin substrates (Aletsee et al., (2001) AUDIOL. NEUROOTOL. 6:57-65). In another example, ephrinB2 and ephrinB3 expression can be altered, such as by silencing with RNAi or overexpression with an exogenously expressed cDNA, to modify EphA4 signaling events. Spiral ganglion neurons have been shown to be guided by signals from EphA4 that are mediated by cell surface expression of ephrin-B2 and -B3 (Brors et al., (2003) J. COMP. NEUROL. 462:90-100). Inactivation of this guidance signal may enhance the number of neurons that reach their target in an adult inner ear. Exogenous factors such as the neurotrophins BDNF and NT3, and LIF can be added to tissue transplants to enhance the extension of neurites and their growth towards a target tissue in vivo and in ex vivo tissue cultures. Neurite extension of sensory neurons can be enhanced by the addition of neurotrophins (BDNF, NT3) and LIF (Gillespie et al. (2010) NEUROREPORT 12:275-279).

4. Measurement of c-myc, Notch or Atoh1 Activity in Target Cells

The methods and compositions described herein can be used to induce cells, e.g., adult mammalian inner ear cells, to reenter the cell cycle and proliferate. For example, the number of hair cells can be increased about 2-, 3-, 4-, 6-, 8-, or 10-fold, or more, as compared to the number of hair cells before treatment. The hair cell can be induced to reenter the cell cycle in vivo or ex vivo. It is contemplated that using these approaches it may be possible to improve the hearing of a recipient. For example, using the methods and compositions described herein, it may be possible to improve the hearing of a recipient by at least about 5, 10, 15, 20, 40, 60, 80, or 90% relative to the hearing prior to the treatment. Tests of auditory or vestibular function also can be performed to measure hearing improvement.

Cells that have been contacted with (i) a c-myc protein or c-myc activator and/or (ii) a Notch protein, NICD protein or Notch activator, can be assayed for markers indicative of cell cycle reentry and proliferation. In one example, a cell can be assayed for incorporation of EdU (5-ethynyl-2'-deoxyuridine) followed sequentially by BrdU (5-bromo-2'-deoxyuridine) by using, for example, an anti-EdU antibody and an anti-BrdU antibody. Labelling by EdU and/or BrdU is indicative of cell proliferation. In addition, double labeling of EdU and BrdU can be used to demonstrate that a cell has undergone division at least two times. Alternatively or in addition, a cell can be assayed for the presence of phosphorylated histone H3 (Ph3) or aurora B, which are indicative of a cell that has reentered the cell cycle and is undergoing metaphase and cytokinesis.

Cell markers can also be used to determine whether a target cell, e.g., a hair cell or a supporting cell, has entered the cell cycle. Exemplary markers indicative of hair cells include Myo7a, Myo6, Prestin, Lhx3, Dner, espin, parvalbumin, and calretinin. Exemplary markers indicative of supporting cells include Sox2, S100a1, Prox1, Rps6, and Jag1. Double labeling of a cell cycle and/or proliferation marker and a cell-type molecule can be used to determine which cells have reentered the cell cycle and are proliferating.

In addition, neuronal markers, e.g., acetylated tubulin, neurofilament and CtBP2, can be used to detect neuronal structure, to determine whether proliferating hair cells are in contact with neurons. The presence of neuronal markers adjacent to or in contact with hair cells suggests that newly-generated hair cells have formed synapses with neurons (e.g., ganglion neurons) and that the hair cells are differentiated.

Where appropriate, following treatment, the subject, for example, a human subject, can be tested for an improvement in hearing or in other symptoms related to inner ear disorders. Methods for measuring hearing are well-known and include pure tone audiometry, air conduction, auditory brainstem response (ABR) and bone conduction tests. These exams measure the limits of loudness (intensity) and pitch (frequency) that a human can hear. Hearing tests in humans include behavioral observation audiometry (for infants to seven months), visual reinforcement orientation audiometry (for children 7 months to 3 years) and play audiometry for children older than 3 years. Oto-acoustic emission testing can be used to test the functioning of the cochlea hair cells, and electro-cochleography provides information about the functioning of the cochlea and the first part of the nerve pathway to the brain. In certain embodiments, treatment can be continued with or without modification or can be stopped.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions may be conducted simultaneously.

EXAMPLES

The invention is further illustrated by the following examples, which are provided for illustrative purposes only, and should not be construed as limiting the scope or content of the invention in any way.

Example 1: In Vivo Induction of Cell Cycle Reentry in Adult Cochlear Cells Via C-Myc and Notch This example demonstrates that providing c-myc and Notch to cells of the inner ear of an adult animal can induce cell cycle reentry and cell proliferation among differentiated cochlear hair and supporting cells.

Adult mice aged between 1 and 15 months were used to investigate the potential for c-myc and Notch to induce cell cycle reentry, proliferation, differentiation, and survival among cochlear hair and supporting cells. In separate experiments, the mice used were either wild type (WT) background mice or mice harboring a LoxP-flanked NICD cassette (NICD$^{flox/flox}$) susceptible to Cre-mediated recombination resulting in activation of NICD expression. The NICD cassette encoded (from 5' to 3') an intracellular fragment of mouse Notch1 (amino acids 1749-2293, lacking the C-terminal PEST domain, see Murthaugh et al. (2003) PROC. NATL. ACAD. SCI. U.S.A. 100(25):14920-14925.) Mice were anaesthetized and cochleostomy was performed to allow injection of adenovirus. Virus was injected via the scala media, facilitating infection of hair and supporting cells within the cochlear sensory epithelium. A mixture of adenovirus carrying a combination of either human c-myc (Ad-Myc) and CRE-GFP (Ad-Cre-GFP) expression cassettes or c-myc and NICD (Ad-NICD) expression cassettes was injected into the cochlea of either NICD$^{flox/flox}$ or WT mice, respectively. One ear per mouse was injected, while the other ear served as an uninjected control. An additional control was used in which cochlea were injected with Ad-Cre-GFP alone. Ad-Myc induced myc overexpression, Ad-NICD induced NICD overexpression, and Ad-CRE-GFP induced overexpression of CRE-GFP, recombination at loci flanked by LoxP sequences, and—in the case of NICD$^{flox/flox}$ mice—NICD overexpression. Virus titered at 2×10$^{12}$ plaque-forming units (pfu) was mixed in equal parts, and a total of 0.6 μL virus was injected per animal. Following viral injection, 5-bromo-2-deoxyuridine (BrdU) was injected daily between 1 and 5 days.

Mice were sacrificed and cochlea were harvested at either 4, 8, 12, 35, or 60 days post-viral injection. Cochlea were dissected, fixed, and decalcified prior to whole mount immunostaining. Hair cells were identified via labeling with antibodies directed against Myo7a and espin. Supporting cells were identified via labeling with antibodies directed against Sox2. Cell cycle reentry and proliferation were assessed via labeling antibodies directed against BrdU. Nuclear labeling was achieved via DAPI exposure.

Figure 7:
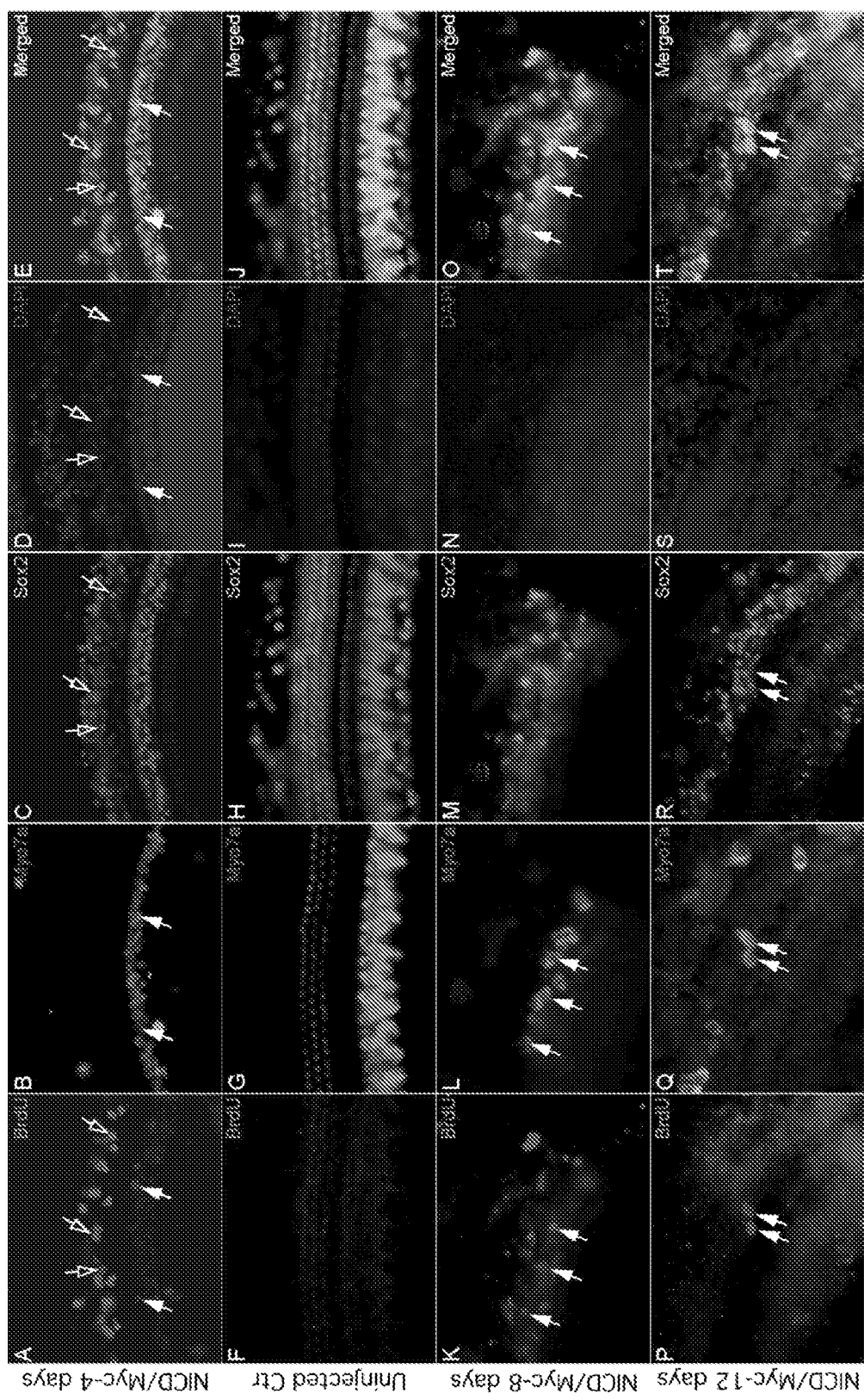
FIG. 7 shows cochlear hair and supporting cells double-labeled with cell-type specific markers and BrdU 4 days (panels A-E), 8 days (panels K-O), or 12 days (panels P-T) post-injection of Ad-Cre-GFP virus and Ad-Myc virus into cochleas of 45-day-old NICD$^{flox/flox}$ mice. Solid arrows indicate BrdU labeled hair cells and open arrows indicate BrdU labeled supporting cells. Panels F-J show an uninjected control cochlea in which no hair and supporting cells double-labeled with cell-type specific markers and BrdU could be found. Panels A, F, K, and P show BrdU labeling. Panels B, G, L, and Q show Myo7a labeling of hair cells. Panels C, H, M, and R show Sox2 labeling of supporting cells. Panels D, I, N, and S show DAPI labeling of cell nuclei. Panels E, J, O, and T show merged images.

Cells of the cochlear epithelium exposed to c-myc and NICD via viral injection were analyzed to determine whether cell cycle reentry and proliferation occurred. Cochlea from NICD$^{flox/flox}$ mice injected with Ad-Cre-GFP and Ad-Myc followed by BrdU administration were harvested at 4, 8, or 12 days post-virus injection and immunostained (FIG. 7). At all time points analyzed, immunostained sections revealed the presence of cycling hair cells as determined by BrdU+/Myo7a+ (FIG. 7, panels A, B, E, K, L, O, P, Q, T, closed arrows) staining. At 4 days post-injection, BrdU+/Sox2+ (FIG. 7, panels A, B, E, open arrows) staining showed that supporting cells also reentered the cell cycle in this population. These findings demonstrate that cochlear hair cells and supporting cells can be induced to reenter the cell cycle following exposure to c-myc and NICD. BrdU-labeled hair cell doublets (assumed to be daughter cells derived from the same cell division) at 12 days post-virus injection were observed, demonstrating that cells induced to reenter the cell cycle following c-Myc and NICD exposure can subsequently proliferate (FIG. 7, panels P-T, arrows). Furthermore, BrdU staining in cochlear cells was not observed in uninjected control ears at any time point (FIG. 7, panels F-J, showing 4 day time point). These observations suggest that exposing differentiated cochlear hair and supporting cells to increased c-myc and Notch activity induces cell cycle reentry within these populations.

Figure 8:
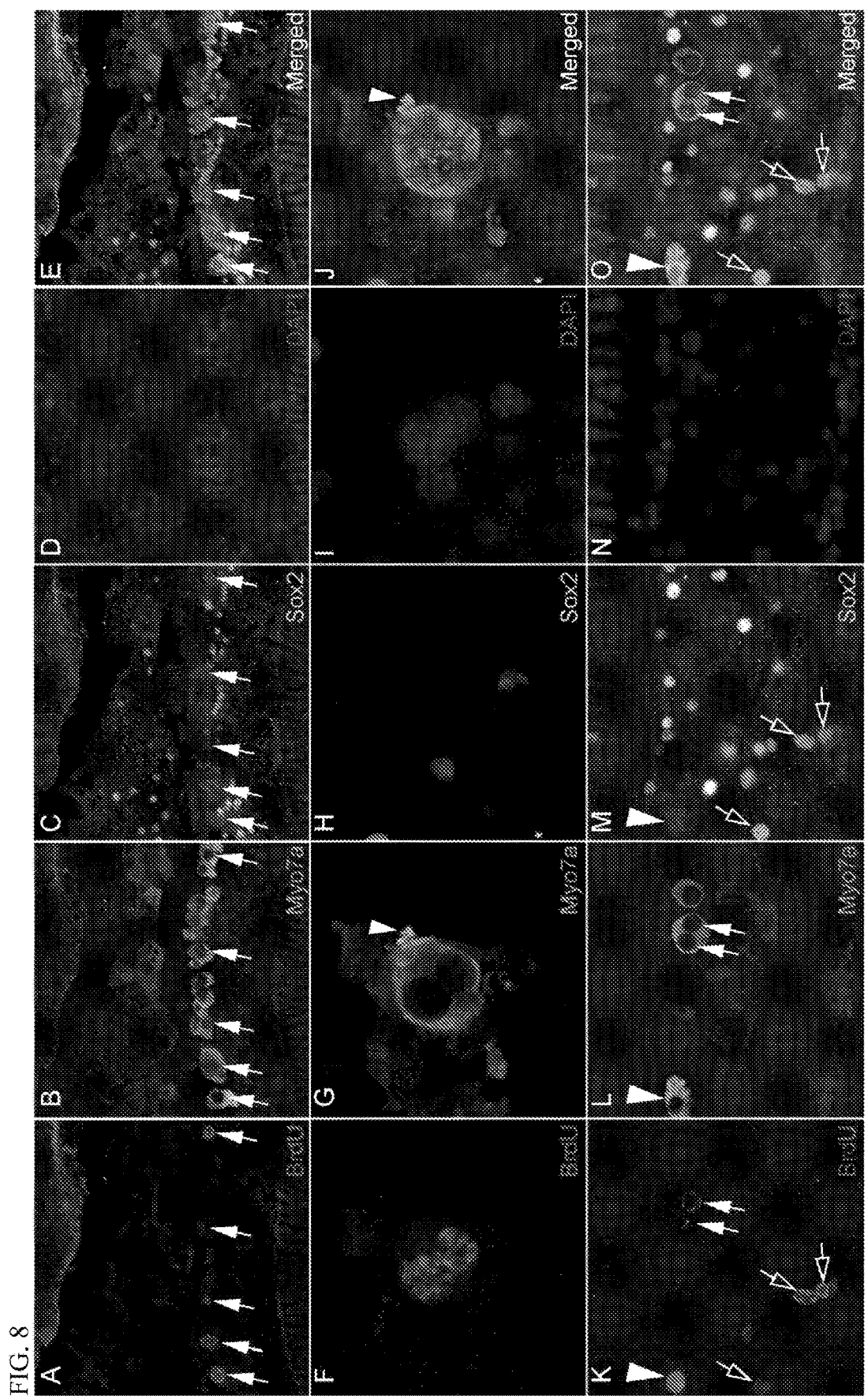
FIG. 8 shows cochlear hair and supporting cells double-labeled with cell-type specific markers and BrdU in the cochlear epithelium of NICD$^{flox/flox}$ mice 35 days post-injection of an Ad-Cre-GFP/Ad-Myc mixture followed by 5 days of daily BrdU administration. Panels A, F, and K show BrdU labeling. Panels B, G, and L show Myo7a labeling of hair cells. Panels C, H, and M show Sox2 labeling of supporting cells. Panels D, I, and N show DAPI labeling of cell nuclei. Panels E, J, and O show merged images. Panels A-E show labeling with BrdU and Myo7a, demonstrating that proliferating hair cells survive 35 days post-injection (solid arrows, panels A, B, C, and E). panels F-J show an enlarged image of two hair cells displaying stereocilia (solid arrowhead, Panel J) derived from division of one mother hair cell. Panels K-O show cells labeled with BrdU and Sox2

The in vivo cell survival of hair and supporting cells induced to reenter the cell cycle at more distant time points after viral injection was assessed. Cochlear tissue from NICD$^{flox/flox}$ mice infected with Ad-Cre-GFP and Ad-Myc virus and subsequently subjected to BrdU injection was harvested 35 days post-virus injection and immunostained to assess cell cycle reentry and survival of cycling hair and supporting cells. Analysis of stained cochlea at this time point again revealed the presence of proliferating hair and supporting cells (FIG. 8). Myo7a-positive hair cells stained positive for BrdU in cochlear epithelia subjected to BrdU labeling and harvested 35 days post-virus injection were observed (FIG. 8, panels A-E, arrows). In the same animals, BrdU-labeled Sox2-positive supporting cells were observed (FIG. 8, panels K-O, open arrows). A dividing hair cell in which Sox2 is activated by Notch is also shown (FIG. 8, panel M, arrowhead). These observations demonstrate that supporting cells and hair cells induced to reenter the cell cycle following exposure to increased c-myc and Notch activity can survive for at least 35 days in vivo. BrdU-labeled hair cells displaying stereocilia following c-Myc and NICD virus exposure at this time point were also observed (FIG. 8, panels F-J, arrowhead in panel J). This finding demonstrates that hair cells induced to reenter the cell cycle or their progeny retain physical characteristics of differentiated hair cells.

In a similar set of experiments, a mixture of Ad-Myc and Ad-NICD was injected into the scala media of WT mice followed by daily administration of BrdU from one to five days. Cochlea were harvested at time points between 2 and 35 days post-virus injection and immunostained. Immunostaining with antibodies directed against BrdU, Myo7a, and Sox2 antigens revealed the presence of double-labeled hair (BrdU+/Myo7a+) and supporting (BrdU+/Sox2+) cells in harvested cochlea. (Data not shown.) Accordingly, exposure to increased c-myc and Notch activity in differentiated hair and supporting cells of WT background also induces cell cycle reentry and proliferation.

Example 2: In Vivo Induction of Cell Cycle Reentry in Cochlear Cells of Aged Mice Via C-Myc and Notch The following example demonstrates that providing c-myc and Notch to cells of the inner ear can also induce cell cycle reentry and cell proliferation among differentiated cochlear hair and supporting cells in aged animal subjects.

Ad-Myc and Ad-Cre-GFP were injected once into 17-month old NICD$^{flox/flox}$ mouse cochlear scala media via cochleostomy and the animals were harvested 15 days later. 0.3 μl of a mixture of an equal amount of Ad-Cre-GFP and Ad-Myc with a titer of 2×10$^{12}$ was injected. BrdU (50 μg/g body weight) was also injected once per day for 15 days to label cycling cells. The same protocol was used as a control, in which only Ad-Cre was injected into the cochlea. Cochlear tissue harvested following BrdU and virus injection demonstrated that cells of the aged mouse cochlea underwent cell re-entry, as evidenced by the presence of double-labeled hair (BrdU+/Myo7a+) and supporting (BrdU+/Sox2+; FIG. 9, panels A-J; arrows identify double-labeled hair cells; arrowheads identify double-labeled support cells). By contrast, no BrdU labeling was observed in Sox2+ support or Myo7a+ hair cells in 17-month old NICD$^{flox/flox}$ control animals injected with Ad-Cre alone and subjected to the same BrdU labeling time course (FIG. 9, panels K-O).

These results demonstrate that inner ear hair and support cell proliferation can be achieved in aged mice, which suggest that similar effects can be achieved in the aged human inner ear.

Example 3: Induction of Cell Cycle Reentry in Cultured Adult Cells Harvested from Inner Ear Tissue of Various Mammals The following example demonstrates that exposure to increased c-myc and Notch activity supports cell cycle reentry and proliferation of adult mouse, monkey and human hair and supporting cells of the inner ear.

In order to investigate whether increased c-myc and Notch activity induce cell cycle reentry and proliferation in human cells, adult human cochlear and utricular tissue was collected. Samples were derived from surgeries during which such tissue was discarded. Cells were cultured in high glucose Dulbecco's modified Eagle's medium and F12 medium supplemented with N2 and B27 (Media and supplements were from Invitrogen/GIBCO/BRL, Carlsbad, CA), and 1% FBS was added.

A working viral titer of 10$^8$ was used for 5 mL of culture. Cultures of harvested tissue and transduced cultured cells were contacted with a mixture of Ad-Myc and Ad-NICD, to elevate cellular levels of c-myc and NICD. Following virus exposure, the cycling cells were labeled via 3 μg/ml BrdU administration to the culture. As in the in vivo studies of transduced mouse tissue, BrdU-labeled supporting (Sox2+) cells and at least one BrdU-labeled hair (Myo7a+) cell in cultured human tissue (FIG. 10) were identified.

BrdU+/Sox2+ supporting cells were identified in the cochlear cultures (FIG. 10, panels A, C, D, E) and utricular cultures (FIG. 10, panels F, H, I, J; all panels, open arrows). The cochlear cell cultures contained virtually no hair cells, so no BrdU-labeled cochlear hair cells were detected. Exposure to virus resulted in few labeled hair cells in utricular cultures, which may be the result of low infection rate of hair cells by adenovirus. However, at least one BrdU+/Myo7a+ hair cell was identified in the human utricular cultures (FIG. 10, panels F, G, I, J; closed arrow).

Similar culture-based experiments were performed utilizing harvested mouse utricle as the culture tissue. In the latter experiments, tissue was derived from either NICD$^{flox/flox}$ or WT mice and infected with a mixture of Ad-Myc/Ad-Cre-GFP or Ad-Myc/Ad-NICD, respectively. Following viral transduction, the cells were exposed to BrdU to label the cycling cells. BrdU was added to a final concentration of 3 μg/ml. As in the human utricle culture-based experiments, BrdU-labeled hair and supporting cells in the murine cultures were observed, demonstrating that these cells can reenter the cell cycle upon exposure to increased levels of Notch and c-myc activity. Examples of BrdU-labeled hair and supporting cells were observed in these cultures, although the majority of BrdU-labeled cells were supporting cells. Based on these findings, it appears that increased c-myc and Notch activity induces cell cycle reentry and proliferation in cultured hair and supporting cells of the inner ear.

Additionally, experiments were performed in cultured cochlea harvested from adult monkeys. The culture medium contained DMEM/F12 supplied with N2 and B27 without serum. Cultured cochlea were exposed to an Ad-Myc/Ad-NICD mixture (final titer of 109) for 16 hours, and the medium was replaced with fresh medium for 4 days. EdU was added at the final concentration of 10 μM. Cycling cells were additionally labeled via EdU administration. Cultured cochlea were fixed and stained for hair and supporting cell markers, as well as EdU. Cycling Sox2+/EdU+ supporting cells were observed following exposure to elevated levels of c-Myc and NICD (FIG. 11, panels G, H, and J; arrowheads). Thus, this example demonstrates that cells of the monkey inner ear can also be induced to proliferate following exposure to elevated levels of c-Myc and Notch activity, suggesting that the disclosed method can be applied to mammals other than mice, e.g., primates. In cultured control monkey cochlea infected with Ad-Cre in the presence of EdU, no EdU labeled cells were seen (FIG. 11, panels A-E), a demonstration that no cells underwent proliferation. It is generally observed, both in cultured mouse and monkey cochlea that surviving inner hair cells rarely re-entered cell cycle, in contrast to mouse cochlea in vivo, in which inner hair cells could readily be induced to proliferation by the combination of c-Myc and NICD. It is likely that inner hair cells require a higher concentration of Myc and NICD and more time to proliferate, as the titer used in culture was not as high as in vivo (10$^9$ vs. 10$^{12}$) and the tissues were harvested within a short period of time after infection (4 days).

Example 4: Dose-Dependent Induction of Cell Proliferation in Cochlear Cell Subpopulations The following example illustrates that different populations of cochlear hair cells are induced to proliferate upon varying degrees of exposure to c-myc and Notch activity.

An osmotic pump (Alzet) was implanted in the back of adult (45-day-old) doxycycline-inducible mice (rtTa/tet-on-Myc/tet-on-NICD) with tubing inserted to the round window niche to continuously dispense doxycycline (150 mg/ml in DMSO) at a rate of 1 μl per hour for 9 days, with concurrent EdU administration (200 μg/g body weight) by ip injection once daily to label proliferating cells. Using this procedure, c-Myc and NICD were activated in all cochlear cell types including supporting cells and hair cells (data not shown). Due to the surgical procedure, the cochlea in this sample lost all outer hair cells with only supporting cells and some inner hair cells remaining. Exposure of cochlear cells to this level of c-myc and NICD resulted in proliferation of Sox2+ supporting cells (FIG. 12, panels B, C, and E; arrows). By contrast Parv+ inner hair cells did not appear to divide upon exposure to these levels of c-myc and NICD (FIG. 12, panels A and E; arrowheads).

Additionally, the rTta/Tet-on-myc/Tet-on-NICD mouse model was used to examine induction of proliferation in outer hair cells. rTta/Tet-on-myc/Tet-on-NICD mice were exposed to doxycycline exposure for 12 days, accompanied by EdU administration once daily during the 12 day period to label cycling cells, following the same procedure described for FIG. 12. Tissue was then harvested and stained for markers of hair cells (Esp) and supporting cells (Sox2). In this case, EdU+/Esp+ proliferating outer hair cells were observed following tissue harvest and staining (FIG. 13, panels A, B, and E; arrows). No cell proliferation was observed in inner hair cells. As this method activates c-Myc and NICD in all cochlear cell types, this example demonstrates that exposure of outer hair cells to elevated c-Myc and Notch activity can selectively induce outer hair cell cycle reentry and proliferation. In the same cochlea, fewer supporting cells (compared to outer hair cells) labeled with EdU were also seen (data not shown), which is consistent with the observation that outer hair cells have a greater capacity for cell cycle re-entry following c-Myc and NICD activation. This sample (FIG. 13) contrasts with the sample shown in FIG. 12 in that most of the outer hair cells survived and showed heightened proliferation capacity. It further indicates that after loss of outer hair cells, supporting cells can be induced to proliferate upon c-Myc and NICD activation (FIG. 12).

Taken together, these results indicate that while all populations of cochlear hair and supporting cells can be induced to differentiate upon exposure to elevated levels of c-myc and Notch activity, different subpopulations within the cochlea respond to different levels of c-myc and Notch exposure. For example, outer hair cells respond to lower levels of c-myc and Notch stimulation than supporting cells and inner hair cells. Supporting cells respond to lower levels of c-myc and Notch stimulation than inner hair cells, but require higher levels of c-myc and Notch stimulation than outer hair cells. Inner hair cells appear to require higher levels of c-myc and Notch stimulation than supporting cells and outer hair cells to promote cell proliferation.

Example 5: Functional Characteristics of Hair Cells Produced by Myc and Notch Exposure The following examples demonstrate that hair cells produced by applying the methods described herein possess characteristics of functional hair cells.

The presence of signal transduction channels necessary for hair cell function was assessed in hair cells produced by elevated Myc and Notch exposure. 45-day-old NICD$^{flox/flox}$ mice were injected with Ad-Cre-GFP and Ad-Myc mixture in the scala media using cochleostomy. EdU was injected for 5 days daily following adenovirus injection to label proliferating hair cells. 35 days post-virus injection, mouse cochleas were dissected and incubated with fluorescence dye FM1-43FX for 30 seconds before cochleas were washed and fixed. Fixed tissues were decalcified and stained with Espin (Esp) for hair cells. Cells that underwent proliferation were labeled by EdU. FIG. 14 shows that control Esp+ hair cells that did not undergo cell cycle reentry following EdU exposure (EdU−) took up FM1-43FX (FIG. 14, panels A-E). Significantly, Esp+ hair cells that reenter the cell cycle following Ad-Myc/Ad-NICD virus injection and EdU exposure (EdU+) also took up FM1-43FX (FIG. 14, panels F-J). As FM1-43FX rapidly enters hair cells through functional transduction channels, labeling by FM1-43FX demonstrates the presence of functional transduction channels in proliferating hair cells similar to non-proliferating hair cells. This result demonstrates that hair cells produced by exposure to elevated Myc and Notch activity possess functional membrane channels that are essential for hair cell function.

Synapse formation was also assessed in cells exposed to elevated levels of c-Myc and Notch activity in vivo. Adult (45-day-old) NICD$^{flox/flox}$ mice were transduced with an Ad-Myc/Ad-Cre virus mixture, exposed to BrdU administration, and analyzed for evidence of functional synapse formation as described for FIG. 9. Tissue was harvested 20 days post-injection of virus and stained for neurofilament (NF) to identify neurofibers of ganglion neurons. Analysis of stained sections revealed the presence of proliferating hair cells (Myo7a+/BrdU+) that were in contact with NF+ neurofibers (FIG. 15, panels A, C, and E; arrows). This result suggests that production of hair cells via the methods disclosed herein is accompanied by regrowth of neurofibers and formation of functional synapses crucial for hair cell function.

Example 6: Hair Cells Induced to Proliferate In Vivo Maintain Specific Hair Cell Identity The following example illustrates that inner hair cells produced in vivo via induced proliferation of existing inner hair cells maintain characteristics specific to inner hair cells.

Cochlea of adult NICD$^{flox/flox}$ mice were transduced in vivo with an Ad-Myc/Ad-Cre virus mixture for 15 days with BrdU injected daily for the first 5 days. The methods used are the same as those described for FIG. 9. Cochlear tissue was harvested and analyzed for inner hair cell-specific markers. Both inner hair cells that underwent cell cycle reentry (FIG. 16, panels A-E; arrow) and those that did not undergo cell cycle reentry (FIG. 16, panels A-E; arrowhead) stained positive for Vesicular Glutamate Transporter-3 (Vglut3), an inner hair cell-specific marker. Furthermore, the same cells also stained positive for C-Terminal Binding Protein 2 (CtBP2) (brackets), a presynaptic marker, indicating the presence of functional synapses. By contrast, in control animals exposed to Ad-GFP, no BrdU labeling was observed, although Vglut3+/CtBP2+ inner hair cells were detected (FIG. 16, panels F-J, bracket). The results show that induced proliferation of inner hair cells via exposure to elevated c-myc and Notch activity produce inner hair cells with markers of functional synapses.

Example 7: Transdifferentiation of Proliferating Supporting Cells in Culture

The following example demonstrates that application of the methods described herein can be used to induce proliferation and transdifferentiation of inner ear support cells to a hair cell fate.

Experiments were performed using a mouse model capable of expressing elevated levels of myc and Notch following doxycycline induction (rTta/Tet-on-Myc/Tet-on-NICD). Adult mouse (rTta/Tet-on-Myc/Tet-on-NICD) cochlea was dissected, with three holes drilled to the bone for efficient media exposure and cultured in the DMEM/F12 supplied with N2 and B27 without serum. Doxycycline (1 mg/ml) was added to the culture for 5 days to activate c-Myc/NICD, followed by Ad-Atoh1 ($2\times10^{12}$, 1:100 dilution) infection for 16 hours. The culture was exchanged with fresh medium for additional 14 days, with medium changed every 3 days. EdU (final concentration 10 M) was added to the culture throughout the entire period. Support cells induced to express elevated NICD and myc levels via doxycycline exposure were observed to undergo cell proliferation as evidenced by EdU labeling (FIG. 17, panels A-E, arrowheads and closed arrows). Furthermore, exposure to Ad-Atoh1 resulted in transdifferentiation of both cycling (FIG. 17, panels A, C, E, closed arrows) and non-cycling (FIG. 17, panels B, C, E, open arrow) support cells to a hair cell fate as evidenced by Myo7a and Parvalbumin (Parv) staining. Control, cultured rTta/Tet-on-Myc/Tet-on-NICD support cells exposed to Ad-Atoh1, but not doxycycline, underwent transdifferentiation but failed to undergo cell cycle reentry (FIG. 17, panels F-J, arrow), as evidenced by the presence of Myo7a+/Parv+/EdU− cells. In a similar experiment, cultured cochlear supporting cells harvested from rTta/Tet-on-Myc/Tet-on-NICD mice were exposed to doxycycline and Ad-Atoh1 virus, and then exposed to FM1-43FX (3 M) for 30 seconds to investigate whether hair cells produced by this process possess characteristics of functional hair cells. Esp staining of cells subjected to this protocol revealed the presence of hair bundles in transdifferentiated supporting cells that also stained positive for FM1 uptake, revealing the presence of functional membrane channels (FIG. 17, panels K and O; arrow). Other transdifferentiated cells were labeled with FM1, but did not show signs of cell cycle reentry as they are EdU negative (FIG. 17, panels K and O; arrowhead). Thus, exposure of cultured cochlear support cells to elevated levels of myc and Notch, followed by Atoh1 induced proliferation of supporting cells and transdifferentiation to a hair cell fate, where the cells generated possessed characteristics of functional hair cells.

Example 8: Induction of Inner Ear Progenitor Gene Expression

In order to understand how cell fate is affected by elevated c-myc and Notch activity, a study of mRNA transcripts expressed following exposure to c-Myc and NICD was performed.

Adult NICD$^{flox/flox}$ mouse cochleas were cultured and infected with Ad-Myc/Ad-Cre-GFP overnight ($2\times10^{12}$ in 1:100 dilution). Beginning the next day, the media was changed daily for the next 4 days. Ad-Cre-GFP infected NICD$^{flox/flox}$ mouse cochleas were used as controls. The infected cochleas were harvested for mRNA isolation using QIAGEN mRNA isolation kit. cDNAs were synthesized using Life Science Technology SuperScript III reverse transcriptase kit. Semi-quantitative RT-PCR was performed using standard protocol. Analysis of different sets of transcripts revealed that stem cell gene transcripts (e.g., Nanog, ALPL, SSEA) were not noticeably upregulated following c-myc and NICD exposure. By contrast, most of the analyzed transcripts specific to ear progenitor cells (e.g., Eya1, DLX5, Six1, Pax2, p27kip1, NICD, Prox1, Hes5) were upregulated following exposure to c-myc and NICD (FIG. 18). GAPDH served as an internal control for normalization of signal intensity. These results suggest a decisive advantage inherent in using the method disclosed herein, as opposed to using embryonic stem cells. Specifically, these results demonstrate that exposure to elevated c-Myc and Notch activity results in elevated levels of progenitor, rather than stem cell gene expression, which likely allows the inner ear cells to both re-enter the cell cycle and maintain the desired cell fate.

INCORPORATION BY REFERENCE

The entire disclosure of each of the patent documents and scientific articles cited herein are incorporated by reference in their entirety for all purposes.

EQUIVALENTS

The invention can be embodied in other specific forms with departing from the essential characteristics thereof. The foregoing embodiments therefore are to be considered illustrative rather than limiting on the invention described herein. The scope of the invention is indicated by the appended claims rather than by the foregoing description, and all changes that come within the meaning and range of equivalency of the claims are intended to be embraced therein.

I claim:

1. A method of inducing proliferation of a mammalian cochlear cell in vivo, the method comprising administering (i) a nucleic acid encoding a c-myc protein and (ii) a nucleic acid encoding a Notch intracellular domain (NICD) protein to the inner ear of a mammal such that a cochlear cell is induced to proliferate.

2. A method of inducing proliferation of a mammalian cochlear cell in vitro, the method comprising administering (i) a nucleic acid encoding a c-myc protein and (ii) a nucleic acid encoding a Notch intracellular domain (NICD) protein to isolated mammalian cochlear cells such that the isolated mammalian cochlear cells are induced to proliferate.

* * * * *

SEQUENCE LISTING

```
<160> NUMBER OF SEQ ID NOS: 28

<210> SEQ ID NO 1
<211> LENGTH: 454
<212> TYPE: PRT
<213> ORGANISM: Homo sapiens

<400> SEQUENCE: 1

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
                20                  25                  30

Ser Val Gln Pro Tyr Phe Tyr Cys Asp Glu Glu Glu Asn Phe Tyr Gln
            35                  40                  45

Gln Gln Gln Gln Ser Glu Leu Gln Pro Pro Ala Pro Ser Glu Asp Ile
        50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
                100                 105                 110
```

Gln Leu Glu Met Val Thr Glu Leu Leu Gly Gly Asp Met Val Asn Gln
            115                 120                 125

Ser Phe Ile Cys Asp Pro Asp Glu Thr Phe Ile Lys Asn Ile Ile
        130                 135                 140

Ile Gln Asp Cys Met Trp Ser Gly Phe Ser Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ser Glu Cys Ile Asp Pro Ser Val
        195                 200                 205

Val Phe Pro Tyr Pro Leu Asn Asp Ser Ser Pro Lys Ser Cys Ala
210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
            260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
        355                 360                 365

Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
        435                 440                 445

Leu Arg Asn Ser Cys Ala
    450

<210> SEQ ID NO 2
<211> LENGTH: 2555
<212> TYPE: PRT
<213> ORGANISM: Homo sapiens

<400> SEQUENCE: 2

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu

```
              20                  25                  30
Asn Gly Gly Lys Cys Glu Ala Ala Asn Gly Thr Glu Ala Cys Val Cys
            35                  40                  45
Gly Gly Ala Phe Val Gly Pro Arg Cys Gln Asp Pro Asn Pro Cys Leu
            50                  55                  60
Ser Thr Pro Cys Lys Asn Ala Gly Thr Cys His Val Val Asp Arg Arg
65                  70                  75                  80
Gly Val Ala Asp Tyr Ala Cys Ser Cys Ala Leu Gly Phe Ser Gly Pro
                        85                  90                  95
Leu Cys Leu Thr Pro Leu Asp Asn Ala Cys Leu Thr Asn Pro Cys Arg
                100                 105                 110
Asn Gly Gly Thr Cys Asp Leu Leu Thr Leu Thr Glu Tyr Lys Cys Arg
            115                 120                 125
Cys Pro Pro Gly Trp Ser Gly Lys Ser Cys Gln Gln Ala Asp Pro Cys
            130                 135                 140
Ala Ser Asn Pro Cys Ala Asn Gly Gly Gln Cys Leu Pro Phe Glu Ala
145                 150                 155                 160
Ser Tyr Ile Cys His Cys Pro Pro Ser Phe His Gly Pro Thr Cys Arg
                    165                 170                 175
Gln Asp Val Asn Glu Cys Gly Gln Lys Pro Gly Leu Cys Arg His Gly
                180                 185                 190
Gly Thr Cys His Asn Glu Val Gly Ser Tyr Arg Cys Val Cys Arg Ala
            195                 200                 205
Thr His Thr Gly Pro Asn Cys Glu Arg Pro Tyr Val Pro Cys Ser Pro
        210                 215                 220
Ser Pro Cys Gln Asn Gly Gly Thr Cys Arg Pro Thr Gly Asp Val Thr
225                 230                 235                 240
His Glu Cys Ala Cys Leu Pro Gly Phe Thr Gly Gln Asn Cys Glu Glu
                245                 250                 255
Asn Ile Asp Asp Cys Pro Gly Asn Asn Cys Lys Asn Gly Gly Ala Cys
            260                 265                 270
Val Asp Gly Val Asn Thr Tyr Asn Cys Arg Cys Pro Pro Glu Trp Thr
        275                 280                 285
Gly Gln Tyr Cys Thr Glu Asp Val Asp Glu Cys Gln Leu Met Pro Asn
        290                 295                 300
Ala Cys Gln Asn Gly Gly Thr Cys His Asn Thr His Gly Gly Tyr Asn
305                 310                 315                 320
Cys Val Cys Val Asn Gly Trp Thr Gly Glu Asp Cys Ser Glu Asn Ile
                325                 330                 335
Asp Asp Cys Ala Ser Ala Ala Cys Phe His Gly Ala Thr Cys His Asp
                340                 345                 350
Arg Val Ala Ser Phe Tyr Cys Glu Cys Pro His Gly Arg Thr Gly Leu
            355                 360                 365
Leu Cys His Leu Asn Asp Ala Cys Ile Ser Asn Pro Cys Asn Glu Gly
            370                 375                 380
Ser Asn Cys Asp Thr Asn Pro Val Asn Gly Lys Ala Ile Cys Thr Cys
385                 390                 395                 400
Pro Ser Gly Tyr Thr Gly Pro Ala Cys Ser Gln Asp Val Asp Glu Cys
                405                 410                 415
Ser Leu Gly Ala Asn Pro Cys Glu His Ala Gly Lys Cys Ile Asn Thr
                420                 425                 430
Leu Gly Ser Phe Glu Cys Gln Cys Leu Gln Gly Tyr Thr Gly Pro Arg
            435                 440                 445
```

```
Cys Glu Ile Asp Val Asn Glu Cys Val Ser Asn Pro Cys Gln Asn Asp
    450                 455                 460

Ala Thr Cys Leu Asp Gln Ile Gly Glu Phe Gln Cys Ile Cys Met Pro
465                 470                 475                 480

Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
            500                 505                 510

Gln Cys Glu Cys Pro Thr Gly Phe Thr Gly His Leu Cys Gln Tyr Asp
        515                 520                 525

Val Asp Glu Cys Ala Ser Thr Pro Cys Lys Asn Gly Ala Lys Cys Leu
    530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Arg
            580                 585                 590

Pro Gly Tyr Thr Gly His His Cys Glu Thr Asn Ile Asn Glu Cys Ser
        595                 600                 605

Ser Gln Pro Cys Arg His Gly Gly Thr Cys Gln Asp Arg Asp Asn Ala
    610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Ile Asn Ile Asp Glu Cys Ala Gly Asn Pro Cys His
        675                 680                 685

Asn Gly Gly Thr Cys Glu Asp Gly Ile Asn Gly Phe Thr Cys Arg Cys
    690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765

Lys Asp Met Thr Ser Gly Tyr Val Cys Thr Cys Arg Glu Gly Phe Ser
    770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
            820                 825                 830

Cys Ala Pro Ser Pro Cys Arg Asn Gly Gly Glu Cys Arg Gln Ser Glu
        835                 840                 845

Asp Tyr Glu Ser Phe Ser Cys Val Cys Pro Thr Gly Trp Gln Gly Gln
    850                 855                 860
```

```
Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
            885                 890                 895

Ala Gly Tyr Ser Gly Arg Asn Cys Glu Thr Asp Ile Asp Asp Cys Arg
        900                 905                 910

Pro Asn Pro Cys His Asn Gly Gly Ser Cys Thr Asp Gly Ile Asn Thr
        915                 920                 925

Ala Phe Cys Asp Cys Leu Pro Gly Phe Arg Gly Thr Phe Cys Glu Glu
    930                 935                 940

Asp Ile Asn Glu Cys Ala Ser Asp Pro Cys Arg Asn Gly Ala Asn Cys
945                 950                 955                 960

Thr Asp Cys Val Asp Ser Tyr Thr Cys Thr Cys Pro Ala Gly Phe Ser
            965                 970                 975

Gly Ile His Cys Glu Asn Asn Thr Pro Asp Cys Thr Glu Ser Ser Cys
        980                 985                 990

Phe Asn Gly Gly Thr Cys Val Asp Gly Ile Asn Ser Phe Thr Cys Leu
    995                 1000                1005

Cys Pro Pro Gly Phe Thr Gly Ser Tyr Cys Gln His Asp Val Asn
    1010                1015                1020

Glu Cys Asp Ser Gln Pro Cys Leu His Gly Gly Thr Cys Gln Asp
    1025                1030                1035

Gly Cys Gly Ser Tyr Arg Cys Thr Cys Pro Gln Gly Tyr Thr Gly
    1040                1045                1050

Pro Asn Cys Gln Asn Leu Val His Trp Cys Asp Ser Ser Pro Cys
    1055                1060                1065

Lys Asn Gly Gly Lys Cys Trp Gln Thr His Thr Gln Tyr Arg Cys
    1070                1075                1080

Glu Cys Pro Ser Gly Trp Thr Gly Leu Tyr Cys Asp Val Pro Ser
    1085                1090                1095

Val Ser Cys Glu Val Ala Ala Gln Arg Gln Gly Val Asp Val Ala
    1100                1105                1110

Arg Leu Cys Gln His Gly Gly Leu Cys Val Asp Ala Gly Asn Thr
    1115                1120                1125

His His Cys Arg Cys Gln Ala Gly Tyr Thr Gly Ser Tyr Cys Glu
    1130                1135                1140

Asp Leu Val Asp Glu Cys Ser Pro Ser Pro Cys Gln Asn Gly Ala
    1145                1150                1155

Thr Cys Thr Asp Tyr Leu Gly Gly Tyr Ser Cys Lys Cys Val Ala
    1160                1165                1170

Gly Tyr His Gly Val Asn Cys Ser Glu Glu Ile Asp Glu Cys Leu
    1175                1180                1185

Ser His Pro Cys Gln Asn Gly Gly Thr Cys Leu Asp Leu Pro Asn
    1190                1195                1200

Thr Tyr Lys Cys Ser Cys Pro Arg Gly Thr Gln Gly Val His Cys
    1205                1210                1215

Glu Ile Asn Val Asp Asp Cys Asn Pro Pro Val Asp Pro Val Ser
    1220                1225                1230

Arg Ser Pro Lys Cys Phe Asn Asn Gly Thr Cys Val Asp Gln Val
    1235                1240                1245

Gly Gly Tyr Ser Cys Thr Cys Pro Pro Gly Phe Val Gly Glu Arg
    1250                1255                1260

Cys Glu Gly Asp Val Asn Glu Cys Leu Ser Asn Pro Cys Asp Ala
```

-continued

```
            1265                1270                1275
Arg Gly Thr Gln Asn Cys Val Gln Arg Val Asn Asp Phe His Cys
       1280                1285                1290
Glu Cys Arg Ala Gly His Thr Gly Arg Arg Cys Glu Ser Val Ile
       1295                1300                1305
Asn Gly Cys Lys Gly Lys Pro Cys Lys Asn Gly Gly Thr Cys Ala
       1310                1315                1320
Val Ala Ser Asn Thr Ala Arg Gly Phe Ile Cys Lys Cys Pro Ala
       1325                1330                1335
Gly Phe Glu Gly Ala Thr Cys Glu Asn Asp Ala Arg Thr Cys Gly
       1340                1345                1350
Ser Leu Arg Cys Leu Asn Gly Gly Thr Cys Ile Ser Gly Pro Arg
       1355                1360                1365
Ser Pro Thr Cys Leu Cys Leu Gly Pro Phe Thr Gly Pro Glu Cys
       1370                1375                1380
Gln Phe Pro Ala Ser Ser Pro Cys Leu Gly Gly Asn Pro Cys Tyr
       1385                1390                1395
Asn Gln Gly Thr Cys Glu Pro Thr Ser Glu Ser Pro Phe Tyr Arg
       1400                1405                1410
Cys Leu Cys Pro Ala Lys Phe Asn Gly Leu Leu Cys His Ile Leu
       1415                1420                1425
Asp Tyr Ser Phe Gly Gly Gly Ala Gly Arg Asp Ile Pro Pro Pro
       1430                1435                1440
Leu Ile Glu Glu Ala Cys Glu Leu Pro Glu Cys Gln Glu Asp Ala
       1445                1450                1455
Gly Asn Lys Val Cys Ser Leu Gln Cys Asn Asn His Ala Cys Gly
       1460                1465                1470
Trp Asp Gly Gly Asp Cys Ser Leu Asn Phe Asn Asp Pro Trp Lys
       1475                1480                1485
Asn Cys Thr Gln Ser Leu Gln Cys Trp Lys Tyr Phe Ser Asp Gly
       1490                1495                1500
His Cys Asp Ser Gln Cys Asn Ser Ala Gly Cys Leu Phe Asp Gly
       1505                1510                1515
Phe Asp Cys Gln Arg Ala Glu Gly Gln Cys Asn Pro Leu Tyr Asp
       1520                1525                1530
Gln Tyr Cys Lys Asp His Phe Ser Asp Gly His Cys Asp Gln Gly
       1535                1540                1545
Cys Asn Ser Ala Glu Cys Glu Trp Asp Gly Leu Asp Cys Ala Glu
       1550                1555                1560
His Val Pro Glu Arg Leu Ala Ala Gly Thr Leu Val Val Val Val
       1565                1570                1575
Leu Met Pro Pro Glu Gln Leu Arg Asn Ser Ser Phe His Phe Leu
       1580                1585                1590
Arg Glu Leu Ser Arg Val Leu His Thr Asn Val Val Phe Lys Arg
       1595                1600                1605
Asp Ala His Gly Gln Gln Met Ile Phe Pro Tyr Tyr Gly Arg Glu
       1610                1615                1620
Glu Glu Leu Arg Lys His Pro Ile Lys Arg Ala Ala Glu Gly Trp
       1625                1630                1635
Ala Ala Pro Asp Ala Leu Leu Gly Gln Val Lys Ala Ser Leu Leu
       1640                1645                1650
Pro Gly Gly Ser Glu Gly Gly Arg Arg Arg Arg Glu Leu Asp Pro
       1655                1660                1665
```

```
Met Asp Val Arg Gly Ser Ile Val Tyr Leu Glu Ile Asp Asn Arg
    1670                1675                1680

Gln Cys Val Gln Ala Ser Ser Gln Cys Phe Gln Ser Ala Thr Asp
    1685                1690                1695

Val Ala Ala Phe Leu Gly Ala Leu Ala Ser Leu Gly Ser Leu Asn
    1700                1705                1710

Ile Pro Tyr Lys Ile Glu Ala Val Gln Ser Glu Thr Val Glu Pro
    1715                1720                1725

Pro Pro Pro Ala Gln Leu His Phe Met Tyr Val Ala Ala Ala Ala
    1730                1735                1740

Phe Val Leu Leu Phe Phe Val Gly Cys Gly Val Leu Leu Ser Arg
    1745                1750                1755

Lys Arg Arg Arg Gln His Gly Gln Leu Trp Phe Pro Glu Gly Phe
    1760                1765                1770

Lys Val Ser Glu Ala Ser Lys Lys Lys Arg Arg Glu Pro Leu Gly
    1775                1780                1785

Glu Asp Ser Val Gly Leu Lys Pro Leu Lys Asn Ala Ser Asp Gly
    1790                1795                1800

Ala Leu Met Asp Asp Asn Gln Asn Glu Trp Gly Asp Glu Asp Leu
    1805                1810                1815

Glu Thr Lys Lys Phe Arg Phe Glu Glu Pro Val Val Leu Pro Asp
    1820                1825                1830

Leu Asp Asp Gln Thr Asp His Arg Gln Trp Thr Gln Gln His Leu
    1835                1840                1845

Asp Ala Ala Asp Leu Arg Met Ser Ala Met Ala Pro Thr Pro Pro
    1850                1855                1860

Gln Gly Glu Val Asp Ala Asp Cys Met Asp Val Asn Val Arg Gly
    1865                1870                1875

Pro Asp Gly Phe Thr Pro Leu Met Ile Ala Ser Cys Ser Gly Gly
    1880                1885                1890

Gly Leu Glu Thr Gly Asn Ser Glu Glu Glu Glu Asp Ala Pro Ala
    1895                1900                1905

Val Ile Ser Asp Phe Ile Tyr Gln Gly Ala Ser Leu His Asn Gln
    1910                1915                1920

Thr Asp Arg Thr Gly Glu Thr Ala Leu His Leu Ala Ala Arg Tyr
    1925                1930                1935

Ser Arg Ser Asp Ala Ala Lys Arg Leu Leu Glu Ala Ser Ala Asp
    1940                1945                1950

Ala Asn Ile Gln Asp Asn Met Gly Arg Thr Pro Leu His Ala Ala
    1955                1960                1965

Val Ser Ala Asp Ala Gln Gly Val Phe Gln Ile Leu Ile Arg Asn
    1970                1975                1980

Arg Ala Thr Asp Leu Asp Ala Arg Met His Asp Gly Thr Thr Pro
    1985                1990                1995

Leu Ile Leu Ala Ala Arg Leu Ala Val Glu Gly Met Leu Glu Asp
    2000                2005                2010

Leu Ile Asn Ser His Ala Asp Val Asn Ala Val Asp Asp Leu Gly
    2015                2020                2025

Lys Ser Ala Leu His Trp Ala Ala Ala Val Asn Asn Val Asp Ala
    2030                2035                2040

Ala Val Val Leu Leu Lys Asn Gly Ala Asn Lys Asp Met Gln Asn
    2045                2050                2055
```

```
Asn Arg Glu Glu Thr Pro Leu Phe Leu Ala Ala Arg Glu Gly Ser
2060             2065             2070

Tyr Glu Thr Ala Lys Val Leu Leu Asp His Phe Ala Asn Arg Asp
2075             2080             2085

Ile Thr Asp His Met Asp Arg Leu Pro Arg Asp Ile Ala Gln Glu
2090             2095             2100

Arg Met His His Asp Ile Val Arg Leu Leu Asp Glu Tyr Asn Leu
2105             2110             2115

Val Arg Ser Pro Gln Leu His Gly Ala Pro Leu Gly Gly Thr Pro
2120             2125             2130

Thr Leu Ser Pro Pro Leu Cys Ser Pro Asn Gly Tyr Leu Gly Ser
2135             2140             2145

Leu Lys Pro Gly Val Gln Gly Lys Lys Val Arg Lys Pro Ser Ser
2150             2155             2160

Lys Gly Leu Ala Cys Gly Ser Lys Glu Ala Lys Asp Leu Lys Ala
2165             2170             2175

Arg Arg Lys Lys Ser Gln Asp Gly Lys Gly Cys Leu Leu Asp Ser
2180             2185             2190

Ser Gly Met Leu Ser Pro Val Asp Ser Leu Glu Ser Pro His Gly
2195             2200             2205

Tyr Leu Ser Asp Val Ala Ser Pro Pro Leu Leu Pro Ser Pro Phe
2210             2215             2220

Gln Gln Ser Pro Ser Val Pro Leu Asn His Leu Pro Gly Met Pro
2225             2230             2235

Asp Thr His Leu Gly Ile Gly His Leu Asn Val Ala Ala Lys Pro
2240             2245             2250

Glu Met Ala Ala Leu Gly Gly Gly Gly Arg Leu Ala Phe Glu Thr
2255             2260             2265

Gly Pro Pro Arg Leu Ser His Leu Pro Val Ala Ser Gly Thr Ser
2270             2275             2280

Thr Val Leu Gly Ser Ser Ser Gly Gly Ala Leu Asn Phe Thr Val
2285             2290             2295

Gly Gly Ser Thr Ser Leu Asn Gly Gln Cys Glu Trp Leu Ser Arg
2300             2305             2310

Leu Gln Ser Gly Met Val Pro Asn Gln Tyr Asn Pro Leu Arg Gly
2315             2320             2325

Ser Val Ala Pro Gly Pro Leu Ser Thr Gln Ala Pro Ser Leu Gln
2330             2335             2340

His Gly Met Val Gly Pro Leu His Ser Ser Leu Ala Ala Ser Ala
2345             2350             2355

Leu Ser Gln Met Met Ser Tyr Gln Gly Leu Pro Ser Thr Arg Leu
2360             2365             2370

Ala Thr Gln Pro His Leu Val Gln Thr Gln Gln Val Gln Pro Gln
2375             2380             2385

Asn Leu Gln Met Gln Gln Gln Asn Leu Gln Pro Ala Asn Ile Gln
2390             2395             2400

Gln Gln Gln Ser Leu Gln Pro Pro Pro Pro Pro Gln Pro His
2405             2410             2415

Leu Gly Val Ser Ser Ala Ala Ser Gly His Leu Gly Arg Ser Phe
2420             2425             2430

Leu Ser Gly Glu Pro Ser Gln Ala Asp Val Gln Pro Leu Gly Pro
2435             2440             2445

Ser Ser Leu Ala Val His Thr Ile Leu Pro Gln Glu Ser Pro Ala
```

```
                2450                2455                2460
Leu Pro Thr Ser Leu Pro Ser Leu Val Pro Val Thr Ala
    2465                2470                2475

Ala Gln Phe Leu Thr Pro Pro Ser Gln His Ser Tyr Ser Ser Pro
    2480                2485                2490

Val Asp Asn Thr Pro Ser His Gln Leu Gln Val Pro Glu His Pro
    2495                2500                2505

Phe Leu Thr Pro Ser Pro Glu Ser Pro Asp Gln Trp Ser Ser Ser
    2510                2515                2520

Ser Pro His Ser Asn Val Ser Asp Trp Ser Glu Gly Val Ser Ser
    2525                2530                2535

Pro Pro Thr Ser Met Gln Ser Gln Ile Ala Arg Ile Pro Glu Ala
    2540                2545                2550

Phe Lys
    2555

<210> SEQ ID NO 3
<211> LENGTH: 354
<212> TYPE: PRT
<213> ORGANISM: Homo sapiens

<400> SEQUENCE: 3

Met Ser Arg Leu Leu His Ala Glu Glu Trp Ala Glu Val Lys Glu Leu
1               5                   10                  15

Gly Asp His His Arg Gln Pro Gln Pro His His Leu Pro Gln Pro Pro
                20                  25                  30

Pro Pro Pro Gln Pro Pro Ala Thr Leu Gln Ala Arg Glu His Pro Val
            35                  40                  45

Tyr Pro Pro Glu Leu Ser Leu Leu Asp Ser Thr Asp Pro Arg Ala Trp
        50                  55                  60

Leu Ala Pro Thr Leu Gln Gly Ile Cys Thr Ala Arg Ala Ala Gln Tyr
65                  70                  75                  80

Leu Leu His Ser Pro Glu Leu Gly Ala Ser Glu Ala Ala Pro Arg
                85                  90                  95

Asp Glu Val Asp Gly Arg Gly Glu Leu Val Arg Arg Ser Gly Gly
            100                 105                 110

Ala Ser Ser Ser Lys Ser Pro Gly Pro Val Lys Val Arg Glu Gln Leu
            115                 120                 125

Cys Lys Leu Lys Gly Gly Val Val Asp Glu Leu Gly Cys Ser Arg
130                 135                 140

Gln Arg Ala Pro Ser Ser Lys Gln Val Asn Gly Val Gln Lys Gln Arg
145                 150                 155                 160

Arg Leu Ala Ala Asn Ala Arg Glu Arg Arg Met His Gly Leu Asn
                165                 170                 175

His Ala Phe Asp Gln Leu Arg Asn Val Ile Pro Ser Phe Asn Asn Asp
                180                 185                 190

Lys Lys Leu Ser Lys Tyr Glu Thr Leu Gln Met Ala Gln Ile Tyr Ile
                195                 200                 205

Asn Ala Leu Ser Glu Leu Leu Gln Thr Pro Ser Gly Gly Glu Gln Pro
            210                 215                 220

Pro Pro Pro Ala Ser Cys Lys Ser Asp His His His Leu Arg Thr
225                 230                 235                 240

Ala Ala Ser Tyr Glu Gly Gly Ala Gly Asn Ala Thr Ala Ala Gly Ala
                245                 250                 255
```

| | | | | | | | | | | | |
|---|---|---|---|---|---|---|---|---|---|---|---|
| Gln | Gln | Ala | Ser | Gly | Gly | Ser | Gln | Arg | Pro | Thr | Pro | Pro | Gly | Ser | Cys |
| | | | 260 | | | | 265 | | | | 270 | | | | |
| Arg | Thr | Arg | Phe | Ser | Ala | Pro | Ala | Ser | Ala | Gly | Gly | Tyr | Ser | Val | Gln |
| | | 275 | | | | | 280 | | | | | 285 | | | |
| Leu | Asp | Ala | Leu | His | Phe | Ser | Thr | Phe | Glu | Asp | Ser | Ala | Leu | Thr | Ala |
| | 290 | | | | | 295 | | | | | 300 | | | | |
| Met | Met | Ala | Gln | Lys | Asn | Leu | Ser | Pro | Ser | Leu | Pro | Gly | Ser | Ile | Leu |
| 305 | | | | | 310 | | | | | 315 | | | | | 320 |
| Gln | Pro | Val | Gln | Glu | Glu | Asn | Ser | Lys | Thr | Ser | Pro | Arg | Ser | His | Arg |
| | | | | 325 | | | | | 330 | | | | | 335 | |
| Ser | Asp | Gly | Glu | Phe | Ser | Pro | His | Ser | His | Tyr | Ser | Asp | Ser | Asp | Glu |
| | | | 340 | | | | | 345 | | | | | 350 | | |
| Ala | Ser | | | | | | | | | | | | | | |

<210> SEQ ID NO 4
<211> LENGTH: 2379
<212> TYPE: DNA
<213> ORGANISM: Homo sapiens

<400> SEQUENCE: 4

| | |
|---|---|
| gacccccgag ctgtgctgct cgcggccgcc accgcgggc cccggccgtc cctggctccc | 60 |
| ctcctgcctc gagaagggca gggcttctca gaggcttggc gggaaaaaga acggagggag | 120 |
| ggatcgcgct gagtataaaa gccggttttc ggggctttat ctaactcgct gtagtaattc | 180 |
| cagcgagagg cagagggagc gagcgggcgg ccggctaggg tggaagagcc gggcgagcag | 240 |
| agctgcgctg cgggcgtcct gggaagggag atccggagcg aatagggggc ttcgcctctg | 300 |
| gcccagccct cccgctgatc ccccagccag cggtccgcaa ccttgccgc atccacgaaa | 360 |
| ctttgcccat agcagcgggc gggcactttg cactggaact acaacaccc gagcaaggac | 420 |
| gcgactctcc cgacgcgggg aggctattct gcccatttgg ggacacttcc ccgccgctgc | 480 |
| caggacccgc ttctctgaaa ggctctcctt gcagctgctt agacgctgga ttttttcgg | 540 |
| gtagtggaaa accagcagcc tcccgcgacg atgcccctca cgttagctt caccaacagg | 600 |
| aactatgacc tcgactacga ctcggtgcag ccgtatttct actgcgacga ggaggagaac | 660 |
| ttctaccagc agcagcagca gagcgagctg cagccccgg cgcccagcga ggatatctgg | 720 |
| aagaaattcg agctgctgcc caccccgccc ctgtccccta gccgccgctc cgggctctgc | 780 |
| tcgcccctcct acgttgcggt cacacccttc tcccttcggg gagacaacga cggcggtggc | 840 |
| gggagcttct ccacggccga ccagctggag atggtgaccg agctgctggg aggagacatg | 900 |
| gtgaaccaga gtttcatctg cgacccggac gacgagacct tcatcaaaaa catcatcatc | 960 |
| caggactgta tgtggagcgg cttctcggcc gccgccaagc tcgtctcaga gaagctggcc | 1020 |
| tcctaccagg ctgcgcgcaa agacagcggc agcccgaacc ccgccgcgg ccacagcgtc | 1080 |
| tgctccacct ccagcttgta cctgcaggat ctgagcgccg ccgcctcaga gtgcatcgac | 1140 |
| ccctcggtgg tcttccccta ccctctcaac gacagcagct cgcccaagtc ctgcgcctcg | 1200 |
| caagactcca gcgccttctc tccgtcctcg gattctctgc tctcctcgac ggagtcctcc | 1260 |
| ccgcagggca gccccgagcc cctggtgctc catgaggaga ccgcccac accagcagc | 1320 |
| gactctgagg aggaacaaga agatgaggaa gaaatcgatg ttgtttctgt ggaaaagagg | 1380 |
| caggctcctg gcaaaaggt agagtctgga tcaccttctg ctggaggcca cagcaaacct | 1440 |
| cctcacagcc cactggtcct caagaggtgc acgtctcca cacatcagca aactacgca | 1500 |
| gcgcctccct ccactcggaa ggactatcct gctgccaaga gggtcaagtt ggacagtgtc | 1560 |

| | | |
|---|---|---|
| agagtcctga dacagatcag caacaaccga aaatgcacca gccccaggtc ctcggacacc | 1620 |
| gaggagaatg tcaagaggcg aacacacaac gtcttggagc gccagaggag gaacgagcta | 1680 |
| aaacggagct ttttttgccct gcgtgaccag atcccggagt tggaaaacaa tgaaaaggcc | 1740 |
| cccaaggtag ttatccttaa aaaagccaca gcatacatcc tgtccgtcca agcagaggag | 1800 |
| caaaagctca tttctgaaga ggacttgttg cggaaacgac gagaacagtt gaaacacaaa | 1860 |
| cttgaacagc tacggaactc ttgtgcgtaa ggaaaagtaa ggaaaacgat tccttctaac | 1920 |
| agaaatgtcc tgagcaatca cctatgaact tgtttcaaat gcatgatcaa atgcaacctc | 1980 |
| acaaccttgg ctgagtcttg agactgaaag atttagccat aatgtaaact gcctcaaatt | 2040 |
| ggactttggg cataaaagaa cttttttatg cttaccatct ttttttttc tttaacagat | 2100 |
| ttgtatttaa gaattgtttt taaaaaattt taagatttac acaatgtttc tctgtaaata | 2160 |
| ttgccattaa atgtaaataa ctttaataaa acgtttatag cagttacaca gaatttcaat | 2220 |
| cctagtatat agtacctagt attataggta ctataaaccc taattttttt tatttaagta | 2280 |
| catttgctt tttaaagttg attttttttct attgttttta gaaaaaataa aataactggc | 2340 |
| aaatatatca ttgagccaaa tcttaaaaaa aaaaaaaaa | 2379 |

<210> SEQ ID NO 5
<211> LENGTH: 9309
<212> TYPE: DNA
<213> ORGANISM: Homo sapiens

<400> SEQUENCE: 5

| | | |
|---|---|---|
| atgccgccgc tcctggcgcc cctgctctgc ctggcgctgc tgcccgcgct cgccgcacga | 60 |
| ggcccgcgat gctcccagcc cggtgagacc tgcctgaatg cgggaagtg tgaagcggcc | 120 |
| aatggcacgg aggcctgcgt ctgtggcggg gccttcgtgg gcccgcgatg ccaggacccc | 180 |
| aacccgtgcc tcagcacccc ctgcaagaac gccgggacat gccacgtggt ggaccgcaga | 240 |
| ggcgtggcag actatgcctg cagctgtgcc ctgggcttct ctgggcccct ctgcctgaca | 300 |
| cccctggaca tgcctgcct caccaacccc tgccgcaacg gggcacctg cgacctgctc | 360 |
| acgctgacgg agtacaagtg ccgctgcccg cccggctggt cagggaaatc gtgccagcag | 420 |
| gctgacccgt gcgcctccaa cccctgcgcc aacggtggcc agtgcctgcc cttcgaggcc | 480 |
| tcctacatct gccactgccc acccagcttc catggcccca cctgccggca ggatgtcaac | 540 |
| gagtgtggcc agaagcccgg gctttgccgc cacggaggca cctgccacaa cgaggtcggc | 600 |
| tcctaccgct gcgtctgccg cgccacccac actggcccca actgcgagcg ccctacgtg | 660 |
| ccctgcagcc cctcgccctg ccagaacggg ggcacctgcc gcccacgggc gacgtcacc | 720 |
| cacgagtgtg cctgcctgcc aggcttcacc ggccagaact gtgaggaaaa tatcgacgat | 780 |
| tgtccaggaa acaactgcaa gaacgggggt gcctgtgtgg acggcgtgaa cacctacaac | 840 |
| tgccgctgcc cgccagagtg gacaggtcag tactgtaccg aggatgtgga cgagtgccag | 900 |
| ctgatgccaa atgcctgcca gaacggcggg acctgccaca cacccacgg tggctacaac | 960 |
| tgcgtgtgtg tcaacggctg gactggtgag gactgcagcg agaacattga tgactgtgcc | 1020 |
| agcgccgcct gcttccacgg cgccacctgc catgaccgtg tggcctcctt ctactgcgag | 1080 |
| tgtccccatg gccgcacagg tctgctgtgc cacctcaacg acgcatgcat cagcaacccc | 1140 |
| tgtaacgagg gctccaactg cgacaccaac cctgtcaatg caaggccat ctgcacctgc | 1200 |
| ccctcggggt acacgggccc ggcctgcagc caggacgtgg atgagtgctc gctgggtgcc | 1260 |

```
aacccctgcg agcatgcggg caagtgcatc aacacgctgg gctccttcga gtgccagtgt  1320
ctgcagggct acacgggccc ccgatgcgag atcgacgtca acgagtgcgt ctcgaacccg  1380
tgccagaacg acgccaccct cctggaccag attggggagt tccagtgcat ctgcatgccc  1440
ggctacgagg tgtgcactg cgaggtcaac acagacgagt gtgccagcag cccctgcctg  1500
cacaatggcc gctgcctgga caagatcaat gagttccagt gcgagtgccc cacgggcttc  1560
actgggcatc tgtgccagta cgatgtggac gagtgtgcca gcaccccctg caagaatggt  1620
gccaagtgcc tggacggacc caacacttac acctgtgtgt gcacggaagg gtacacgggg  1680
acgcactgcg aggtggacat cgatgagtgc gaccccgacc cctgccacta cggctcctgc  1740
aaggacggcg tcgccacctt cacctgcctc tgccgcccag gctacacggg ccaccactgc  1800
gagaccaaca tcaacgagtg ctccagccag ccctgccgcc acgggggcac ctgccaggac  1860
cgcgacaacg cctacctctg cttctgcctg aaggggacca caggacccaa ctgcgagatc  1920
aacctggatg actgtgccag cagcccctgc gactcgggca cctgtctgga caagatcgat  1980
ggctacgagt gtgcctgtga gccgggctac acagggagca tgtgtaacat caacatcgat  2040
gagtgtgcgg gcaacccctg ccacaacggg ggcacctgcg aggacggcat caatggcttc  2100
acctgccgct gccccgaggg ctaccacgac cccacctgcc tgtctgaggt caatgagtgc  2160
aacagcaacc cctgcgtcca ggggcctgc cgggacagcc tcaacgggta caagtgcgac  2220
tgtgaccctg ggtggagtgg gaccaactgt gacatcaaca caatgagtg tgaatccaac  2280 ccttgtgtca acggcggcac ctgcaaagac atgaccagtg gctacgtgtg cacctgccgg  2340
gagggcttca cgcgtcccaa ctgccagacc aacatcaacg agtgtgcgtc caacccatgt  2400
ctgaaccagg gcacgtgtat tgacgacgtt gccgggtaca agtgcaactg cctgctgccc  2460
tacacaggtg ccacgtgtga ggtggtgctg gcccgtgtg cccccagccc ctgcagaaac  2520
ggcggggagt gcaggcaatc cgaggactat gagagcttct cctgtgtctg ccccacgggc  2580
tggcaagggc agacctgtga ggtcgacatc aacgagtgcg ttctgagccc gtgccggcac  2640
ggcgcatcct gccagaacac ccacggcggc taccgctgcc actgccaggc cggctacagt  2700
gggcgcaact gcgagaccga catcgacgac tgccggccca cccgtgtca caacgggggc  2760 tcctgcacag acggcatcaa cacggccttc tgcgactgcc tgcccggctt ccggggcact  2820
ttctgtgagg aggacatcaa cgagtgtgcc agtgaccccct gccgcaacgg ggccaactgc  2880
acggactgcg tggacagcta cacgtgcacc tgccccgcag gcttcagcgg gatccactgt  2940
gagaacaaca cgcctgactg cacagagagc tcctgcttca cggtggcac ctgcgtggac  3000 ggcatcaact cgttcacctg cctgtgtcca cccggcttca cgggcagcta ctgccagcac  3060
gatgtcaatg agtgcgactc acagccctgc ctgcatggcg gcacctgtca ggacggctgc  3120
ggctcctaca ggtgcacctg cccccagggc tacactggcc ccaactgcca gaaccttgtg  3180
cactggtgtg actcctcgcc ctgcaagaac ggcggcaaat gctggcagac ccacacccag  3240
taccgctgcg agtgccccag cggctggacc ggcctttact cgacgtgcc cagcgtgtcc  3300 tgtgaggtgg ctgcgcagcg acaaggtgtt gacgttgccc gcctgtgcca gcatggaggg  3360
ctctgtgtgg acgcgggcaa cacgcaccac tgccgctgcc aggcgggcta cacaggcagc  3420
tactgtgagg acctggtgga cgagtgctca cccagcccct gccagaacgg ggccacctgc  3480
acggactacc tggcggcta ctcctgcaag tgcgtggccg gctaccacgg ggtgaactgc  3540
tctgaggaga tcgacgagtg cctctcccac ccctgccaga cgggggcac ctgcctcgac  3600 ctccccaaca cctacaagtg ctcctgccca cggggcactc agggtgtgca ctgtgagatc  3660
```

```
aacgtggacg actgcaatcc ccccgttgac cccgtgtccc ggagcccaa  gtgctttaac   3720
aacggcacct gcgtggacca ggtgggcggc tacagctgca cctgcccgcc gggcttcgtg   3780
ggtgagcgct gtgagggga  tgtcaacgag tgcctgtcca atccctgcga cgcccgtggc   3840
acccagaact gcgtgcagcg cgtcaatgac ttccactgcg agtgccgtgc tggtcacacc   3900
gggcgccgct gcgagtccgt catcaatggc tgcaaaggca agccctgcaa gaatggggc   3960
acctgcgccg tggcctccaa caccgcccgc gggttcatct gcaagtgccc tgcgggcttc   4020
gagggcgcca cgtgtgagaa tgacgctcgt acctgcggca gcctgcgctg cctcaacggc   4080
ggcacatgca tctccggccc cgcgcagccc acctgcctgt gcctgggccc cttcacgggc   4140
cccgaatgcc agttcccggc cagcagcccc tgcctgggcg caacccctg  ctacaaccag   4200
gggacctgtg agcccacatc cgagagcccc ttctaccgtt gcctgtgccc cgccaaattc   4260
aacgggctct tgtgccacat cctggactac agcttcgggg gtgggccgg  gcgcgacatc   4320
cccccgccgc tgatcgagga ggcgtgcgag ctgcccgagt gccaggagga cgcgggcaac   4380
aaggtctgca gcctgcagtg caacaaccac gcgtgcggct gggacggcgg tgactgctcc   4440
ctcaacttca atgaccctg  gaagaactgc acgcagtctc tgcagtgctg gaagtacttc   4500
agtgacggcc actgtgacag ccagtgcaac tcagccggct gcctcttcga cggctttgac   4560
tgccagcgtg cggaaggcca gtgcaacccc ctgtacgacc agtactgcaa ggaccacttc   4620
agcgacgggc actgcgacca gggctgcaac agcgcggagt gcgagtggga cgggctggac   4680
tgtgcggagc atgtacccga gaggctggcg gccggcacgc tggtggtggt ggtgctgatg   4740
ccgccggagc agctgcgcaa cagctccttc cacttcctgc gggagctcag ccgcgtgctg   4800
cacaccaacg tggtcttcaa gcgtgacgca cacggccagc agatgatctt ccctactac    4860
ggccgcgagg aggagctgcg caagcacccc atcaagcgtg ccgccgaggg ctgggccgca   4920
cctgacgccc tgctgggcca ggtgaaggcc tcgctgctcc ctggtggcag cgagggtggg   4980
cggcggcgga gggagctgga ccccatggac gtccgcggct ccatcgtcta cctggagatt   5040
gacaaccggc agtgtgtgca ggcctcctcg cagtgcttcc agagtgccac cgacgtggcc   5100
gcattcctgg gagcgctcgc ctcgctgggc agcctcaaca tccctacaa  gatcgaggcc   5160
gtgcagagtg agaccgtgga gccgccccg  ccggcgcagc tgcacttcat gtacgtggcg   5220
gcggccgcct ttgtgcttct gttcttcgtg ggctgcgggg tgctgctgtc ccgcaagcgc   5280
cggcggcagc atggccagct ctggttccct gagggcttca agtgtctga  ggccagcaag   5340
aagaagcggc gggagcccct cggcgaggac tccgtgggcc tcaagcccct gaagaacgct   5400
tcagacggtg ccctcatgga cgacaaccag aatgagtggg gggacgagga cctggagacc   5460
aagaagttcc ggttcgagga gcccgtggtt ctgcctgacc tggacgacca gacagaccac   5520
cggcagtgga ctcagcagca cctggatgcc gctgacctgc gcatgtctgc catggccccc   5580
acaccgcccc agggtgaggt tgacgccgac tgcatggacg tcaatgtccg gggcctgat   5640
ggcttcaccc cgctcatgat cgcctcctgc agcggggcg  gcctggagac gggcaacagc   5700
gaggaagagg aggacgcgcc ggccgtcatc tccgacttca tctaccaggg cgccagcctg   5760
cacaaccaga cagaccgcac gggcgagacc gccttgcacc tggccgcccg ctactcacgc   5820
tctgatgccg ccaagcgcct gctggaggcc agcgcagatg ccaacatcca ggacaacatg   5880
ggccgcaccc cgctgcatgc ggctgtgtct gccgacgcac aaggtgtctt ccagatcctg   5940
atccggaacc gagccacaga cctggatgcc cgcatgcatg atggcacgac gccactgatc   6000
```

```
ctggctgccc gcctggccgt ggagggcatg ctggaggacc tcatcaactc acacgccgac      6060
gtcaacgccg tagatgacct gggcaagtcc gccctgcact gggccgccgc cgtgaacaat      6120
gtggatgccg cagttgtgct cctgaagaac ggggctaaca agatatgca gaacaacagg      6180 gaggagacac ccctgtttct ggccgcccgg gagggcagct acgagaccgc caaggtgctg      6240
ctggaccact ttgccaaccg ggacatcacg gatcatatgg accgcctgcc gcgcgacatc      6300
gcacaggagc gcatgcatca cgacatcgtg aggctgctgg acgagtacaa cctggtgcgc      6360
agcccgcagc tgcacggagc cccgctgggg ggcacgccca ccctgtcgcc cccgctctgc      6420
tcgcccaacg gctacctggg cagcctcaag cccggcgtgc agggcaagaa ggtccgcaag      6480
cccagcagca aaggcctggc ctgtggaagc aaggaggcca aggacctcaa ggcacggagg      6540
aagaagtccc aggacggcaa gggctgcctg ctggacagct ccggcatgct ctcgcccgtg      6600
gactccctgg agtcacccca tggctacctg tcagacgtgg cctcgccgcc actgctgccc      6660
tccccgttcc agcagtctcc gtccgtgccc ctcaaccacc tgcctgggat gcccgacacc      6720
cacctgggca tcgggcacct gaacgtgccg gccaagcccg agatggccgg gctgggtggg      6780
ggcggccggc tggcctttga gactggccca cctcgtctct cccacctgcc tgtggcctct      6840
ggcaccagca ccgtcctggg ctccagcagc ggaggggccc tgaatttcac gtgggcgggg      6900
tccaccagtt tgaatggtca atgcgagtgg ctgtcccggc tgcagagcgg catggtgccg      6960
aaccaataca ccctctgcg ggggagtgtg gcaccaggcc ccctgagcac acaggccccc      7020
tccctgcagc atggcatggt aggcccgctg cacagtagcc ttgctgccag cgccctgtcc      7080
cagatgatga gctaccaggg cctgcccagc acccggctgg ccacccagcc tcacctggtg      7140
cagacccagc aggtgcagcc acaaaactta cagatgcagc agcagaacct gcagccagca      7200
aacatccagc agcagcaaag cctgcagccg ccaccaccac caccacagcc gcaccttggc      7260
gtgagctcag cagccagcgg ccacctgggc cggagcttcc tgagtggaga gccgagccag      7320
gcagacgtgc agccactggg ccccagcagc ctggcggtgc acactattct gccccaggag      7380
agccccgccc tgcccacgtc gctgccatcc tcgctggtcc cacccgtgac cgcagcccag      7440
ttcctgacgc cccctcgca gcacagctac tcctcgcctg tggacaacac ccccagccac      7500
cagctacagg tgcctgagca cccccttcctc acccccgtccc ctgagtcccc tgaccagtgg      7560
tccagctcgt ccccgcattc caacgtctcc gactggtccg agggcgtctc cagccctccc      7620
accagcatgc agtcccagat cgcccgcatt ccggaggcct tcaagtaaac ggcgcgcccc      7680 acgagaccccc ggcttccttt cccaagcctt cgggcgtctg tgtgcgctct gtggatgcca      7740
gggccgacca gaggagcctt tttaaaacac atgttttat acaaaataag aacgaggatt      7800
ttaatttttt ttagtattta tttatgtact tttattttac acagaaacac tgcctttta      7860 tttatatgta ctgtttatc tggccccagg tagaaacttt tatctattct gagaaaacaa      7920
gcaagttctg agagccaggg ttttcctacg taggatgaaa agattcttct gtgtttataa      7980
aatataaaca aagattcatg atttataaat gccatttatt tattgattcc ttttttcaaa      8040
atccaaaaag aaatgatgtt ggagaaggga agttgaacga gcatagtcca aaaagctcct      8100
ggggcgtcca ggccgcgccc ttttccccgac gcccacccaa ccccaagcca gcccggccgc      8160
tccaccagca tcacctgcct gttaggagaa gctgcatcca gaggcaaacg gaggcaaagc      8220
tggctcacct tccgcacgcg gattaatttg catctgaaat aggaaacaag tgaaagcata      8280
tgggttagat gttgccatgt gttttagatg gtttcttgca agcatgcttg tgaaaatgtg      8340
ttctcggagt gtgtatgcca agagtgcacc catggtacca atcatgaatc tttgtttcag      8400
```

```
gttcagtatt atgtagttgt tcgttggtta tacaagttct tggtccctcc agaaccaccc    8460
cggccccctg cccgttcttg aaatgtaggc atcatgcatg tcaaacatga gatgtgtgga    8520
ctgtggcact tgcctgggtc acacacggag gcatcctacc cttttctggg gaaagacact    8580
gcctgggctg accccggtgg cggccccagc acctcagcct gcacagtgtc cccaggttc     8640 cgaagaagat gctccagcaa cacagcctgg gccccagctc gcgggacccg accccccgtg    8700
ggctcccgtg ttttgtagga gacttgccag agccgggcac attgagctgt gcaacgccgt    8760
gggctgcgtc ctttggtcct gtccccgcag ccctggcagg gggcatgcgg tcgggcaggg    8820
gctggaggga ggcgggggct gcccttgggc caccctcct agtttgggag gagcagattt    8880
ttgcaatacc aagtatagcc tatggcagaa aaaatgtctg taaatatgtt tttaaaggtg    8940
gattttgttt aaaaaatctt aatgaatgag tctgttgtgt gtcatgccag tgagggacgt    9000
cagacttggc tcagctcggg gagccttagc cgcccatgca ctggggacgc tccgctgccg    9060
tgccgcctgc actcctcagg gcagcctccc ccggctctac gggggccgcg tggtgccatc    9120 cccaggggc atgaccagat gcgtcccaag atgttgattt ttactgtgtt ttataaaata    9180
gagtgtagtt tacagaaaaa gactttaaaa gtgatctaca tgaggaactg tagatgatgt    9240 attttttca tcttttttgt taactgattt gcaataaaaa tgatactgat ggtgaaaaaa    9300
aaaaaaaa                                                             9309

<210> SEQ ID NO 6
<211> LENGTH: 1065
<212> TYPE: DNA
<213> ORGANISM: Homo sapiens

<400> SEQUENCE: 6
atgtcccgcc tgctgcatgc agaagagtgg gctgaagtga aggagttggg agaccaccat      60
cgccagcccc agccgcatca tctcccgcaa ccgccgccgc cgccgcagcc acctgcaact    120
ttgcaggcga gagagcatcc cgtctacccg cctgagctgt ccctcctgga cagcaccgac    180
ccacgcgcct ggctggctcc cactttgcag ggcatctgca cggcacgcgc cgcccagtat    240
ttgctacatt ccccggagct gggtgcctca gaggccgctg cgccccggga cgaggtggac    300 ggccggggg agctggtaag gaggagcagc ggcggtgcca gcagcagcaa gagccccggg    360
ccggtgaaag tgcgggaaca gctgtgcaag ctgaaaggcg gggtggtggt agacgagctg    420
ggctgcagcc gccaacgggc cccttccagc aaacaggtga atggggtgca gaagcagaga    480
cggctagcag ccaacgccag ggagcggcgc aggatgcatg gctgaaccca gccttcgac    540 cagctgcgca atgttatccc gtcgttcaac aacgacaaga agctgtccaa atatgagacc    600
ctgcagatgg cccaaatcta catcaacgcc ttgtccgagc tgctacaaac gcccagcgga    660
ggggaacagc caccgccgcc tccagcctcc tgcaaaagcg accaccacca ccttcgcacc    720
gcggcctcct atgaagggg gcgggcaac gcgaccgcag ctggggctca gcaggcttcc    780
ggagggagcc agcggccgac cccgcccggg agttgccgga ctcgcttctc agccccagct    840
tctgcgggag ggtactcggt gcagctggac gctctgcact tctcgacttt cgaggacagc    900
gccctgacag cgatgatggc gcaaaagaat ttgtctcctt ctctccccgg gagcatcttg    960
cagccagtgc aggaggaaaa cagcaaaact tcgcctcggt cccacagaag cgacggggaa    1020 ttttccccccc attcccatta cagtgactcg gatgaggcaa gttag                   1065

<210> SEQ ID NO 7
```

-continued

```
<211> LENGTH: 802
<212> TYPE: PRT
<213> ORGANISM: Homo sapiens

<400> SEQUENCE: 7

Val Leu Leu Ser Arg Lys Arg Arg Gln His Gly Gln Leu Trp Phe
1               5                   10                  15

Pro Glu Gly Phe Lys Val Ser Glu Ala Ser Lys Lys Arg Arg Glu
            20                  25                  30

Pro Leu Gly Glu Asp Ser Val Gly Leu Lys Pro Leu Lys Asn Ala Ser
        35                  40                  45

Asp Gly Ala Leu Met Asp Asp Asn Gln Asn Glu Trp Gly Asp Glu Asp
    50                  55                  60

Leu Glu Thr Lys Lys Phe Arg Phe Glu Glu Pro Val Val Leu Pro Asp
65                  70                  75                  80

Leu Asp Asp Gln Thr Asp His Arg Gln Trp Thr Gln Gln His Leu Asp
                85                  90                  95

Ala Ala Asp Leu Arg Met Ser Ala Met Ala Pro Thr Pro Pro Gln Gly
            100                 105                 110

Glu Val Asp Ala Asp Cys Met Asp Val Asn Val Arg Gly Pro Asp Gly
        115                 120                 125

Phe Thr Pro Leu Met Ile Ala Ser Cys Ser Gly Gly Gly Leu Glu Thr
    130                 135                 140

Gly Asn Ser Glu Glu Glu Glu Asp Ala Pro Ala Val Ile Ser Asp Phe
145                 150                 155                 160

Ile Tyr Gln Gly Ala Ser Leu His Asn Gln Thr Asp Arg Thr Gly Glu
                165                 170                 175

Thr Ala Leu His Leu Ala Ala Arg Tyr Ser Arg Ser Asp Ala Ala Lys
            180                 185                 190

Arg Leu Leu Glu Ala Ser Ala Asp Ala Asn Ile Gln Asp Asn Met Gly
        195                 200                 205

Arg Thr Pro Leu His Ala Ala Val Ser Ala Asp Ala Gln Gly Val Phe
    210                 215                 220

Gln Ile Leu Ile Arg Asn Arg Ala Thr Asp Leu Asp Ala Arg Met His
225                 230                 235                 240

Asp Gly Thr Thr Pro Leu Ile Leu Ala Ala Arg Leu Ala Val Glu Gly
                245                 250                 255

Met Leu Glu Asp Leu Ile Asn Ser His Ala Asp Val Asn Ala Val Asp
            260                 265                 270

Asp Leu Gly Lys Ser Ala Leu His Trp Ala Ala Val Asn Asn Val
        275                 280                 285

Asp Ala Ala Val Val Leu Leu Lys Asn Gly Ala Asn Lys Asp Met Gln
    290                 295                 300

Asn Asn Arg Glu Glu Thr Pro Leu Phe Leu Ala Ala Arg Glu Gly Ser
305                 310                 315                 320

Tyr Glu Thr Ala Lys Val Leu Leu Asp His Phe Ala Asn Arg Asp Ile
                325                 330                 335

Thr Asp His Met Asp Arg Leu Pro Arg Asp Ile Ala Gln Glu Arg Met
            340                 345                 350

His His Asp Ile Val Arg Leu Leu Asp Glu Tyr Asn Leu Val Arg Ser
        355                 360                 365

Pro Gln Leu His Gly Ala Pro Leu Gly Gly Thr Pro Thr Leu Ser Pro
    370                 375                 380

Pro Leu Cys Ser Pro Asn Gly Tyr Leu Gly Ser Leu Lys Pro Gly Val
```

```
            385                 390                 395                 400
        Gln Gly Lys Lys Val Arg Lys Pro Ser Ser Lys Gly Leu Ala Cys Gly
                        405                 410                 415

Ser Lys Glu Ala Lys Asp Leu Lys Ala Arg Arg Lys Lys Ser Gln Asp
                        420                 425                 430

Gly Lys Gly Cys Leu Leu Asp Ser Gly Met Leu Ser Pro Val Asp
                        435                 440                 445

Ser Leu Glu Ser Pro His Gly Tyr Leu Ser Asp Val Ala Ser Pro Pro
                    450                 455                 460

Leu Leu Pro Ser Pro Phe Gln Gln Ser Pro Ser Val Pro Leu Asn His
        465                 470                 475                 480

Leu Pro Gly Met Pro Asp Thr His Leu Gly Ile Gly His Leu Asn Val
                        485                 490                 495

Ala Ala Lys Pro Glu Met Ala Ala Leu Gly Gly Gly Arg Leu Ala
                    500                 505                 510

Phe Glu Thr Gly Pro Pro Arg Leu Ser His Leu Pro Val Ala Ser Gly
                    515                 520                 525

Thr Ser Thr Val Leu Gly Ser Ser Gly Gly Ala Leu Asn Phe Thr
                    530                 535                 540

Val Gly Gly Ser Thr Ser Leu Asn Gly Gln Cys Glu Trp Leu Ser Arg
        545                 550                 555                 560

Leu Gln Ser Gly Met Val Pro Asn Gln Tyr Asn Pro Leu Arg Gly Ser
                        565                 570                 575

Val Ala Pro Gly Pro Leu Ser Thr Gln Ala Pro Ser Leu Gln His Gly
                    580                 585                 590

Met Val Gly Pro Leu His Ser Ser Leu Ala Ala Ser Ala Leu Ser Gln
                        595                 600                 605

Met Met Ser Tyr Gln Gly Leu Pro Ser Thr Arg Leu Ala Thr Gln Pro
                    610                 615                 620

His Leu Val Gln Thr Gln Gln Val Gln Pro Gln Asn Leu Gln Met Gln
        625                 630                 635                 640

Gln Gln Asn Leu Gln Pro Ala Asn Ile Gln Gln Gln Ser Leu Gln
                        645                 650                 655

Pro Pro Pro Pro Pro Gln Pro His Leu Gly Val Ser Ser Ala Ala
                        660                 665                 670

Ser Gly His Leu Gly Arg Ser Phe Leu Ser Gly Glu Pro Ser Gln Ala
                    675                 680                 685

Asp Val Gln Pro Leu Gly Pro Ser Ser Leu Ala Val His Thr Ile Leu
                    690                 695                 700

Pro Gln Glu Ser Pro Ala Leu Pro Thr Ser Leu Pro Ser Ser Leu Val
        705                 710                 715                 720

Pro Pro Val Thr Ala Ala Gln Phe Leu Thr Pro Pro Ser Gln His Ser
                        725                 730                 735

Tyr Ser Ser Pro Val Asp Asn Thr Pro Ser His Gln Leu Gln Val Pro
                    740                 745                 750

Glu His Pro Phe Leu Thr Pro Ser Pro Glu Ser Pro Asp Gln Trp Ser
                    755                 760                 765

Ser Ser Ser Pro His Ser Asn Val Ser Asp Trp Ser Glu Gly Val Ser
                    770                 775                 780

Ser Pro Pro Thr Ser Met Gln Ser Gln Ile Ala Arg Ile Pro Glu Ala
        785                 790                 795                 800

Phe Lys
```

<210> SEQ ID NO 8
<211> LENGTH: 2406
<212> TYPE: DNA
<213> ORGANISM: Homo sapiens

<400> SEQUENCE: 8

| | | | | | |
|---|---|---|---|---|---|
| gtgctgctgt | cccgcaagcg | ccggcggcag | catggccagc | tctggttccc | tgagggcttc | 60 |
| aaagtgtctg | aggccagcaa | gaagaagcgg | cgggagcccc | tcggcgagga | ctccgtgggc | 120 |
| ctcaagcccc | tgaagaacgc | ttcagacggt | gccctcatgg | acgacaacca | gaatgagtgg | 180 |
| ggggacgagg | acctggagac | caagaagttc | cggttcgagg | agcccgtggt | tctgcctgac | 240 |
| ctggacgacc | agacagacca | ccggcagtgg | actcagcagc | acctggatgc | cgctgacctg | 300 |
| cgcatgtctg | ccatggcccc | cacaccgccc | caggtgagg | ttgacgccga | ctgcatggac | 360 |
| gtcaatgtcc | gcgggcctga | tggcttcacc | ccgctcatga | tcgcctcctg | cagcggggc | 420 |
| ggcctggaga | cgggcaacag | cgaggaagag | gaggacgcgc | cggccgtcat | ctccgacttc | 480 |
| atctaccagg | gcgccagcct | gcacaaccag | acagaccgca | cgggcgagac | cgccttgcac | 540 |
| ctggccgccc | gctactcacg | ctctgatgcc | gccaagcgcc | tgctggaggc | cagcgcagat | 600 |
| gccaacatcc | aggacaacat | gggccgcacc | ccgctgcatg | cggctgtgtc | tgccgacgca | 660 |
| caaggtgtct | tccagatcct | gatccggaac | cgagccacag | acctggatgc | ccgcatgcat | 720 |
| gatggcacga | cgccactgat | cctggctgcc | cgcctggccg | tggagggcat | gctggaggac | 780 |
| ctcatcaact | cacacgccga | cgtcaacgcc | gtagatgacc | tgggcaagtc | cgccctgcac | 840 |
| tgggccgccg | ccgtgaacaa | tgtggatgcc | gcagttgtgc | tcctgaagaa | cggggctaac | 900 |
| aaagatatgc | agaacaacag | ggaggagaca | cccctgtttc | tggccgcccg | ggagggcagc | 960 |
| tacgagaccg | ccaaggtgct | gctggaccac | tttgccaacc | gggacatcac | ggatcatatg | 1020 |
| gaccgcctgc | cgcgcgacat | cgcacaggag | cgcatgcatc | acgacatcgt | gaggctgctg | 1080 |
| gacgagtaca | acctggtgcg | cagccccgca | gctgcacggag | ccccgctggg | gggcacgccc | 1140 |
| accctgtcgc | ccccgctctg | ctcgcccaac | ggctacctgg | gcagcctcaa | gcccggcgtg | 1200 |
| cagggcaaga | aggtccgcaa | gcccagcagc | aaaggcctgg | cctgtggaag | caaggaggcc | 1260 |
| aaggacctca | aggcacggag | gaagaagtcc | caggacggca | agggctgcct | gctggacagc | 1320 |
| tccggcatgc | tctcgcccgt | ggactccctg | gagtcacccc | catggctacct | gtcagacgtg | 1380 |
| gcctcgccgc | cactgctgcc | ctccccgttc | cagcagtctc | cgtccgtgcc | cctcaaccac | 1440 |
| ctgcctggga | tgcccgacac | ccacctgggc | atcgggcacc | tgaacgtggc | ggccaagccc | 1500 |
| gagatggcgg | cgctgggtgg | gggcggccgg | ctggcctttg | agactggccc | acctcgtctc | 1560 |
| tcccacctgc | ctgtggcctc | tggcaccagc | accgtcctgg | gctccagcag | cggagggggcc | 1620 |
| ctgaatttca | ctgtgggcgg | gtccaccagt | ttgaatggtc | aatgcgagtg | gctgtcccgg | 1680 |
| ctgcagagcg | gcatggtgcc | gaaccaatac | aaccctctgc | gggggagtgt | ggcaccaggc | 1740 |
| cccctgagca | cacaggcccc | ctccctgcag | catggcatgt | taggcccgct | gcacagtagc | 1800 |
| cttgctgcca | gcgccctgtc | ccagatgatg | agctaccagg | gcctgccag | cacccggctg | 1860 |
| gccacccagc | ctcacctggt | gcagacccag | caggtgcagc | cacaaaactt | acagatgcag | 1920 |
| cagcagaacc | tgcagccagc | aaacatccag | cagcagcaaa | gcctgcagcc | gccaccacca | 1980 |
| ccaccacagc | cgcaccttgg | cgtgagctca | gcagccagcg | gccacctggg | ccggagcttc | 2040 |
| ctgagtggag | agccgagcca | ggcagacgtg | cagccactgg | gccccagcag | cctgcggtg | 2100 |
| cacactattc | tgcccaggga | gagccccgcc | ctgcccacgt | cgctgccatc | ctcgctggtc | 2160 |

```
ccacccgtga ccgcagccca gttcctgacg ccccccctcgc agcacagcta ctcctcgcct    2220
gtggacaaca cccccagcca ccagctacag gtgcctgagc accccttcct cacccgtcc      2280 cctgagtccc ctgaccagtg gtccagctcg tccccgcatt ccaacgtctc cgactggtcc    2340
gagggcgtct ccagccctcc caccagcatg cagtcccaga tcgcccgcat tccggaggcc    2400
ttcaag                                                                2406
```

```
<210> SEQ ID NO 9
<211> LENGTH: 440
<212> TYPE: PRT
<213> ORGANISM: Artificial Sequence
<220> FEATURE:
<223> OTHER INFORMATION: Description of Artificial Sequence: Synthetic
      C-myc consensus protein sequence
<220> FEATURE:
<221> NAME/KEY: MOD_RES
<222> LOCATION: (6)..(6)
<223> OTHER INFORMATION: Ser or Asn
<220> FEATURE:
<221> NAME/KEY: MOD_RES
<222> LOCATION: (8)..(8)
<223> OTHER INFORMATION: Thr or Ala
<220> FEATURE:
<221> NAME/KEY: MOD_RES
<222> LOCATION: (24)..(24)
<223> OTHER INFORMATION: Tyr or Ile
<220> FEATURE:
<221> NAME/KEY: MOD_RES
<222> LOCATION: (33)..(33)
<223> OTHER INFORMATION: Gln or His
<220> FEATURE:
<221> NAME/KEY: MOD_RES
<222> LOCATION: (78)..(78)
<223> OTHER INFORMATION: Thr or Ala
<220> FEATURE:
<221> NAME/KEY: MOD_RES
<222> LOCATION: (79)..(79)
<223> OTHER INFORMATION: Pro or Thr
<220> FEATURE:
<221> NAME/KEY: MOD_RES
<222> LOCATION: (80)..(80)
<223> OTHER INFORMATION: May or may not be present
<220> FEATURE:
<221> NAME/KEY: MOD_RES
<222> LOCATION: (83)..(83)
<223> OTHER INFORMATION: Leu or Pro
<220> FEATURE:
<221> NAME/KEY: MOD_RES
<222> LOCATION: (85)..(85)
<223> OTHER INFORMATION: Gly or Glu
<220> FEATURE:
<221> NAME/KEY: MOD_RES
<222> LOCATION: (87)..(87)
<223> OTHER INFORMATION: Asn or Asp
<220> FEATURE:
<221> NAME/KEY: MOD_RES
<222> LOCATION: (93)..(93)
<223> OTHER INFORMATION: Ser or Asn
<220> FEATURE:
<221> NAME/KEY: MOD_RES
<222> LOCATION: (103)..(103)
<223> OTHER INFORMATION: Val or Met
<220> FEATURE:
<221> NAME/KEY: MOD_RES
<222> LOCATION: (161)..(161)
<223> OTHER INFORMATION: Gly or Thr
<220> FEATURE:
<221> NAME/KEY: MOD_RES
<222> LOCATION: (163)..(163)
<223> OTHER INFORMATION: Pro or Leu
<220> FEATURE:
<221> NAME/KEY: MOD_RES
<222> LOCATION: (164)..(164)
<223> OTHER INFORMATION: Asn or Ser
```

-continued

```
<220> FEATURE:
<221> NAME/KEY: MOD_RES
<222> LOCATION: (183)..(183)
<223> OTHER INFORMATION: Ser or Thr
<220> FEATURE:
<221> NAME/KEY: MOD_RES
<222> LOCATION: (210)..(210)
<223> OTHER INFORMATION: Pro, Ala or Thr
<220> FEATURE:
<221> NAME/KEY: MOD_RES
<222> LOCATION: (212)..(212)
<223> OTHER INFORMATION: Gln or Ser
<220> FEATURE:
<221> NAME/KEY: MOD_RES
<222> LOCATION: (215)..(215)
<223> OTHER INFORMATION: Ser or Thr
<220> FEATURE:
<221> NAME/KEY: MOD_RES
<222> LOCATION: (219)..(219)
<223> OTHER INFORMATION: Pro or Ser
<220> FEATURE:
<221> NAME/KEY: MOD_RES
<222> LOCATION: (228)..(228)
<223> OTHER INFORMATION: May or may not be present
<220> FEATURE:
<221> NAME/KEY: MOD_RES
<222> LOCATION: (233)..(233)
<223> OTHER INFORMATION: Gln or Arg
<220> FEATURE:
<221> NAME/KEY: MOD_RES
<222> LOCATION: (234)..(234)
<223> OTHER INFORMATION: Ala or Gly
<220> FEATURE:
<221> NAME/KEY: MOD_RES
<222> LOCATION: (235)..(235)
<223> OTHER INFORMATION: Ser or Thr
<220> FEATURE:
<221> NAME/KEY: MOD_RES
<222> LOCATION: (258)..(258)
<223> OTHER INFORMATION: Glu or Asp
<220> FEATURE:
<221> NAME/KEY: MOD_RES
<222> LOCATION: (273)..(273)
<223> OTHER INFORMATION: Ala, Thr or Pro
<220> FEATURE:
<221> NAME/KEY: MOD_RES
<222> LOCATION: (275)..(275)
<223> OTHER INFORMATION: Gly or Ala
<220> FEATURE:
<221> NAME/KEY: MOD_RES
<222> LOCATION: (283)..(283)
<223> OTHER INFORMATION: Pro or Ser
<220> FEATURE:
<221> NAME/KEY: MOD_RES
<222> LOCATION: (284)..(284)
<223> OTHER INFORMATION: Pro or Ser
<220> FEATURE:
<221> NAME/KEY: MOD_RES
<222> LOCATION: (285)..(285)
<223> OTHER INFORMATION: Ala or Ser
<220> FEATURE:
<221> NAME/KEY: MOD_RES
<222> LOCATION: (326)..(326)
<223> OTHER INFORMATION: Val or Ala
<220> FEATURE:
<221> NAME/KEY: MOD_RES
<222> LOCATION: (331)..(331)
<223> OTHER INFORMATION: Val or Gly
<220> FEATURE:
<221> NAME/KEY: MOD_RES
<222> LOCATION: (335)..(335)
<223> OTHER INFORMATION: Lys or Arg
<220> FEATURE:
<221> NAME/KEY: MOD_RES
<222> LOCATION: (344)..(344)
<223> OTHER INFORMATION: Thr or Ser
<220> FEATURE:
<221> NAME/KEY: MOD_RES
<222> LOCATION: (355)..(355)
```

```
<223> OTHER INFORMATION: Asp or Val
<220> FEATURE:
<221> NAME/KEY: MOD_RES
<222> LOCATION: (407)..(407)
<223> OTHER INFORMATION: Val or Ile
<220> FEATURE:
<221> NAME/KEY: MOD_RES
<222> LOCATION: (410)..(410)
<223> OTHER INFORMATION: Glu or Asp
<220> FEATURE:
<221> NAME/KEY: MOD_RES
<222> LOCATION: (412)..(412)
<223> OTHER INFORMATION: Gln or His
<220> FEATURE:
<221> NAME/KEY: MOD_RES
<222> LOCATION: (415)..(415)
<223> OTHER INFORMATION: Thr or Ile
<220> FEATURE:
<221> NAME/KEY: MOD_RES
<222> LOCATION: (418)..(418)
<223> OTHER INFORMATION: Glu or Lys
<220> FEATURE:
<221> NAME/KEY: MOD_RES
<222> LOCATION: (439)..(439)
<223> OTHER INFORMATION: Cys or Gly

<400> SEQUENCE: 9

Met Pro Leu Asn Val Xaa Phe Xaa Asn Arg Asn Tyr Asp Leu Asp Tyr
1               5                   10                  15

Asp Ser Val Gln Pro Tyr Phe Xaa Cys Asp Glu Glu Glu Asn Phe Tyr
            20                  25                  30

Xaa Gln Gln Gln Gln Ser Glu Leu Gln Pro Pro Ala Pro Ser Glu Asp
        35                  40                  45

Ile Trp Lys Lys Phe Glu Leu Leu Pro Thr Pro Pro Leu Ser Pro Ser
50                  55                  60

Arg Arg Ser Gly Leu Cys Ser Pro Ser Tyr Val Ala Val Xaa Xaa Ser
65                  70                  75                  80

Phe Ser Xaa Arg Xaa Asp Xaa Asp Gly Gly Gly Xaa Phe Ser Thr
                85                  90                  95

Ala Asp Gln Leu Glu Met Xaa Thr Glu Leu Leu Gly Gly Asp Met Val
            100                 105                 110

Asn Gln Ser Phe Ile Cys Asp Pro Asp Asp Glu Thr Phe Ile Lys Asn
        115                 120                 125

Ile Ile Ile Gln Asp Cys Met Trp Ser Gly Phe Ser Ala Ala Ala Lys
130                 135                 140

Leu Val Ser Glu Lys Leu Ala Ser Tyr Gln Ala Ala Arg Lys Asp Ser
145                 150                 155                 160

Xaa Ser Xaa Xaa Pro Ala Arg Gly His Ser Val Cys Ser Thr Ser Ser
                165                 170                 175

Leu Tyr Leu Gln Asp Leu Xaa Ala Ala Ala Ser Glu Cys Ile Asp Pro
            180                 185                 190

Ser Val Val Phe Pro Tyr Pro Leu Asn Asp Ser Ser Ser Pro Lys Ser
        195                 200                 205

Cys Xaa Ser Xaa Asp Ser Xaa Ala Phe Ser Xaa Ser Ser Asp Ser Leu
210                 215                 220

Leu Ser Ser Thr Glu Ser Ser Pro Xaa Xaa Xaa Pro Glu Pro Leu Val
225                 230                 235                 240

Leu His Glu Glu Thr Pro Pro Thr Thr Ser Ser Asp Ser Glu Glu Glu
            245                 250                 255

Gln Xaa Asp Glu Glu Glu Ile Asp Val Val Ser Val Glu Lys Arg Gln
        260                 265                 270
```

Xaa Pro Xaa Lys Arg Ser Glu Ser Gly Ser Xaa Xaa Gly Gly His
            275                 280                 285

Ser Lys Pro Pro His Ser Pro Leu Val Leu Lys Arg Cys His Val Ser
290                 295                 300

Thr His Gln His Asn Tyr Ala Ala Pro Pro Ser Thr Arg Lys Asp Tyr
305                 310                 315                 320

Pro Ala Ala Lys Arg Xaa Lys Leu Asp Ser Xaa Arg Val Leu Xaa Gln
                325                 330                 335

Ile Ser Asn Asn Arg Lys Cys Xaa Ser Pro Arg Ser Ser Asp Thr Glu
            340                 345                 350

Glu Asn Xaa Lys Arg Arg Thr His Asn Val Leu Glu Arg Gln Arg Arg
        355                 360                 365

Asn Glu Leu Lys Arg Ser Phe Phe Ala Leu Arg Asp Gln Ile Pro Glu
370                 375                 380

Leu Glu Asn Asn Glu Lys Ala Pro Lys Val Val Ile Leu Lys Lys Ala
385                 390                 395                 400

Thr Ala Tyr Ile Leu Ser Xaa Gln Ala Xaa Glu Xaa Lys Leu Xaa Ser
                405                 410                 415

Glu Xaa Asp Leu Leu Arg Lys Arg Arg Glu Gln Leu Lys His Lys Leu
    420                 425                 430

Glu Gln Leu Arg Asn Ser Xaa Ala
        435                 440

<210> SEQ ID NO 10
<211> LENGTH: 803
<212> TYPE: PRT
<213> ORGANISM: Artificial Sequence
<220> FEATURE:
<223> OTHER INFORMATION: Description of Artificial Sequence: Synthetic
      Notch Intracellular Domain consensus protein sequence
<220> FEATURE:
<221> NAME/KEY: MOD_RES
<222> LOCATION: (82)..(82)
<223> OTHER INFORMATION: Asp or Ser
<220> FEATURE:
<221> NAME/KEY: MOD_RES
<222> LOCATION: (102)..(102)
<223> OTHER INFORMATION: Met or Val
<220> FEATURE:
<221> NAME/KEY: MOD_RES
<222> LOCATION: (228)..(228)
<223> OTHER INFORMATION: Leu or Ile
<220> FEATURE:
<221> NAME/KEY: MOD_RES
<222> LOCATION: (307)..(307)
<223> OTHER INFORMATION: Lys or Arg
<220> FEATURE:
<221> NAME/KEY: MOD_RES
<222> LOCATION: (374)..(374)
<223> OTHER INFORMATION: Thr or Ala
<220> FEATURE:
<221> NAME/KEY: MOD_RES
<222> LOCATION: (375)..(375)
<223> OTHER INFORMATION: Ala or Pro
<220> FEATURE:
<221> NAME/KEY: MOD_RES
<222> LOCATION: (385)..(385)
<223> OTHER INFORMATION: Thr or Pro
<220> FEATURE:
<221> NAME/KEY: MOD_RES
<222> LOCATION: (395)..(395)
<223> OTHER INFORMATION: Ser or Asn
<220> FEATURE:
<221> NAME/KEY: MOD_RES
<222> LOCATION: (398)..(398)
<223> OTHER INFORMATION: Ser or Pro
<220> FEATURE:
<221> NAME/KEY: MOD_RES

```
<222> LOCATION: (399)..(399)
<223> OTHER INFORMATION: Ala or Gly
<220> FEATURE:
<221> NAME/KEY: MOD_RES
<222> LOCATION: (400)..(400)
<223> OTHER INFORMATION: Thr or Val
<220> FEATURE:
<221> NAME/KEY: MOD_RES
<222> LOCATION: (405)..(405)
<223> OTHER INFORMATION: Ala or Val
<220> FEATURE:
<221> NAME/KEY: MOD_RES
<222> LOCATION: (410)..(410)
<223> OTHER INFORMATION: Thr or Ser
<220> FEATURE:
<221> NAME/KEY: MOD_RES
<222> LOCATION: (416)..(416)
<223> OTHER INFORMATION: Gly or Ser
<220> FEATURE:
<221> NAME/KEY: MOD_RES
<222> LOCATION: (442)..(442)
<223> OTHER INFORMATION: Gly or Ser
<220> FEATURE:
<221> NAME/KEY: MOD_RES
<222> LOCATION: (476)..(476)
<223> OTHER INFORMATION: Met or Val
<220> FEATURE:
<221> NAME/KEY: MOD_RES
<222> LOCATION: (479)..(479)
<223> OTHER INFORMATION: Ser or Asn
<220> FEATURE:
<221> NAME/KEY: MOD_RES
<222> LOCATION: (492)..(492)
<223> OTHER INFORMATION: Ser or Gly
<220> FEATURE:
<221> NAME/KEY: MOD_RES
<222> LOCATION: (506)..(506)
<223> OTHER INFORMATION: Ala or Gly
<220> FEATURE:
<221> NAME/KEY: MOD_RES
<222> LOCATION: (509)..(509)
<223> OTHER INFORMATION: Ser or Gly
<220> FEATURE:
<221> NAME/KEY: MOD_RES
<222> LOCATION: (515)..(515)
<223> OTHER INFORMATION: Pro or Thr
<220> FEATURE:
<221> NAME/KEY: MOD_RES
<222> LOCATION: (516)..(516)
<223> OTHER INFORMATION: Pro or Gly
<220> FEATURE:
<221> NAME/KEY: MOD_RES
<222> LOCATION: (528)..(528)
<223> OTHER INFORMATION: Ser or Gly
<220> FEATURE:
<221> NAME/KEY: MOD_RES
<222> LOCATION: (529)..(529)
<223> OTHER INFORMATION: Ala or Thr
<220> FEATURE:
<221> NAME/KEY: MOD_RES
<222> LOCATION: (534)..(534)
<223> OTHER INFORMATION: Ser or Gly
<220> FEATURE:
<221> NAME/KEY: MOD_RES
<222> LOCATION: (535)..(535)
<223> OTHER INFORMATION: Thr or Ser
<220> FEATURE:
<221> NAME/KEY: MOD_RES
<222> LOCATION: (536)..(536)
<223> OTHER INFORMATION: Asn or Ser
<220> FEATURE:
<221> NAME/KEY: MOD_RES
<222> LOCATION: (537)..(537)
<223> OTHER INFORMATION: Gly or Ser
<220> FEATURE:
<221> NAME/KEY: MOD_RES
<222> LOCATION: (538)..(538)
<223> OTHER INFORMATION: Thr or Gly
<220> FEATURE:
```

```
<221> NAME/KEY: MOD_RES
<222> LOCATION: (541)..(541)
<223> OTHER INFORMATION: Met or Leu
<220> FEATURE:
<221> NAME/KEY: MOD_RES
<222> LOCATION: (547)..(547)
<223> OTHER INFORMATION: Ala or Gly
<220> FEATURE:
<221> NAME/KEY: MOD_RES
<222> LOCATION: (548)..(548)
<223> OTHER INFORMATION: Pro or Ser
<220> FEATURE:
<221> NAME/KEY: MOD_RES
<222> LOCATION: (549)..(549)
<223> OTHER INFORMATION: Ala or Thr
<220> FEATURE:
<221> NAME/KEY: MOD_RES
<222> LOCATION: (559)..(559)
<223> OTHER INFORMATION: Pro or Ser
<220> FEATURE:
<221> NAME/KEY: MOD_RES
<222> LOCATION: (563)..(563)
<223> OTHER INFORMATION: Asn or Ser
<220> FEATURE:
<221> NAME/KEY: MOD_RES
<222> LOCATION: (568)..(568)
<223> OTHER INFORMATION: Ser or Asn
<220> FEATURE:
<221> NAME/KEY: MOD_RES
<222> LOCATION: (575)..(575)
<223> OTHER INFORMATION: Pro or Gly
<220> FEATURE:
<221> NAME/KEY: MOD_RES
<222> LOCATION: (576)..(576)
<223> OTHER INFORMATION: Gly or Ser
<220> FEATURE:
<221> NAME/KEY: MOD_RES
<222> LOCATION: (578)..(578)
<223> OTHER INFORMATION: Thr or Ala
<220> FEATURE:
<221> NAME/KEY: MOD_RES
<222> LOCATION: (581)..(581)
<223> OTHER INFORMATION: Thr or Pro
<220> FEATURE:
<221> NAME/KEY: MOD_RES
<222> LOCATION: (587)..(587)
<223> OTHER INFORMATION: Ala or Pro
<220> FEATURE:
<221> NAME/KEY: MOD_RES
<222> LOCATION: (588)..(588)
<223> OTHER INFORMATION: Gly or Ser
<220> FEATURE:
<221> NAME/KEY: MOD_RES
<222> LOCATION: (592)..(592)
<223> OTHER INFORMATION: Gly or Ser
<220> FEATURE:
<221> NAME/KEY: MOD_RES
<222> LOCATION: (594)..(594)
<223> OTHER INFORMATION: Met or Val
<220> FEATURE:
<221> NAME/KEY: MOD_RES
<222> LOCATION: (597)..(597)
<223> OTHER INFORMATION: Leu or Ile
<220> FEATURE:
<221> NAME/KEY: MOD_RES
<222> LOCATION: (602)..(602)
<223> OTHER INFORMATION: Ser or Ala
<220> FEATURE:
<221> NAME/KEY: MOD_RES
<222> LOCATION: (603)..(603)
<223> OTHER INFORMATION: Thr or Ala
<220> FEATURE:
<221> NAME/KEY: MOD_RES
<222> LOCATION: (604)..(604)
<223> OTHER INFORMATION: Asn or Ser
<220> FEATURE:
<221> NAME/KEY: MOD_RES
<222> LOCATION: (605)..(605)
<223> OTHER INFORMATION: Thr or Ala
```

```
<220> FEATURE:
<221> NAME/KEY: MOD_RES
<222> LOCATION: (608)..(608)
<223> OTHER INFORMATION: Pro or Gln
<220> FEATURE:
<221> NAME/KEY: MOD_RES
<222> LOCATION: (609)..(609)
<223> OTHER INFORMATION: Met or Ile
<220> FEATURE:
<221> NAME/KEY: MOD_RES
<222> LOCATION: (610)..(610)
<223> OTHER INFORMATION: Met or Ile
<220> FEATURE:
<221> NAME/KEY: MOD_RES
<222> LOCATION: (611)..(611)
<223> OTHER INFORMATION: May or may not be present
<220> FEATURE:
<221> NAME/KEY: MOD_RES
<222> LOCATION: (617)..(617)
<223> OTHER INFORMATION: Ser or Asn
<220> FEATURE:
<221> NAME/KEY: MOD_RES
<222> LOCATION: (639)..(639)
<223> OTHER INFORMATION: Leu, Ile or Met
<220> FEATURE:
<221> NAME/KEY: MOD_RES
<222> LOCATION: (641)..(641)
<223> OTHER INFORMATION: Gln or Pro
<220> FEATURE:
<221> NAME/KEY: MOD_RES
<222> LOCATION: (646)..(659)
<223> OTHER INFORMATION: May or may not be present
<220> FEATURE:
<221> NAME/KEY: MOD_RES
<222> LOCATION: (662)..(662)
<223> OTHER INFORMATION: Pro or Ser
<220> FEATURE:
<221> NAME/KEY: MOD_RES
<222> LOCATION: (667)..(667)
<223> OTHER INFORMATION: Ser or Gly
<220> FEATURE:
<221> NAME/KEY: MOD_RES
<222> LOCATION: (673)..(673)
<223> OTHER INFORMATION: Asn or Ser
<220> FEATURE:
<221> NAME/KEY: MOD_RES
<222> LOCATION: (699)..(699)
<223> OTHER INFORMATION: Pro or Ala
<220> FEATURE:
<221> NAME/KEY: MOD_RES
<222> LOCATION: (709)..(709)
<223> OTHER INFORMATION: Gln or Pro
<220> FEATURE:
<221> NAME/KEY: MOD_RES
<222> LOCATION: (719)..(719)
<223> OTHER INFORMATION: Met or Leu
<220> FEATURE:
<221> NAME/KEY: MOD_RES
<222> LOCATION: (723)..(723)
<223> OTHER INFORMATION: Met or Val
<220> FEATURE:
<221> NAME/KEY: MOD_RES
<222> LOCATION: (725)..(725)
<223> OTHER INFORMATION: Thr or Ala
<220> FEATURE:
<221> NAME/KEY: MOD_RES
<222> LOCATION: (726)..(726)
<223> OTHER INFORMATION: Thr or Ala
<220> FEATURE:
<221> NAME/KEY: MOD_RES
<222> LOCATION: (740)..(740)
<223> OTHER INFORMATION: May or may not be present
<220> FEATURE:
<221> NAME/KEY: MOD_RES
<222> LOCATION: (773)..(773)
<223> OTHER INFORMATION: Pro or Arg
<220> FEATURE:
<221> NAME/KEY: MOD_RES
<222> LOCATION: (777)..(777)
```

```
<223> OTHER INFORMATION: Ile or Val
<220> FEATURE:
<221> NAME/KEY: MOD_RES
<222> LOCATION: (784)..(784)
<223> OTHER INFORMATION: Ile or Val
<220> FEATURE:
<221> NAME/KEY: MOD_RES
<222> LOCATION: (790)..(790)
<223> OTHER INFORMATION: Thr or Ser
<220> FEATURE:
<221> NAME/KEY: MOD_RES
<222> LOCATION: (792)..(792)
<223> OTHER INFORMATION: Pro or Gln
<220> FEATURE:
<221> NAME/KEY: MOD_RES
<222> LOCATION: (796)..(796)
<223> OTHER INFORMATION: Thr or Ala
<220> FEATURE:
<221> NAME/KEY: MOD_RES
<222> LOCATION: (797)..(797)
<223> OTHER INFORMATION: His or Arg

<400> SEQUENCE: 10

Val Leu Leu Ser Arg Lys Arg Arg Gln His Gly Gln Leu Trp Phe
 1               5                  10                  15

Pro Glu Gly Phe Lys Val Ser Glu Ala Ser Lys Lys Arg Arg Glu
            20                  25                  30

Pro Leu Gly Glu Asp Ser Val Gly Leu Lys Pro Leu Lys Asn Ala Ser
        35                  40                  45

Asp Gly Ala Leu Met Asp Asp Asn Gln Asn Glu Trp Gly Asp Glu Asp
50                  55                  60

Leu Glu Thr Lys Lys Phe Arg Phe Glu Glu Pro Val Val Leu Pro Asp
65                  70                  75                  80

Leu Xaa Asp Gln Thr Asp His Arg Gln Trp Thr Gln Gln His Leu Asp
                85                  90                  95

Ala Ala Asp Leu Arg Xaa Ser Ala Met Ala Pro Thr Pro Pro Gln Gly
            100                 105                 110

Glu Val Asp Ala Asp Cys Met Asp Val Asn Val Arg Gly Pro Asp Gly
        115                 120                 125

Phe Thr Pro Leu Met Ile Ala Ser Cys Ser Gly Gly Gly Leu Glu Thr
130                 135                 140

Gly Asn Ser Glu Glu Glu Glu Asp Ala Pro Ala Val Ile Ser Asp Phe
145                 150                 155                 160

Ile Tyr Gln Gly Ala Ser Leu His Asn Gln Thr Asp Arg Thr Gly Glu
                165                 170                 175

Thr Ala Leu His Leu Ala Ala Arg Tyr Ser Arg Ser Asp Ala Ala Lys
            180                 185                 190

Arg Leu Leu Glu Ala Ser Ala Asp Ala Asn Ile Gln Asp Asn Met Gly
        195                 200                 205

Arg Thr Pro Leu His Ala Ala Val Ser Ala Asp Ala Gln Gly Val Phe
210                 215                 220

Gln Ile Leu Xaa Arg Asn Arg Ala Thr Asp Leu Asp Ala Arg Met His
225                 230                 235                 240

Asp Gly Thr Thr Pro Leu Ile Leu Ala Ala Arg Leu Ala Val Glu Gly
                245                 250                 255

Met Leu Glu Asp Leu Ile Asn Ser His Ala Asp Val Asn Ala Val Asp
            260                 265                 270

Asp Leu Gly Lys Ser Ala Leu His Trp Ala Ala Val Asn Asn Val
        275                 280                 285

Asp Ala Ala Val Val Leu Leu Lys Asn Gly Ala Asn Lys Asp Met Gln
```

```
            290                 295                 300
Asn Asn Xaa Glu Glu Thr Pro Leu Phe Leu Ala Ala Arg Glu Gly Ser
305                 310                 315                 320

Tyr Glu Thr Ala Lys Val Leu Leu Asp His Phe Ala Asn Arg Asp Ile
                    325                 330                 335

Thr Asp His Met Asp Arg Leu Pro Arg Asp Ile Ala Gln Glu Arg Met
                340                 345                 350

His His Asp Ile Val Arg Leu Leu Asp Glu Tyr Asn Leu Val Arg Ser
            355                 360                 365

Pro Gln Leu His Gly Xaa Xaa Leu Gly Gly Thr Pro Thr Leu Ser Pro
        370                 375                 380

Xaa Leu Cys Ser Pro Asn Gly Tyr Leu Gly Xaa Leu Lys Xaa Xaa Xaa
385                 390                 395                 400

Gln Gly Lys Lys Xaa Arg Lys Pro Ser Xaa Lys Gly Leu Ala Cys Xaa
                405                 410                 415

Ser Lys Glu Ala Lys Asp Leu Lys Ala Arg Arg Lys Lys Ser Gln Asp
                420                 425                 430

Gly Lys Gly Cys Leu Leu Asp Ser Ser Xaa Met Leu Ser Pro Val Asp
            435                 440                 445

Ser Leu Glu Ser Pro His Gly Tyr Leu Ser Asp Val Ala Ser Pro Pro
        450                 455                 460

Leu Leu Pro Ser Pro Phe Gln Gln Ser Pro Ser Xaa Pro Leu Xaa His
465                 470                 475                 480

Leu Pro Gly Met Pro Asp Thr His Leu Gly Ile Xaa His Leu Asn Val
                485                 490                 495

Ala Ala Lys Pro Glu Met Ala Ala Leu Xaa Gly Gly Xaa Arg Leu Ala
                500                 505                 510

Phe Glu Xaa Xaa Pro Pro Arg Leu Ser His Leu Pro Val Ala Ser Xaa
            515                 520                 525

Xaa Ser Thr Val Leu Xaa Xaa Xaa Xaa Gly Ala Xaa Asn Phe Thr
        530                 535                 540

Val Gly Xaa Xaa Xaa Ser Leu Asn Gly Gln Cys Glu Trp Leu Xaa Arg
545                 550                 555                 560

Leu Gln Xaa Gly Met Val Pro Xaa Gln Tyr Asn Pro Leu Arg Xaa Xaa
                565                 570                 575

Val Xaa Pro Gly Xaa Leu Ser Thr Gln Ala Xaa Xaa Leu Gln His Xaa
            580                 585                 590

Met Xaa Gly Pro Xaa His Ser Ser Leu Xaa Xaa Xaa Xaa Leu Ser Xaa
        595                 600                 605

Xaa Xaa Ser Tyr Gln Gly Leu Pro Xaa Thr Arg Leu Ala Thr Gln Pro
610                 615                 620

His Leu Val Gln Thr Gln Val Gln Pro Gln Asn Leu Gln Xaa Gln
625                 630                 635                 640

Xaa Gln Asn Leu Gln Pro Ala Asn Ile Gln Gln Gln Ser Leu Gln
                645                 650                 655

Pro Pro Pro Pro Pro Xaa Gln Pro His Leu Xaa Val Ser Ser Ala Ala
                660                 665                 670

Xaa Gly His Leu Gly Arg Ser Phe Leu Ser Gly Glu Pro Ser Gln Ala
            675                 680                 685

Asp Val Gln Pro Leu Gly Pro Ser Ser Leu Xaa Val His Thr Ile Leu
        690                 695                 700

Pro Gln Glu Ser Xaa Ala Leu Pro Thr Ser Leu Pro Ser Ser Xaa Val
705                 710                 715                 720
```

```
Pro Pro Xaa Thr Xaa Xaa Gln Phe Leu Thr Pro Pro Ser Gln His Ser
            725                 730                 735

Tyr Ser Ser Ser Pro Val Asp Asn Thr Pro Ser His Gln Leu Gln Val
            740                 745                 750

Pro Glu His Pro Phe Leu Thr Pro Ser Pro Glu Ser Pro Asp Gln Trp
            755                 760                 765

Ser Ser Ser Ser Xaa His Ser Asn Xaa Ser Asp Trp Ser Glu Gly Xaa
            770                 775                 780

Ser Ser Pro Pro Thr Xaa Met Xaa Ser Gln Ile Xaa Xaa Ile Pro Glu
785                 790                 795                 800

Ala Phe Lys

<210> SEQ ID NO 11
<211> LENGTH: 354
<212> TYPE: PRT
<213> ORGANISM: Artificial Sequence
<220> FEATURE:
<223> OTHER INFORMATION: Description of Artificial Sequence: Synthetic
      Atoh1 consensus protein sequence
<220> FEATURE:
<221> NAME/KEY: MOD_RES
<222> LOCATION: (22)..(22)
<223> OTHER INFORMATION: Gln or His
<220> FEATURE:
<221> NAME/KEY: MOD_RES
<222> LOCATION: (28)..(28)
<223> OTHER INFORMATION: Leu or Val
<220> FEATURE:
<221> NAME/KEY: MOD_RES
<222> LOCATION: (30)..(31)
<223> OTHER INFORMATION: May or may not be present
<220> FEATURE:
<221> NAME/KEY: MOD_RES
<222> LOCATION: (34)..(35)
<223> OTHER INFORMATION: May or may not be present
<220> FEATURE:
<221> NAME/KEY: MOD_RES
<222> LOCATION: (45)..(45)
<223> OTHER INFORMATION: Glu or Asp
<220> FEATURE:
<221> NAME/KEY: MOD_RES
<222> LOCATION: (46)..(46)
<223> OTHER INFORMATION: His or Leu
<220> FEATURE:
<221> NAME/KEY: MOD_RES
<222> LOCATION: (51)..(51)
<223> OTHER INFORMATION: Pro or Ala
<220> FEATURE:
<221> NAME/KEY: MOD_RES
<222> LOCATION: (66)..(66)
<223> OTHER INFORMATION: Ala or Thr
<220> FEATURE:
<221> NAME/KEY: MOD_RES
<222> LOCATION: (72)..(72)
<223> OTHER INFORMATION: Ile or Leu
<220> FEATURE:
<221> NAME/KEY: MOD_RES
<222> LOCATION: (88)..(88)
<223> OTHER INFORMATION: Ser or Gly
<220> FEATURE:
<221> NAME/KEY: MOD_RES
<222> LOCATION: (99)..(99)
<223> OTHER INFORMATION: Val or Ala
<220> FEATURE:
<221> NAME/KEY: MOD_RES
<222> LOCATION: (101)..(101)
<223> OTHER INFORMATION: Gly or Ser
<220> FEATURE:
<221> NAME/KEY: MOD_RES
<222> LOCATION: (102)..(102)
<223> OTHER INFORMATION: Arg or Gln
<220> FEATURE:
```

```
<221> NAME/KEY: MOD_RES
<222> LOCATION: (110)..(110)
<223> OTHER INFORMATION: Ser or Gly
<220> FEATURE:
<221> NAME/KEY: MOD_RES
<222> LOCATION: (111)..(111)
<223> OTHER INFORMATION: Gly or Cys
<220> FEATURE:
<221> NAME/KEY: MOD_RES
<222> LOCATION: (113)..(113)
<223> OTHER INFORMATION: Ala or Gly
<220> FEATURE:
<221> NAME/KEY: MOD_RES
<222> LOCATION: (114)..(114)
<223> OTHER INFORMATION: May or may not be present
<220> FEATURE:
<221> NAME/KEY: MOD_RES
<222> LOCATION: (115)..(115)
<223> OTHER INFORMATION: Ser or Leu
<220> FEATURE:
<221> NAME/KEY: MOD_RES
<222> LOCATION: (219)..(219)
<223> OTHER INFORMATION: Ser or Asn
<220> FEATURE:
<221> NAME/KEY: MOD_RES
<222> LOCATION: (220)..(220)
<223> OTHER INFORMATION: Gly or Val
<220> FEATURE:
<221> NAME/KEY: MOD_RES
<222> LOCATION: (228)..(228)
<223> OTHER INFORMATION: Pro or Thr
<220> FEATURE:
<221> NAME/KEY: MOD_RES
<222> LOCATION: (233)..(233)
<223> OTHER INFORMATION: Ser or Asn
<220> FEATURE:
<221> NAME/KEY: MOD_RES
<222> LOCATION: (242)..(242)
<223> OTHER INFORMATION: Ala or Ser
<220> FEATURE:
<221> NAME/KEY: MOD_RES
<222> LOCATION: (250)..(250)
<223> OTHER INFORMATION: Ala or Asn
<220> FEATURE:
<221> NAME/KEY: MOD_RES
<222> LOCATION: (251)..(251)
<223> OTHER INFORMATION: Ala or Ser
<220> FEATURE:
<221> NAME/KEY: MOD_RES
<222> LOCATION: (252)..(252)
<223> OTHER INFORMATION: Thr or Ala
<220> FEATURE:
<221> NAME/KEY: MOD_RES
<222> LOCATION: (253)..(253)
<223> OTHER INFORMATION: Ala or Val
<220> FEATURE:
<221> NAME/KEY: MOD_RES
<222> LOCATION: (258)..(258)
<223> OTHER INFORMATION: Gln or Pro
<220> FEATURE:
<221> NAME/KEY: MOD_RES
<222> LOCATION: (260)..(260)
<223> OTHER INFORMATION: Ser or Pro
<220> FEATURE:
<221> NAME/KEY: MOD_RES
<222> LOCATION: (263)..(263)
<223> OTHER INFORMATION: Ser or Gly
<220> FEATURE:
<221> NAME/KEY: MOD_RES
<222> LOCATION: (264)..(264)
<223> OTHER INFORMATION: Gln or Pro
<220> FEATURE:
<221> NAME/KEY: MOD_RES
<222> LOCATION: (271)..(271)
<223> OTHER INFORMATION: Ser or Pro
<220> FEATURE:
<221> NAME/KEY: MOD_RES
<222> LOCATION: (278)..(278)
<223> OTHER INFORMATION: Ala or Gly
```

```
<220> FEATURE:
<221> NAME/KEY: MOD_RES
<222> LOCATION: (282)..(282)
<223> OTHER INFORMATION: Ala or Ser
<220> FEATURE:
<221> NAME/KEY: MOD_RES
<222> LOCATION: (295)..(295)
<223> OTHER INFORMATION: Ser or Pro
<220> FEATURE:
<221> NAME/KEY: MOD_RES
<222> LOCATION: (296)..(296)
<223> OTHER INFORMATION: Thr or Ala
<220> FEATURE:
<221> NAME/KEY: MOD_RES
<222> LOCATION: (300)..(300)
<223> OTHER INFORMATION: Ser or Arg
<220> FEATURE:
<221> NAME/KEY: MOD_RES
<222> LOCATION: (310)..(310)
<223> OTHER INFORMATION: Asn or Asp
<220> FEATURE:
<221> NAME/KEY: MOD_RES
<222> LOCATION: (318)..(318)
<223> OTHER INFORMATION: Ser or Gly
<220> FEATURE:
<221> NAME/KEY: MOD_RES
<222> LOCATION: (326)..(326)
<223> OTHER INFORMATION: Glu or Asp

<400> SEQUENCE: 11

Met Ser Arg Leu Leu His Ala Glu Glu Trp Ala Glu Val Lys Glu Leu
1               5                   10                  15

Gly Asp His His Arg Xaa Pro Gln Pro His His Xaa Pro Gln Pro Pro
            20                  25                  30

Pro Pro Pro Gln Pro Pro Ala Thr Leu Gln Ala Arg Xaa Xaa Pro Val
        35                  40                  45

Tyr Pro Xaa Glu Leu Ser Leu Leu Asp Ser Thr Asp Pro Arg Ala Trp
    50                  55                  60

Leu Xaa Pro Thr Leu Gln Gly Xaa Cys Thr Ala Arg Ala Ala Gln Tyr
65                  70                  75                  80

Leu Leu His Ser Pro Glu Leu Xaa Ala Ser Glu Ala Ala Ala Pro Arg
                85                  90                  95

Asp Glu Xaa Asp Xaa Xaa Gly Glu Leu Val Arg Arg Ser Xaa Xaa Gly
            100                 105                 110

Xaa Ser Xaa Ser Lys Ser Pro Gly Pro Val Lys Val Arg Glu Gln Leu
        115                 120                 125

Cys Lys Leu Lys Gly Gly Val Val Asp Glu Leu Gly Cys Ser Arg
130                 135                 140

Gln Arg Ala Pro Ser Ser Lys Gln Val Asn Gly Val Gln Lys Gln Arg
145                 150                 155                 160

Arg Leu Ala Ala Asn Ala Arg Glu Arg Arg Met His Gly Leu Asn
                165                 170                 175

His Ala Phe Asp Gln Leu Arg Asn Val Ile Pro Ser Phe Asn Asn Asp
            180                 185                 190

Lys Lys Leu Ser Lys Tyr Glu Thr Leu Gln Met Ala Gln Ile Tyr Ile
        195                 200                 205

Asn Ala Leu Ser Glu Leu Leu Gln Thr Pro Xaa Xaa Gly Glu Gln Pro
210                 215                 220

Pro Pro Pro Xaa Ala Ser Cys Lys Xaa Asp His His His Leu Arg Thr
225                 230                 235                 240

Ala Xaa Ser Tyr Glu Gly Gly Ala Gly Xaa Xaa Xaa Xaa Ala Gly Ala
                245                 250                 255
```

```
Gln Xaa Ala Xaa Gly Gly Xaa Xaa Arg Pro Thr Pro Pro Gly Xaa Cys
            260                 265                 270

Arg Thr Arg Phe Ser Xaa Pro Ala Ser Xaa Gly Gly Tyr Ser Val Gln
        275                 280                 285

Leu Asp Ala Leu His Phe Xaa Xaa Phe Glu Asp Xaa Ala Leu Thr Ala
    290                 295                 300

Met Met Ala Gln Lys Xaa Leu Ser Pro Ser Leu Pro Gly Xaa Ile Leu
305                 310                 315                 320

Gln Pro Val Gln Glu Xaa Asn Ser Lys Thr Ser Pro Arg Ser His Arg
                325                 330                 335

Ser Asp Gly Glu Phe Ser Pro His Ser His Tyr Ser Asp Ser Asp Glu
            340                 345                 350

Ala Ser

<210> SEQ ID NO 12
<211> LENGTH: 462
<212> TYPE: PRT
<213> ORGANISM: Homo sapiens

<400> SEQUENCE: 12

Met Pro Ser Cys Ser Thr Ser Thr Met Pro Gly Met Ile Cys Lys Asn
1               5                   10                  15

Pro Asp Leu Glu Phe Asp Ser Leu Gln Pro Cys Phe Tyr Pro Asp Glu
            20                  25                  30

Asp Asp Phe Tyr Phe Gly Gly Pro Asp Ser Thr Pro Pro Gly Glu Asp
        35                  40                  45

Ile Trp Lys Lys Phe Glu Leu Leu Pro Thr Pro Pro Leu Ser Pro Ser
50                  55                  60

Arg Gly Phe Ala Glu His Ser Ser Glu Pro Pro Ser Trp Val Thr Glu
65                  70                  75                  80

Met Leu Leu Glu Asn Glu Leu Trp Gly Ser Pro Ala Glu Glu Asp Ala
                85                  90                  95

Phe Gly Leu Gly Gly Leu Gly Gly Leu Thr Pro Asn Pro Val Ile Leu
            100                 105                 110

Gln Asp Cys Met Trp Ser Gly Phe Ser Ala Arg Glu Lys Leu Glu Arg
        115                 120                 125

Ala Val Ser Glu Lys Leu Gln His Gly Arg Gly Pro Pro Thr Ala Gly
    130                 135                 140

Ser Thr Ala Gln Ser Pro Gly Ala Gly Ala Ala Ser Pro Ala Gly Arg
145                 150                 155                 160

Gly His Gly Gly Ala Ala Gly Ala Gly Arg Ala Gly Ala Ala Leu Pro
                165                 170                 175

Ala Glu Leu Ala His Pro Ala Ala Glu Cys Val Asp Pro Ala Val Val
            180                 185                 190

Phe Pro Phe Pro Val Asn Lys Arg Glu Pro Ala Pro Val Pro Ala Ala
        195                 200                 205

Pro Ala Ser Ala Pro Ala Ala Gly Pro Ala Val Ala Ser Gly Ala Gly
    210                 215                 220

Ile Ala Ala Pro Ala Gly Ala Pro Gly Val Ala Pro Arg Pro Gly Gly
225                 230                 235                 240

Gly Arg Gln Thr Ser Gly Gly Asp His Lys Ala Leu Ser Thr Ser Gly
                245                 250                 255

Glu Asp Thr Leu Ser Asp Ser Asp Asp Glu Asp Asp Glu Glu Glu Asp
            260                 265                 270
```

Glu Glu Glu Glu Ile Asp Val Val Thr Val Glu Lys Arg Arg Ser Ser
            275                 280                 285

Ser Asn Thr Lys Ala Val Thr Thr Phe Thr Ile Thr Val Arg Pro Lys
        290                 295                 300

Asn Ala Ala Leu Gly Pro Gly Arg Ala Gln Ser Ser Glu Leu Ile Leu
305                 310                 315                 320

Lys Arg Cys Leu Pro Ile His Gln Gln His Asn Tyr Ala Ala Pro Ser
                325                 330                 335

Pro Tyr Val Glu Ser Glu Asp Ala Pro Gln Lys Lys Ile Lys Ser
            340                 345                 350

Glu Ala Ser Pro Arg Pro Leu Lys Ser Val Ile Pro Pro Lys Ala Lys
        355                 360                 365

Ser Leu Ser Pro Arg Asn Ser Asp Ser Glu Asp Ser Glu Arg Arg Arg
    370                 375                 380

Asn His Asn Ile Leu Glu Arg Gln Arg Arg Asn Asp Leu Arg Ser Ser
385                 390                 395                 400

Phe Leu Thr Leu Arg Asp His Val Pro Glu Leu Val Lys Asn Glu Lys
                405                 410                 415

Ala Ala Lys Val Leu Lys Lys Ala Thr Glu Tyr Val His Ser Leu Gln
            420                 425                 430

Ala Glu Glu His Gln Leu Leu Leu Glu Lys Glu Lys Leu Gln Ala Arg
        435                 440                 445

Gln Gln Gln Leu Leu Lys Lys Ile Glu His Ala Arg Thr Cys
    450                 455                 460

<210> SEQ ID NO 13
<211> LENGTH: 2613
<212> TYPE: DNA
<213> ORGANISM: Homo sapiens

<400> SEQUENCE: 13
gtcatctgtc tggacgcgct gggtggatgc gggggctcc tgggaactgt gttggagccg      60
agcaagcgct agccaggcgc aagcgcgcac agactgtagc catccgagga caccccgcc    120
cccccggccc acccggagac acccgcgcag aatcgcctcc ggatccctg cagtcggcgg    180
gagtgttgga ggtcggcgcc ggccccgcc ttccgcgccc ccacgggaa ggaagcaccc    240
ccggtattaa aacgaacggg gcggaaagaa gccctcagtc gccggccggg aggcgagccg    300
atgccgagct gctccacgtc caccatgccg gcatgatct gcaagaaccc agacctcgag    360
tttgactcgc tacagccctg cttctacccg gacgaagatg acttctactt cggcggcccc    420
gactcgaccc cccggggga ggacatctgg aagaagtttg agctgctgcc cacgccccg    480
ctgtcgccca gccgtggctt cgcggagcac agctccgagc cccgagctg ggtcacggag    540
atgctgcttg agaacgagct gtgggcagc ccggccgagg aggacgcgtt cggcctgggg    600
ggactgggtg gcctcacccc caacccggtc atcctccagg actgcatgtg gagcggcttc    660
tccgcccgcg agaagctgga gcgcgccgtg agcgagaagc tgcagcacgg ccgcgggccg    720
ccaaccgccg gttccaccgc ccagtccccg ggagccggcg ccgccagccc tgcgggtcgc    780
gggcacggcg gggctgcggg agccggccgc gccggggccg ccctgcccgc cgagctcgcc    840
cacccggccg ccgagtgcgt ggatcccgcc gtggtcttcc cctttcccgt gaacaagcgc    900
gagccagcgc ccgtgcccgc agcccggcc agtgccccgg cggcgggccc tgcggtcgcc    960
tcggggcgg gtattgccgc ccagccgggg gccccgggg tcgcccctcc gcgcccaggc   1020
ggccgccaga ccagcggcgg cgaccacaag gccctcagta cctccggaga ggacaccctg   1080

```
agcgattcag atgatgaaga tgatgaagag gaagatgaag aggaagaaat cgacgtggtc    1140
actgtggaga agcggcgttc ctcctccaac accaaggctg tcaccacatt caccatcact    1200
gtgcgtccca agaacgcagc cctgggtccc gggagggctc agtccagcga gctgatcctc    1260
aaacgatgcc ttcccatcca ccagcagcac aactatgccg ccccctctcc ctacgtggag    1320
agtgaggatg cacccccaca gaagaagata aagagcgagg cgtccccacg tccgctcaag    1380
agtgtcatcc cccaaaggc taagagcttg agcccccgaa actctgactc ggaggacagt    1440
gagcgtcgca gaaaccacaa catcctggag cgccagcgcc gcaacgacct tcggtccagc    1500
tttctcacgc tcagggacca cgtgccgagt tggtaaaga atgagaaggc cgccaaggtg    1560
gtcattttga aaaaggccac tgagtatgtc cactccctcc aggccgagga gcaccagctt    1620
ttgctggaaa aggaaaaatt gcaggcaaga cagcagcagt tgctaaagaa aattgaacac    1680
gctcggactt gctagacgct ctcaaaact ggacagtcac tgccactttg cacattttga    1740 ttttttttt aaacaaacat tgtgttgaca ttaagaatgt tggtttactt tcaaatcggt    1800
cccctgtcga gttcggctct gggtgggcag taggaccacc agtgtggggt tctgctggga    1860
ccttggagag cctgcatccc aggatgctgg gtggccctgc agcctcctcc acctcacctc    1920
catgacagcg ctaaacgttg gtgacggttg ggagcctctg gggctgttga agtcaccttg    1980
tgtgttccaa gttccaaac aacagaaagt cattccttct ttttaaaatg gtgcttaagt    2040
tccagcagat gccacataag gggtttgcca tttgatatccc ctggggaaca tttctgtaaa    2100
taccattgac acatccgcct tttgtataca tcctgggtaa tgagaggtgg cttttgcggc    2160
cagtattaga ctggaagttc atacctaagt actgtaataa tacctcaatg tttgaggagc    2220
atgttttgta tacaaatata ttgttaatct ctgttatgta ctgtactaat tcttacactg    2280
cctgtatact ttagtatgac gctgatacat aactaaattt gatacttata ttttcgtatg    2340
aaaatgagtt gtgaaagttt tgagtagata ttactttatc acttttttgaa ctaagaaact    2400 tttgtaaaga aatttactat atatatatgc cttttttccta gcctgtttct tcctgttaat    2460
gtatttgttc atgtttggtg catagaactg ggtaaatgca aagttctgtg tttaatttct    2520
tcaaaatgta tatatttagt gctgcatctt atagcacttt gaaataacctc atgtttatga    2580 aaataaatag cttaaaatta aatgaaaaaa aaa                                 2613
```

<210> SEQ ID NO 14
<211> LENGTH: 2471
<212> TYPE: PRT
<213> ORGANISM: Homo sapiens

<400> SEQUENCE: 14

Met Pro Ala Leu Arg Pro Ala Leu Leu Trp Ala Leu Leu Ala Leu Trp
1               5                   10                  15

Leu Cys Cys Ala Ala Pro Ala His Ala Leu Gln Cys Arg Asp Gly Tyr
                20                  25                  30

Glu Pro Cys Val Asn Glu Gly Met Cys Val Thr Tyr His Asn Gly Thr
            35                  40                  45

Gly Tyr Cys Lys Cys Pro Glu Gly Phe Leu Gly Glu Tyr Cys Gln His
        50                  55                  60

Arg Asp Pro Cys Glu Lys Asn Arg Cys Gln Asn Gly Gly Thr Cys Val
65                  70                  75                  80

Ala Gln Ala Met Leu Gly Lys Ala Thr Cys Arg Cys Ala Ser Gly Phe
                85                  90                  95

```
Thr Gly Glu Asp Cys Gln Tyr Ser Thr Ser His Pro Cys Phe Val Ser
            100                 105                 110

Arg Pro Cys Leu Asn Gly Gly Thr Cys His Met Leu Ser Arg Asp Thr
        115                 120                 125

Tyr Glu Cys Thr Cys Gln Val Gly Phe Thr Gly Lys Glu Cys Gln Trp
    130                 135                 140

Thr Asp Ala Cys Leu Ser His Pro Cys Ala Asn Gly Ser Thr Cys Thr
145                 150                 155                 160

Thr Val Ala Asn Gln Phe Ser Cys Lys Cys Leu Thr Gly Phe Thr Gly
                165                 170                 175

Gln Lys Cys Glu Thr Asp Val Asn Glu Cys Asp Ile Pro Gly His Cys
            180                 185                 190

Gln His Gly Gly Thr Cys Leu Asn Leu Pro Gly Ser Tyr Gln Cys Gln
        195                 200                 205

Cys Pro Gln Gly Phe Thr Gly Gln Tyr Cys Asp Ser Leu Tyr Val Pro
    210                 215                 220

Cys Ala Pro Ser Pro Cys Val Asn Gly Gly Thr Cys Arg Gln Thr Gly
225                 230                 235                 240

Asp Phe Thr Phe Glu Cys Asn Cys Leu Pro Gly Phe Glu Gly Ser Thr
                245                 250                 255

Cys Glu Arg Asn Ile Asp Asp Cys Pro Asn His Arg Cys Gln Asn Gly
            260                 265                 270

Gly Val Cys Val Asp Gly Val Asn Thr Tyr Asn Cys Arg Cys Pro Pro
        275                 280                 285

Gln Trp Thr Gly Gln Phe Cys Thr Glu Asp Val Asp Glu Cys Leu Leu
    290                 295                 300

Gln Pro Asn Ala Cys Gln Asn Gly Gly Thr Cys Ala Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
            340                 345                 350

Cys Ile Asp Arg Val Ala Ser Phe Ser Cys Met Cys Pro Glu Gly Lys
        355                 360                 365

Ala Gly Leu Leu Cys His Leu Asp Asp Ala Cys Ile Ser Asn Pro Cys
    370                 375                 380

His Lys Gly Ala Leu Cys Asp Thr Asn Pro Leu Asn Gly Gln Tyr Ile
385                 390                 395                 400

Cys Thr Cys Pro Gln Gly Tyr Lys Gly Ala Asp Cys Thr Glu Asp Val
                405                 410                 415

Asp Glu Cys Ala Met Ala Asn Ser Asn Pro Cys Glu His Ala Gly Lys
            420                 425                 430

Cys Val Asn Thr Asp Gly Ala Phe His Cys Glu Cys Leu Lys Gly Tyr
        435                 440                 445

Ala Gly Pro Arg Cys Glu Met Asp Ile Asn Glu Cys His Ser Asp Pro
    450                 455                 460

Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu Glu Ile Asn
                485                 490                 495

Glu Cys Gln Ser Asn Pro Cys Val Asn Asn Gly Gln Cys Val Asp Lys
            500                 505                 510

Val Asn Arg Phe Gln Cys Leu Cys Pro Pro Gly Phe Thr Gly Pro Val
```

```
              515                 520                 525
Cys Gln Ile Asp Ile Asp Asp Cys Ser Ser Thr Pro Cys Leu Asn Gly
        530                 535                 540

Ala Lys Cys Ile Asp His Pro Asn Gly Tyr Glu Cys Gln Cys Ala Thr
545                 550                 555                 560

Gly Phe Thr Gly Val Leu Cys Glu Glu Asn Ile Asp Asn Cys Asp Pro
                565                 570                 575

Asp Pro Cys His His Gly Gln Cys Gln Asp Gly Ile Asp Ser Tyr Thr
            580                 585                 590

Cys Ile Cys Asn Pro Gly Tyr Met Gly Ala Ile Cys Ser Asp Gln Ile
        595                 600                 605

Asp Glu Cys Tyr Ser Ser Pro Cys Leu Asn Asp Gly Arg Cys Ile Asp
    610                 615                 620

Leu Val Asn Gly Tyr Gln Cys Asn Cys Gln Pro Gly Thr Ser Gly Val
625                 630                 635                 640

Asn Cys Glu Ile Asn Phe Asp Asp Cys Ala Ser Asn Pro Cys Ile His
                645                 650                 655

Gly Ile Cys Met Asp Gly Ile Asn Arg Tyr Ser Cys Val Cys Ser Pro
            660                 665                 670

Gly Phe Thr Gly Gln Arg Cys Asn Ile Asp Ile Asp Glu Cys Ala Ser
        675                 680                 685

Asn Pro Cys Arg Lys Gly Ala Thr Cys Ile Asn Gly Val Asn Gly Phe
    690                 695                 700

Arg Cys Ile Cys Pro Glu Gly Pro His His Pro Ser Cys Tyr Ser Gln
705                 710                 715                 720

Val Asn Glu Cys Leu Ser Asn Pro Cys Ile His Gly Asn Cys Thr Gly
                725                 730                 735

Gly Leu Ser Gly Tyr Lys Cys Leu Cys Asp Ala Gly Trp Val Gly Ile
            740                 745                 750

Asn Cys Glu Val Asp Lys Asn Glu Cys Leu Ser Asn Pro Cys Gln Asn
        755                 760                 765

Gly Gly Thr Cys Asp Asn Leu Val Asn Gly Tyr Arg Cys Thr Cys Lys
    770                 775                 780

Lys Gly Phe Lys Gly Tyr Asn Cys Gln Val Asn Ile Asp Glu Cys Ala
785                 790                 795                 800

Ser Asn Pro Cys Leu Asn Gln Gly Thr Cys Phe Asp Asp Ile Ser Gly
                805                 810                 815

Tyr Thr Cys His Cys Val Leu Pro Tyr Thr Gly Lys Asn Cys Gln Thr
            820                 825                 830

Val Leu Ala Pro Cys Ser Pro Asn Pro Cys Glu Asn Ala Ala Val Cys
        835                 840                 845

Lys Glu Ser Pro Asn Phe Glu Ser Tyr Thr Cys Leu Cys Ala Pro Gly
    850                 855                 860

Trp Gln Gly Gln Arg Cys Thr Ile Asp Ile Asp Glu Cys Ile Ser Lys
865                 870                 875                 880

Pro Cys Met Asn His Gly Leu Cys His Asn Thr Gln Gly Ser Tyr Met
                885                 890                 895

Cys Glu Cys Pro Pro Gly Phe Ser Gly Met Asp Cys Glu Glu Asp Ile
            900                 905                 910

Asp Asp Cys Leu Ala Asn Pro Cys Gln Asn Gly Gly Ser Cys Met Asp
        915                 920                 925

Gly Val Asn Thr Phe Ser Cys Leu Cys Leu Pro Gly Phe Thr Gly Asp
    930                 935                 940
```

```
Lys Cys Gln Thr Asp Met Asn Glu Cys Leu Ser Glu Pro Cys Lys Asn
945                 950                 955                 960

Gly Gly Thr Cys Ser Asp Tyr Val Asn Ser Tyr Thr Cys Lys Cys Gln
            965                 970                 975

Ala Gly Phe Asp Gly Val His Cys Glu Asn Asn Ile Asn Glu Cys Thr
                980                 985                 990

Glu Ser Ser Cys Phe Asn Gly Gly Thr Cys Val Asp Gly Ile Asn Ser
        995                 1000                1005

Phe Ser Cys Leu Cys Pro Val Gly Phe Thr Gly Ser Phe Cys Leu
    1010                1015                1020

His Glu Ile Asn Glu Cys Ser Ser His Pro Cys Leu Asn Glu Gly
    1025                1030                1035

Thr Cys Val Asp Gly Leu Gly Thr Tyr Arg Cys Ser Cys Pro Leu
    1040                1045                1050

Gly Tyr Thr Gly Lys Asn Cys Gln Thr Leu Val Asn Leu Cys Ser
    1055                1060                1065

Arg Ser Pro Cys Lys Asn Lys Gly Thr Cys Val Gln Lys Lys Ala
    1070                1075                1080

Glu Ser Gln Cys Leu Cys Pro Ser Gly Trp Ala Gly Ala Tyr Cys
    1085                1090                1095

Asp Val Pro Asn Val Ser Cys Asp Ile Ala Ala Ser Arg Arg Gly
    1100                1105                1110

Val Leu Val Glu His Leu Cys Gln His Ser Gly Val Cys Ile Asn
    1115                1120                1125

Ala Gly Asn Thr His Tyr Cys Gln Cys Pro Leu Gly Tyr Thr Gly
    1130                1135                1140

Ser Tyr Cys Glu Glu Gln Leu Asp Glu Cys Ala Ser Asn Pro Cys
    1145                1150                1155

Gln His Gly Ala Thr Cys Ser Asp Phe Ile Gly Gly Tyr Arg Cys
    1160                1165                1170

Glu Cys Val Pro Gly Tyr Gln Gly Val Asn Cys Glu Tyr Glu Val
    1175                1180                1185

Asp Glu Cys Gln Asn Gln Pro Cys Gln Asn Gly Gly Thr Cys Ile
    1190                1195                1200

Asp Leu Val Asn His Phe Lys Cys Ser Cys Pro Pro Gly Thr Arg
    1205                1210                1215

Gly Leu Leu Cys Glu Glu Asn Ile Asp Asp Cys Ala Arg Gly Pro
    1220                1225                1230

His Cys Leu Asn Gly Gly Gln Cys Met Asp Arg Ile Gly Gly Tyr
    1235                1240                1245

Ser Cys Arg Cys Leu Pro Gly Phe Ala Gly Glu Arg Cys Glu Gly
    1250                1255                1260

Asp Ile Asn Glu Cys Leu Ser Asn Pro Cys Ser Ser Glu Gly Ser
    1265                1270                1275

Leu Asp Cys Ile Gln Leu Thr Asn Asp Tyr Leu Cys Val Cys Arg
    1280                1285                1290

Ser Ala Phe Thr Gly Arg His Cys Glu Thr Phe Val Asp Val Cys
    1295                1300                1305

Pro Gln Met Pro Cys Leu Asn Gly Gly Thr Cys Ala Val Ala Ser
    1310                1315                1320

Asn Met Pro Asp Gly Phe Ile Cys Arg Cys Pro Pro Gly Phe Ser
    1325                1330                1335
```

```
Gly Ala Arg Cys Gln Ser Ser Cys Gly Gln Val Lys Cys Arg Lys
    1340                1345                1350

Gly Glu Gln Cys Val His Thr Ala Ser Gly Pro Arg Cys Phe Cys
    1355                1360                1365

Pro Ser Pro Arg Asp Cys Glu Ser Gly Cys Ala Ser Ser Pro Cys
    1370                1375                1380

Gln His Gly Gly Ser Cys His Pro Gln Arg Gln Pro Pro Tyr Tyr
    1385                1390                1395

Ser Cys Gln Cys Ala Pro Pro Phe Ser Gly Ser Arg Cys Glu Leu
    1400                1405                1410

Tyr Thr Ala Pro Pro Ser Thr Pro Pro Ala Thr Cys Leu Ser Gln
    1415                1420                1425

Tyr Cys Ala Asp Lys Ala Arg Asp Gly Val Cys Asp Glu Ala Cys
    1430                1435                1440

Asn Ser His Ala Cys Gln Trp Asp Gly Gly Asp Cys Ser Leu Thr
    1445                1450                1455

Met Glu Asn Pro Trp Ala Asn Cys Ser Ser Pro Leu Pro Cys Trp
    1460                1465                1470

Asp Tyr Ile Asn Asn Gln Cys Asp Glu Leu Cys Asn Thr Val Glu
    1475                1480                1485

Cys Leu Phe Asp Asn Phe Glu Cys Gln Gly Asn Ser Lys Thr Cys
    1490                1495                1500

Lys Tyr Asp Lys Tyr Cys Ala Asp His Phe Lys Asp Asn His Cys
    1505                1510                1515

Asp Gln Gly Cys Asn Ser Glu Glu Cys Gly Trp Asp Gly Leu Asp
    1520                1525                1530

Cys Ala Ala Asp Gln Pro Glu Asn Leu Ala Glu Gly Thr Leu Val
    1535                1540                1545

Ile Val Val Leu Met Pro Pro Glu Gln Leu Leu Gln Asp Ala Arg
    1550                1555                1560

Ser Phe Leu Arg Ala Leu Gly Thr Leu Leu His Thr Asn Leu Arg
    1565                1570                1575

Ile Lys Arg Asp Ser Gln Gly Glu Leu Met Val Tyr Pro Tyr Tyr
    1580                1585                1590

Gly Glu Lys Ser Ala Ala Met Lys Lys Gln Arg Met Thr Arg Arg
    1595                1600                1605

Ser Leu Pro Gly Glu Gln Glu Gln Glu Val Ala Gly Ser Lys Val
    1610                1615                1620

Phe Leu Glu Ile Asp Asn Arg Gln Cys Val Gln Asp Ser Asp His
    1625                1630                1635

Cys Phe Lys Asn Thr Asp Ala Ala Ala Ala Leu Leu Ala Ser His
    1640                1645                1650

Ala Ile Gln Gly Thr Leu Ser Tyr Pro Leu Val Ser Val Val Ser
    1655                1660                1665

Glu Ser Leu Thr Pro Glu Arg Thr Gln Leu Leu Tyr Leu Leu Ala
    1670                1675                1680

Val Ala Val Val Ile Ile Leu Phe Ile Ile Leu Leu Gly Val Ile
    1685                1690                1695

Met Ala Lys Arg Lys Arg Lys His Gly Ser Leu Trp Leu Pro Glu
    1700                1705                1710

Gly Phe Thr Leu Arg Arg Asp Ala Ser Asn His Lys Arg Arg Glu
    1715                1720                1725

Pro Val Gly Gln Asp Ala Val Gly Leu Lys Asn Leu Ser Val Gln
```

-continued

```
            1730                1735                1740
Val Ser Glu Ala Asn Leu Ile Gly Thr Gly Thr Ser Glu His Trp
    1745                1750                1755

Val Asp Asp Glu Gly Pro Gln Pro Lys Lys Val Lys Ala Glu Asp
    1760                1765                1770

Glu Ala Leu Leu Ser Glu Glu Asp Asp Pro Ile Asp Arg Arg Pro
    1775                1780                1785

Trp Thr Gln Gln His Leu Glu Ala Ala Asp Ile Arg Arg Thr Pro
    1790                1795                1800

Ser Leu Ala Leu Thr Pro Pro Gln Ala Glu Gln Glu Val Asp Val
    1805                1810                1815

Leu Asp Val Asn Val Arg Gly Pro Asp Gly Cys Thr Pro Leu Met
    1820                1825                1830

Leu Ala Ser Leu Arg Gly Gly Ser Ser Asp Leu Ser Asp Glu Asp
    1835                1840                1845

Glu Asp Ala Glu Asp Ser Ser Ala Asn Ile Ile Thr Asp Leu Val
    1850                1855                1860

Tyr Gln Gly Ala Ser Leu Gln Ala Gln Thr Asp Arg Thr Gly Glu
    1865                1870                1875

Met Ala Leu His Leu Ala Ala Arg Tyr Ser Arg Ala Asp Ala Ala
    1880                1885                1890

Lys Arg Leu Leu Asp Ala Gly Ala Asp Ala Asn Ala Gln Asp Asn
    1895                1900                1905

Met Gly Arg Cys Pro Leu His Ala Ala Val Ala Ala Asp Ala Gln
    1910                1915                1920

Gly Val Phe Gln Ile Leu Ile Arg Asn Arg Val Thr Asp Leu Asp
    1925                1930                1935

Ala Arg Met Asn Asp Gly Thr Thr Pro Leu Ile Leu Ala Ala Arg
    1940                1945                1950

Leu Ala Val Glu Gly Met Val Ala Glu Leu Ile Asn Cys Gln Ala
    1955                1960                1965

Asp Val Asn Ala Val Asp Asp His Gly Lys Ser Ala Leu His Trp
    1970                1975                1980

Ala Ala Ala Val Asn Asn Val Glu Ala Thr Leu Leu Leu Leu Lys
    1985                1990                1995

Asn Gly Ala Asn Arg Asp Met Gln Asp Asn Lys Glu Glu Thr Pro
    2000                2005                2010

Leu Phe Leu Ala Ala Arg Glu Gly Ser Tyr Glu Ala Ala Lys Ile
    2015                2020                2025

Leu Leu Asp His Phe Ala Asn Arg Asp Ile Thr Asp His Met Asp
    2030                2035                2040

Arg Leu Pro Arg Asp Val Ala Arg Asp Arg Met His His Asp Ile
    2045                2050                2055

Val Arg Leu Leu Asp Glu Tyr Asn Val Thr Pro Ser Pro Pro Gly
    2060                2065                2070

Thr Val Leu Thr Ser Ala Leu Ser Pro Val Ile Cys Gly Pro Asn
    2075                2080                2085

Arg Ser Phe Leu Ser Leu Lys His Thr Pro Met Gly Lys Lys Ser
    2090                2095                2100

Arg Arg Pro Ser Ala Lys Ser Thr Met Pro Thr Ser Leu Pro Asn
    2105                2110                2115

Leu Ala Lys Glu Ala Lys Asp Ala Lys Gly Ser Arg Arg Lys Lys
    2120                2125                2130
```

| | | | | | | | | | | |
|---|---|---|---|---|---|---|---|---|---|---|
| Ser | Leu | Ser | Glu | Lys | Val | Gln | Leu | Ser | Glu | Ser | Ser | Val | Thr | Leu |
| | | 2135 | | | | 2140 | | | | 2145 | | | | |
| Ser | Pro | Val | Asp | Ser | Leu | Glu | Ser | Pro | His | Thr | Tyr | Val | Ser | Asp |
| 2150 | | | | | 2155 | | | | | 2160 | | | | |
| Thr | Thr | Ser | Ser | Pro | Met | Ile | Thr | Ser | Pro | Gly | Ile | Leu | Gln | Ala |
| | 2165 | | | | | 2170 | | | | | 2175 | | | |
| Ser | Pro | Asn | Pro | Met | Leu | Ala | Thr | Ala | Ala | Pro | Pro | Ala | Pro | Val |
| 2180 | | | | | 2185 | | | | | 2190 | | | | |
| His | Ala | Gln | His | Ala | Leu | Ser | Phe | Ser | Asn | Leu | His | Glu | Met | Gln |
| 2195 | | | | | 2200 | | | | | 2205 | | | | |
| Pro | Leu | Ala | His | Gly | Ala | Ser | Thr | Val | Leu | Pro | Ser | Val | Ser | Gln |
| | 2210 | | | | | 2215 | | | | | 2220 | | | |
| Leu | Leu | Ser | His | His | His | Ile | Val | Ser | Pro | Gly | Ser | Gly | Ser | Ala |
| | 2225 | | | | | 2230 | | | | | 2235 | | | |
| Gly | Ser | Leu | Ser | Arg | Leu | His | Pro | Val | Pro | Val | Pro | Ala | Asp | Trp |
| 2240 | | | | | 2245 | | | | | 2250 | | | | |
| Met | Asn | Arg | Met | Glu | Val | Asn | Glu | Thr | Gln | Tyr | Asn | Glu | Met | Phe |
| | 2255 | | | | | 2260 | | | | | 2265 | | | |
| Gly | Met | Val | Leu | Ala | Pro | Ala | Glu | Gly | Thr | His | Pro | Gly | Ile | Ala |
| 2270 | | | | | 2275 | | | | | 2280 | | | | |
| Pro | Gln | Ser | Arg | Pro | Pro | Glu | Gly | Lys | His | Ile | Thr | Thr | Pro | Arg |
| 2285 | | | | | 2290 | | | | | 2295 | | | | |
| Glu | Pro | Leu | Pro | Pro | Ile | Val | Thr | Phe | Gln | Leu | Ile | Pro | Lys | Gly |
| 2300 | | | | | 2305 | | | | | 2310 | | | | |
| Ser | Ile | Ala | Gln | Pro | Ala | Gly | Ala | Pro | Gln | Pro | Gln | Ser | Thr | Cys |
| | 2315 | | | | | 2320 | | | | | 2325 | | | |
| Pro | Pro | Ala | Val | Ala | Gly | Pro | Leu | Pro | Thr | Met | Tyr | Gln | Ile | Pro |
| | 2330 | | | | | 2335 | | | | | 2340 | | | |
| Glu | Met | Ala | Arg | Leu | Pro | Ser | Val | Ala | Phe | Pro | Thr | Ala | Met | Met |
| 2345 | | | | | 2350 | | | | | 2355 | | | | |
| Pro | Gln | Gln | Asp | Gly | Gln | Val | Ala | Gln | Thr | Ile | Leu | Pro | Ala | Tyr |
| | 2360 | | | | | 2365 | | | | | 2370 | | | |
| His | Pro | Phe | Pro | Ala | Ser | Val | Gly | Lys | Tyr | Pro | Thr | Pro | Pro | Ser |
| | 2375 | | | | | 2380 | | | | | 2385 | | | |
| Gln | His | Ser | Tyr | Ala | Ser | Ser | Asn | Ala | Ala | Glu | Arg | Thr | Pro | Ser |
| | 2390 | | | | | 2395 | | | | | 2400 | | | |
| His | Ser | Gly | His | Leu | Gln | Gly | Glu | His | Pro | Tyr | Leu | Thr | Pro | Ser |
| 2405 | | | | | 2410 | | | | | 2415 | | | | |
| Pro | Glu | Ser | Pro | Asp | Gln | Trp | Ser | Ser | Ser | Ser | Pro | His | Ser | Ala |
| 2420 | | | | | 2425 | | | | | 2430 | | | | |
| Ser | Asp | Trp | Ser | Asp | Val | Thr | Thr | Ser | Pro | Thr | Pro | Gly | Gly | Ala |
| 2435 | | | | | 2440 | | | | | 2445 | | | | |
| Gly | Gly | Gly | Gln | Arg | Gly | Pro | Gly | Thr | His | Met | Ser | Glu | Pro | Pro |
| 2450 | | | | | 2455 | | | | | 2460 | | | | |
| His | Asn | Asn | Met | Gln | Val | Tyr | Ala | | | | | | | |
| 2465 | | | | | 2470 | | | | | | | | | |

<210> SEQ ID NO 15
<211> LENGTH: 11474
<212> TYPE: DNA
<213> ORGANISM: Homo sapiens

<400> SEQUENCE: 15
gcttgcggtg ggaggaggcg gctgaggcgg aaggacacac gaggctgctt cgttgcacac     60

-continued

```
ccgagaaagt tcagccaaa cttcgggcgg cggctgaggc ggcggccgag gagcggcgga    120
ctcggggcgc ggggagtcga ggcatttgcg cctgggcttc ggagcgtagc gccagggcct    180
gagcctttga agcaggagga ggggaggaga gagtggggct cctctatcgg gaccccctcc    240
ccatgtggat ctgcccaggc ggcggcgcg gcggcggagg aggaggcgac cgagaagatg    300
cccgccctgc gccccgctct gctgtgggcg ctgctggcgc tctggctgtg ctgcgcggcc    360
cccgcgcatg cattgcagtg tcgagatggc tatgaaccct gtgtaaatga aggaatgtgt    420
gttacctacc acaatggcac aggatactgc aaatgtccag aaggcttctt gggggaatat    480
tgtcaacatc gagaccctg tgagaagaac cgctgccaga atggtgggac ttgtgtggcc    540
caggccatgc tggggaaagc cacgtgccga tgtgcctcag ggtttacagg agaggactgc    600
cagtactcaa catctcatcc atgctttgtg tctcgaccct gcctgaatgg cggcacatgc    660
catatgctca gccgggatac ctatgagtgc acctgtcaag tcgggtttac aggtaaggag    720
tgccaatgga cggatgcctg cctgtctcat ccctgtgcaa atggaagtac ctgtaccact    780
gtggccaacc agttctcctg caaatgcctc acaggcttca cagggcagaa atgtgagact    840
gatgtcaatg agtgtgacat tccaggacac tgccagcatg gtggcacctg cctcaacctg    900
cctggttcct accagtgcca gtgccctcag ggcttcacag ccagtactg tgacagcctg    960 tatgtgccct gtgcaccctc accttgtgtc aatggaggca cctgtcggca gactggtgac   1020
ttcacttttg agtgcaactg ccttccaggt tttgaaggga gcacctgtga ggaatatatt   1080
gatgactgcc ctaaccacag gtgtcagaat ggaggggttt gtgtggatgg ggtcaacact   1140
tacaactgcc gctgtccccc acaatggaca ggacagttct gcacagagga tgtggatgaa   1200
tgcctgctgc agcccaatgc ctgtcaaaat ggggcacct gtgccaaccg caatggaggc   1260
tatggctgtg tatgtgtcaa cggctggagt ggagatgact gcagtgagaa cattgatgat   1320
tgtgccttcg cctcctgtac tccaggctcc acctgcatcg accgtgtggc ctccttctct   1380
tgcatgtgcc cagaggggaa ggcaggtctc ctgtgtcatc tggatgatgc atgcatcagc   1440
aatccttgcc acaaggggc actgtgtgac accaacccc taatgggca atatatttgc   1500 acctgcccac aaggctacaa agggctgac tgcacagaag atgtggatga atgtgccatg   1560
gccaatagca atccttgtga gcatgcagga aaatgtgtga acacggatgg cgccttccac   1620
tgtgagtgtc tgaagggtta tgcaggacct cgttgtgaga tggacatcaa tgagtgccat   1680
tcagacccct gccagaatga tgctacctgt ctggataaga ttggaggctt cacatgtctg   1740
tgcatgccag gtttcaaagg tgtgcattgt gaattagaaa taaatgaatg tcagagcaac   1800
ccttgtgtga acaatgggca gtgtgtggat aaagtcaatc gtttccagtg cctgtgtcct   1860
cctggtttca ctgggccagt ttgccagatt gatattgatg actgttccag tactccgtgt   1920
ctgaatgggg caaagtgtat cgatcacccg aatggctatg aatgccagtg tgccacaggt   1980
ttcactggtg tgttgtgtga ggagaacatt gacaactgtg accccgatcc ttgccaccat   2040
ggtcagtgtc aggatggtat tgattcctac acctgcatct gcaatcccgg gtacatgggc   2100
gccatctgca gtgaccagat tgatgaatgt acagcagcc cttgcctgaa cgatggtcgc   2160
tgcattgacc tggtcaatgg ctaccagtgc aactgccagc aggcacgtc agggggttaat   2220 tgtgaaatta atttgatga ctgtgcaagt aacccttgta tccatggaat ctgtatggat   2280
ggcattaatc gctacagttg tgtctgctca ccaggattca cagggcagag atgtaacatt   2340
gacattgatg agtgtgcctc caatcctgt cgcaagggtg caacatgtat caacggtgtg   2400
```

```
aatggtttcc gctgtatatg ccccgaggga ccccatcacc ccagctgcta ctcacaggtg      2460
aacgaatgcc tgagcaatcc ctgcatccat ggaaactgta ctggaggtct cagtggatat      2520
aagtgtctct gtgatgcagg ctgggttggc atcaactgtg aagtggacaa aaatgaatgc      2580
ctttcgaatc catgccagaa tggaggaact tgtgacaatc tggtgaatgg atacaggtgt      2640
acttgcaaga agggctttaa aggctataac tgccaggtga atattgatga atgtgcctca      2700
aatccatgcc tgaaccaagg aacctgcttt gatgacataa gtggctacac ttgccactgt      2760
gtgctgccat acacaggcaa gaattgtcag acagtattgg ctccctgttc cccaaaccct      2820
tgtgagaatg ctgctgtttg caaagagtca ccaaattttg agagttatac ttgcttgtgt      2880
gctcctggct ggcaaggtca gcggtgtacc attgacattg acgagtgtat ctccaagccc      2940
tgcatgaacc atggtctctg ccataacacc cagggcagct acatgtgtga atgtccacca      3000
ggcttcagtg gtatggactg tgaggaggac attgatgact gccttgccaa tccttgccag      3060
aatggaggtt cctgtatgga tggagtgaat actttctcct gcctctgcct tccgggtttc      3120
actggggata agtgccagac agacatgaat gagtgtctga gtgaaccctg taagaatgga      3180
gggacctgct ctgactacgt caacagttac acttgcaagt gccaggcagg atttgatgga      3240
gtccattgtg agaacaacat caatgagtgc actgagagct cctgtttcaa tggtggcaca      3300
tgtgttgatg ggattaactc cttctcttgc ttgtgccctg tgggtttcac tggatccttc      3360
tgcctccatg agatcaatga atgcagctct catccatgcc tgaatgaggg aacgtgtgtt      3420
gatggcctgg gtacctaccg ctgcagctgc ccctgggct acactgggaa aaactgtcag      3480
accctggtga atctctgcag tcggtctcca tgtaaaaaca aaggtacttg cgttcagaaa      3540
aaagcagagt cccagtgcct atgtccatct ggatgggctg gtgcctattg tgacgtgccc      3600
aatgtctctt gtgacatagc agcctccagg agaggtgtgc ttgttgaaca cttgtgccag      3660
cactcaggtg tctgcatcaa tgctggcaac acgcattact gtcagtgccc cctgggctat      3720
actgggagct actgtgagga gcaactcgat gagtgtgcgt ccaaccctg ccagcacggg      3780 gcaacatgca gtgacttcat tggtggatac agatgcgagt gtgtcccagg ctatcagggt      3840
gtcaactgtg agtatgaagt ggatgagtgc cagaatcagc cctgccagaa tggaggcacc      3900
tgtattgacc ttgtgaacca tttcaagtgc tcttgcccac caggcactcg gggcctactc      3960
tgtgaagaga acattgatga ctgtgcccgg ggtcccatt gccttaatgg tggtcagtgc      4020
atggatagga ttggaggcta cagttgtcgc tgcttgcctg gctttgctgg ggagcgttgt      4080
gagggagaca tcaacgagtg cctctccaac ccctgcagct ctgagggcag cctggactgt      4140
atacagctca ccaatgacta cctgtgtgtt tgccgtagtg cctttactgg ccggcactgt      4200
gaaaccttcg tcgatgtgtg tccccagatg ccctgcctga atggagggac ttgtgctgtg      4260
gccagtaaca tgcctgatgg tttcatttgc cgttgtcccc cgggattttc cggggcaagg      4320
tgccagagca gctgtggaca agtgaaatgt aggaagggg agcagtgtgt gcacaccgcc      4380
tctggacccc gctgcttctg ccccagtccc cgggactgcg agtcaggctg tgccagtagc      4440
ccctgccagc acggggcag ctgccaccct cagcgccagc ctccttatta ctcctgccag      4500
tgtgccccac cattctcggg tagccgctgt gaactctaca cggcaccccc cagcaccct      4560 cctgccacct gtctgagcca gtattgtgcc gacaaagctc gggatggcgt ctgtgatgag      4620
gcctgcaaca gccatgcctg ccagtgggat ggggtgact gttctctcac catggagaac      4680
ccctgggcca actgctcctc cccacttccc tgctgggatt atatcaacaa ccagtgtgat      4740
gagctgtgca acacggtcga gtgcctgttt gacaactttg aatgccaggg gaacagcaag      4800
```

```
acatgcaagt atgacaaata ctgtgcagac cacttcaaag acaaccactg tgaccagggg    4860
tgcaacagtg aggagtgtgg ttgggatggg ctggactgtg ctgctgacca acctgagaac    4920
ctggcagaag gtaccctggt tattgtggta ttgatgccac ctgaacaact gctccaggat    4980
gctcgcagct tcttgcgggc actgggtacc ctgctccaca ccaacctgcg cattaagcgg    5040
gactcccagg gggaactcat ggtgtacccc tattatggtg agaagtcagc tgctatgaag    5100
aaacagagga tgacacgcag atcccttcct ggtgaacaag aacaggaggt ggctggctct    5160
aaagtctttc tggaaattga caaccgccag tgtgttcaag actcagacca ctgcttcaag    5220
aacacggatc agcagcagc tctcctggcc tctcacgcca tacaggggac cctgtcatac      5280
cctcttgtgt ctgtcgtcag tgaatccctg actccagaac gcactcagct cctctatctc    5340
cttgctgttg ctgttgtcat cattctgttt attattctgc tgggggtaat catggcaaaa    5400
cgaaagcgta agcatggctc tctctggctg cctgaaggtt tcactcttcg ccgagatgca    5460
agcaatcaca agcgtcgtga gccagtggga caggatgctg tggggctgaa aaatctctca    5520
gtgcaagtct cagaagctaa cctaattggt actggaacaa gtgaacactg ggtcgatgat    5580
gaagggcccc agccaaagaa agtaaaggct gaagatgagg ccttactctc agaagaagat    5640
gaccccattg atcgacggcc atggacacag cagcaccttg aagctgcaga catccgtagg    5700
acaccatcgc tggctctcac ccctcctcag gcagagcagg aggtggatgt gttagatgtg    5760
aatgtccgtg gcccagatgg ctgcaccca ttgatgttgg cttctctccg aggaggcagc     5820
tcagatttga gtgatgaaga tgaagatgca gaggactctt ctgctaacat catcacagac    5880
ttggtctacc agggtgccag cctccaggcc cagacagacc ggactggtga gatggccctg    5940
caccttgcag cccgctactc acgggctgat gctgccaagc gtctcctgga tgcaggtgca    6000
gatgccaatg cccaggacaa catgggccgc tgtccactcc atgctgcagt ggcagctgat    6060
gcccaaggtg tcttccagat tctgattcgc aaccgagtaa ctgatctaga tgccaggatg    6120
aatgatggta ctacaccct gatcctggct gcccgcctgg ctgtggaggg aatggtggca     6180
gaactgatca actgccaagc ggatgtgaat gcagtggatg accatggaaa atctgctctt    6240
cactgggcag ctgctgtcaa taatgtggag gcaactcttt tgttgttgaa aaatggggcc    6300
aaccgagaca tgcaggacaa caaggaagag acacctctgt ttcttgctgc ccgggagggg    6360
agctatgaag cagccaagat cctgttagac cattttgcca atcgagacat cacagaccat    6420
atggatcgtc ttccccggga tgtggctcgg gatcgcatgc accatgacat tgtgcgcctt    6480
ctggatgaat acaatgtgac cccaagccct ccaggcaccg tgttgacttc tgctctctca    6540
cctgtcatct gtgggcccaa cagatctttc ctcagcctga agcacacccc aatgggcaag    6600
aagtctagac ggcccagtgc caagagtacc atgcctacta gcctccctaa ccttgccaag    6660
gaggcaaagg atgccaaggg tagtaggagg aagaagtctc tgagtgagaa ggtccaactg    6720
tctgagagtt cagtaacttt atccctgtt gattccctag aatctcctca cacgtatgtt     6780
tccgacacca catcctctcc aatgattaca tcccctggga tcttacaggc ctcacccaac    6840
cctatgttgg ccactgccgc ccctcctgcc ccagtccatg cccagcatgc actatctttt    6900
tctaaccttc atgaaatgca gcctttggca catgggccaa gcactgtgct tccctcagtg    6960
agccagttgc tatcccacca ccacattgtg tctccaggca gtggcagtgc tggaagcttg    7020
agtaggctcc atccagtccc agtcccagca gattggatga accgcatgga ggtgaatgag    7080
acccagtaca atgagatgtt tggtatggtc ctggctccag ctgagggcac ccatcctggc    7140
```

```
atagctcccc agagcaggcc acctgaaggg aagcacataa ccaccccctcg ggagcccttg    7200 cccccattg tgactttcca gctcatccct aaaggcagta ttgcccaacc agcgggggct      7260
ccccagcctc agtccacctg ccctccagct gttgcgggcc cctgcccac catgtaccag     7320 attccagaaa tggcccgttt gcccagtgtg gctttcccca ctgccatgat gccccagcag    7380
gacgggcagg tagctcagac cattctccca gcctatcatc ctttcccagc ctctgtgggc    7440
aagtacccca cacccccttc acagcacagt tatgcttcct caaatgctgc tgagcgaaca    7500
cccagtcaca gtggtcacct ccagggtgag catccctacc tgacaccatc cccagagtct    7560
cctgaccagt ggtcaagttc atcaccccac tctgcttctg actggtcaga tgtgaccacc    7620
agccctaccc ctgggggtgc tggaggaggt cagcgggac ctgggacaca catgtctgag     7680
ccaccacaca acaacatgca ggtttatgcg tgagagagtc cacctccagt gtagagacat    7740
aactgacttt tgtaaatgct gctgaggaac aaatgaaggt catccgggag agaaatgaag    7800
aaatctctgg agccagcttc tagaggtagg aaagagaaga tgttcttatt cagataatgc    7860
aagagaagca attcgtcagt ttcactgggt atctgcaagg cttattgatt attctaatct    7920
aataagacaa gtttgtggaa atgcaagatg aatacaagcc ttgggtccat gtttactctc    7980
ttctatttgg agaataagat ggatgcttat tgaagcccag acattcttgc agcttggact    8040
gcattttaag ccctgcaggc ttctgccata tccatgagaa gattctacac tagcgtcctg    8100
ttgggaatta tgccctggaa ttctgcctga attgacctac gcatctcctc ctccttggac    8160
attcttttgt cttcatttgg tgcttttggt tttgcacctc tccgtgattg tagccctacc    8220
agcatgttat agggcaagac ctttgtgctt ttgatcattc tggcccatga aagcaacttt    8280
ggtctccttt cccctcctgt cttcccggta tcccttggag tctcacaagg tttactttgg    8340 tatgttctc agcacaaacc tttcaagtat gttgtttctt tggaaaatgg acatactgta    8400
ttgtgttctc ctgcatatat cattcctgga gagagaaggg gagaagaata cttttcttca    8460
acaaattttg ggggcaggag atcccttcaa gaggctgcac cttaatttttt cttgtctgtg    8520 tgcaggtctt catataaact ttaccaggaa gaagggtgtg agtttgttgt ttttctgtgt    8580
atgggcctgg tcagtgtaaa gttttatcct tgatagtcta gttactatga ccctccccac    8640
ttttttaaaa ccagaaaaag gtttggaatg ttggaatgac caagagacaa gttaactcgt    8700
gcaagagcca gttacccacc cacaggtccc cctacttcct gccaagcatt ccattgactg    8760
cctgtatgga acacatttgt cccagatctg agcattctag gcctgtttca ctcactcacc    8820
cagcatatga aactagtctt aactgttgag cctttccttt catatccaca gaagacactg    8880
tctcaaatgt tgtaccctgg ccatttagga ctgaactttc cttagcccaa gggacccagt    8940
gacagttgtc ttccgtttgt cagatgatca gtctctactg attatcttgc tgcttaaagg    9000
cctgctcacc aatctttctt tcacaccgtg tggtccgtgt tactggtata cccagtatgt    9060
tctcactgaa gacatggact ttatatgttc aagtgcagga attggaaagt tggacttgtt    9120
ttctatgatc caaaacagcc ctataagaag gttggaaaag gaggaactat atagcagcct    9180
ttgctatttt ctgctaccat ttcttttcct ctgaagcggc catgacattc cctttggcaa    9240
ctaacgtaga aactcaacag aacatttttcc tttcctagag tcacctttta gatgataatg    9300
gacaactata gacttgctca ttgttcagac tgattgcccc tcacctgaat ccactctctg    9360
tattcatgct cttggcaatt tctttgactt tctttttaagg gcagaagcat tttagttaat    9420
tgtagataaa gaatagtttt cttcctcttc tccttgggcc agttaataat tggtccatgg    9480
ctacactgca acttccgtcc agtgctgtga tgcccatgac acctgcaaaa taagttctgc    9540
```

```
ctgggcattt tgtagatatt aacaggtgaa ttcccgactc ttttggtttg aatgacagtt    9600
ctcattcctt ctatggctgc aagtatgcat cagtgcttcc cacttacctg atttgtctgt    9660
cggtggcccc atatggaaac cctgcgtgtc tgttggcata atagtttaca aatggttttt    9720
tcagtcctat ccaaatttat tgaaccaaca aaaataatta cttctgccct gagataagca    9780
gattaagttt gttcattctc tgctttattc tctccatgtg gcaacattct gtcagcctct    9840
ttcatagtgt gcaaacattt tatcattcta aatggtgact ctctgccctt ggacccattt    9900
attattcaca gatggggaga acctatctgc atggacctct gtggaccaca gcgtacctgc    9960 cccctttctgc cctcctgctc cagccccact tctgaaagta tcagctactg atccagccac   10020
tggatatttt atatcctccc ttttccttaa gcacaatgtc agaccaaatt gcttgtttct   10080
ttttcttgga ctactttaat ttggatcctt tgggtttgga gaaagggaat gtgaaagctg   10140
tcattacaga caacaggttt cagtgatgag gaggacaaca ctgcctttca aacttttttac  10200 tgatctctta gattttaaga actcttgaat tgtgtggtat ctaataaaag ggaaggtaag   10260
atggataatc actttctcat ttgggttctg aattggagac tcagttttta tgagacacat   10320
cttttatgcc atgtatagat cctcccctgc tattttggt ttatttttat tgttataaat   10380
gctttctttc tttgactcct cttctgcctg cctttgggga taggttttt tgtttgttta   10440 tttgcttcct ctgttttgtt ttaagcatca ttttcttatg tgaggtgggg aagggaaagg   10500
tatgagggaa agagagtctg agaattaaaa tattttagta taagcaattg gctgtgatgc   10560
tcaaatccat tgcatcctct tattgaattt gccaatttgt aatttttgca taataaagaa   10620
ccaaaggtgt aatgttttgt tgagaggtgg tttagggatt ttggccctaa ccaatacatt   10680
gaatgtatga tgactatttg ggaggacaca tttatgtacc cagaggcccc cactaataag   10740
tggtactatg gttacttcct tgtgtacatt tctcttaaaa gtgatattat atctgtttgt   10800
atgagaaacc cagtaaccaa taaaatgacc gcatattcct gactaaacgt agtaaggaaa   10860
atgcacactt tgtttttact tttccgtttc attctaaagg tagttaagat gaaatttata   10920
tgaaagcatt tttatcacaa aataaaaaag gtttgccaag ctcagtggtg ttgtatttt    10980 tatttccaa tactgcatcc atggcctggc agtgttacct catgatgtca taatttgctg    11040
agagagcaaa ttttcttttc tttctgaatc ccacaaagcc tagcaccaaa cttctttttt   11100 tcttcccttta attagatcat aaataaatga tcctggggaa aaagcatctg tcaaatagga   11160
aacatcacaa aactgagcac tcttctgtgc actagccata gctggtgaca aacagatggt   11220
tgctcaggga caaggtgcct tccaatgaa atgcgaagta gttgctatag caagaattgg    11280
gaactgggat ataagtcata atattaatta tgctgttatg taaatgattg gtttgtaaca   11340
ttccttaagt gaaatttgtg tagaacttaa tatacaggat tataaaataa tattttgtgt   11400
ataaatttgt tataagttca cattcataca tttatttata aagtcagtga gatatttgaa   11460
catgaaaaaa aaaa                                                     11474
```

<210> SEQ ID NO 16
<211> LENGTH: 2318
<212> TYPE: PRT
<213> ORGANISM: Homo sapiens

<400> SEQUENCE: 16

```
Met Gly Pro Gly Ala Arg Gly Arg Arg Arg Arg Arg Pro Met Ser
1               5                   10                  15

Pro Pro Pro Pro Pro Pro Pro Val Arg Ala Leu Pro Leu Leu Leu Leu
```

```
            20                  25                  30
Leu Ala Gly Pro Gly Ala Ala Pro Pro Cys Leu Asp Gly Ser Pro
            35                  40                  45
Cys Ala Asn Gly Gly Arg Cys Thr Gln Leu Pro Ser Arg Glu Ala Ala
 50                      55                  60
Cys Leu Cys Pro Pro Gly Trp Val Gly Glu Arg Cys Gln Leu Glu Asp
 65                      70                  75                  80
Pro Cys His Ser Gly Pro Cys Ala Gly Arg Gly Val Cys Gln Ser Ser
                    85                  90                  95
Val Val Ala Gly Thr Ala Arg Phe Ser Cys Arg Cys Pro Arg Gly Phe
                   100                 105                 110
Arg Gly Pro Asp Cys Ser Leu Pro Asp Pro Cys Leu Ser Ser Pro Cys
                   115                 120                 125
Ala His Gly Ala Arg Cys Ser Val Gly Pro Asp Gly Arg Phe Leu Cys
                   130                 135                 140
Ser Cys Pro Pro Gly Tyr Gln Gly Arg Ser Cys Arg Ser Asp Val Asp
145                     150                 155                 160
Glu Cys Arg Val Gly Glu Pro Cys Arg His Gly Gly Thr Cys Leu Asn
                        165                 170                 175
Thr Pro Gly Ser Phe Arg Cys Gln Cys Pro Ala Gly Tyr Thr Gly Pro
                    180                 185                 190
Leu Cys Glu Asn Pro Ala Val Pro Cys Ala Pro Ser Pro Cys Arg Asn
                    195                 200                 205
Gly Gly Thr Cys Arg Gln Ser Gly Asp Leu Thr Tyr Asp Cys Ala Cys
                    210                 215                 220
Leu Pro Gly Phe Glu Gly Gln Asn Cys Glu Val Asn Val Asp Asp Cys
225                     230                 235                 240
Pro Gly His Arg Cys Leu Asn Gly Gly Thr Cys Val Asp Gly Val Asn
                        245                 250                 255
Thr Tyr Asn Cys Gln Cys Pro Pro Glu Trp Thr Gly Gln Phe Cys Thr
                    260                 265                 270
Glu Asp Val Asp Glu Cys Gln Leu Gln Pro Asn Ala Cys His Asn Gly
                    275                 280                 285
Gly Thr Cys Phe Asn Thr Leu Gly Gly His Ser Cys Val Cys Val Asn
                    290                 295                 300
Gly Trp Thr Gly Glu Ser Cys Ser Gln Asn Ile Asp Asp Cys Ala Thr
305                     310                 315                 320
Ala Val Cys Phe His Gly Ala Thr Cys His Asp Arg Val Ala Ser Phe
                        325                 330                 335
Tyr Cys Ala Cys Pro Met Gly Lys Thr Gly Leu Leu Cys His Leu Asp
                    340                 345                 350
Asp Ala Cys Val Ser Asn Pro Cys His Glu Asp Ala Ile Cys Asp Thr
                    355                 360                 365
Asn Pro Val Asn Gly Arg Ala Ile Cys Thr Cys Pro Pro Gly Phe Thr
                    370                 375                 380
Gly Gly Ala Cys Asp Gln Asp Val Asp Glu Cys Ser Ile Gly Ala Asn
385                     390                 395                 400
Pro Cys Glu His Leu Gly Arg Cys Val Asn Thr Gln Gly Ser Phe Leu
                        405                 410                 415
Cys Gln Cys Gly Arg Gly Tyr Thr Gly Pro Arg Cys Glu Thr Asp Val
                    420                 425                 430
Asn Glu Cys Leu Ser Gly Pro Cys Arg Asn Gln Ala Thr Cys Leu Asp
                    435                 440                 445
```

```
Arg Ile Gly Gln Phe Thr Cys Ile Cys Met Ala Gly Phe Thr Gly Thr
            450                 455                 460

Tyr Cys Glu Val Asp Ile Asp Glu Cys Gln Ser Ser Pro Cys Val Asn
465                 470                 475                 480

Gly Gly Val Cys Lys Asp Arg Val Asn Gly Phe Ser Cys Thr Cys Pro
                    485                 490                 495

Ser Gly Phe Ser Gly Ser Thr Cys Gln Leu Asp Val Asp Glu Cys Ala
            500                 505                 510

Ser Thr Pro Cys Arg Asn Gly Ala Lys Cys Val Asp Gln Pro Asp Gly
            515                 520                 525

Tyr Glu Cys Arg Cys Ala Glu Gly Phe Glu Gly Thr Leu Cys Asp Arg
            530                 535                 540

Asn Val Asp Asp Cys Ser Pro Asp Pro Cys His His Gly Arg Cys Val
545                 550                 555                 560

Asp Gly Ile Ala Ser Phe Ser Cys Ala Cys Ala Pro Gly Tyr Thr Gly
                565                 570                 575

Thr Arg Cys Glu Ser Gln Val Asp Glu Cys Arg Ser Gln Pro Cys Arg
            580                 585                 590

His Gly Gly Lys Cys Leu Asp Leu Val Asp Lys Tyr Leu Cys Arg Cys
            595                 600                 605

Pro Ser Gly Thr Thr Gly Val Asn Cys Glu Val Asn Ile Asp Asp Cys
            610                 615                 620

Ala Ser Asn Pro Cys Thr Phe Gly Val Cys Arg Asp Gly Ile Asn Arg
625                 630                 635                 640

Tyr Asp Cys Val Cys Gln Pro Gly Phe Thr Gly Pro Leu Cys Asn Val
                645                 650                 655

Glu Ile Asn Glu Cys Ala Ser Ser Pro Cys Gly Glu Gly Gly Ser Cys
            660                 665                 670

Val Asp Gly Glu Asn Gly Phe Arg Cys Leu Cys Pro Pro Gly Ser Leu
            675                 680                 685

Pro Pro Leu Cys Leu Pro Pro Ser His Pro Cys Ala His Glu Pro Cys
            690                 695                 700

Ser His Gly Ile Cys Tyr Asp Ala Pro Gly Gly Phe Arg Cys Val Cys
705                 710                 715                 720

Glu Pro Gly Trp Ser Gly Pro Arg Cys Ser Gln Ser Leu Ala Arg Asp
                725                 730                 735

Ala Cys Glu Ser Gln Pro Cys Arg Ala Gly Gly Thr Cys Ser Ser Asp
            740                 745                 750

Gly Met Gly Phe His Cys Thr Cys Pro Pro Gly Val Gln Gly Arg Gln
            755                 760                 765

Cys Glu Leu Leu Ser Pro Cys Thr Pro Asn Pro Cys Glu His Gly Gly
770                 775                 780

Arg Cys Glu Ser Ala Pro Gly Gln Leu Pro Val Cys Ser Cys Pro Gln
785                 790                 795                 800

Gly Trp Gln Gly Pro Arg Cys Gln Gln Asp Val Asp Glu Cys Ala Gly
                805                 810                 815

Pro Ala Pro Cys Gly Pro His Gly Ile Cys Thr Asn Leu Ala Gly Ser
            820                 825                 830

Phe Ser Cys Thr Cys His Gly Gly Tyr Thr Gly Pro Ser Cys Asp Gln
            835                 840                 845

Asp Ile Asn Asp Cys Asp Pro Asn Pro Cys Leu Asn Gly Gly Ser Cys
850                 855                 860
```

```
Gln Asp Gly Val Gly Ser Phe Ser Cys Ser Cys Leu Pro Gly Phe Ala
865                 870                 875                 880

Gly Pro Arg Cys Ala Arg Asp Val Asp Glu Cys Leu Ser Asn Pro Cys
            885                 890                 895

Gly Pro Gly Thr Cys Thr Asp His Val Ala Ser Phe Thr Cys Thr Cys
            900                 905                 910

Pro Pro Gly Tyr Gly Gly Phe His Cys Glu Gln Asp Leu Pro Asp Cys
            915                 920                 925

Ser Pro Ser Ser Cys Phe Asn Gly Gly Thr Cys Val Asp Gly Val Asn
930                 935                 940

Ser Phe Ser Cys Leu Cys Arg Pro Gly Tyr Thr Gly Ala His Cys Gln
945                 950                 955                 960

His Glu Ala Asp Pro Cys Leu Ser Arg Pro Cys Leu His Gly Gly Val
            965                 970                 975

Cys Ser Ala Ala His Pro Gly Phe Arg Cys Thr Cys Leu Glu Ser Phe
            980                 985                 990

Thr Gly Pro Gln Cys Gln Thr Leu Val Asp Trp Cys Ser Arg Gln Pro
            995                 1000                1005

Cys Gln Asn Gly Gly Arg Cys Val Gln Thr Gly Ala Tyr Cys Leu
    1010            1015            1020

Cys Pro Pro Gly Trp Ser Gly Arg Leu Cys Asp Ile Arg Ser Leu
    1025            1030            1035

Pro Cys Arg Glu Ala Ala Ala Gln Ile Gly Val Arg Leu Glu Gln
    1040            1045            1050

Leu Cys Gln Ala Gly Gly Gln Cys Val Asp Glu Asp Ser Ser His
    1055            1060            1065

Tyr Cys Val Cys Pro Glu Gly Arg Thr Gly Ser His Cys Glu Gln
    1070            1075            1080

Glu Val Asp Pro Cys Leu Ala Gln Pro Cys Gln His Gly Gly Thr
    1085            1090            1095

Cys Arg Gly Tyr Met Gly Gly Tyr Met Cys Glu Cys Leu Pro Gly
    1100            1105            1110

Tyr Asn Gly Asp Asn Cys Glu Asp Asp Val Asp Glu Cys Ala Ser
    1115            1120            1125

Gln Pro Cys Gln His Gly Gly Ser Cys Ile Asp Leu Val Ala Arg
    1130            1135            1140

Tyr Leu Cys Ser Cys Pro Pro Gly Thr Leu Gly Val Leu Cys Glu
    1145            1150            1155

Ile Asn Glu Asp Asp Cys Gly Pro Gly Pro Pro Leu Asp Ser Gly
    1160            1165            1170

Pro Arg Cys Leu His Asn Gly Thr Cys Val Asp Leu Val Gly Gly
    1175            1180            1185

Phe Arg Cys Thr Cys Pro Pro Gly Tyr Thr Gly Leu Arg Cys Glu
    1190            1195            1200

Ala Asp Ile Asn Glu Cys Arg Ser Gly Ala Cys His Ala Ala His
    1205            1210            1215

Thr Arg Asp Cys Leu Gln Asp Pro Gly Gly Gly Phe Arg Cys Leu
    1220            1225            1230

Cys His Ala Gly Phe Ser Gly Pro Arg Cys Gln Thr Val Leu Ser
    1235            1240            1245

Pro Cys Glu Ser Gln Pro Cys Gln His Gly Gly Gln Cys Arg Pro
    1250            1255            1260

Ser Pro Gly Pro Gly Gly Gly Leu Thr Phe Thr Cys His Cys Ala
```

-continued

```
            1265                1270                1275

Gln Pro Phe Trp Gly Pro Arg Cys Glu Arg Val Ala Arg Ser Cys
        1280                1285                1290

Arg Glu Leu Gln Cys Pro Val Gly Val Pro Cys Gln Gln Thr Pro
        1295                1300                1305

Arg Gly Pro Arg Cys Ala Cys Pro Pro Gly Leu Ser Gly Pro Ser
        1310                1315                1320

Cys Arg Ser Phe Pro Gly Ser Pro Pro Gly Ala Ser Asn Ala Ser
        1325                1330                1335

Cys Ala Ala Ala Pro Cys Leu His Gly Gly Ser Cys Arg Pro Ala
        1340                1345                1350

Pro Leu Ala Pro Phe Phe Arg Cys Ala Cys Ala Gln Gly Trp Thr
        1355                1360                1365

Gly Pro Arg Cys Glu Ala Pro Ala Ala Ala Pro Glu Val Ser Glu
        1370                1375                1380

Glu Pro Arg Cys Pro Arg Ala Ala Cys Gln Ala Lys Arg Gly Asp
        1385                1390                1395

Gln Arg Cys Asp Arg Glu Cys Asn Ser Pro Gly Cys Gly Trp Asp
        1400                1405                1410

Gly Gly Asp Cys Ser Leu Ser Val Gly Asp Pro Trp Arg Gln Cys
        1415                1420                1425

Glu Ala Leu Gln Cys Trp Arg Leu Phe Asn Asn Ser Arg Cys Asp
        1430                1435                1440

Pro Ala Cys Ser Ser Pro Ala Cys Leu Tyr Asp Asn Phe Asp Cys
        1445                1450                1455

His Ala Gly Gly Arg Glu Arg Thr Cys Asn Pro Val Tyr Glu Lys
        1460                1465                1470

Tyr Cys Ala Asp His Phe Ala Asp Gly Arg Cys Asp Gln Gly Cys
        1475                1480                1485

Asn Thr Glu Glu Cys Gly Trp Asp Gly Leu Asp Cys Ala Ser Glu
        1490                1495                1500

Val Pro Ala Leu Leu Ala Arg Gly Val Leu Val Leu Thr Val Leu
        1505                1510                1515

Leu Pro Pro Glu Glu Leu Leu Arg Ser Ser Ala Asp Phe Leu Gln
        1520                1525                1530

Arg Leu Ser Ala Ile Leu Arg Thr Ser Leu Arg Phe Arg Leu Asp
        1535                1540                1545

Ala His Gly Gln Ala Met Val Phe Pro Tyr His Arg Pro Ser Pro
        1550                1555                1560

Gly Ser Glu Pro Arg Ala Arg Arg Glu Leu Ala Pro Glu Val Ile
        1565                1570                1575

Gly Ser Val Val Met Leu Glu Ile Asp Asn Arg Leu Cys Leu Gln
        1580                1585                1590

Ser Pro Glu Asn Asp His Cys Phe Pro Asp Ala Gln Ser Ala Ala
        1595                1600                1605

Asp Tyr Leu Gly Ala Leu Ser Ala Val Glu Arg Leu Asp Phe Pro
        1610                1615                1620

Tyr Pro Leu Arg Asp Val Arg Gly Glu Pro Leu Glu Pro Pro Glu
        1625                1630                1635

Pro Ser Val Pro Leu Leu Pro Leu Leu Val Ala Gly Ala Val Leu
        1640                1645                1650

Leu Leu Val Ile Leu Val Leu Gly Val Met Val Ala Arg Arg Lys
        1655                1660                1665
```

-continued

Arg Glu His Ser Thr Leu Trp Phe Pro Glu Gly Phe Ser Leu His
1670                1675                1680

Lys Asp Val Ala Ser Gly His Lys Gly Arg Glu Pro Val Gly
1685                1690                1695

Gln Asp Ala Leu Gly Met Lys Asn Met Ala Lys Gly Glu Ser Leu
1700                1705                1710

Met Gly Glu Val Ala Thr Asp Trp Met Asp Thr Glu Cys Pro Glu
1715                1720                1725

Ala Lys Arg Leu Lys Val Glu Glu Pro Gly Met Gly Ala Glu Glu
1730                1735                1740

Ala Val Asp Cys Arg Gln Trp Thr Gln His His Leu Val Ala Ala
1745                1750                1755

Asp Ile Arg Val Ala Pro Ala Met Ala Leu Thr Pro Pro Gln Gly
1760                1765                1770

Asp Ala Asp Ala Asp Gly Met Asp Val Asn Val Arg Gly Pro Asp
1775                1780                1785

Gly Phe Thr Pro Leu Met Leu Ala Ser Phe Cys Gly Gly Ala Leu
1790                1795                1800

Glu Pro Met Pro Thr Glu Glu Asp Glu Ala Asp Asp Thr Ser Ala
1805                1810                1815

Ser Ile Ile Ser Asp Leu Ile Cys Gln Gly Ala Gln Leu Gly Ala
1820                1825                1830

Arg Thr Asp Arg Thr Gly Glu Thr Ala Leu His Leu Ala Ala Arg
1835                1840                1845

Tyr Ala Arg Ala Asp Ala Ala Lys Arg Leu Leu Asp Ala Gly Ala
1850                1855                1860

Asp Thr Asn Ala Gln Asp His Ser Gly Arg Thr Pro Leu His Thr
1865                1870                1875

Ala Val Thr Ala Asp Ala Gln Gly Val Phe Gln Ile Leu Ile Arg
1880                1885                1890

Asn Arg Ser Thr Asp Leu Asp Ala Arg Met Ala Asp Gly Ser Thr
1895                1900                1905

Ala Leu Ile Leu Ala Ala Arg Leu Ala Val Glu Gly Met Val Glu
1910                1915                1920

Glu Leu Ile Ala Ser His Ala Asp Val Asn Ala Val Asp Glu Leu
1925                1930                1935

Gly Lys Ser Ala Leu His Trp Ala Ala Ala Val Asn Asn Val Glu
1940                1945                1950

Ala Thr Leu Ala Leu Leu Lys Asn Gly Ala Asn Lys Asp Met Gln
1955                1960                1965

Asp Ser Lys Glu Glu Thr Pro Leu Phe Leu Ala Ala Arg Glu Gly
1970                1975                1980

Ser Tyr Glu Ala Ala Lys Leu Leu Leu Asp His Phe Ala Asn Arg
1985                1990                1995

Glu Ile Thr Asp His Leu Asp Arg Leu Pro Arg Asp Val Ala Gln
2000                2005                2010

Glu Arg Leu His Gln Asp Ile Val Arg Leu Leu Asp Gln Pro Ser
2015                2020                2025

Gly Pro Arg Ser Pro Pro Gly Pro His Gly Leu Gly Pro Leu Leu
2030                2035                2040

Cys Pro Pro Gly Ala Phe Leu Pro Gly Leu Lys Ala Ala Gln Ser
2045                2050                2055

| | | | | | | | | | | |
|---|---|---|---|---|---|---|---|---|---|---|
| Gly | Ser 2060 | Lys | Lys | Ser | Arg 2065 | Arg | Pro | Pro | Gly 2070 | Lys | Ala | Gly | Leu | Gly |

Pro Gln Gly Pro Arg Gly Arg Gly Lys Lys Leu Thr Leu Ala Cys
    2075              2080              2085

Pro Gly Pro Leu Ala Asp Ser Ser Val Thr Leu Ser Pro Val Asp
    2090              2095              2100

Ser Leu Asp Ser Pro Arg Pro Phe Gly Pro Pro Ala Ser Pro
    2105              2110              2115

Gly Gly Phe Pro Leu Glu Gly Pro Tyr Ala Ala Ala Thr Ala Thr
    2120              2125              2130

Ala Val Ser Leu Ala Gln Leu Gly Gly Pro Gly Arg Ala Gly Leu
    2135              2140              2145

Gly Arg Gln Pro Pro Gly Gly Cys Val Leu Ser Leu Gly Leu Leu
    2150              2155              2160

Asn Pro Val Ala Val Pro Leu Asp Trp Ala Arg Leu Pro Pro Pro
    2165              2170              2175

Ala Pro Pro Gly Pro Ser Phe Leu Leu Pro Leu Ala Pro Gly Pro
    2180              2185              2190

Gln Leu Leu Asn Pro Gly Thr Pro Val Ser Pro Gln Glu Arg Pro
    2195              2200              2205

Pro Pro Tyr Leu Ala Val Pro Gly His Gly Glu Glu Tyr Pro Ala
    2210              2215              2220

Ala Gly Ala His Ser Ser Pro Pro Lys Ala Arg Phe Leu Arg Val
    2225              2230              2235

Pro Ser Glu His Pro Tyr Leu Thr Pro Ser Pro Glu Ser Pro Glu
    2240              2245              2250

His Trp Ala Ser Pro Ser Pro Ser Leu Ser Asp Trp Ser Glu
    2255              2260              2265

Ser Thr Pro Ser Pro Ala Thr Ala Thr Gly Ala Met Thr Gly Ala
    2270              2275              2280

Leu Pro Ala Gln Pro Leu Pro Leu Ser Val Pro Ser Ser Leu Ala
    2285              2290              2295

Gln Ala Gln Thr Gln Leu Gly Pro Gln Pro Glu Val Thr Pro Lys
    2300              2305              2310

Arg Gln Val Leu Ala
    2315

<210> SEQ ID NO 17
<211> LENGTH: 8089
<212> TYPE: DNA
<213> ORGANISM: Homo sapiens

<400> SEQUENCE: 17
gcggcgcgga ggctggcccg ggacgcgccc ggagcccagg gaaggaggga ggaggggagg    60
gtcgcggccg ccgccatgg ggccgggggc ccgtggccgc cgccgccgcc gtcgcccgat   120
gtcgccgcca ccgccaccgc cacccgtgcg ggcgctgccc ctgctgctgc tgctagcggg   180
gccgggggct gcagcccccc cttgcctgga cggaagcccg tgtgcaaatg gaggtcgttg   240
cacccagctg ccctcccggg aggctgcctg cctgtgcccg cctggctggg tgggtgagcg   300
gtgtcagctg gaggaccct gtcactcagg cccctgtgct ggccgtggtg tctgccagag   360
ttcagtggtg gctggcaccg cccgattctc atgccggtgc cccgtggct tccgaggccc   420 tgactgctcc ctgccagatc cctgcctcag cagcccttgt gccacgtgg cccgctgctc   480 agtgggccc gatggacgct tcctctgctc ctgcccacct ggctaccagg ccgcagctg   540

```
ccgaagcgac gtggatgagt gccgggtggg tgagccctgc cgccatggtg gcacctgcct    600
caacacacct ggctccttcc gctgccagtg tccagctggc tacacagggc cactatgtga    660
gaaccccgcg gtgccctgtg caccctcacc atgccgtaac gggggcacct gcaggcagag    720
tggcgacctc acttacgact gtgcctgtct tcctgggttt gagggtcaga attgtgaagt    780
gaacgtggac gactgtccag gacaccgatg tctcaatggg gggacatgcg tggatggcgt    840
caacacctat aactgccagt gccctcctga gtggacaggc cagttctgca cggaggacgt    900
ggatgagtgt cagctgcagc ccaacgcctg ccacaatggg ggtacctgct caacacgct    960 gggtggccac agctgcgtgt gtgtcaatgg ctggacaggc gagagctgca gtcagaatat   1020
cgatgactgt gccacagccg tgtgcttcca tggggccacc tgccatgacc gcgtggcttc   1080
tttctactgt gcctgcccca tgggcaagac tggcctcctg tgtcacctgg atgacgcctg   1140
tgtcagcaac ccctgccacg aggatgctat ctgtgacaca aatccggtga acggccgggc   1200
catttgcacc tgtcctcccg gcttcacggg tgggcatgt gaccaggatg tggacgagtg   1260
ctctatcggc gccaaccccct gcgagcactt gggcaggtgc gtgaacacgc agggctcctt   1320
cctgtgccag tgcggtcgtg gctacactgg acctcgctgt gagaccgatg tcaacgagtg   1380
tctgtcgggg ccctgccgaa accaggccac gtgcctcgac cgcataggcc agttcacctg   1440
tatctgtatg gcaggcttca caggaaccta ttgcgaggtg gacattgacg agtgtcagag   1500
tagcccctgt gtcaacggtg gggtctgcaa ggaccgagtc aatggcttca gctgcacctg   1560
cccctcgggg ttcagcggct ccacgtgtca gctggacgtg gacgaatgcg ccagcacgcc   1620
ctgcaggaat ggcgccaaat gcgtggacca gcccgatggc tacgagtgcc gctgtgccga   1680
gggctttgag gcacgctgt gtgatcgcaa cgtggacgac tgctcccctg acccatgcca   1740
ccatggtcgc tgcgtggatg catcgccag cttctcatgt gcctgtgctc ctggctacac   1800
gggcacacgc tgcgagagcc aggtggacga atgccgcagc cagccctgcc gccatggcgg   1860
caaatgccta gacctggtgg acaagtacct ctgccgctgc ccttctggga ccacaggtgt   1920
gaactgcgaa gtgaacattg acgactgtgc cagcaacccc tgcacctttg gagtctgccg   1980
tgatggcatc aaccgctacg actgtgtctg ccaacctggc ttcacagggc cccttttgtaa   2040 cgtggagatc aatgagtgtg cttccagccc atgcggcgag ggaggttcct gtgtggatgg   2100
ggaaaatggc ttccgctgcc tctgcccgcc tggctccttg ccccccactct gcctccccc   2160 gagccatccc tgtgccatg agccctgcag tcacggcatc tgctatgatg cacctggcgg   2220
gttccgctgt gtgtgtgagc ctggctggag tggccccgc tgcagccaga gcctggcccg   2280
agacgcctgt gagtcccagc cgtgcagggc cggtgggaca tgcagcagcg atggaatggg   2340
tttccactgc acctgcccgc ctggtgtcca gggacgtcag tgtgaactcc tctcccctg   2400 caccccgaac ccctgtgagc atgggggccg ctgcgagtct gcccctggcc agctgcctgt   2460
ctgctcctgc ccccagggct ggcaaggccc acgatgccag caggatgtgg acagtgtgc   2520 tggcccccgca ccctgtggcc ctcatggtat ctgcaccaac ctggcaggga gtttcagctg   2580
cacctgccat ggagggtaca ctggcccctt ctgcgatcag gacatcaatg actgtgaccc   2640
caacccatgc ctgaacggtg gctcgtgcca agacggcgtg ggctccttt cctgctcctg   2700 cctccctggt ttcgccggcc acgatgcgc ccgcgatgtg gatgagtgcc tgagcaaccc   2760
ctgcggcccg gcacctgta ccgaccacgt ggcctccttc acctgcacct gcccgccagg   2820
ctacggaggc ttccactgcg aacaggacct gcccgactgc agcccagct cctgcttcaa   2880
```

```
tggcgggacc tgtgtggacg gcgtgaactc gttcagctgc ctgtgccgtc ccggctacac    2940
aggagcccac tgccaacatg aggcagaccc ctgcctctcg cggccctgcc tacacggggg    3000
cgtctgcagc gccgcccacc ctggcttccg ctgcacctgc ctcgagagct tcacgggccc    3060
gcagtgccag acgctggtgg attggtgcag ccgccagcct tgtcaaaacg ggggtcgctg    3120
cgtccagact ggggcctatt gcctttgtcc ccctggatgg agcggacgcc tctgtgacat    3180
ccgaagcttg ccctgcaggg aggccgcagc ccagatcggg gtgcggctgg agcagctgtg    3240
tcaggcgggt gggcagtgtg tggatgaaga cagctcccac tactgcgtgt gcccagaggg    3300
ccgtactggt agccactgtg agcaggaggt ggacccctgc ttggcccagc ctgccagca    3360 tgggggggacc tgccgtggct atatggggggg ctacatgtgt gagtgtcttc ctggctacaa    3420
tggtgataac tgtgaggacg acgtggacga gtgtgcctcc cagccctgcc agcacggggg    3480
ttcatgcatt gacctcgtgg cccgctatct ctgctcctgt cccccaggaa cgctgggggt    3540
gctctgcgag attaatgagg atgactgcgg cccaggccca ccgctggact cagggccccg    3600
gtgcctacac aatggcacct gcgtggacct ggtgggtggt ttccgctgca cctgtccccc    3660
aggatacact ggtttgcgct gcgaggcaga catcaatgag tgtcgctcag gtgcctgcca    3720
cgcggcacac acccgggact gcctgcagga cccaggcgga ggtttccgtt gcctttgtca    3780
tgctggcttc tcaggtcctc gctgtcagac tgtcctgtct ccctgcgagt cccagccatg    3840
ccagcatgga ggccagtgcc gtcctagccc gggtcctggg ggtgggctga ccttcacctg    3900
tcactgtgcc cagccgttct ggggtccgcg ttgcgagcgg gtggcgcgct cctgccggga    3960
gctgcagtgc ccggtgggcg tcccatgcca gcagacgccc cgcgggccgc gctgcgcctg    4020 cccccccaggg ttgtcgggac cctcctgccg cagcttcccg gggtcgccgc cgggggccag    4080
caacgccagc tgcgcggccg cccctgtct ccacgggggc tcctgccgcc ccgcgccgct    4140 cgcgccctttc ttccgctgcg cttgcgcgca gggctggacc gggccgcgct gcgaggcgcc    4200
cgccgcggca cccgaggtct cggaggagcc gcggtgcccg cgcgccgcct gccaggccaa    4260
gcgcggggac cagcgctgcg accgcgagtg caacagccca ggctgcggct gggacggcgg    4320
cgactgctcg ctgagcgtgg gcgacccctg cggcaatgc gaggcgctgc agtgctggcg    4380
cctcttcaac aacagccgct cgaccccgc ctgcagctcg cccgcctgcc tctacgacaa    4440
cttcgactgc cacgccggtg gccgcgacg cacttgcaac ccggtgtacg agaagtactg    4500
cgccgaccac tttgccgacg gccgctgcga ccagggctgc aacacggagg agtgcggctg    4560
ggatgggctg gattgtgcca gcgaggtgcc ggccctgctg gccgcgggcg tgctggtgct    4620
cacagtgctg ctgccgccag aggagctact gcgttccagc gccgactttc tgcagcggct    4680
cagcgccatc ctgcgcacct cgctgcgctt ccgcctggac gcgcacggcc aggccatggt    4740
cttcccttac caccggccta gtcctggctc cgaaccccgg gccgtcgggg agctggcccc    4800
cgaggtgatc ggctcggtag taatgctgga gattgacaac cggctctgcc tgcagtcgcc    4860
tgagaatgat cactgcttcc ccgatgccca gagcgccgct gactacctgg gagcgttgtc    4920
agcggtggag cgcctggact tcccgtaccc actgcgggac gtgcgggggg agccgctgga    4980
gcctccagaa cccagcgtcc cgctgctgcc actgctagtg gcgggcgctg tcttgctgct    5040
ggtcattctc gtcctgggtg tcatggtggc ccggcgcaag cgcgagcaca gcaccctctg    5100
gttccctgag ggcttctcac tgcacaagga cgtggcctct ggtcacaagg ccggcggaa    5160 acccgtgggc caggacgcgc tgggcatgaa gaacatggcc aagggtgaga gcctgatggg    5220
ggaggtggcc acagactgga tggacacaga gtgcccagag gccaagcggc taaaggtaga    5280
```

```
ggagccaggc atgggggctg aggaggctgt ggattgccgt cagtggactc aacaccatct    5340
ggttgctgct gacatccgcg tggcaccagc catggcactg acaccaccac agggcgacgc    5400
agatgctgat ggcatggatg tcaatgtgcg tggcccagat ggcttcaccc cgctaatgct    5460
ggcttccttc tgtgggggg ctctggagcc aatgccaact gaagaggatg aggcagatga    5520
cacatcagct agcatcatct ccgacctgat ctgccagggg gctcagcttg gggcacggac    5580
tgaccgtact ggcgagactg ctttgcacct ggctgcccgt tatgcccgtg ctgatgcagc    5640
caagcggctg ctggatgctg gggcagacac caatgcccag gaccactcag ccgcactcc    5700 cctgcacaca gctgtcacag ccgatgccca gggtgtcttc cagattctca tccgaaaccg    5760
ctctacagac ttggatgccc gcatggcaga tggctcaacg gcactgatcc tggcggcccg    5820
cctggcagta gagggcatgg tggaagagct catcgccagc catgctgatg tcaatgctgt    5880
ggatgagctt gggaaatcag ccttacactg gctgcggct gtgaacaacg tggaagccac    5940
tttggccctg ctcaaaaatg gagccaataa ggacatgcag gatagcaagg aggagacccc    6000
cctattcctg gccgcccgcg agggcagcta tgaggctgcc aagctgctgt ggaccactt    6060 tgccaaccgt gagatcaccg accacctgga caggctgccg cggacgtag cccaggagag    6120 actgcaccag gacatcgtgc gcttgctgga tcaacccagt gggccccgca gcccccccgg    6180
tccccacggc ctggggcctc tgctctgtcc tccaggggcc ttcctccctg gcctcaaagc    6240
ggcacagtcg gggtccaaga agagcaggag gcccccggg aaggcggggc tggggccgca    6300
ggggccccgg gggcggggca agaagctgac gctggcctgc ccgggccccc tggctgacag    6360
ctcggtcacg ctgtcgcccg tggactcgct ggactcccg cggcctttcg gtgggccccc    6420
tgcttcccct ggtggcttcc cccttgaggg gccctatgca gctgccactg ccactgcagt    6480
gtctctggca cagcttggtg gcccaggccg ggcgggtcta gggcgccagc cccctggagg    6540
atgtgtactc agcctgggcc tgctgaaccc tgtggctgtg ccctcgatt gggcccggct    6600 gccccacct gccccctccag gccctcgtt cctgctgcca ctggcgccgg accccagct    6660 gctcaaccca gggaccccg tctccccgca ggagcggccc ccgccttacc tggcagtccc    6720
aggacatggc gaggagtacc cggcggctgg ggcacacagc agccccccaa aggcccgctt    6780
cctgcgggtt cccagtgagc acccttacct gaccccatcc cccgaatccc ctgagcactg    6840
ggccagcccc tcacctccct ccctctcaga ctggtccgaa tccacgccta gcccagccac    6900
tgccactggg gccatggcca ccaccactgg ggcactgcct gcccagccac ttcccttgtc    6960
tgttcccagc tcccttgctc aggcccagac ccagctgggg cccagccgg aagttacccc    7020 caagaggcaa gtgttggcct gagacgctcg tcagttctta gatcttgggg gcctaaagag    7080 accccgtcc tgcctccttt cttctctgt ctcttcctc ctttagtct ttttcatcct    7140 cttctctttc caccaaccct cctgcatcct tgccttgcag cgtgaccgag ataggtcatc    7200
agcccagggc ttcagtcttc ctttatttat aatgggtggg ggctaccacc caccctctca    7260
gtcttgtgaa gagtctggga cctccttctt ccccacttct ctcttccctc attcctttct    7320
ctctccttct ggcctctcat ttccttacac tctgacatga atgaattatt attattttta    7380
tttttctttt ttttttaca ttttgtatag aaacaaattc atttaaacaa acttattatt    7440 attattttt acaaaatata tatatggaga tgctccctcc cctgtgaac ccccagtgc    7500 ccccgtgggg ctgagtctgt gggcccattc ggccaagctg gattctgtgt acctagtaca    7560
caggcatgac tgggatcccg tgtaccgagt acacgaccca ggtatgtacc aagtaggcac    7620
```

```
ccttgggcgc acccactggg gccaggggtc gggggagtgt tgggagcctc ctccccaccc    7680
cacctccctc acttcactgc attccagatg ggacatgttc catagccttg ctggggaagg    7740
gcccactgcc aactccctct gccccagccc caccccttggc catctccctt tgggaactag    7800
ggggctgctg gtgggaaatg ggagccaggg cagatgtatg cattcctttg tgtccctgta    7860
aatgtgggac tacaagaaga ggagctgcct gagtggtact ttctcttcct ggtaatcctc    7920
tggcccagcc tcatggcaga atagaggtat ttttaggcta tttttgtaat atggcttctg    7980
gtcaaaatcc ctgtgtagct gaattcccaa gccctgcatt gtacagcccc ccactcccct    8040
caccacctaa taaaggaata gttaacactc aaaaaaaaaa aaaaaaaa                 8089
```

<210> SEQ ID NO 18
<211> LENGTH: 2003
<212> TYPE: PRT
<213> ORGANISM: Homo sapiens

<400> SEQUENCE: 18

```
Met Gln Pro Pro Ser Leu Leu Leu Leu Leu Leu Leu Leu Leu Leu Leu
1               5                   10                  15

Cys Val Ser Val Val Arg Pro Arg Gly Leu Leu Cys Gly Ser Phe Pro
            20                  25                  30

Glu Pro Cys Ala Asn Gly Gly Thr Cys Leu Ser Leu Ser Leu Gly Gln
        35                  40                  45

Gly Thr Cys Gln Cys Ala Pro Gly Phe Leu Gly Glu Thr Cys Gln Phe
    50                  55                  60

Pro Asp Pro Cys Gln Asn Ala Gln Leu Cys Gln Asn Gly Gly Ser Cys
65                  70                  75                  80

Gln Ala Leu Leu Pro Ala Pro Leu Gly Leu Pro Ser Ser Pro Ser Pro
                85                  90                  95

Leu Thr Pro Ser Phe Leu Cys Thr Cys Leu Pro Gly Phe Thr Gly Glu
            100                 105                 110

Arg Cys Gln Ala Lys Leu Glu Asp Pro Cys Pro Pro Ser Phe Cys Ser
        115                 120                 125

Lys Arg Gly Arg Cys His Ile Gln Ala Ser Gly Arg Pro Gln Cys Ser
    130                 135                 140

Cys Met Pro Gly Trp Thr Gly Glu Gln Cys Gln Leu Arg Asp Phe Cys
145                 150                 155                 160

Ser Ala Asn Pro Cys Val Asn Gly Gly Val Cys Leu Ala Thr Tyr Pro
                165                 170                 175

Gln Ile Gln Cys His Cys Pro Pro Gly Phe Glu Gly His Ala Cys Glu
            180                 185                 190

Arg Asp Val Asn Glu Cys Phe Gln Asp Pro Gly Pro Cys Pro Lys Gly
        195                 200                 205

Thr Ser Cys His Asn Thr Leu Gly Ser Phe Gln Cys Leu Cys Pro Val
    210                 215                 220

Gly Gln Glu Gly Pro Arg Cys Glu Leu Arg Ala Gly Pro Cys Pro Pro
225                 230                 235                 240

Arg Gly Cys Ser Asn Gly Gly Thr Cys Gln Leu Met Pro Glu Lys Asp
                245                 250                 255

Ser Thr Phe His Leu Cys Leu Cys Pro Pro Gly Phe Ile Gly Pro Asp
            260                 265                 270

Cys Glu Val Asn Pro Asp Asn Cys Val Ser His Gln Cys Gln Asn Gly
        275                 280                 285

Gly Thr Cys Gln Asp Gly Leu Asp Thr Tyr Thr Cys Leu Cys Pro Glu
```

```
                290                 295                 300
Thr Trp Thr Gly Trp Asp Cys Ser Glu Asp Val Asp Glu Cys Glu Thr
305                 310                 315                 320

Gln Gly Pro Pro His Cys Arg Asn Gly Gly Thr Cys Gln Asn Ser Ala
                325                 330                 335

Gly Ser Phe His Cys Val Cys Val Ser Gly Trp Gly Gly Thr Ser Cys
                340                 345                 350

Glu Glu Asn Leu Asp Asp Cys Ile Ala Ala Thr Cys Ala Pro Gly Ser
                355                 360                 365

Thr Cys Ile Asp Arg Val Gly Ser Phe Ser Cys Leu Cys Pro Pro Gly
370                 375                 380

Arg Thr Gly Leu Leu Cys His Leu Glu Asp Met Cys Leu Ser Gln Pro
385                 390                 395                 400

Cys His Gly Asp Ala Gln Cys Ser Thr Asn Pro Leu Thr Gly Ser Thr
                405                 410                 415

Leu Cys Leu Cys Gln Pro Gly Tyr Ser Gly Pro Thr Cys His Gln Asp
                420                 425                 430

Leu Asp Glu Cys Leu Met Ala Gln Gln Gly Pro Ser Pro Cys Glu His
                435                 440                 445

Gly Gly Ser Cys Leu Asn Thr Pro Gly Ser Phe Asn Cys Leu Cys Pro
                450                 455                 460

Pro Gly Tyr Thr Gly Ser Arg Cys Glu Ala Asp His Asn Glu Cys Leu
465                 470                 475                 480

Ser Gln Pro Cys His Pro Gly Ser Thr Cys Leu Asp Leu Leu Ala Thr
                485                 490                 495

Phe His Cys Leu Cys Pro Pro Gly Leu Glu Gly Gln Leu Cys Glu Val
                500                 505                 510

Glu Thr Asn Glu Cys Ala Ser Ala Pro Cys Leu Asn His Ala Asp Cys
                515                 520                 525

His Asp Leu Leu Asn Gly Phe Gln Cys Ile Cys Leu Pro Gly Phe Ser
                530                 535                 540

Gly Thr Arg Cys Glu Glu Asp Ile Asp Glu Cys Arg Ser Ser Pro Cys
545                 550                 555                 560

Ala Asn Gly Gly Gln Cys Gln Asp Gln Pro Gly Ala Phe His Cys Lys
                565                 570                 575

Cys Leu Pro Gly Phe Glu Gly Pro Arg Cys Gln Thr Glu Val Asp Glu
                580                 585                 590

Cys Leu Ser Asp Pro Cys Pro Val Gly Ala Ser Cys Leu Asp Leu Pro
                595                 600                 605

Gly Ala Phe Phe Cys Leu Cys Pro Ser Gly Phe Thr Gly Gln Leu Cys
610                 615                 620

Glu Val Pro Leu Cys Ala Pro Asn Leu Cys Gln Pro Lys Gln Ile Cys
625                 630                 635                 640

Lys Asp Gln Lys Asp Lys Ala Asn Cys Leu Cys Pro Asp Gly Ser Pro
                645                 650                 655

Gly Cys Ala Pro Pro Glu Asp Asn Cys Thr Cys His His Gly His Cys
                660                 665                 670

Gln Arg Ser Ser Cys Val Cys Asp Val Gly Trp Thr Gly Pro Glu Cys
                675                 680                 685

Glu Ala Glu Leu Gly Gly Cys Ile Ser Ala Pro Cys Ala His Gly Gly
                690                 695                 700

Thr Cys Tyr Pro Gln Pro Ser Gly Tyr Asn Cys Thr Cys Pro Thr Gly
705                 710                 715                 720
```

```
Tyr Thr Gly Pro Thr Cys Ser Glu Glu Met Thr Ala Cys His Ser Gly
                725                 730                 735

Pro Cys Leu Asn Gly Gly Ser Cys Asn Pro Ser Pro Gly Tyr Tyr
            740                 745                 750

Cys Thr Cys Pro Pro Ser His Thr Gly Pro Gln Cys Gln Thr Ser Thr
            755                 760                 765

Asp Tyr Cys Val Ser Ala Pro Cys Phe Asn Gly Gly Thr Cys Val Asn
    770                 775                 780

Arg Pro Gly Thr Phe Ser Cys Leu Cys Ala Met Gly Phe Gln Gly Pro
785                 790                 795                 800

Arg Cys Glu Gly Lys Leu Arg Pro Ser Cys Ala Asp Ser Pro Cys Arg
                805                 810                 815

Asn Arg Ala Thr Cys Gln Asp Ser Pro Gln Gly Pro Arg Cys Leu Cys
                820                 825                 830

Pro Thr Gly Tyr Thr Gly Gly Ser Cys Gln Thr Leu Met Asp Leu Cys
            835                 840                 845

Ala Gln Lys Pro Cys Pro Arg Asn Ser His Cys Leu Gln Thr Gly Pro
850                 855                 860

Ser Phe His Cys Leu Cys Leu Gln Gly Trp Thr Gly Pro Leu Cys Asn
865                 870                 875                 880

Leu Pro Leu Ser Ser Cys Gln Lys Ala Ala Leu Ser Gln Gly Ile Asp
                885                 890                 895

Val Ser Ser Leu Cys His Asn Gly Gly Leu Cys Val Asp Ser Gly Pro
            900                 905                 910

Ser Tyr Phe Cys His Cys Pro Pro Gly Phe Gln Gly Ser Leu Cys Gln
            915                 920                 925

Asp His Val Asn Pro Cys Glu Ser Arg Pro Cys Gln Asn Gly Ala Thr
            930                 935                 940

Cys Met Ala Gln Pro Ser Gly Tyr Leu Cys Gln Cys Ala Pro Gly Tyr
945                 950                 955                 960

Asp Gly Gln Asn Cys Ser Lys Glu Leu Asp Ala Cys Gln Ser Gln Pro
                965                 970                 975

Cys His Asn His Gly Thr Cys Thr Pro Lys Pro Gly Gly Phe His Cys
                980                 985                 990

Ala Cys Pro Pro Gly Phe Val Gly Leu Arg Cys Glu Gly Asp Val Asp
            995                 1000                1005

Glu Cys Leu Asp Gln Pro Cys His Pro Thr Gly Thr Ala Ala Cys
    1010                1015                1020

His Ser Leu Ala Asn Ala Phe Tyr Cys Gln Cys Leu Pro Gly His
    1025                1030                1035

Thr Gly Gln Trp Cys Glu Val Glu Ile Asp Pro Cys His Ser Gln
    1040                1045                1050

Pro Cys Phe His Gly Gly Thr Cys Glu Ala Thr Ala Gly Ser Pro
    1055                1060                1065

Leu Gly Phe Ile Cys His Cys Pro Lys Gly Phe Glu Gly Pro Thr
    1070                1075                1080

Cys Ser His Arg Ala Pro Ser Cys Gly Phe His His Cys His His
    1085                1090                1095

Gly Gly Leu Cys Leu Pro Ser Pro Lys Pro Gly Phe Pro Pro Arg
    1100                1105                1110

Cys Ala Cys Leu Ser Gly Tyr Gly Gly Pro Asp Cys Leu Thr Pro
    1115                1120                1125
```

```
Pro Ala Pro Lys Gly Cys Gly Pro Pro Ser Pro Cys Leu Tyr Asn
    1130            1135            1140

Gly Ser Cys Ser Glu Thr Thr Gly Leu Gly Gly Pro Gly Phe Arg
    1145            1150            1155

Cys Ser Cys Pro His Ser Ser Pro Gly Pro Arg Cys Gln Lys Pro
    1160            1165            1170

Gly Ala Lys Gly Cys Glu Gly Arg Ser Gly Asp Gly Ala Cys Asp
    1175            1180            1185

Ala Gly Cys Ser Gly Pro Gly Gly Asn Trp Asp Gly Asp Cys
    1190            1195            1200

Ser Leu Gly Val Pro Asp Pro Trp Lys Gly Cys Pro Ser His Ser
    1205            1210            1215

Arg Cys Trp Leu Leu Phe Arg Asp Gly Gln Cys His Pro Gln Cys
    1220            1225            1230

Asp Ser Glu Glu Cys Leu Phe Asp Gly Tyr Asp Cys Glu Thr Pro
    1235            1240            1245

Pro Ala Cys Thr Pro Ala Tyr Asp Gln Tyr Cys His Asp His Phe
    1250            1255            1260

His Asn Gly His Cys Glu Lys Gly Cys Asn Thr Ala Glu Cys Gly
    1265            1270            1275

Trp Asp Gly Gly Asp Cys Arg Pro Glu Asp Gly Asp Pro Glu Trp
    1280            1285            1290

Gly Pro Ser Leu Ala Leu Leu Val Val Leu Ser Pro Pro Ala Leu
    1295            1300            1305

Asp Gln Gln Leu Phe Ala Leu Ala Arg Val Leu Ser Leu Thr Leu
    1310            1315            1320

Arg Val Gly Leu Trp Val Arg Lys Asp Arg Asp Gly Arg Asp Met
    1325            1330            1335

Val Tyr Pro Tyr Pro Gly Ala Arg Ala Glu Glu Lys Leu Gly Gly
    1340            1345            1350

Thr Arg Asp Pro Thr Tyr Gln Glu Arg Ala Ala Pro Gln Thr Gln
    1355            1360            1365

Pro Leu Gly Lys Glu Thr Asp Ser Leu Ser Ala Gly Phe Val Val
    1370            1375            1380

Val Met Gly Val Asp Leu Ser Arg Cys Gly Pro Asp His Pro Ala
    1385            1390            1395

Ser Arg Cys Pro Trp Asp Pro Gly Leu Leu Leu Arg Phe Leu Ala
    1400            1405            1410

Ala Met Ala Ala Val Gly Ala Leu Glu Pro Leu Leu Pro Gly Pro
    1415            1420            1425

Leu Leu Ala Val His Pro His Ala Gly Thr Ala Pro Pro Ala Asn
    1430            1435            1440

Gln Leu Pro Trp Pro Val Leu Cys Ser Pro Val Ala Gly Val Ile
    1445            1450            1455

Leu Leu Ala Leu Gly Ala Leu Leu Val Leu Gln Leu Ile Arg Arg
    1460            1465            1470

Arg Arg Arg Glu His Gly Ala Leu Trp Leu Pro Pro Gly Phe Thr
    1475            1480            1485

Arg Arg Pro Arg Thr Gln Ser Ala Pro His Arg Arg Pro Pro
    1490            1495            1500

Leu Gly Glu Asp Ser Ile Gly Leu Lys Ala Leu Lys Pro Lys Ala
    1505            1510            1515

Glu Val Asp Glu Asp Gly Val Val Met Cys Ser Gly Pro Glu Glu
```

```
            1520                1525                1530
Gly Glu Glu Val Gly Gln Ala Glu Glu Thr Gly Pro Pro Ser Thr
    1535                1540                1545
Cys Gln Leu Trp Ser Leu Ser Gly Gly Cys Gly Ala Leu Pro Gln
    1550                1555                1560
Ala Ala Met Leu Thr Pro Pro Gln Glu Ser Glu Met Glu Ala Pro
    1565                1570                1575
Asp Leu Asp Thr Arg Gly Pro Asp Gly Val Thr Pro Leu Met Ser
    1580                1585                1590
Ala Val Cys Cys Gly Glu Val Gln Ser Gly Thr Phe Gln Gly Ala
    1595                1600                1605
Trp Leu Gly Cys Pro Glu Pro Trp Glu Pro Leu Leu Asp Gly Gly
    1610                1615                1620
Ala Cys Pro Gln Ala His Thr Val Gly Thr Gly Glu Thr Pro Leu
    1625                1630                1635
His Leu Ala Ala Arg Phe Ser Arg Pro Thr Ala Ala Arg Arg Leu
    1640                1645                1650
Leu Glu Ala Gly Ala Asn Pro Asn Gln Pro Asp Arg Ala Gly Arg
    1655                1660                1665
Thr Pro Leu His Ala Ala Val Ala Ala Asp Ala Arg Glu Val Cys
    1670                1675                1680
Gln Leu Leu Leu Arg Ser Arg Gln Thr Ala Val Asp Ala Arg Thr
    1685                1690                1695
Glu Asp Gly Thr Thr Pro Leu Met Leu Ala Ala Arg Leu Ala Val
    1700                1705                1710
Glu Asp Leu Val Glu Glu Leu Ile Ala Ala Gln Ala Asp Val Gly
    1715                1720                1725
Ala Arg Asp Lys Trp Gly Lys Thr Ala Leu His Trp Ala Ala Ala
    1730                1735                1740
Val Asn Asn Ala Arg Ala Ala Arg Ser Leu Leu Gln Ala Gly Ala
    1745                1750                1755
Asp Lys Asp Ala Gln Asp Asn Arg Glu Gln Thr Pro Leu Phe Leu
    1760                1765                1770
Ala Ala Arg Glu Gly Ala Val Glu Val Ala Gln Leu Leu Leu Gly
    1775                1780                1785
Leu Gly Ala Ala Arg Glu Leu Arg Asp Gln Ala Gly Leu Ala Pro
    1790                1795                1800
Ala Asp Val Ala His Gln Arg Asn His Trp Asp Leu Leu Thr Leu
    1805                1810                1815
Leu Glu Gly Ala Gly Pro Pro Glu Ala Arg His Lys Ala Thr Pro
    1820                1825                1830
Gly Arg Glu Ala Gly Pro Phe Pro Arg Ala Arg Thr Val Ser Val
    1835                1840                1845
Ser Val Pro Pro His Gly Gly Gly Ala Leu Pro Arg Cys Arg Thr
    1850                1855                1860
Leu Ser Ala Gly Ala Gly Pro Arg Gly Gly Gly Ala Cys Leu Gln
    1865                1870                1875
Ala Arg Thr Trp Ser Val Asp Leu Ala Ala Arg Gly Gly Gly Ala
    1880                1885                1890
Tyr Ser His Cys Arg Ser Leu Ser Gly Val Gly Ala Gly Gly Gly
    1895                1900                1905
Pro Thr Pro Arg Gly Arg Arg Phe Ser Ala Gly Met Arg Gly Pro
    1910                1915                1920
```

| Arg | Pro | Asn | Pro | Ala | Ile | Met | Arg | Gly | Arg | Tyr | Gly | Val | Ala | Ala |
| | 1925 | | | | 1930 | | | | | 1935 | | | | |

| Gly | Arg | Gly | Gly | Arg | Val | Ser | Thr | Asp | Asp | Trp | Pro | Cys | Asp | Trp |
| | 1940 | | | | | 1945 | | | | | 1950 | | | |

| Val | Ala | Leu | Gly | Ala | Cys | Gly | Ser | Ala | Ser | Asn | Ile | Pro | Ile | Pro |
| | 1955 | | | | | 1960 | | | | | 1965 | | | |

| Pro | Pro | Cys | Leu | Thr | Pro | Ser | Pro | Glu | Arg | Gly | Ser | Pro | Gln | Leu |
| | 1970 | | | | | 1975 | | | | | 1980 | | | |

| Asp | Cys | Gly | Pro | Pro | Ala | Leu | Gln | Glu | Met | Pro | Ile | Asn | Gln | Gly |
| | 1985 | | | | | 1990 | | | | | 1995 | | | |

| Gly | Glu | Gly | Lys | Lys |
| | 2000 | | | |

```
<210> SEQ ID NO 19
<211> LENGTH: 6762
<212> TYPE: DNA
<213> ORGANISM: Homo sapiens

<400> SEQUENCE: 19
agacgtgagg cttgcagcag gccgaggagg aagaagaggg gcagtgggag cagaggaggt      60
ggctcctgcc ccagtgagag ctctgagggt ccctgcctga agagggacag ggaccggggc     120
ttggagaagg ggctgtggaa tgcagccccc ttcactgctg ctgctgctgc tgctgctgct     180
gctgctatgt gtctcagtgg tcagacccag agggctgctg tgtgggagtt tcccagaacc     240
ctgtgccaat ggaggcacct gcctgagcct gtctctggga caagggacct gccagtgtgc     300
ccctggcttc ctgggtgaga cgtgccagtt tcctgacccc tgccagaacg cccagctctg     360
ccaaaatgga ggcagctgcc aagccctgct tcccgctccc ctagggctcc ccagctctcc     420
ctctccattg acacccagct tcttgtgcac ttgcctccct ggcttcactg gtgagagatg     480
ccaggccaag cttgaagacc cttgtcctcc ctccttctgt tccaaaaggg gccgctgcca     540
catccaggcc tcgggccgcc cacagtgctc ctgcatgcct ggatggacag tgagcagtg     600 ccagcttcgg gacttctgtt cagccaaccc atgtgttaat ggaggggtgt gtctggccac     660 ataccccag atccagtgcc actgcccacc gggcttcgag ggccatgcct gtgaacgtga     720
tgtcaacgag tgcttccagg acccaggacc ctgccccaaa ggcacctcct gccataacac     780
cctgggctcc ttccagtgcc tctgcccgtgggcaggag gtccacgtt gtgagctgcg     840 ggcaggaccc tgccctccta ggggctgttc gaatgggggc acctgccagc tgatgccaga     900
gaaagactcc acctttcacc tctgcctctg tcccccaggt ttcataggcc agactgtga     960 ggtgaatcca gacaactgtg tcagccacca gtgtcagaat ggggggcactt gccaggatgg    1020 gctggacacc tacacctgcc tctgcccaga aacctggaca ggctgggact gctccgaaga    1080
tgtggatgag tgtgagaccc agggtcccc tcactgcaga aacggggca cctgccagaa    1140 ctctgctggt agctttcact gcgtgtgtgt gagtggctgg ggcggacaa gctgtgagga    1200 gaacctggat gactgtattg ctgccacctg tgccccggga tccacctgca ttgaccgggt    1260
gggctctttc tcctgcctct gcccacctgg acgcacagga ctcctgtgcc acttggaaga    1320
catgtgtctg agccagccgt gccatgggga tgcccaatgc agcaccaacc ccctcacagg    1380
ctccacactc tgcctgtgtc agcctggcta ttcggggccc acctgccacc aggacctgga    1440
cgagtgtctg atggcccagc aaggcccaag tccctgtgaa catggcggtt cctgcctcaa    1500
cactcctggc tccttcaact gcctctgtcc acctggctac acaggctccc gttgtgaggc    1560
```

```
tgatcacaat gagtgcctct cccagccctg ccacccagga agcacctgtc tggacctact      1620
tgccaccttc cactgcctct gcccgccagg cttagaaggg cagctctgtg aggtggagac      1680
caacgagtgt gcctcagctc cctgcctgaa ccacgcggat tgccatgacc tgctcaacgg      1740
cttccagtgc atctgcctgc ctggattctc cggcacccga tgtgaggagg atatcgatga      1800
gtgcagaagc tctccctgtg ccaatggtgg gcagtgccag gaccagcctg gagccttcca      1860
ctgcaagtgt ctcccaggct ttgaagggcc acgctgtcaa acagaggtgg atgagtgcct      1920
gagtgaccca tgtcccgttg gagccagctg ccttgatctt ccaggagcct tcttttgcct      1980
ctgcccctct ggtttcacag gccagctctg tgaggttccc ctgtgtgctc ccaacctgtg      2040
ccagcccaag cagatatgta aggaccagaa agacaaggcc aactgcctct gtcctgatgg      2100
aagccctggc tgtgccccac ctgaggacaa ctgcacctgc caccacgggc actgccagag      2160
atcctcatgt gtgtgtgacg tgggttggac ggggccagag tgtgaggcag agctagggg       2220 ctgcatctct gcaccctgtg cccatggggg gacctgctac ccccagccct ctggctacaa      2280
ctgcacctgc cctacaggct acacaggacc cacctgtagt gaggagatga cagcttgtca      2340
ctcagggcca tgtctcaatg gcggctcctg caaccctagc cctggaggct actactgcac      2400
ctgccctcca agccacacag ggccccagtg ccaaaccagc actgactact gtgtgtctgc      2460
cccgtgcttc aatgggggta cctgtgtgaa caggcctggc accttctcct gcctctgtgc      2520
catgggcttc cagggcccgc gctgtgaggg aaagctccgc cccagctgtg cagacagccc      2580
ctgtaggaat agggcaacct gccaggacag ccctcagggt cccgctgcc tctgccccac       2640 tggctacacc ggaggcagct gccagactct gatggactta tgtgcccaga agccctgccc      2700
acgcaattcc cactgcctcc agactgggcc ctccttccac tgcttgtgcc tccagggatg      2760
gaccgggcct ctctgcaacc ttccactgtc ctcctgccag aaggctgcac tgagccaagg      2820
catagacgtc tcttcccttt gccacaatgg aggcctctgt gtcgacagcg ccccctccta      2880
tttctgccac tgccccccctg gattccaagg cagcctgtgc caggatcacg tgaacccatg      2940
tgagtccagg ccttgccaga acggggccac ctgcatggcc cagcccagtg ggtatctctg      3000
ccagtgtgcc ccaggctacg atggacagaa ctgctcaaag gaactcgatg cttgtcagtc      3060
ccaaccctgt cacaaccatg gaacctgtac tcccaaacct ggaggattcc actgtgcctg      3120
ccctccaggc tttgtggggc tacgctgtga gggagacgtg gacgagtgtc tggaccagcc      3180
ctgccacccc acaggcactg cagcctgcca ctctctggcc aatgccttct actgccagtg      3240
tctgcctgga cacacaggcc agtggtgtga ggtggagata gacccctgcc acagccaacc      3300
ctgctttcat ggagggacct gtgaggccac agcaggatca cccctgggtt tcatctgcca      3360
ctgccccaag ggttttgaag gccccacctg cagccacagg gccccttcct gcggcttcca      3420
tcactgccac cacggaggcc tgtgtctgcc ctcccctaag ccaggcttcc caccacgctg      3480
tgcctgcctc agtggctatg ggggtcctga ctgcctgacc ccaccagctc ctaaaggctg      3540
tggccctccc tccccatgcc tatacaatgg cagctgctca gagaccacgg gcttgggggg      3600
cccaggcttt cgatgctcct gccctcacag ctctccaggg cccggtgtc agaaacccgg       3660 agccaagggg tgtgagggca gaagtggaga tgggcctgc gatgctggct gcagtggccc       3720
gggaggaaac tgggatggag gggactgctc tctgggagtc ccagacccct ggaagggctg      3780
cccctcccac tctcggtgct ggcttctctt ccgggacggg cagtgccacc cacagtgtga      3840 ctctgaaagag tgtctgtttg atggctacga ctgtgagacc cctccagcct gcactccagc      3900
ctatgaccag tactgccatg atcacttcca caacgggcac tgtgagaaag ctgcaacac       3960
```

```
tgcagagtgt ggctgggatg gaggtgactg caggcctgaa gatggggacc cagagtgggg    4020
gccctccctg gccctgctgg tggtactgag ccccccagcc ctagaccagc agctgtttgc    4080
cctggcccgg gtgctgtccc tgactctgag ggtaggactc tgggtaagga aggatcgtga    4140
tggcagggac atggtgtacc cctatcctgg ggcccgggct gaagaaaagc taggaggaac    4200
tcgggacccc acctatcagg agagagcagc ccctcaaacg cagcccctgg gcaaggagac    4260
cgactccctc agtgctgggt tgtggtggt catgggtgtg gatttgtccc gctgtggccc    4320
tgaccacccg gcatcccgct gtccctggga ccctgggctt ctactccgct tccttgctgc    4380
gatggctgca gtgggagccc tggagcccct gctgctgga ccactgctgg ctgtccaccc    4440
tcatgcaggg accgcacccc ctgccaacca gcttccctgg cctgtgctgt gctccccagt    4500
ggccggggtg attctcctgg ccctagggc tcttctcgtc ctccagctca tccggcgtcg    4560
acgccgagag catggagctc tctggctgcc ccctggtttc actcgacggc ctcggactca    4620
gtcagctccc caccgacgcc ggcccccact aggcgaggac agcattggtc tcaaggcact    4680
gaagccaaag gcagaagttg atgaggatgg agttgtgatg tgctcaggcc ctgaggaggg    4740
agaggaggtg ggccaggctg aagaaacagg cccacccctcc acgtgccagc tctggtctct    4800
gagtggtggc tgtgggcgc tccctcaggc agccatgcta actcctcccc aggaatctga    4860
gatggaagcc cctgacctgg acacccgtgg acctgatggg gtgacacccc tgatgtcagc    4920
agtttgctgt ggggaagtac agtccgggac cttccaaggg gcatggttgg gatgtcctga    4980
gccctgggaa cctctgctgg atggagggc ctgtccccag gctcacaccg tgggcactgg    5040
ggagaccccc ctgcacctgg ctgcccgatt ctccccggcca accgctgccc gccgcctcct    5100
tgaggctgga gccaaccca accagccaga ccgggcaggg cgcacacccc ttcatgctgc    5160
tgtggctgct gatgctcggg aggtctgcca gcttctgctc cgtagcagac aaactgcagt    5220
ggacgctcgc acagaggacg ggaccacacc cttgatgctg gctgccaggc tggcggtgga    5280
agacctggtt gaagaactga ttgcagccca agcagacgtg ggggccagag ataaatgggg    5340
gaaaactgcg ctgcactggg ctgctgccgt gaacaacgcc cgagccgccc gctcgcttct    5400
ccaggccgga gccgataaag atgcccagga caacaggag cagacgccgc tattcctggc    5460
ggcgcgggaa ggagcggtgg aagtagccca gctactgctg gggctggggg cagcccgaga    5520
gctgcgggac caggctgggc tagcgccggc ggacgtcgct caccaacgta accactggga    5580
tctgctgacg ctgctggaag gggctgggcc accagaggcc cgtcacaaag ccacgccggg    5640
ccgcgaggct gggcccttcc cgcgcgcacg gacggtgtca gtaagcgtgc ccccgcatgg    5700
gggcggggct ctgccgcgct gccggacgct gtcagccgga gcaggccctc gtgggggcgg    5760
agcttgtctg caggctcgga cttggtccgt agacttggct gcgcgggggg gcggggccta    5820
ttctcattgc cggagcctct cgggagtagg agcaggagga ggcccgaccc ctcgcggccg    5880
taggttttct gcaggcatgc gcgggcctcg gcccaaccct gcgataatgc gaggaagata    5940
cggagtggct gccgggcgcg gaggcagggt ctcaacggat gactggccct gtgattgggt    6000
ggccctggga gcttgcggtt ctgcctccaa cattccgatc ccgcctcctt gccttactcc    6060
gtccccggag cggggatcac ctcaacttga ctgtggtccc ccagcccctcc aagaaatgcc    6120 cataaaccaa ggaggagagg gtaaaaaata gaagaataca tggtagggag gaattccaaa    6180
aatgattacc cattaaaagg caggctggaa ggccttcctg gttttaagat ggatccccca    6240
aaatgaaggg ttgtgagttt agtttctctc ctaaaatgaa tgtatgccca ccagagcaga    6300
```

```
catcttccac gtggagaagc tgcagctctg gaaagagggt ttaagatgct aggatgaggc    6360
aggcccagtc ctcctccaga aaataagaca ggccacagga gggcagagtg gagtggaaat    6420 accctaagt tggaaccaag aattgcaggc atatgggatg taagatgttc tttcctatat    6480
atggtttcca aagggtgccc ctatgatcca ttgtccccac tgcccacaaa tggctgacaa    6540
atatttattg ggcacctact atgtgccagg cactgtgtag gtgctgaaaa gtggccaagg    6600 gccaccccg ctgatgactc cttgcattcc ctcccctcac aacaaagaac tccactgtgg    6660
ggatgaagcg cttcttctag ccactgctat cgctatttaa gaaccctaaa tctgtcaccc    6720
ataataaagc tgatttgaag tgttaaaaaa aaaaaaaaa aa                        6762
```

<210> SEQ ID NO 20
<211> LENGTH: 152
<212> TYPE: PRT
<213> ORGANISM: Homo sapiens

<400> SEQUENCE: 20

```
Met Lys Ser Cys Lys Pro Ser Gly Pro Pro Ala Gly Ala Arg Val Ala
1               5                   10                  15

Pro Pro Cys Ala Gly Gly Thr Glu Cys Ala Gly Thr Cys Ala Gly Ala
            20                  25                  30

Gly Arg Leu Glu Ser Ala Ala Arg Arg Leu Ala Ala Asn Ala Arg
        35                  40                  45

Glu Arg Arg Met Gln Gly Leu Asn Thr Ala Phe Asp Arg Leu Arg
    50                  55                  60

Arg Val Val Pro Gln Trp Gly Gln Asp Lys Lys Leu Ser Lys Tyr Glu
65                  70                  75                  80

Thr Leu Gln Met Ala Leu Ser Tyr Ile Met Ala Leu Thr Arg Ile Leu
                85                  90                  95

Ala Glu Ala Glu Arg Phe Gly Ser Glu Arg Asp Trp Val Gly Leu His
            100                 105                 110

Cys Glu His Phe Gly Arg Asp His Tyr Leu Pro Phe Pro Gly Ala Lys
        115                 120                 125

Leu Pro Gly Glu Ser Glu Leu Tyr Ser Gln Arg Leu Phe Gly Phe Gln
    130                 135                 140

Pro Glu Pro Phe Gln Met Ala Thr
145                 150
```

<210> SEQ ID NO 21
<211> LENGTH: 1534
<212> TYPE: DNA
<213> ORGANISM: Homo sapiens

<400> SEQUENCE: 21

```
ctgcactctc cgacagctac tgcgctaaaa gcgctccttc cctgagcttc gggaaagagt      60
tcatcttcct gcaaaggagt ctcaggcttt cccagaggac ttgaaaggcc ttcctcgaac     120
cagccacacc aaactctgct gcagaaggtt tccttctctt tttcaacttc atgttgagaa     180
aatgactttc tcttgagcat ctcattttcc cctaaatttg ggcaagtgaa gagatatcag     240
cctggtcatc cagtagaaca gaaggccgag tcccgcactc ccccactgta aactatttga     300
ttgcacgtga gttgctttgt ttatgactta tttgctcaga agaggcacgt tgggaagcgg     360
ctcgagagac cagcccacgc gcaggtcctg agcgggcggg cgtgcgaggt cggcgcctcg     420
ctgcttgggg ccggggatga agtcctgcaa gcccagcggc cgccggcgg gagcgcgcgt     480 tgcacccccg tgcgcgggcg gcaccgagtg cgcgggcacg tgcgccgggg ccgggcggct     540
```

```
ggagagcgcg gcgcgcaggc gcctggcggc caacgcgcgc gagcgccgcc gcatgcaggg      600
gctcaacact gccttcgacc gcttacgcag ggtggttccc cagtgggggcc aggataaaaa      660
gctgtccaag tacgagaccc tgcagatggc cctgagctac atcatggctc tgacccggat      720
cctggccgag gccgagcgat tcggctcgga gcgggactgg gtgggtctcc actgtgagca      780
cttcggccgc gaccactacc tcccgttccc gggcgcgaag ctgccggggcg agagcgagct      840
gtacagccag agactcttcg gcttccagcc cgagcccttc cagatggcca cctagggcgc      900
gcgcctccgc gggggtgggt gtccggcagc cgctccgagc ctcggccctg ccccaagtag      960
cccagaagcc tccggcggcc caggattcta aggatgcaat cctcgaggaa aattagtcga     1020
ttctcagatt acctttattc gcatcatcag acctatggac gcaatcattt aattgccttt     1080
cttttcccct cctcctttgt attttgtaga tttcattaat ggatcttgtg aatgggttga     1140
ttgctgtgaa aataatgccc cctttcccct tttctgggct actttgaggg aaaacaatct     1200
taagaaaaat aggattaagc tattctgttc cagtcctcag agaaataatc actttcttaa     1260
actttgtgag tttgtcctgt tcgggtgaag ttacagtatc cattacttgt gtttgctcac     1320
aacagagcta ccttcctgtt gtgtaaatgc gttttttgctt tagtgcattg tgtgtgcaag     1380
catgaagtag aaacactttt ttttttctggg tacagtacat gggtatcggt gctctgtatt     1440
tttttaaact gtgtacacat tattaaaata tacattttat aaaatataaa taaaaacgtg     1500
gatttgtttt tcatgccaaa aaaaaaaaaa aaaa                                 1534

<210> SEQ ID NO 22
<211> LENGTH: 1385
<212> TYPE: DNA
<213> ORGANISM: Unknown
<220> FEATURE:
<223> OTHER INFORMATION: Description of Unknown: Atoh1 enhancer
      polynucleotide

<400> SEQUENCE: 22
tccaaggtcc ggcaatgaag tttgcataac aaacgtttgg cagctccctc tctcacaccc       60
cattaacaag ctgtaacata tagctgcagg ttgctataat ctcattaata ttttggaaac      120
ttgaatattg agtatttctg agcgctcatt ccccatatgc cagaccactc ctgccatgct      180
gactggttcc tttctctcca ttattagcaa ttagcttcta ccttccaaag tcagatccaa      240
gtatctaaga tactaccaaa ggcatcaact atgtatgcaa gttaggcatg cttaatatca      300
cccaaacaaa caaagagtca gcacttctta aagtaatgaa gatagataaa tcgggttagt      360
tctttgggac accgctgttg ttttccagag ttttttctata ctttaagcag cttgttttat      420
attctgtctt tgccctcagc cagctaacat tttatttgtt gagggttttg gctcaccaca      480
cttttggaaa cttatttgat ttcacgggga gctgaaggaa gattgttttt ggcaacaggc      540
aagtttaaca cgttcttcat ggggcattgc gaatggcaca tctaccagaa agggaggggg      600
agtaacttcc tcgtgctgaa ccagcaggag accagagctt cctgaggtc ttcctattga      660
ttttaaagat ttaaaactga gccccaaagt tgtaatgtta ttgaagtttg tcttggaata      720
tacatctcct ctgctaactt aaaagttcaa gaaaggaaag gaaagaaata gaacccccttg     780
ctaactacaa cctagactga gaggtgaaga tcgcgggcaa agacaggtgg tcactgaaac     840
gtttgcagtt ctttctcttcc gaaggcttag gacacagggt aaggaggagc taaaataaag      900
ccgagtgtac gtttagtctt ctctgcaccc caggcctagt gtctccccag gcaaggagtc      960
acccccctttg cttctggctc ctaactgaaa aaggcaaaag ggagtggaga atgggttaaa     1020
```

| | |
|---|---:|
| tcccaggaca caggggagag gcaggggagg agagaagtcg gaggaagata aaggaaagga | 1080 |
| caggaaccaa gaagcgtggg ggtagtttgc cgtaatgtga gtgtttctta attagagagc | 1140 |
| ggctgacaat agaggggctg gcagaggctc ctggccccgg tgcggagcgt ctggagcgga | 1200 |
| gcacgcgctg tcagctggtg agcgcactcg ctttcaggcc gctccccggg gagctgagcg | 1260 |
| gccacattta acaccgtcgt caccctcccc ggcctcctca acatcggcct cctcctcgta | 1320 |
| gacagccttg ctcggccccc caccggcaga gtttacagaa gccagagcct ctcgccgttc | 1380 |
| ccccg | 1385 |

<210> SEQ ID NO 23
<211> LENGTH: 8501
<212> TYPE: DNA
<213> ORGANISM: Unknown
<220> FEATURE:
<223> OTHER INFORMATION: Description of Unknown: Pou4f3 promoter
      polynucleotide

<400> SEQUENCE: 23

| | |
|---|---:|
| agggggtggc acggcgcggc gcggcgcggc gcggcgcggc gcggcgggtg tctcacagtt | 60 |
| ggcctctggc tccctggtcc ctctgggcat ctcggatcct ccctgggctg ggcagacaat | 120 |
| gagaggcagc ggccgacagg cgagtccagt agcagctgtg caggcggagg ttacatgtga | 180 |
| gaagtttgtg aaagaaactg agagaaagag agaggaaggc aaggcaggct gcagacacct | 240 |
| ggccccggtg cctcaccagc tgccctcctg cgatggcatc ttgagttcgg gcagctccta | 300 |
| tcgaagccat cttgcctggc atcctccccg ccccctctcc agcatgccta ggtgaggctg | 360 |
| agctgatgga ggcttagctg tggttccaac taactgccct gtaccagcag aggaagctag | 420 |
| cttagttcaa aacctagtaa agcaaacact ctgtcagggg aacttgcctt ccccttcaca | 480 |
| ttgagcattc ctctggcagg agtcctgaag aagatttatt aatatgtcca ttctaaaatg | 540 |
| acatagactt cttaaggact gtttgggaca cataagaact gataagactc accctctaaa | 600 |
| agtctccaga gtctttgaag gaacagacat tcatcgtcac atgcttttga agagataaca | 660 |
| gagcagggct ggagaaatgg ctcagcagtt aagaagactt ccagaggacc tggtgagatt | 720 |
| cccagtcccc tgtaattcca gttccagtga atctgatgcc ttcttctggc cagcagcact | 780 |
| cacgctagac acaaatgtgg tatacaaaca tacatgcaag caaaacaaaa gtgtgtgtta | 840 |
| agtgtttgtg catcatgtgc atactacgtg cctggtaagg ccagaagaag atgttggatc | 900 |
| ccctggaact cttagagatg gttgtgagct gccatgtagg tgctggaaat tgtatcaggg | 960 |
| ccctctggag aggtcaataa atgctcttaa gtgttgagcc atctctccac tcctcatata | 1020 |
| cattaaagga ataatttttt tgtacaggct acaggggagg ttgaggcagg aaggtctcaa | 1080 |
| ggccaaggcc aggcttagtt acatagaggg aactgtctca aaataagagt ggaggatctg | 1140 |
| gagaaatgga aagagcactg ttgttcttac aggggaccaa ttcctagcat ccacatggag | 1200 |
| gtccaagatc cttttctgac tctgaaggta tcagacactc atatggtaga catacataca | 1260 |
| tgcaggcaaa acacttatac acataagata atctgaaaaa aattaataaa ggggggaatc | 1320 |
| taactcattg gcagaccact cgccttgaat gcacgaggcc ctaggttcag tttatcatat | 1380 |
| gcagagagta gagttagtca cattgggata gacaataagc agagagaagc gggatgctag | 1440 |
| ctgtctcctt tcttccattg tgtgtgtgta tatatatata tgtatacata tatatacaca | 1500 |
| cacacatata catacacaca cacacacaca cacacacaca cacactgtat atactgtagt | 1560 |
| tgtcttcagc cataccagaa gagggcatca gatcctatta cagctgattt tgagccacct | 1620 |

-continued

```
tgtggttgct gggagttgaa cttaagacct tggcaagagc agccaatgct cttaaccact   1680
gggccgtctc tccaatcccc tcccttctc cattttgttc ctttgtgtat acccgcccct   1740
gggatgatga cacttggatc caaggtggat cttctctcct cgatcaatcc ttcaagaaac   1800
acctcacacg tgtccttctt aagttttctc tttttccaa gacaggattt ctctgtgtag   1860
ccatggctgg cctgtaacca tctttataga ccaggctggc ctcgaactca cagagatcca   1920
cctgctaatg aaagaactca gtggggaaac ccccactcag ctcccgattc ggcgtgcacc   1980
caagaatcgc gaatagaaca caacaccttg atgtaacaac aagaggtttt ttaatggcgg   2040
agctccgggt cgaaacgtat ctcacacaac aggagacagt ggattcgacc acgaggctta   2100
gaagctaggg gttttttatag aaaaggagtg gggctgggga aggaattgac gcggtttcac   2160
atgattggtc catttaaaca tcagcagcct gtaacattta acttaggtca gagggtggg   2220
agctagggag gcgaagggct tgcccgggca tgtcctggtc tgttctgctg tgttctcagc   2280
cccaggtttc aaagcgcaca aacaactctt tgggctattt aacatacatt acatgaatta   2340
cagttttatt tcctttcact tctactgtct gagtgcttgg cctaaaggcg tgctccacca   2400
cctggatcct taggcttggc aaccacatct actccttgtt acttaacact gaaatacacc   2460
actttagcca caacattcca tcctgtcccc caagtgttcc gatatatcgt atctcataac   2520
gcaaaacatt ctatccaatt tcaagaattc ccatagttat aaaagtccca acatgattga   2580
aaagtccaag ttcaataaaa tctctgggtc tccaagaaaa tccttaaatg tgagttctgg   2640
taacaatcca gaaatattct acatccaata tacaatggta ccaggtgaac atcacattcc   2700
aaaagacggg aaggagagca tagaacaaat ggatgggacc aagtcaagac taaaacccag   2760
gagaggaaat acgaaactct gcagctccat ttgtagcacc gagggcacgt catataatga   2820
cgtgcggttg aagatggttg ttagctgctg tgtgggtcct gggttctctg gatgaacatt   2880
gactagtaaa aaaatttttt tgaatgaatt aatttactta tcttctgggt gaggcaggat   2940
ctgaatgtgg aggccagagg gcaactgtgg gagtcacttg tctcctatgt gttagatctg   3000
gggagacaac tgaggaatcc aggtccccaa gcttcatgcc aggcacctt actagcggag   3060
tcatctcact gaccttggca ctcatcactt aataacagt taccttttaa ttcattcatt   3120
taatttaatt aatgataatt ccacagcatt caactcaatc cttttctgg ccatatggtt   3180
ttcaaaatct tttgctgtct tgagtctcat tataaaccca actaaacaca atgaccacaa   3240
cacctaacta aatgctatgc tgtcttgaaa tgtcctccac caaatgtgtc tgtcacccat   3300
gtttccctac acacacaaag tttatggaca cagacaaaat actttgccag aatagaattc   3360
aaatgatctt tagtcaagct cccaatagag acctcatttg catcgaaaac ctcaggggc   3420
caagcttttca tcctttgagt ctagtccact gaactcttgt gcatctagac cactgaactc   3480
cagacagaat tccccaccaa gctctgctca ccacactctc agcacctcta gtctaccttc   3540
ccctaccaac ccccttcaag caaacaagtt ccaaaggcgt gagaactagc tggttagcaa   3600
gaatgtaact tctgggtgcc aactttctgt attagatagt ttttcctca ctaatcagat   3660
acttgataga aacaacttaa gagagagaag atatattttg tatccagtgt cagagttttc   3720
agtgtgagag agctagagca cagaattctg tgctgggtcc cgaggtagag aaaggagaat   3780
gctagctcct gtcaactttc cctctttaac ccatttattc cagcaaagtc caaagccatg   3840
aggatggcac cactcacatt caagatgagt cttttttttt ttttttgccc cttacttaat   3900
cctcacactc acaggtagat ctcaccagtc tttcaggtaa ttctaaatat agtctagttg   3960
```

-continued

```
acaaggagga ttaaaccacc acagcccttg tcaaaacctc tgagtccgag tttcgtgct      4020
ctgttttatg aaactggagt tgcttctttc ttattcattc taatgttgaa agccactagc      4080
ccacagaaaa atgtccttgt ccctgatttg aatctctctg gagaacacag tgctctgagt      4140
cctgatttat gtggcaatct catgtcctgg ccaagatctt ggttttttgt tttttgtttt      4200
gttttgtttt ttttgttttt tttttttttt ttttttttt tgagataggg tctcacttat      4260
gtagccctgg ctgtcctgaa actccctatg tagaccaggc tggccttgaa ctcacagaga      4320
tccacctgcc tctgcctcct caagtgccac tacactgcct taaaccctaa gatcttgaaa      4380
cagtgctctc tgtatctgca gaacctgcca tgaaatccag ctagcagtgg gtatttcaaa      4440
gaccttatag aatgaaaaaa atgtgactcc tttggtgccc ttgactgaac cctgagatta      4500
ttttggact caatgggtgt agggtatttc cttatttgtt tgtgctctag gtggggtccc      4560
cattatgtag cttagctgac cttgaactct tgatgtagaa cagactgccc cccccacctg      4620
tctctctatg tgtgttttaa ttacaataaa atgccacggt ataagcgtaa gtttacctca      4680
ggccaacctc tcttgcatga ccaactacaa atagtagttg actggttttt attagatttt      4740
catctaattg aatttaagtt tgtaagttct gaaaaaaatg tgtcctaagg cttatcttgt      4800
actttcatcc cccccccgc ccaccaatct attatttat gtgtatggag gttttgtatg      4860
tatatatgtt tgtgtacctc ctatgtgaag taccccctgga ggtccgaaaa gggcatcaga      4920
ttcattggaa ttaacaaata gttctgagct accatgtgtg tgctgggaac tgaacttggg      4980
tcttctgaaa gacccagcca atgctcttaa tctcagggtc acttctacag accctgccgt      5040
tgcaattttt aaaaattatt tgttgttccc ttgtcatcat gtgtgtgtct ccctgccctt      5100
gttccacccc cattccccac cgatttcccc agcattatct aaagaccttg ataaggcctg      5160
tggtgtgaca gaaaacagtt gataaaggag atcagcatta cctttttaca ggtcctttaa      5220
aaagccaagt aagtacatgt atgactacac ttaattgatt tttaaaattt cagccccttt      5280
ctgtagctgg gtgtctttgc atgtagtttc actctgtctc catcaatagg tttatgttca      5340
ggcaaagcca taatcagatt ttctaagagt catctccagt gacaattatt caggtcttat      5400
tactattaat tattatttaa tatttaatta attgattaac aatcattatt aatcattagt      5460
ttttcatgtt attattcgtt tcgttttgtt taagatctcg cacagcccaa gctggccttg      5520
aactcagtct gtcatccatg tgagtacaga actcccagtt tccttcaccc acatcccaag      5580
tgctgaggtt acaggtgtga acagccacat ctatcttaca gatttacaat ggtttcatgc      5640
ccttttctga tgctatagaa taagaaaat gtatttttgc cagctaaaga agaaaaaaat      5700
gattccctta caatttgtat ttcttatctt tcaggctaat tgatgattga gttccaacca      5760
ggttgactat agcaatgtat aaaagattaa ttttaaagtg tgacacaaaa ataaatattc      5820
aaaatggtgg acacacacac acacacacac acagaggcta gttttactga taggtgtcag      5880
cttactactg accattgcta gtggacctta tgggaagaaa agacagaaag gtgttttcta      5940
ggggcctgag ggaagtagtg gtattgtcct ggtcagcatt ttttgatgac ttatttatt      6000
ttatgtgcat tgatgttttg cctacatata tgtctgttga accgcattgg atcccctgaa      6060
actgcagtta caggctacca tgtgggtgtt gggaattgag cccaggtcct ctggaagatc      6120
agtcagtgtt gttaaccact gagccatctc tccagtccca cctagtcagt attttccaag      6180
tccatgagtg acagagcagt gaaggggatg ggtatgaatg cgtctttccc aagtattcct      6240
cttcacagac aacgaggata ttatggcatg aaaagagacc cttaagaggc tccatggggt      6300
caggcaaaat gtaggtccac tacctccatg tttattcccg cttcccttt ggactccaca      6360
```

```
ctggtcagga acaatactg aggagtctta aaagctagtg ggagataaaa atcacccatg    6420
tttgacttct ggggacttga ggggcttgtg ttgtggcaca aagccagtaa taaggagagg    6480
aacagttcac atctgcagag agaccacatc cctggagaga ctgcaggctg ttctttaggt    6540
taaaaaggag gtgctaacat tgttccatc ctttcaacat gttggatgcc gtttcaagtg    6600
cttaccacca agtaaccctc actacagtag gggaaactac tgtatgcatc tgtatacaga    6660
tgggcactgc agtatagagg cctcaagatg actgtctcct ggcctctcag ccagtagaag    6720
tagaagcagc agtgtgctct gagtctgatg gcagcatgca ctgggttgtg aagaagtgtc    6780
ctgagtgcac agtgaggtca tcatcatcat ccttctcctc cagcaagacc caagaaagct    6840
acctgagtac catttcagtt ggcctccctc acagattgat gattgattga ttgattgatt    6900
gttgttgttg ttttgccaca gcaaggaagg acctagaatg tgttttggga tgagttgaga    6960
aaggactggc tggcagtcct gaggaaagag ggggagccag gtcagtgtag ggtgtcatct    7020
tagactaaat tcatccctgg gtcctagact ttccacactc tgcccctca gtgttaagat    7080 tctgggaaac ccagcactct tgagcacaga gacagtgctg caggacacag ctgggcagga    7140
agaatttctc ttccaacccg aaggcagctc tccagccggc cacagtccca ggattcccca    7200
tccattattc atggtgttta ttagctccca ggaagggaga ggaaagaagg agaggaggcg    7260
ctagggaaat aggggacaca gaggatgggg cagagacaaa cttaggaccc ttaagttggg    7320
ggaacttcta aaggaagaag aggaggctaa gaggtgaaga gcccaaagtc agacatggtg    7380
ttggctccaa accagtgagt gaatgacact gctcacaggt aggagatctt gggctaactt    7440
atttggctct tgtttccttt ggctgtctaa tgggatagca gtagctactc tgtagtgtcc    7500
tgtaggaacg ttggtcctat acactaacaa tacttttaa atattgagtg ctcaatactt    7560
ttctcattat gttattatta ttattattat tattattatt attattatta ttatcattgc    7620
ctcgcacaaa tcagtagctc aaaaatgata gctgttgtta caggtattgg ggctgctaag    7680
ctctacagaa gtatgcagaa gaattgctcc agctaggcca gctgtcctct actgttcctt    7740
agcaagcttt ctgggggggtg ggggggaaag ggagaacttg gcccacaagt tctgtttctc    7800
agatgaaagc tgaaacagcc agggttagga agaagccaca ggcttgtgga tcaggaagcc    7860
tttcttccac ccaagctcac agaggggagt atcacccgat aagcattctg gtaacctctg    7920
gtccttgccc aggctggttt ctgagtttgg aggcaccttt tcgctatgca ctgggatgca    7980
ggctttgagc ttcagactca gagcaccttg aaaatagcca gtttggggtg tgtgtgtgtg    8040
tgtgtgtgtg tgtgtgtgtg tgtgtgtgtg tctcaggagc ttaagtctgc cctttcatcc    8100
aggcagctcg agctgggaca ggacagaggt ttaggacttt atgcaaagaa gtccaggagg    8160
aagaagaaag aatctgtaaa gtctggcaag ctggagccag gtgggcggg gcggacagga    8220 agaggccctg ccaggccggg gtataaatgc tgtggagggg ggcggccgca tcaggctcag    8280
agtggcgcgc cgagacctgc ggtcccgcct tgcctcccgg gccgcccctg cgagtcccgg    8340
gcgcgtgtgc acgtctgcgc gtgcccgggc ccttcctggc agactgcttg taagatgagt    8400
gaagaagcag gtgggggaga ggggaggcag caagcgagag ggcgagggga gcgctggcgc    8460
tgagcggcgc tcacttggag cgcggagagc tagcaagacg a                      8501
```

<210> SEQ ID NO 24
<211> LENGTH: 3833
<212> TYPE: DNA
<213> ORGANISM: Unknown
<220> FEATURE:

<223> OTHER INFORMATION: Description of Unknown: Myo7a promoter
      polynucleotide

<400> SEQUENCE: 24

| | | | | | |
|---|---|---|---|---|---|
| ctagagggat | ctgtctgttt | cattttccc | gtaccccgca | cccccccaca | cacaagggta | 60 |
| aagacagagg | gcacaatggg | tagctgacct | ctggtcagaa | ggatgagcaa | ggaaggcctt | 120 |
| gggaatcaca | gataaaagct | ggccttgctg | gttacctagt | gagtcagagc | ccagctctgt | 180 |
| ggaatccttc | aggttccctg | cttccagtca | gtgtggggct | ggctttgctg | agctctgccc | 240 |
| atctcaggcc | ctggggacat | gggggcacac | agttcctgct | ctgcagcagc | cttccagcaa | 300 |
| ctggggaaaa | tgtacaaatc | atgtctgatc | gaagtactgt | agtgtccttg | ataagcagtg | 360 |
| tccctaggag | ctgactctta | gtctctgagt | tcaagatctg | tgccctgttc | tagtggagag | 420 |
| gagagactta | catgcaggcc | acagacggag | gtggcagagc | agatcctg | ggaaggtgcg | 480 |
| gtagctagag | ctaggaattt | atgggcaggg | ccacgggtag | aagctgggtc | gggttgtgga | 540 |
| aaacgaaatg | atggaatacg | acgatagatt | ggatttgaag | gggcgagggt | tgtatgaact | 600 |
| aagaccagtt | ctgcagtggt | tcagatgtgg | tgcccttaag | aggctcaggt | gccagaaacc | 660 |
| agtgcccctt | ctggataggg | cagaaaacag | gcagaacctg | gagaggtacg | gtggagcatg | 720 |
| aggtggtaag | gacacacacc | atctcaggtg | gtttgttttg | gggaaaacaa | gcatggattt | 780 |
| ctaggtttct | ccgatcgggt | gacctgctta | gccgagtttg | ggtgctgagg | aaatgtctcc | 840 |
| gttatggttc | tgagaccact | ttctcaccca | cccactgcct | tcccagcatg | cacctcagcc | 900 |
| tcaacgaagc | acacctgccc | cagttgccgc | cttgtcgatt | gggctctgga | tgctccaacc | 960 |
| tgtgtctctc | ccactctgtg | taggctcatg | ctactcacct | gactcataag | tatcagtttc | 1020 |
| gtaggtgaag | gctgcgttgg | gtgcaagtca | accttggacc | ctggtctcac | tgtggcaccc | 1080 |
| tggtatgagg | aagttgaccg | gcttttcctt | agtcttgtag | cagttggctg | tgcccagcag | 1140 |
| gtggcaccat | tgcaccattg | attctcccca | ctccatacca | ctatagattc | caccccaccc | 1200 |
| tattcccctc | cccaccttaa | cccacccacc | cccaccgaaa | agcagctttc | ctgagtagat | 1260 |
| gtcccagctg | gcaagtgtgg | gcagaagaag | gggccaggtc | tcaggaggag | gaggaggagg | 1320 |
| aggaggagga | ggaagaggaa | gaggagtcct | tcagcctcct | tcctcatcta | ccatgatgag | 1380 |
| tatttgtgtc | ctgttcattc | ccacccactc | ccttttttaa | atcacacatt | taaatcacac | 1440 |
| acacacacac | acacacacac | acacacacac | acacacacac | acaccgggta | agtctgtcct | 1500 |
| gcgtgaggtg | gctcctactc | aggtggcttt | gcaaactgtc | tggataacag | cacactcaag | 1560 |
| actcctagga | caggctgtgg | gggccagttg | tagagcctgg | gggtggggtg | catcttgggg | 1620 |
| agtcctggtt | tggatgttgt | gtccagccaa | ggctccaggt | attgccaagc | ctgctcattt | 1680 |
| atatggtctc | tagtagtgcc | ctgacgaggg | aagctgggtg | agcaggggag | gctactggga | 1740 |
| actgagaccc | agcaaaatca | tgaggaagat | gggacgtgat | caggtgtcct | aaccatgcag | 1800 |
| agatggcagg | tagtaacaca | tgtgacaaga | gaccctgagg | tcctgatggt | tggccccagg | 1860 |
| cccgaggttc | ccactggcca | gcagtgcccc | ctggagcttc | tatgccttgc | atccctgctg | 1920 |
| gttagcttta | cacagcacct | tgggcaacct | ctagacgtta | gtcagcagcc | ccagcacagc | 1980 |
| ccgcccctca | tgctgatgtc | accacatcca | gaccttcgag | gccccaggg | ctccgcctcc | 2040 |
| tgggagaagg | ctttggaggg | agagggcggg | tggcagtgca | ggctggacag | ctgccctgaa | 2100 |
| cagaaagaaa | gagtgaccca | gggagacaag | aaacagagta | gcccaaggga | agcccacagc | 2160 |
| agcagcagat | caaggctcaa | gctggagctg | aaaatttgca | ggctccagcc | tcagcttcca | 2220 |

| | |
|---|---|
| gagtcctcct gacctgtgac ccctggctcc tggctgggag gtggtgactc ggagggtgtg | 2280 |
| gataaaccc aggtaaggat gggctgccct ggctggaact tttggactgg ggaggagtta | 2340 |
| caggctgggg cctcctctgg agcctctgcc cttaggttcc tgggactgga ctcccctgaa | 2400 |
| cctacagggg ccttgccacc ataggcatgg aaagaaaatg ccccgagccg tgcacatgga | 2460 |
| ggcttatgcc ctagatgagg aatagctga agagcacagg gcctgtggag ttgtttccgg | 2520 |
| gttggagctg ggtcaggggt atccagaggc aggggtgaaa gatgggagtg gaggctgggg | 2580 |
| gggcaagtgt ggatgcctct ctctgcttgg tcttttggtc atctccctga taatctatct | 2640 |
| ctccttgcac acgttgtttc ttctttgtgt gccttacatt ctctatccgt gacccaagaa | 2700 |
| catgaaggtt accatctggg gttgcccagg ggtcaaggta aaatcagttg tgggtctagg | 2760 |
| gaaaaaaaca aaacaaaaca aaaaactatg gttctttgtt ctcaatttga aaagcaacag | 2820 |
| tcttacacac tagtctagtc tgggatggag aggtagagcc tcatgcatgg ggtagaagag | 2880 |
| acctgagctt ttccatgggt cttcagctct accctccaag tctacagtcc cagtctgtcc | 2940 |
| tgcagccttg taccagcatg agtgaggcag gggccaggca gcctcttcag acgccagctc | 3000 |
| tcataactac tgctgctgcc tttgggatta tcccctgcc aggacccag cgtggtgtag | 3060 |
| gtctcccgaa ggaccatatg cccatagaga cccaggcgt ggggtcaggg ctcaggtgtc | 3120 |
| aggcagtgtc gtgggcagag gatcagatgt cccagtgcct ctgaatggac ccttgtgaaa | 3180 |
| acttaatgct cactcgaggg gcaggccagg cagggatgga ggggcctcac accaagacct | 3240 |
| atgggctggg gctgcttctg gtgaccacac tcgaggcagc aaatccatct cgagcctatt | 3300 |
| cctgggtcca gctctgtgct ggatgaggta agagatgagg gccacgaaca ggtgttagat | 3360 |
| cattctgcca tgtgtcctaa aactcctaaa gcagtcctga accaggagca gagtccaaat | 3420 |
| cttacttagt gccaagtctt ccctgccctg ctgtgtgacc ttgggtaaga gatagtcctt | 3480 |
| ctctgaactt tgggcagcct caggacatta gtccctgtcc cagcacagcc caccctcac | 3540 |
| gctgatgtct ggtacagggc tgactacact cctttcaaag ccctttggga tgacgagggc | 3600 |
| agctttgggc agtggaggtg gtgacggtaa ctgaggctct ggtcacatag actgagcttt | 3660 |
| aatcagaagg atggaaacca agaaagattt ccgtgaggga ggaggggtag gggtggggtt | 3720 |
| ggggaggagt ctaggtggcc ctgcagatcc aagctgcctg ggctcagggc gtgccatggt | 3780 |
| ctcttcccac agagctgtgt ctggtcactc cggcaggtgt gctgacgtag aag | 3833 |

<210> SEQ ID NO 25
<211> LENGTH: 1600
<212> TYPE: DNA
<213> ORGANISM: Unknown
<220> FEATURE:
<223> OTHER INFORMATION: Description of Unknown: Hes5 promoter
    polynucleotide

<400> SEQUENCE: 25

| | |
|---|---|
| acctctgtca gagctcgggt gagggttgtg gcagggacta agggaggtga attctgcact | 60 |
| tatatcttgc actggacaga ccatcctgtg ctgcctcaaa gccaagcctt cccctctgtc | 120 |
| ccagatgctt ccatccatgg taacccaaca accccttgtg ctaagagctt ctggagcaag | 180 |
| accttcggaa tagatcattt acagcagtgg gtcactacca tagcaggagg gcgtttccct | 240 |
| agtgggcact gtgaaggccc ttcagttcct gagctcagac atgctgaca tccatccaga | 300 |
| gaacctggtt tcattccaca ctggctattg tgctctgatg ccagcctcct ggtttgggcc | 360 |
| tggctaggtc ttaggttgac cctaggagga agcacggggc cttatctcct ccctcagccc | 420 |

```
ctgcagagta ttggggaaat agtacaggtt ccagatggag ggacgctcct acatggccat        480
cccctaggtg tctagggtgt gactagtaag gtcacctggt taggaaccac ggttatcagt        540
tcttacaaag aggcccatcc acactggcac agcattcata tgggggctta ttttaggtc         600 tcccaccttc tacctgccaa cacaaaatgc tgaatgaaac tggaacacac acacagaggc        660
atgcacgcgc gcgcccgcac gagctgaggg ggatgtcatg agaggagtta agggcagcca        720
tggtttccta aaagccacgc gggagtagtg atcacggaca gcatgaagga ggcacggtcc        780
tcctgtttca gagatgcatg tggcacctgg tgacacaaga gcagtccaga taccctgtgg        840
gttcaggggt tcctgagggc ttcctaggta tggggctttg tgctaggcat tatccaaagc        900
aaattcagct agcctagaag tacgcttggc aggctccgcg cgtggccatt tctagctgcg        960
gagaagtcac tcctctcaac tgacagaact ggcaataaag cgcctaaatt ctaaatacat       1020
gagtccctct ctcatcctgt acctgcgaat ggcatggcgg cagcatctgt ttgagagaat       1080
gtggcccact ttaacccact gtgcctgtgg gcaacaggtc ccagctgggg agggtgccca       1140
ctcctctgga agtcgctgtc tgttcattgt aaaactctca tttctctgcg cctgtggcct       1200
ctgccagcca gcggtgggga gcctctgggg agtgggaggg aagaagggag agaagggggg       1260
gggagagcac tccttcctgc cctccccacc tccccgcggc ctgggaaaag gcagcatatt       1320
gaggcgcggg gctctcagca tcaggccccg ggatgctaat gagggcgagc gcgttcccac       1380
agcccggaca ttgtgccgcg cggcccacct gctcctcggg gagcgaccat tgtgcccgcg       1440
ccaattcaca ggcaatttag cgtgcgctaa tgggccggcg cctttgtgcg gccggcgccg       1500
ccattggccg ccgagtgtgg gaacggccgc ggcgcccgga ccccaggcgc cgggccgctg       1560
cccgcgccta tagggctg gcgtgctggg gtccaggtcg                                1600
```

<210> SEQ ID NO 26
<211> LENGTH: 2211
<212> TYPE: DNA
<213> ORGANISM: Unknown
<220> FEATURE:
<223> OTHER INFORMATION: Description of Unknown: GFAP promoter
      polynucleotide

<400> SEQUENCE: 26

```
aggagctccc acctccctct ctgtgctggg actcacagag ggagacctca ggaggcagtc         60
tgtccatcac atgtccaaat gcagagcata ccctgggctg gcgcagtgg cgcacaactg         120 taattccagc actttgggag gctgatgtgg aaggatcact tgagcccaga agttctagac        180
cagcctggga acatggcaa gaccctatct ctacaaaaaa agttaaaaaa tcagccacgt         240
gtggtgacac acacctgtag tcccagctat tcaggaggct gaggtgaggg gatcacttaa        300 ggctggagg ttgaggctgc agtgagtcgt ggttgcgcca ctgcactcca gcctgggcaa         360
cagtgagacc ctgtctcaaa agacaaaaaa aaaaaaaaa aaaaaagaa catatcctgg         420 tgtggagtag gggacgctgc tctgacagag gctcggggc ctgagctggc tctgtgagct         480
ggggaggagg cagacagcca ggccttgtct gcaagcagac ctggcagcat tgggctggcc        540
gccccccagg gcctcctctt catgcccagt gaatgactca ccttggcaca gacacaatgt        600
tcggggtggg cacagtgcct gcttcccgcc gcacccagc cccctcaaa tgccttccga         660 gaagcccatt gagcaggggg cttgcattgc accccagcct gacagcctgg catcttggga        720
taaaagcagc acagccccct aggggctgcc cttgctgtgt ggcgccaccg gcggtggaga       780
acaaggctct attcagcctg tgcccaggaa aggggatcag gggatgccca ggcatggaca       840
```

```
gtgggtggca ggggggggaga ggagggctgt ctgcttccca gaagtccaag gacacaaatg   900
ggtgagggga ctgggcaggg ttctgaccct gtgggaccag agtggagggc gtagatggac   960
ctgaagtctc cagggacaac agggcccagg tctcaggctc ctagttgggc ccagtggctc  1020
cagcgtttcc aaacccatcc atccccagag gttcttccca tctctccagg ctgatgtgtg  1080
ggaactcgag gaaataaatc tccagtggga gacggagggg tggccaggga acggggcgc   1140 tgcaggaata agacgagcc agcacagcca gctcatgtgt aacggctttg tggagctgtc   1200
aaggcctggt ctctgggaga gaggcacagg gaggccagac aaggaagggg tgacctggag  1260
ggacagatcc aggggctaaa gtcctgataa ggcaagagag tgccggcccc ctcttgccct  1320
atcaggacct ccactgccac atagaggcca tgattgaccc ttagacaaag gctggtgtc   1380 caatcccagc ccccagcccc agaactccag ggaatgaatg ggcagagagc aggaatgtgg  1440
gacatctgtg ttcaagggaa ggactccagg agtctgctgg gaatgaggcc tagtaggaaa  1500
tgaggtggcc cttgagggta cagaacaggt tcattcttcg ccaaattccc agcaccttgc  1560
aggcacttac agctgagtga gataatgcct gggttatgaa atcaaaaagt tggaaagcag  1620
gtcagaggtc atctggtaca gcccttcctt ccctttttt tttttttttt tgtgagacaa   1680
ggtctctctc tgttgcccag gctggagtgg cgcaaacaca gctcactgca gcctcaacct  1740
actgggctca agcaatcctc cagcctcagc ctcccaaagt gctgggatta caagcatgag  1800
ccaccccact cagccctttc cttcctttt aattgatgca taataattgt aagtattcat   1860
catggtccaa ccaacccttt cttgacccac cttcctagag agagggtcct cttgcttcag  1920
cggtcagggc cccagaccca tggtctggct ccaggtacca cctgcctcat gcaggagttg  1980
gcgtgcccag gaagctctgc ctctgggcac agtgacctca gtggggtgag gggagctctc  2040
cccatagctg ggctgcggcc caaccccacc ccctcaggct atgccagggg gtgttgccag  2100
gggcacccgg gcatcgccag tctagcccac tccttcataa agccctcgca tcccaggagc  2160
gagcagagcc agagcaggat ggagaggaga cgcatcacct ccgctgctcg c            2211
```

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Glu Ala Pro Pro Ala Pro Pro Gln Ser Pro
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Lys Glu Ala Pro Pro Ala Pro Pro Gln Ser Pro
1               5                   10